US011243210B2

(12) United States Patent
Igawa et al.

(10) Patent No.: US 11,243,210 B2
(45) Date of Patent: Feb. 8, 2022

(54) ION CONCENTRATION-DEPENDENT BINDING MOLECULE LIBRARY

(71) Applicant: Chugai Seiyaku Kabushiki Kaisha, Tokyo (JP)

(72) Inventors: Tomoyuki Igawa, Shizuoka (JP); Shinya Ishii, Shizuoka (JP); Miho Funaki, Shizuoka (JP); Naoka Hironiwa, Shizuoka (JP); Shun Shimizu, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 230 days.

(21) Appl. No.: 16/010,929

(22) Filed: Jun. 18, 2018

(65) Prior Publication Data
US 2019/0041396 A1    Feb. 7, 2019

Related U.S. Application Data

(63) Continuation of application No. 14/348,511, filed as application No. PCT/JP2012/006254 on Sep. 28, 2012, now Pat. No. 10,024,867.

(30) Foreign Application Priority Data

Sep. 30, 2011 (JP) ................................ 2011-218006
May 30, 2012 (JP) ................................ 2012-123479

(51) Int. Cl.
| | | |
|---|---|---|
| G01N 33/68 | (2006.01) | |
| C07K 16/00 | (2006.01) | |
| C07K 16/24 | (2006.01) | |
| C07K 16/26 | (2006.01) | |
| C07K 16/40 | (2006.01) | |
| C07K 16/28 | (2006.01) | |
| C40B 40/10 | (2006.01) | |

(52) U.S. Cl.
CPC ......... *G01N 33/6854* (2013.01); *C07K 16/00* (2013.01); *C07K 16/005* (2013.01); *C07K 16/24* (2013.01); *C07K 16/26* (2013.01); *C07K 16/2866* (2013.01); *C07K 16/40* (2013.01); *G01N 33/6845* (2013.01); *C07K 2317/14* (2013.01); *C07K 2317/21* (2013.01); *C07K 2317/55* (2013.01); *C07K 2317/565* (2013.01); *C07K 2317/72* (2013.01); *C07K 2317/92* (2013.01); *C07K 2317/94* (2013.01); *C40B 40/10* (2013.01)

(58) Field of Classification Search
None
See application file for complete search history.

(56) References Cited

U.S. PATENT DOCUMENTS

| | | |
|---|---|---|
| 2005/0123546 A1 | 6/2005 | Umana et al. |
| 2010/0239577 A1 | 9/2010 | Igawa et al. |
| 2010/0249377 A1 | 9/2010 | Wang et al. |
| 2011/0111406 A1* | 5/2011 | Igawa et al. .......... A61K 39/145 435/6.14 |
| 2013/0336963 A1 | 12/2013 | Igawa et al. |

FOREIGN PATENT DOCUMENTS

| | | | |
|---|---|---|---|
| CN | 102056946 A | 5/2011 | |
| EA | 015009 B1 | 12/2006 | |
| EP | 2275443 A1 | 1/2011 | |
| JP | 2163085 A | 6/1990 | |
| JP | 2011507520 A | 3/2011 | |
| JP | 2011184418 A | 9/2011 | |
| JP | 4954326 B2 | 6/2012 | |
| KR | 20110004435 A | 1/2011 | |
| WO | WO 2003105757 A2 | 12/2003 | |
| WO | WO-2009125825 A1 * | 10/2009 | ......... C07K 16/2866 |
| WO | WO 2009125825 A1 | 10/2009 | |
| WO | WO 2010058860 A1 | 5/2010 | |
| WO | WO 2011111007 A2 | 9/2011 | |

OTHER PUBLICATIONS

Communication dated Feb. 22, 2016, from the Intellectual Property Office of Taiwan in corresponding Application No. 101136222.
Luttrell, B. M., et al., "Reaction coupling of chelation and antigen binding in the calcium iondependent antibody binding of cyclic AMP," The Journal of Biological Chemistry, 266(32):21626-21630 (1991).
Communication from the Chinese Patent Office dated Dec. 26, 2014 in counterpart Chinese Application No. 201280058080.5.
Reichert, J. M., et al., "Monoclonal antibody successes in the clinic," Nature Biotechnology, 23(9):1073-1078 (2005).
Pavlou, A. K., "The therapeutic antibodies market to 2008," European Journal of Pharmaceutical and Biopharmaceutics, 59(3):389-396 (2005).
Kim, S. J., et al., "Antibody Engineering for the Development of Therapeutic Antibodies," Molecules and Cells, 20(1):17-29 (2005).
Hinton, P. R., et al., "An Engineered Human IgG1 Antibody with Longer Serum Half-life," The Journal Immunology, 176(1):346-356 (2006).

(Continued)

*Primary Examiner* — Kaijiang Zhang
(74) *Attorney, Agent, or Firm* — Nixon & Vanderhye P.C.

(57) ABSTRACT

Disclosed is a library consisting essentially of a plurality of antigen-binding molecules differing in sequence from each other, wherein an antigen-binding domain in each of the antigen-binding molecules comprises at least one amino acid residue that changes the antigen-binding activity of the antigen-binding molecule depending on ion concentration conditions. Also disclosed are a composition comprising a plurality of polynucleotide molecules each encoding the antigen-binding molecules, a composition comprising a plurality of vectors each comprising the polynucleotide molecules, a method for selecting the antigen-binding molecules, a method for isolating the polynucleotide molecules, a method for producing the antigen-binding molecules, and a pharmaceutical composition comprising any of the antigen-binding molecules.

11 Claims, 21 Drawing Sheets

Specification includes a Sequence Listing.

(56) References Cited

OTHER PUBLICATIONS

Ghetie, V., et al., "Increasing the serum persistence of an IgG fragment by random mutagenesis," Nature Biotechnology, 15(7):637-640 (1997).
Rajpal, A., et al., "A general method for greatly improving the affinity of antibodies by using combinatorial libraries," Proc Natl Acad Sci., USA, 102(24):8466-8471 (2005).
Wu, H., et al., "Development of Motavizumab, an Ultra-potent Antibody for the Prevention of Respiratory Syncytial Virus Infection in the Upper and Lower Respiratory Tract," J Mol Biol., 368:652-665 (2007).
Hanson, C. V., et al., "Catalytic antibodies and the applications," Current Opinion in Biotechnology, 16(6):631-636 (2005).
Rathanaswami, P., et al., "Demonstration of an in vivo generated sub-picomolar affinity fully human monoclonal antibody to interleukin-8," Biochemical Biophysical Research Communications, 334(4):1004-1013 (2005).
Springer, T. A., et al., "A Novel $Ca^{2+}$ Binding B Hairpin Loop Better Resembles Integrin Sequence Motifs Than the EF Hand," Cell, 102:275-277 (2000).
Kawasaki, H., et al., "Calcium-Binding Proteins 1," Protein Profile, 2:305-490 (1995).
Moncrief, N. D., et al., "Evolution of EF-Hand Calcium-Modulated Proteins. I. Relationships Based on Amino Acid Sequences," J Mol Evol., 30:522-562 (1995).
Chauvaux, S., et al., "Calcium-binding affinity and calcium-enhanced activity of *Clostridium thermocellum* endoglucanase D," Biochem J., 265:261-265 (1990).
Bairoch, A., et al., "EF-hand motifs in inositol phospholid-specific phospholipase C," FEBS Lett., 269(2):454-456 (1990).
Davis, C. G., "The Many Faces of Epidermal Growth Factor Repeats," The New Biologist, 2(5):410-419 (1990).
Schafer, B. W., "Isolation of a YAC Clone Covering a Cluster of Nine S100 Genes on Human Chromosome 1q21: Rationale fora New Nomenclature of the S100 Calcium-Binding Protein Family," Genomics, 25:638-643 (1995).
Economou, A., et al., "The *Rhizobium* nodulation gene nodO encodes $Ca2^+$-binding protein that is exported without N-terminal cleavage and is homologous to haemolysin and related proteins," The EMBO Journal, 9(2):349-354 (1990).
Wurzburg, B. A., et al., "Structural Changes in the Lectin Domain of CD23, the Low-Affinity IgE Receptor, upon Calcium Binding," Structure, 14(6):1049-1058 (2006).
Knappik, A., et al., "Fully Synthetic Human Combinatorial Antibody Libraries (HuCAL) Based on Modular Consensus Frameworks and CDRs Randomized with Trinucleotides," J Mol Biol., 296:57-86 (2000).
Glanville, J., et al., "Precise determination of the diversity of a combinatorial antibody library gives insight into the human immunoglobulin repertoire," Proc Natl Acad Sci., 106(48):20216-20221 (2009).
Hopp, T. P., et al., "Metal-binding Properties of a Calcium-dependent Monoclonal Antibody," Molecular Immunology, 33(7/8):601-608 (1996).
Einhauer, A., et al., "Complex formation of a calcium-dependent antibody: A thermodynamical consideration," Journal of Chromatography A, 1009(1-2):81-87 (2003).
O'Connor, S. J., et al., "Humanization of an antibody against human protein C and calcium-dependence involving framework residues," Protein Engineering, 11(4):321-328 (1998).
Dixit, V. M., et al., "Monoclonal Antibodies That Recognize Calcium-dependent Structures of Human Thrombospondin," The Journal of Biological Chemistry, 261 (4):1962-1968 (1986).
Sigma-Aldrich, Product Information Sheet, 1 page, http://www.sigmaaldrich.com/content/dam/sigmaaldrich/docs/Sigma/Datasheet/f3040dat.pdf.
Zhou, T., et al., "Interfacial metal and antibody recognition," PNAS, 102(41):14575-14580 (2009).
Wojciak, J. M., "The crystal structure of sphingosine-1-phosphate in complex with a Fab fragment reveals metal bridging of an antibody and its antigen," PNAS, 106(42):17717-17722 (2009).
International Search Report for PCT/JP2012/006254 dated Dec. 25, 2012.
Sigma-Aldrich, Product Information Sheet and Product Specification Sheet, (2 pages) http://www.sigmaaldrich.com/content/dam/sigmaaldrich/docs/Sigma/Datasheet/f3040dat.pdf. (dated Nov. 23, 2010).
Murtaugh, et al., "A Combinatorial Histidine Scanning Library Approach to Engineer Highly pH-Dependent Protein Switches," Protein Science, 20(9):1619-1631 (2011).
Ito, et al., "The His-probe method: effects of histidine residues introduced into the complementarity-determining regions of antibodies on antigen-antibody interactions at different pH values," FEBS Letters, 309(1):85-88 (1992).
Igawa, et al., "Antibody recycling by engineered pH-dependent antigen binding improves the duration of antigen neutralization," Nature Biotechnology, 28(11):1203-1207 (2010).
Communication dated Mar. 26, 2015, issued by the European Patent Office in corresponding Application No. 12835490.9.
Communication dated Jan. 4, 2016 from the Intellectual Property of Singapore in counterpart Application No. 11201401102V.
Reverberi, R. and Reverberi, L., "Factors affecting the antigen-antibody reaction," Blood Transfusion, 5(4):227-240 (2007).
Rudikoff, S., et al., "Single amino acid substitution altering antigen-binding specificity," Proc Natl Acad Sci., USA, 79(6):1979-1983 (1982).
Chen, et al., "Selection and Analysis of an Optimized Anti-VEGF Antibody: Crystal Structure of an Affinity-matured Fab in Complex with Antigen," J M Biol., 293:865-881 (1999).
Schier, et al., "Isolation of Picomolar Affinity Anti-c-erbB-2 Single-chain Fv by Molecular Evolution of the Complementarity Determining Regions in the Center of the Antibody Binding Site," J M Biol., 263:551-567 (1996).
Yang, et al., "CDR Walking Mutagenesis for the Affinity Maturation of a Potent Human Anti-HIV-1 Antibody into the Picomolar Range," J M Biol., 254:392-403 (1995).
Osbourn, et al., "Generation of a panel of related human scFv antibodies with high affinities for human CEA," Immunotechnology, 2:181-196 (1996).
Wu, et al., "Stepwise in vitro affinity maturation of Vitaxin, an $alpha_v beta_3$-specific humanized mAb," 95:6037-6042 (1998).
Pancook, et al., "In Vitro Affinity Maturation of Human IgM Antibodies Reactive with Tumor-Associated Antigens," Hybridoma and Hybridomics, 20(6):383-396 (2001).
Fiedler, et al., "An engineered IN-1 $F_{ab}$ fragment with improved affinity for the Nogo-A axonal growth inhibitor permits immunochemical detection and shows enhanced neutralizing activity," Protein Engineering, 15(11):931-941 (2002).
Japanese Office Action dated Aug. 9, 2016 in corresponding Japanese Patent Application No. 2013-535944.
Invitation to Respond to Written Opinion dated Mar. 19, 2018 in corresponding Singaporean Patent Application No. 11201401102V.
Christensen, K. A., et al., "pH-dependent regulation of lysosomal calcium in macrophages," J Cell Science, 115:599-607 (2002).
Kim, J., et al., "Kinetics of FcRn-mediated recycling of IgG and albumin in human: Pathophysiology and therapeutic implications using a simplified mechanism-based model," Clin Immunol., 122(2):146-155 (2007).
Russian Decision to Grant dated May 27, 2020 in Russian Patent Application No. 2014117636.
Singaporean Examination Review Report dated Jul. 9, 2020 in Singaporean Patent Application No. 11201401102V.
Hironiwa, N., et al., "Calcium-dependent antigen binding as a novel modality for antibody recycling by endosomal antigen dissociation," mAbs, 8(1):65-73 (2016), published online Dec. 19, 2015.
Sergeeva, A., et al., "Display technologies: Application for the discovery of drug and gene delivery agents," Adv Drug Del Rev., 58:1622-1654 (2006).
Canadian Office Action dated Jul. 11, 2019 from the Canadian Intellectual Property Office in corresponding Application No. 2,850,041, 6 pages.

(56) References Cited

OTHER PUBLICATIONS

Russian Office Action dated Feb. 1, 2021 in corresponding Application No. 2020124650, 15 pages.
Filipovich, Y. B., et al., "Biohimicheskie osnovy zhiznedeyatelnosti cheloveka," Moscow, Vlados, 49-50, 70 (2005).
Yarilin, A. A., "Osnovy immunologii," (English: Fundamentals of immunology), Moscow, Medicina, 171, second paragraph (1999).

* cited by examiner

FIG.4A
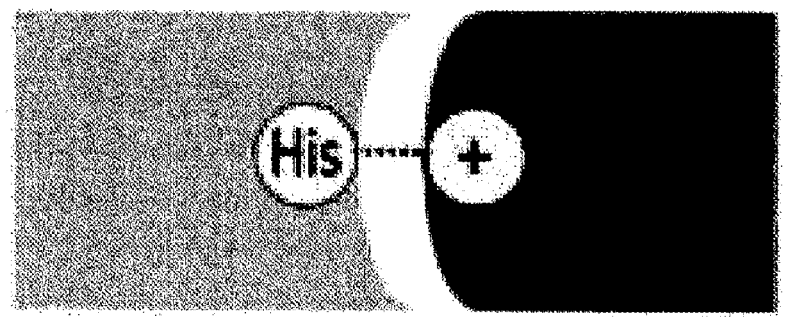
pH7.4
Interaction
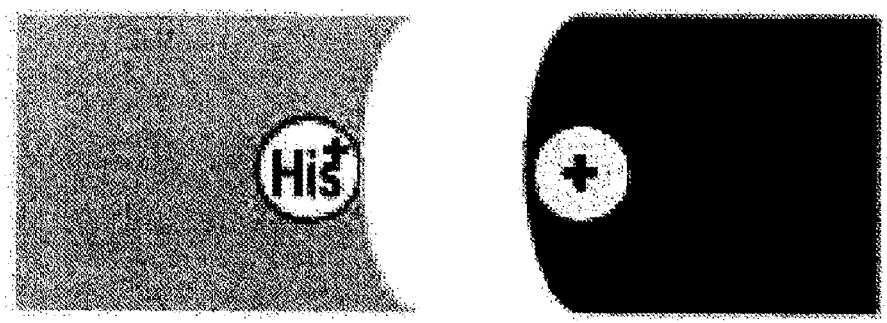
pH6.0
Repulsion

FIG.4B
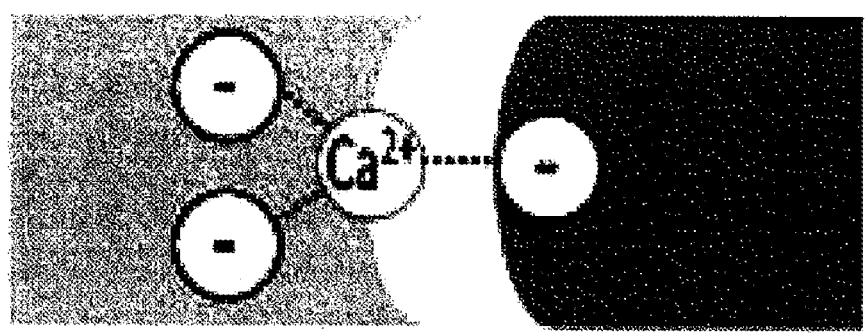
Interaction
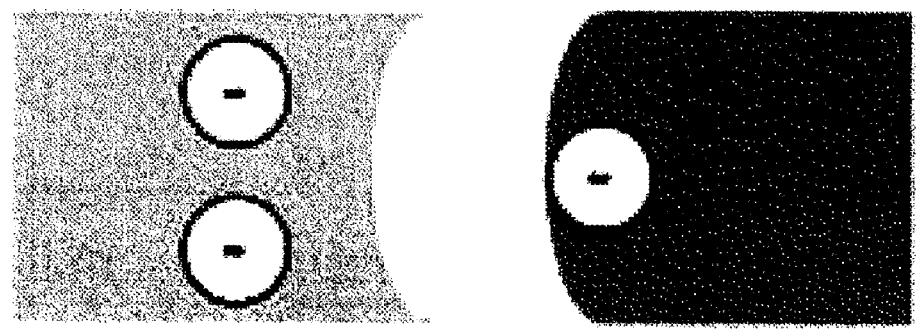
Repulsion

FIG.4C
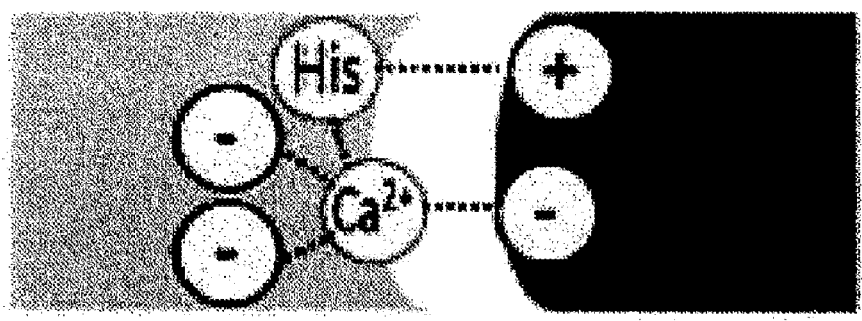
Interaction
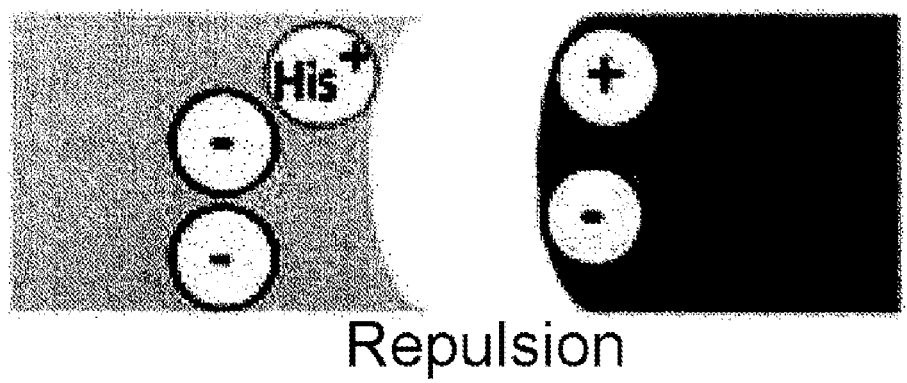
Repulsion

FIG.7
(i) Light chain LfVk1_Ca
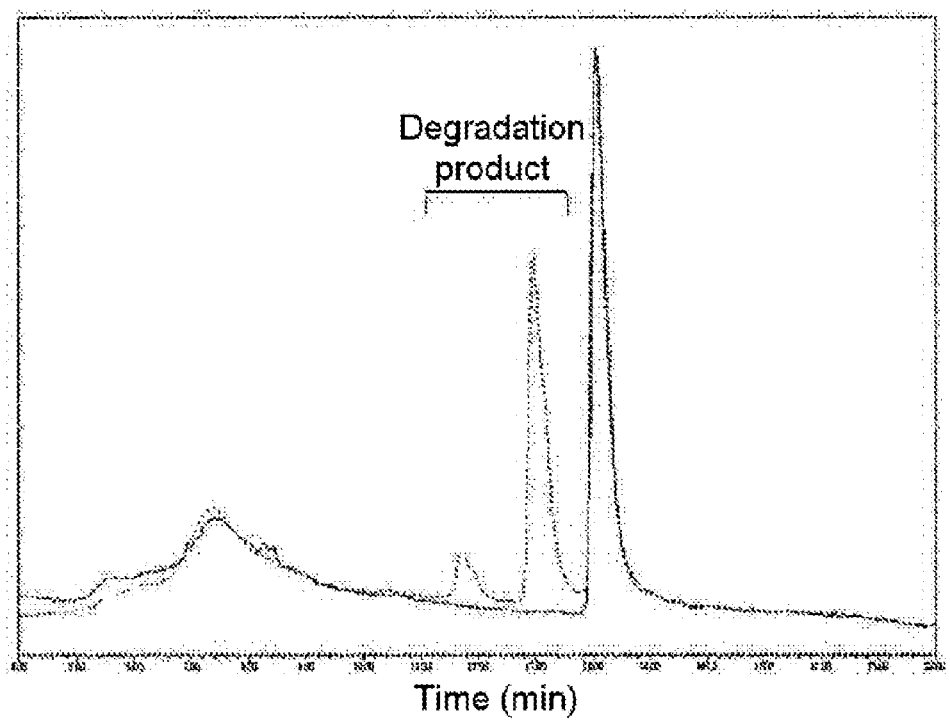
(ii) Light chain LfVk1_Ca6
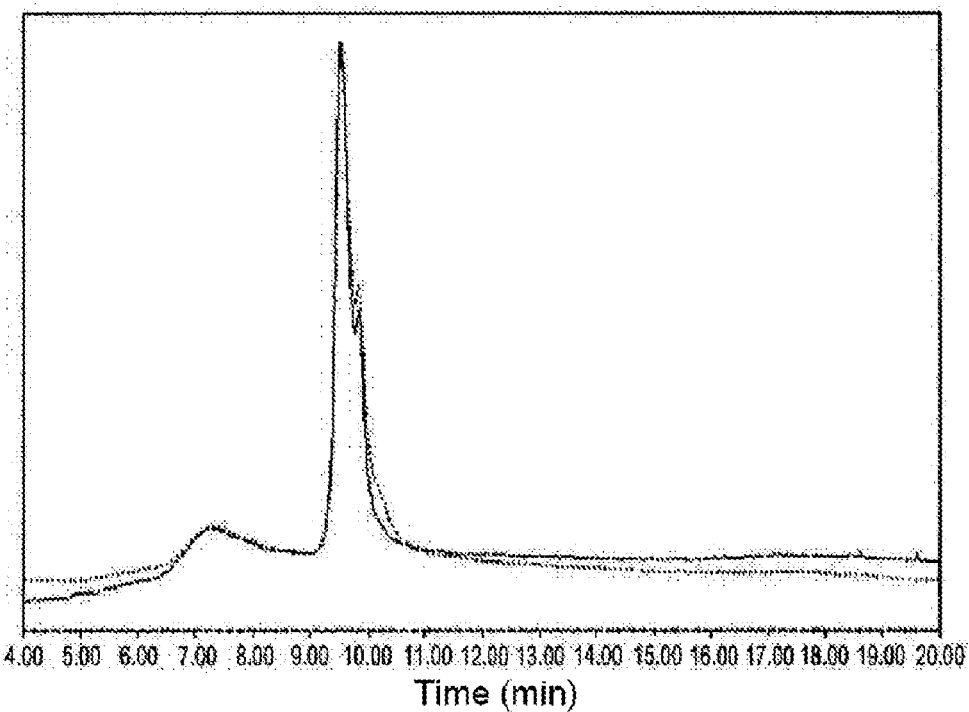

FIG.11
(i) Crystal structure in presence of calcium ion
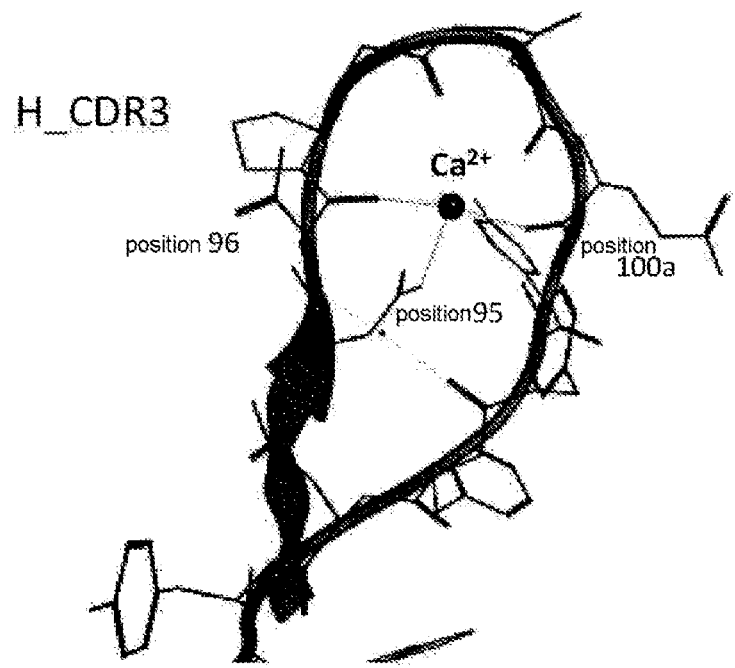
(ii) Crystal structure in absence of calcium ion
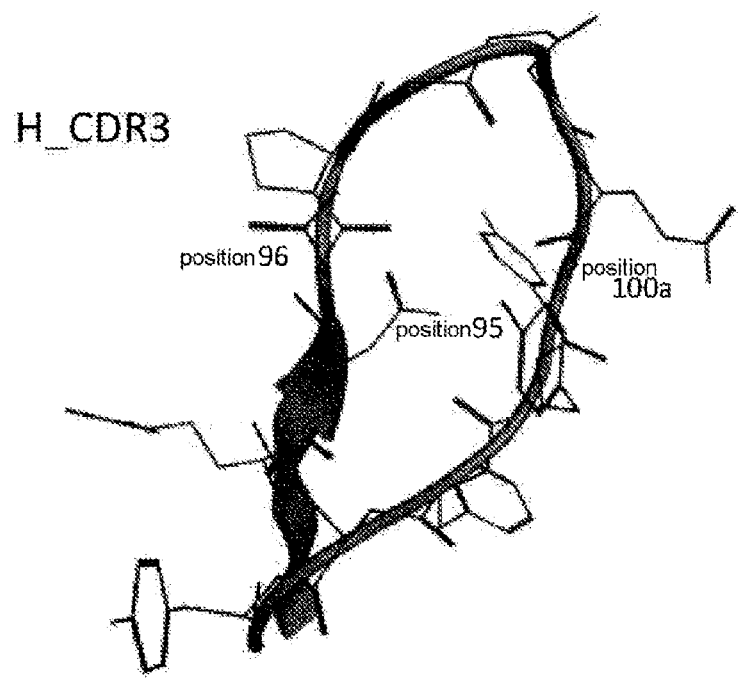

FIG.13
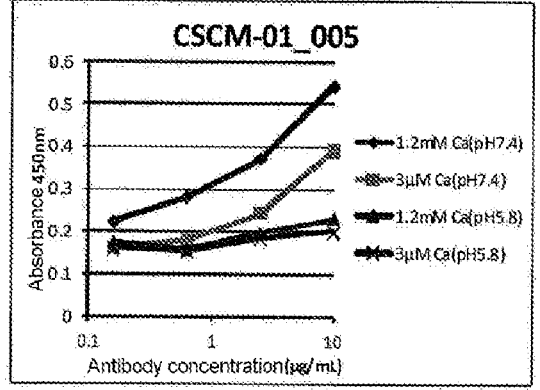
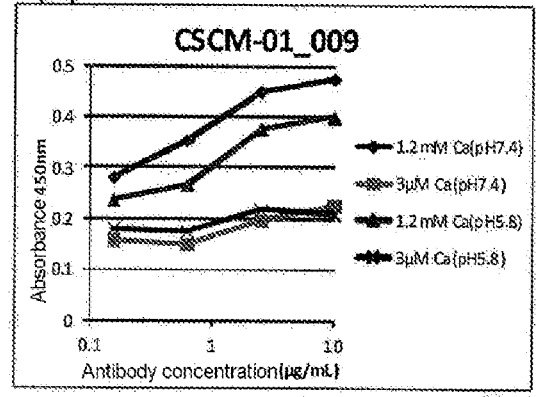
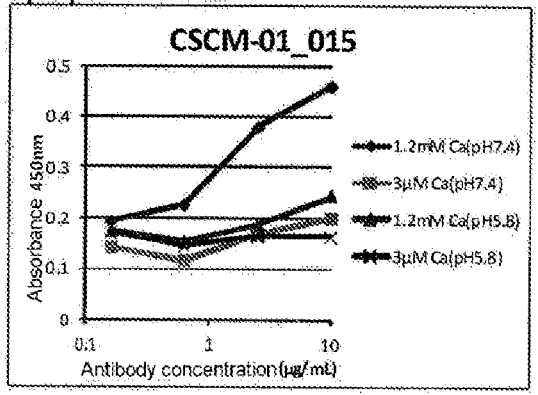
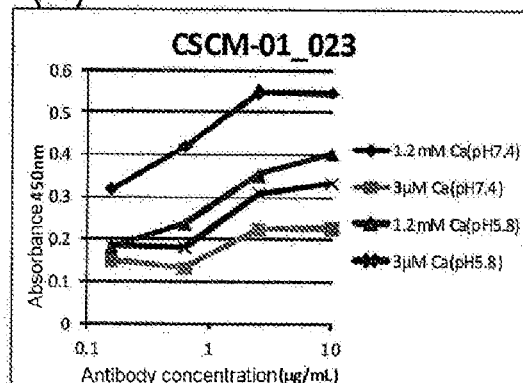
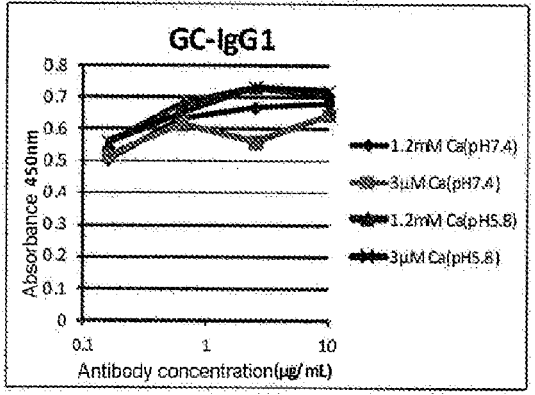

SEQUENCE LISTING

```
<160> NUMBER OF SEQ ID NOS: 136

<210> SEQ ID NO 1
<211> LENGTH: 107
<212> TYPE: PRT
<213> ORGANISM: Artificial Sequence
<220> FEATURE:
<223> OTHER INFORMATION: Synthetic antibody fragment

<400> SEQUENCE: 1

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys
                100                 105

<210> SEQ ID NO 2
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 2

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
    210
```

<210> SEQ ID NO 3
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 3

```
Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Glu Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
    210
```

<210> SEQ ID NO 4
<211> LENGTH: 445
<212> TYPE: PRT
<213> ORGANISM: Artificial Sequence
<220> FEATURE:
<223> OTHER INFORMATION: Synthetic antibody fragment

<400> SEQUENCE: 4

```
Gln Val Gln Leu Val Gln Ser Gly Ala Glu Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Ser Cys
        210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
        290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415
```

Trp Gln Glu Gly Asn Val Phe Ser Cys Ser Val Met His Glu Ala Leu
            420                 425                 430
His Asn His Tyr Thr Gln Lys Ser Leu Ser Leu Ser Pro
        435                 440                 445

<210> SEQ ID NO 5
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 5

Glu Thr Thr Leu Thr Gln Ser Pro Ala Phe Met Ser Ala Thr Pro Gly
1               5                   10                  15
Asp Lys Val Thr Ile Ser Cys Lys Ala Ser Gln Asp Ile Asp Asp Asp
            20                  25                  30
Met Asn Trp Tyr Gln Gln Lys Pro Gly Glu Ala Ala Ile Phe Ile Ile
        35                  40                  45
Gln Glu Ala Thr Thr Leu Val Pro Gly Ile Ser Pro Arg Phe Ser Gly
    50                  55                  60
Ser Gly Tyr Gly Thr Asp Phe Thr Leu Thr Ile Asn Asn Ile Glu Ser
65                  70                  75                  80
Glu Asp Ala Ala Tyr Tyr Phe Cys Leu Gln His Asp Asn Phe Pro Tyr
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 6
<211> LENGTH: 107
<212> TYPE: PRT
<213> ORGANISM: Artificial Sequence
<220> FEATURE:
<223> OTHER INFORMATION: Synthetic antibody fragment

<400> SEQUENCE: 6

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Phe
                 85                  90                  95

Thr Phe Gly Pro Gly Thr Lys Val Asp Ile Lys
            100                 105

<210> SEQ ID NO 7
<211> LENGTH: 112
<212> TYPE: PRT
<213> ORGANISM: Artificial Sequence
<220> FEATURE:
<223> OTHER INFORMATION: Synthetic antibody fragment

<400> SEQUENCE: 7

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Asp Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Val
                 85                  90                  95

Leu Arg Asn Pro Leu Thr Phe Gly Gly Gly Thr Lys Val Glu Ile Gln
            100                 105                 110

<210> SEQ ID NO 8
<211> LENGTH: 107
<212> TYPE: PRT
<213> ORGANISM: Artificial Sequence
<220> FEATURE:
<223> OTHER INFORMATION: Synthetic antibody fragment

<400> SEQUENCE: 8

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Glu Ile Lys
            100                 105

<210> SEQ ID NO 9
<211> LENGTH: 112
<212> TYPE: PRT
<213> ORGANISM: Artificial Sequence
<220> FEATURE:
<223> OTHER INFORMATION: Synthetic antibody fragment
```

<400> SEQUENCE: 9

Asp Ile Val Met Thr Gln Ser Pro Glu Ser Leu Val Leu Ser Leu Gly
1               5                   10                  15

Gly Thr Ala Thr Ile Asn Cys Arg Ser Ser Gln Ser Val Leu Tyr Ser
            20                  25                  30

Ser Asn Asn Lys Asn Tyr Leu Thr Trp Tyr Gln Gln Lys Pro Gly Gln
        35                  40                  45

Pro Pro Thr Leu Leu Phe Ser Trp Ala Ser Ile Arg Asp Ser Gly Val
    50                  55                  60

Pro Asp Arg Phe Ser Ala Ser Gly Ser Gly Thr Glu Phe Thr Leu Thr
65                  70                  75                  80

Ile Ser Asp Leu Gln Ala Glu Asp Ala Ala Val Tyr Tyr Cys Gln Gln
                85                  90                  95

Tyr Tyr Arg Ala Pro Ser Phe Gly Gln Gly Thr Lys Leu Gln Ile Lys
            100                 105                 110

<210> SEQ ID NO 10
<211> LENGTH: 121
<212> TYPE: PRT
<213> ORGANISM: Artificial Sequence
<220> FEATURE:
<223> OTHER INFORMATION: Synthetic antibody fragment

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Pro Gly Gly Gly Glu Tyr Tyr Phe Asp Tyr Trp Gly
            100                 105                 110

Gln Gly Thr Leu Val Thr Val Ser Ser
        115                 120

<210> SEQ ID NO 11
<211> LENGTH: 126
<212> TYPE: PRT
<213> ORGANISM: Artificial Sequence
<220> FEATURE:
<223> OTHER INFORMATION: Synthetic antibody fragment

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser
        115                 120                 125

<210> SEQ ID NO 12
<211> LENGTH: 35
<212> TYPE: PRT
<213> ORGANISM: Artificial Sequence
<220> FEATURE:
<223> OTHER INFORMATION: Synthetic antibody fragment

<400> SEQUENCE: 12

Gly Arg Met Lys Gln Leu Glu Asp Lys Val Glu Glu Leu Leu Ser Lys
1               5                  10                  15

Asn Tyr His Leu Glu Asn Glu Val Ala Arg Leu Lys Lys Leu Val Gly
            20                  25                  30

Glu Arg Gly
        35

<210> SEQ ID NO 13
<211> LENGTH: 19
<212> TYPE: PRT
<213> ORGANISM: Artificial Sequence
<220> FEATURE:
<223> OTHER INFORMATION: Synthetic antibody fragment

<400> SEQUENCE: 13

Met Gly Trp Ser Cys Ile Ile Leu Phe Leu Val Ala Thr Ala Thr Gly
1               5                  10                  15

Val His Ser

<210> SEQ ID NO 14
<211> LENGTH: 330
<212> TYPE: PRT
<213> ORGANISM: Artificial Sequence
<220> FEATURE:
<223> OTHER INFORMATION: Synthetic antibody fragment

<400> SEQUENCE: 14

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
                115                 120                 125
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 326
<212> TYPE: PRT
<213> ORGANISM: Artificial Sequence
<220> FEATURE:
<223> OTHER INFORMATION: Synthetic antibody fragment

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
```

```
             145                 150                 155                 160
    Val Glu Val His Asn Ala Lys Thr Lys Pro Arg Glu Glu Gln Phe Asn
                     165                 170                 175

Ser Thr Phe Arg Val Val Ser Val Leu Thr Val Val His Gln Asp Trp
                     180                 185                 190

Leu Asn Gly Lys Glu Tyr Lys Cys Lys Val Ser Asn Lys Gly Leu Pro
                     195                 200                 205

Ala Pro Ile Glu Lys Thr Ile Ser Lys Thr Lys Gly Gln Pro Arg Glu
                     210                 215                 220

Pro Gln Val Tyr Thr Leu Pro Pro Ser Arg Glu Glu Met Thr Lys Asn
    225                 230                 235                 240

Gln Val Ser Leu Thr Cys Leu Val Lys Gly Phe Tyr Pro Ser Asp Ile
                     245                 250                 255

Ala Val Glu Trp Glu Ser Asn Gly Gln Pro Glu Asn Asn Tyr Lys Thr
                     260                 265                 270

Thr Pro Pro Met Leu Asp Ser Asp Gly Ser Phe Phe Leu Tyr Ser Lys
                     275                 280                 285

Leu Thr Val Asp Lys Ser Arg Trp Gln Gln Gly Asn Val Phe Ser Cys
                     290                 295                 300

Ser Val Met His Glu Ala Leu His Asn His Tyr Thr Gln Lys Ser Leu
    305                 310                 315                 320

Ser Leu Ser Pro Gly Lys
                     325

<210> SEQ ID NO 16
<211> LENGTH: 377
<212> TYPE: PRT
<213> ORGANISM: Artificial Sequence
<220> FEATURE:
<223> OTHER INFORMATION: Synthetic antibody fragment

<400> SEQUENCE: 16

Ala Ser Thr Lys Gly Pro Ser Val Phe Pro Leu Ala Pro Cys Ser Arg
    1               5                   10                  15

Ser Thr Ser Gly Gly Thr Ala Ala Leu Gly Cys Leu Val Lys Asp Tyr
                     20                 25                  30

Phe Pro Glu Pro Val Thr Val Ser Trp Asn Ser Gly Ala Leu Thr Ser
                     35                 40                  45

Gly Val His Thr Phe Pro Ala Val Leu Gln Ser Ser Gly Leu Tyr Ser
                     50                 55                  60

Leu Ser Ser Val Val Thr Val Pro Ser Ser Ser Leu Gly Thr Gln Thr
    65                  70                 75                  80

Tyr Thr Cys Asn Val Asn His Lys Pro Ser Asn Thr Lys Val Asp Lys
                     85                 90                  95

Arg Val Glu Leu Lys Thr Pro Leu Gly Asp Thr Thr His Thr Cys Pro
                     100                105                 110

Arg Cys Pro Glu Pro Lys Ser Cys Asp Thr Pro Pro Cys Pro Arg
                     115                120                 125

Cys Pro Glu Pro Lys Ser Cys Asp Thr Pro Pro Cys Pro Arg Cys
                     130                135                 140

Pro Glu Pro Lys Ser Cys Asp Thr Pro Pro Cys Pro Arg Cys Pro
    145                 150                155                 160

Ala Pro Glu Leu Leu Gly Gly Pro Ser Val Phe Leu Phe Pro Pro Lys
                     165                170                 175

Pro Lys Asp Thr Leu Met Ile Ser Arg Thr Pro Glu Val Thr Cys Val
```

```
            180                 185                 190
Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
            210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 17
<211> LENGTH: 327
<212> TYPE: PRT
<213> ORGANISM: Artificial Sequence
<220> FEATURE:
<223> OTHER INFORMATION: Synthetic antibody fragment

<400> SEQUENCE: 17

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
```

```
                165                 170                 175
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 18
<211> LENGTH: 458
<212> TYPE: PRT
<213> ORGANISM: Artificial Sequence
<220> FEATURE:
<223> OTHER INFORMATION: Synthetic antibody fragment

<400> SEQUENCE: 18

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ala Ser Ile Tyr Cys Ser Ser Thr Ser Cys Tyr Glu Pro Pro
            100                 105                 110

Tyr Tyr Tyr Tyr Met Asp Val Trp Gly Lys Gly Thr Met Val Thr Val
            115                 120                 125

Ser Ser Ala Ser Thr Lys Gly Pro Ser Val Phe Pro Leu Ala Pro Ser
            130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
            165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
```

```
                195                 200                 205
Gln Thr Tyr Ile Cys Asn Val Asn His Lys Pro Ser Asn Thr Lys Val
    210                 215                 220
Asp Lys Lys Val Glu Pro Lys Ser Cys Asp Lys Thr His Thr Cys Pro
225                 230                 235                 240
Pro Cys Pro Ala Pro Glu Leu Leu Gly Gly Pro Ser Val Phe Leu Phe
                245                 250                 255
Pro Pro Lys Pro Lys Asp Thr Leu Met Ile Ser Arg Thr Pro Glu Val
            260                 265                 270
Thr Cys Val Val Val Asp Val Ser His Glu Asp Pro Glu Val Lys Phe
        275                 280                 285
Asn Trp Tyr Val Asp Gly Val Glu Val His Asn Ala Lys Thr Lys Pro
    290                 295                 300
Arg Glu Glu Gln Tyr Asn Ser Thr Tyr Arg Val Val Ser Val Leu Thr
305                 310                 315                 320
Val Leu His Gln Asp Trp Leu Asn Gly Lys Glu Tyr Lys Cys Lys Val
                325                 330                 335
Ser Asn Lys Ala Leu Pro Ala Pro Ile Glu Lys Thr Ile Ser Lys Ala
            340                 345                 350
Lys Gly Gln Pro Arg Glu Pro Gln Val Tyr Thr Leu Pro Pro Ser Arg
        355                 360                 365
Asp Glu Leu Thr Lys Asn Gln Val Ser Leu Thr Cys Leu Val Lys Gly
    370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Val Leu Asp Ser Asp Gly Ser
                405                 410                 415
Phe Phe Leu Tyr Ser Lys Leu Thr Val Asp Lys Ser Arg Trp Gln Gln
            420                 425                 430
Gly Asn Val Phe Ser Cys Ser Val Met His Glu Ala Leu His Asn His
        435                 440                 445
Tyr Thr Gln Lys Ser Leu Ser Leu Ser Pro
    450                 455

<210> SEQ ID NO 19
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 19

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser His
            20                  25                  30
Leu Ala Trp Tyr Gln Gln Lys Pro Gly Lys Ala Pro Lys Leu Leu Ile
        35                  40                  45
Tyr Ala Ala Ser His Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser His Asn Tyr Pro Leu
                85                  90                  95
Thr Phe Gly Gln Gly Thr Lys Val Glu Ile Lys Arg Thr Val Ala Ala
```

```
                    100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 20
<211> LENGTH: 447
<212> TYPE: PRT
<213> ORGANISM: Artificial Sequence
<220> FEATURE:
<223> OTHER INFORMATION: Synthetic antibody fragment

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Met Ile Asn Gly Val Trp Glu Gly Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                        245                 250                 255
Arg Thr Pro Glu Val Thr Cys Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 21
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile His Ser His
            20                  25                  30

Leu Asn Trp Tyr Gln Gln Lys Pro Gly Lys Ala Pro Lys Leu Leu Ile
        35                  40                  45

Tyr His Ala Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Gly Asn Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                    165                 170                 175
Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 22
<211> LENGTH: 451
<212> TYPE: PRT
<213> ORGANISM: Artificial Sequence
<220> FEATURE:
<223> OTHER INFORMATION: Synthetic antibody fragment

<400> SEQUENCE: 22

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ile Trp Val Arg Gln Ala Pro Gly Lys Gly Leu Glu Trp Val
        35                  40                  45

Gly Arg Ile Lys Ser Lys Val Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asp Ser Leu Lys Thr Glu Asp Thr Ala Val Tyr
                85                  90                  95

Tyr Cys Val Ala Asp Val Pro Ala Ser Asn Pro Tyr Gly Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
```

```
            305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Asp Glu Leu Thr Lys Asn Gln
                355                 360                 365
Val Ser Leu Thr Cys Leu Val Lys Gly Phe Tyr Pro Ser Asp Ile Ala
            370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
            435                 440                 445
Leu Ser Pro
    450

<210> SEQ ID NO 23
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 23

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Asn Ser His
                20                  25                  30
Leu Asn Trp Tyr Gln Gln Lys Pro Gly Lys Ala Pro Lys Leu Leu Ile
            35                  40                  45
Tyr Asp Ala Ser His Leu Gln Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln His Asn Asn Tyr Pro Leu
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
```

<210> SEQ ID NO 24
<211> LENGTH: 449
<212> TYPE: PRT
<213> ORGANISM: Artificial Sequence
<220> FEATURE:
<223> OTHER INFORMATION: Synthetic antibody fragment

<400> SEQUENCE: 24

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
                355              360             365
Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
                405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys

<210> SEQ ID NO 25
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 25

Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Ile Ser Ser Tyr
            20              25              30

Leu Asn Trp Tyr Gln Gln Lys Pro Gly Lys Ala Pro Lys Leu Leu Ile
        35              40              45

Tyr Tyr Thr Ser Arg Leu His Ser Gly Val Pro Ser Arg Phe Ser Gly
    50              55              60

Ser Gly Ser Gly Thr Asp Phe Thr Phe Thr Ile Ser Ser Leu Gln Pro
65              70              75              80

Glu Asp Ile Ala Thr Tyr Tyr Cys Gln Gln Gly Asn Thr Leu Pro Tyr
                85              90              95

Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210

<210> SEQ ID NO 26
<211> LENGTH: 107
<212> TYPE: PRT
<213> ORGANISM: Artificial Sequence
<220> FEATURE:
<223> OTHER INFORMATION: Synthetic antibody fragment
```

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 27
<211> LENGTH: 128
<212> TYPE: PRT
<213> ORGANISM: Artificial Sequence
<220> FEATURE:
<223> OTHER INFORMATION: Synthetic antibody fragment

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Thr Leu Tyr Asp Phe Trp Ser Gly Tyr Tyr Ser Tyr
            100                 105                 110

Asp Ala Phe Asp Ile Trp Gly Gln Gly Thr Met Val Thr Val Ser Ser
        115                 120                 125

<210> SEQ ID NO 28
<211> LENGTH: 122
<212> TYPE: PRT
<213> ORGANISM: Artificial Sequence
<220> FEATURE:
<223> OTHER INFORMATION: Synthetic antibody fragment

<400> SEQUENCE: 28

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Leu Asp Thr Gly Pro Tyr Tyr Tyr Gly Met Asp Val Trp
            100                 105                 110

Gly Gln Gly Thr Met Val Thr Val Ser Ser
            115                 120

<210> SEQ ID NO 29
<211> LENGTH: 124
<212> TYPE: PRT
<213> ORGANISM: Artificial Sequence
<220> FEATURE:
<223> OTHER INFORMATION: Synthetic antibody fragment

<400> SEQUENCE: 29

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ser Pro Val Pro Gly Val Tyr Tyr Tyr Gly Met Asp
            100                 105                 110

Val Trp Gly Gln Gly Thr Met Val Thr Val Ser Ser
            115                 120

<210> SEQ ID NO 30
<211> LENGTH: 119
<212> TYPE: PRT
<213> ORGANISM: Artificial Sequence
<220> FEATURE:
<223> OTHER INFORMATION: Synthetic antibody fragment

<400> SEQUENCE: 30

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Arg Ala Gly Asp Leu Gly Gly Asp Tyr Trp Gly Gln Gly
            100                 105                 110

Thr Leu Val Thr Val Ser Ser
            115
```

```
<210> SEQ ID NO 31
<211> LENGTH: 107
<212> TYPE: PRT
<213> ORGANISM: Artificial Sequence
<220> FEATURE:
<223> OTHER INFORMATION: Synthetic antibody fragment

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asp Asp Asp
            20                  25                  30

Met Asn Trp Tyr Gln Gln Lys Pro Gly Lys Ala Pro Lys Leu Leu Ile
        35                  40                  45

Tyr Glu Ala Thr Thr Leu Val Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Asn Phe Pro Tyr
                85                  90                  95

Thr Phe Gly Gln Gly Thr Lys Val Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: Synthetic antibody fragment

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Lys Ala Ser Gln Asp Ile Asp Asp Asp
            20                  25                  30

Met Asn Trp Tyr Leu Gln Lys Pro Gly Gln Ser Pro Gln Leu Leu Ile
        35                  40                  45

Tyr Glu Ala Thr Thr Leu Val Pro Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Leu Gln His Asp Asn Phe Pro Tyr
                85                  90                  95

Thr Phe Gly Gln Gly Thr Lys Leu Glu Ile Lys
            100                 105

<210> SEQ ID NO 33
<211> LENGTH: 107
<212> TYPE: PRT
<213> ORGANISM: Artificial Sequence
<220> FEATURE:
<223> OTHER INFORMATION: Synthetic antibody fragment

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asp Asp
            20                  25                  30
```

```
Met Asn Trp Tyr Gln Gln Lys Pro Gly Gln Ala Pro Arg Leu Leu Ile
            35                  40                  45

Tyr Glu Ala Thr Thr Leu Val Pro Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Leu Gln His Asp Asn Phe Pro Tyr
                 85                  90                  95

Thr Phe Gly Gln Gly Thr Lys Val Glu Ile Lys
            100                 105
```

<210> SEQ ID NO 34
<211> LENGTH: 107
<212> TYPE: PRT
<213> ORGANISM: Artificial Sequence
<220> FEATURE:
<223> OTHER INFORMATION: Synthetic antibody fragment

<400> SEQUENCE: 34

```
Asp Ile Val Met Thr Gln Ser Pro Asp Ser Leu Ala Val Ser Leu Gly
 1               5                   10                  15

Glu Arg Ala Thr Ile Asn Cys Lys Ala Ser Gln Asp Ile Asp Asp Asp
            20                  25                  30

Met Asn Trp Tyr Gln Gln Lys Pro Gly Gln Pro Pro Lys Leu Leu Ile
            35                  40                  45

Tyr Glu Ala Thr Thr Leu Val Pro Gly Val Pro Asp Arg Phe Ser Gly
 50                  55                  60

Ser Gly Ser Gly Thr Asp Phe Thr Leu Thr Ile Ser Ser Leu Gln Ala
 65                  70                  75                  80

Glu Asp Val Ala Val Tyr Tyr Cys Leu Gln His Asp Asn Phe Pro Tyr
                 85                  90                  95

Thr Phe Gly Gln Gly Thr Lys Leu Glu Ile Lys
            100                 105
```

<210> SEQ ID NO 35
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 35

```
Glu Thr Thr Leu Thr Gln Ser Pro Ala Phe Met Ser Ala Thr Pro Gly
 1               5                   10                  15

Asp Lys Val Thr Ile Ser Cys Lys Ala Ser Gln Asp Ile Ala Asp Asp
            20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Ser Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 36
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 36

```
Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Ala Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 37
<211> LENGTH: 214
<212> TYPE: PRT
<213> ORGANISM: Artificial Sequence
<220> FEATURE:
<223> OTHER INFORMATION: Synthetic antibody fragment -continued

<400> SEQUENCE: 37

```
Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Ala
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 38
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 38

```
Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Ala Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                130               135                140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 39
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 39

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Ala
                20                  25                  30

Met Asn Trp Tyr Gln Gln Lys Pro Gly Glu Ala Ala Ile Phe Ile Ile
                35                  40                  45

Gln Glu Ala Thr Thr Leu Val Pro Gly Ile Ser Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 40
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 40
```

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Asp
                20                  25                  30

Met Asn Trp Tyr Gln Gln Lys Pro Gly Glu Ala Ala Ile Phe Ile Ile
            35                  40                  45

Gln Ala Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 41
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 41

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Ala
                20                  25                  30

Met Asn Trp Tyr Gln Gln Lys Pro Gly Glu Ala Ala Ile Phe Ile Ile
            35                  40                  45

Gln Ala Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 42
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 42

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Ala Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 43
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 44
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 45
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 46
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ala Asp

```
                20                  25                  30
Leu Asn Trp Tyr Gln Gln Lys Pro Gly Lys Ala Pro Lys Leu Leu Ile
            35                  40                  45
Tyr Glu Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Asp Ser Thr Pro Tyr
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 47
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 47

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Asp Asp Ala
            20                  25                  30
Leu Asn Trp Tyr Gln Gln Lys Pro Gly Lys Ala Pro Lys Leu Leu Ile
        35                  40                  45
Tyr Glu Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Asp Ser Thr Pro Tyr
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
```

```
                    165                 170                 175
Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 48
<211> LENGTH: 443
<212> TYPE: PRT
<213> ORGANISM: Artificial Sequence
<220> FEATURE:
<223> OTHER INFORMATION: Synthetic antibody fragment

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
```

```
                305                 310                 315                 320
Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro
                435                 440

<210> SEQ ID NO 49
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
                20                  25                  30

Leu Asn Trp Tyr Gln Gln Lys Pro Gly Lys Ala Pro Lys Leu Leu Ile
                35                  40                  45

Tyr Glu Ala Ser Ser Leu Gln Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Thr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210
```

-continued

```
<210> SEQ ID NO 50
<211> LENGTH: 456
<212> TYPE: PRT
<213> ORGANISM: Artificial Sequence
<220> FEATURE:
<223> OTHER INFORMATION: Synthetic antibody fragment

<400> SEQUENCE: 50
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Pro Pro Tyr Ser Ser Ser Tyr Tyr Tyr Tyr Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr

```
                370                 375                 380
Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
                435                 440                 445

Gln Lys Ser Leu Ser Leu Ser Pro
                450                 455

<210> SEQ ID NO 51
<211> LENGTH: 452
<212> TYPE: PRT
<213> ORGANISM: Artificial Sequence
<220> FEATURE:
<223> OTHER INFORMATION: Synthetic antibody fragment

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
                50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Ala Pro Gly Ile Gln Leu Trp Leu Arg Pro Tyr Phe Asp
                100                 105                 110

Tyr Trp Gly Gln Gly Thr Leu Val Thr Val Ser Ser Ala Ser Thr Lys
                115                 120                 125

Gly Pro Ser Val Phe Pro Leu Ala Pro Ser Ser Lys Ser Thr Ser Gly
                130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Val Glu Pro
                210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
```

```
              275                 280                 285
Val Glu Val His Asn Ala Lys Thr Lys Pro Arg Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
    450

<210> SEQ ID NO 52
<211> LENGTH: 447
<212> TYPE: PRT
<213> ORGANISM: Artificial Sequence
<220> FEATURE:
<223> OTHER INFORMATION: Synthetic antibody fragment

<400> SEQUENCE: 52

Gln Val Gln Leu Gln Glu Ser Gly Pro Gly Leu Val Lys Pro Trp Glu
1               5                   10                  15

Thr Leu Ser Leu Thr Cys Thr Val Ala Gly Asp Ser Ile Lys Tyr Ser
            20                  25                  30

Ser Asp Tyr Trp Gly Trp Val Arg Gln Ser Pro Gly Lys Gly Leu Glu
        35                  40                  45

Trp Ile Gly Ser Ser Tyr Leu Ser Gly Thr Thr Gln Tyr Asn Pro Ser
    50                  55                  60

Leu Lys Ser Arg Val Thr Met Ser Val Asp Thr Ser Lys Asn Gln Phe
65                  70                  75                  80

Ser Leu Arg Leu Ser Ser Val Thr Ala Ala Asp Thr Ala Val Tyr Tyr
            85                  90                  95

Cys Ala Arg His Arg Gly Pro Thr Gly Val Asp Gln Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
        210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro
            435                 440                 445

<210> SEQ ID NO 53
<211> LENGTH: 449
<212> TYPE: PRT
<213> ORGANISM: Artificial Sequence
<220> FEATURE:
<223> OTHER INFORMATION: Synthetic antibody fragment

<400> SEQUENCE: 53

Glu Val Gln Leu Val Gln Ser Gly Gly Gly Leu Val Gln Pro Gly Arg
1               5                   10                  15
Ser Leu Thr Leu Ser Cys Val Gly Tyr Gly Phe Thr Phe His Glu Asn
                20                  25                  30
Asp Met His Trp Leu Arg Gln Pro Leu Gly Lys Gly Leu Glu Trp Val
            35                  40                  45
Ser His Ile Gly Trp Asn Asn Asn Arg Val Ala Tyr Ala Asp Ser Val
        50                  55                  60
Lys Gly Arg Phe Ala Val Ser Arg Asp Asn Lys Asn Ser Leu Phe
65                  70                  75                  80
Leu His Met Asn Ser Leu Arg Pro Asp Asp Thr Ala Leu Tyr Tyr Cys
                85                  90                  95
Ala Lys Asp Leu Gly Asn Pro Ile Tyr Asp Val Phe Asp Val Trp Gly
```

```
            100                 105                 110
Gln Gly Thr Met Val Thr Val Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro

<210> SEQ ID NO 54
<211> LENGTH: 452
<212> TYPE: PRT
<213> ORGANISM: Artificial Sequence
<220> FEATURE:
<223> OTHER INFORMATION: Synthetic antibody fragment

<400> SEQUENCE: 54

Gln Pro Ala Leu Ala Gln Met Gln Leu Val Glu Ser Gly Gly Gly Leu
1               5                   10                  15
```

```
Val Gln Pro Gly Arg Ser Leu Arg Leu Ser Cys Ala Ala Ser Gly Phe
         20                  25                  30

Thr Phe Asp Asp Tyr Ala Met His Trp Val Arg Gln Ala Pro Gly Lys
         35                  40                  45

Gly Leu Glu Trp Val Ser Gly Ile Ser Trp Asn Ser Gly Ser Ile Gly
 50                  55                  60

Tyr Ala Asp Ser Val Lys Gly Arg Phe Thr Ile Ser Arg Asp Asn Ala
 65                  70                  75                  80

Lys Asn Ser Leu Tyr Leu Gln Met Asn Ser Leu Arg Ala Glu Asp Thr
             85                  90                  95

Ala Leu Tyr Tyr Cys Ala Arg Glu Gly Val Leu Gly Asp Ala Phe Asp
            100                 105                 110

Ile Trp Gly Gln Gly Thr Met Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430
```

```
Ser Val Met His Glu Ala Leu His Asn His Tyr Thr Gln Lys Ser Leu
        435                 440                 445

Ser Leu Ser Pro
    450

<210> SEQ ID NO 55
<211> LENGTH: 454
<212> TYPE: PRT
<213> ORGANISM: Artificial Sequence
<220> FEATURE:
<223> OTHER INFORMATION: Synthetic antibody fragment

<400> SEQUENCE: 55

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Arg Val Arg Ser Gly Ser Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335
```

```
Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
450

<210> SEQ ID NO 56
<211> LENGTH: 450
<212> TYPE: PRT
<213> ORGANISM: Artificial Sequence
<220> FEATURE:
<223> OTHER INFORMATION: Synthetic antibody fragment

<400> SEQUENCE: 56

Gln Val Gln Leu Gln Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Ile Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Lys Asp Pro Arg Val Trp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240
```

```
Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro
    450

<210> SEQ ID NO 57
<211> LENGTH: 449
<212> TYPE: PRT
<213> ORGANISM: Artificial Sequence
<220> FEATURE:
<223> OTHER INFORMATION: Synthetic antibody fragment

<400> SEQUENCE: 57

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Arg Ile Ile Pro Val Leu Ala Ile Ala Asn Tyr Ala Gln Lys Phe
50                  55                  60

Gln Gly Arg Val Thr Ile Thr Ala Asp Lys Ser Thr His Thr Ala Tyr
65                  70                  75                  80

Met Glu Leu Ser Ser Leu Arg Ser Gly Asp Thr Ala Val Tyr Tyr Cys
            85                  90                  95

Ala Arg Asp Ser Gly Tyr Ser Ala Gly Tyr Gly Gly Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro

<210> SEQ ID NO 58
<211> LENGTH: 447
<212> TYPE: PRT
<213> ORGANISM: Artificial Sequence
<220> FEATURE:
<223> OTHER INFORMATION: Synthetic antibody fragment

<400> SEQUENCE: 58

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Lys Thr Tyr
            20                  25                  30

Trp Met Asn Trp Val Arg Gln Ala Pro Gly Lys Gly Leu Glu Trp Val
        35                  40                  45

Ala Asn Ile Arg Ala Asp Gly Gly Gln Met Tyr Tyr Ala Asp Ser Val
```

```
            50                  55                  60
Lys Gly Arg Phe Thr Ile Ser Arg Asp Asn Ala Lys Asp Ser Leu Tyr
 65                  70                  75                  80

Leu Gln Met Ile Ser Leu Arg Pro Glu Asp Thr Ala Leu Tyr Tyr Cys
                 85                  90                  95

Ala Arg Asp Pro Phe Ala Ser Gly Gly Leu Asp Gln Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 59
<211> LENGTH: 450
<212> TYPE: PRT
<213> ORGANISM: Artificial Sequence
```

<220> FEATURE:
<223> OTHER INFORMATION: Synthetic antibody fragment

<400> SEQUENCE: 59

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Glu Trp Val Arg Gln Ala Pro Gly Lys Gly Leu Glu Trp Val
        35                  40                  45

Ala Leu Ile Ser His Asp Gly Asn Asn Lys Tyr Tyr Ala Asp Ser Val
    50                  55                  60

Glu Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Val Arg Tyr Phe Asp Ser Tyr Gly Met Asp Val Trp
            100                 105                 110

Gly His Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro
    450

<210> SEQ ID NO 60
<211> LENGTH: 449
<212> TYPE: PRT
<213> ORGANISM: Artificial Sequence
<220> FEATURE:
<223> OTHER INFORMATION: Synthetic antibody fragment

<400> SEQUENCE: 60

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Phe
            20                  25                  30

Trp Ile Asn Trp Val Arg Gln Met Pro Gly Lys Gly Leu Glu Trp Met
        35                  40                  45

Gly Asn Ile Asp Pro Ser Asp Ser Tyr Thr Asn Tyr Ser Pro Ser Phe
    50                  55                  60

Gln Gly His Val Ala Ile Ser Ala Asp Lys Ser Ile Ser Thr Ala Tyr
65                  70                  75                  80

Leu His Trp Asn Ser Leu Lys Ala Ser Asp Thr Ala Met Tyr Tyr Cys
                85                  90                  95

Ala Arg His Arg Tyr Leu Gly Gln Leu Ala Pro Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro

<210> SEQ ID NO 61
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210
```

<210> SEQ ID NO 62
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 62

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr His Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 63
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 63

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Ser Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 64
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 64

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Gly Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 65
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 65

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Asn Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Ser Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 66
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Tyr
```

```
                85                  90                  95
Thr Phe Gly Gln Gly Thr Lys Val Glu Ile Lys Arg Thr Val Ala Ala
               100                 105                 110
Pro Ser Val Phe Ile Phe Pro Pro Ser Asp Glu Gln Leu Lys Ser Gly
               115                 120                 125
Thr Ala Ser Val Val Cys Leu Leu Asn Asn Phe Tyr Pro Arg Glu Ala
               130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
               165                 170                 175
Ser Thr Leu Thr Leu Ser Lys Ala Asp Tyr Glu Lys His Lys Val Tyr
               180                 185                 190
Ala Cys Glu Val Thr His Gln Gly Leu Ser Ser Pro Val Thr Lys Ser
               195                 200                 205
Phe Asn Arg Gly Glu Cys
               210

<210> SEQ ID NO 67
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 67

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Asp Asp
                20                  25                  30
Leu Ala Trp Tyr Gln Gln Lys Pro Gly Lys Ala Pro Lys Leu Leu Ile
            35                  40                  45
Tyr His Ala Ser His Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asp Asn Ser Pro Leu
                85                  90                  95
Thr Phe Gly Gln Gly Thr Lys Val Glu Ile Lys Arg Thr Val Ala Ala
               100                 105                 110
Pro Ser Val Phe Ile Phe Pro Pro Ser Asp Glu Gln Leu Lys Ser Gly
               115                 120                 125
Thr Ala Ser Val Val Cys Leu Leu Asn Asn Phe Tyr Pro Arg Glu Ala
               130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
               165                 170                 175
Ser Thr Leu Thr Leu Ser Lys Ala Asp Tyr Glu Lys His Lys Val Tyr
               180                 185                 190
Ala Cys Glu Val Thr His Gln Gly Leu Ser Ser Pro Val Thr Lys Ser
               195                 200                 205
Phe Asn Arg Gly Glu Cys
               210
```

```
<210> SEQ ID NO 68
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
            20                  25                  30

Leu Ala Trp Tyr Gln Gln Lys Pro Gly Lys Ala Pro Lys Leu Leu Ile
        35                  40                  45

Tyr His Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asn Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 69
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Ser Pro Tyr
                85                  90                  95
```

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 70
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
                20                  25                  30

Leu Asn Trp Tyr Gln Gln Lys Pro Gly Lys Ala Pro Lys Leu Leu Ile
            35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Asp Tyr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 71
<211> LENGTH: 214

```
<212> TYPE: PRT
<213> ORGANISM: Artificial Sequence
<220> FEATURE:
<223> OTHER INFORMATION: Synthetic antibody fragment

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Asn Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
<211> LENGTH: 453
<212> TYPE: PRT
<213> ORGANISM: Artificial Sequence
<220> FEATURE:
<223> OTHER INFORMATION: Synthetic antibody fragment

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ala Phe Leu Glu Trp Pro Ile Trp Gly Ser Glu Tyr Phe
            100                 105                 110
```

```
Gln His Trp Gly Gln Gly Thr Leu Val Thr Val Ser Ser Ala Ser Thr
            115                 120                 125
Lys Gly Pro Ser Val Phe Pro Leu Ala Pro Ser Ser Lys Ser Thr Ser
        130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Leu Gly Thr Gln Thr Tyr Ile Cys
        195                 200                 205
Asn Val Asn His Lys Pro Ser Asn Thr Lys Val Asp Lys Lys Val Glu
            210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro
    450

<210> SEQ ID NO 73
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 73

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr His Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 74
<211> LENGTH: 451
<212> TYPE: PRT
<213> ORGANISM: Artificial Sequence
<220> FEATURE:
<223> OTHER INFORMATION: Synthetic antibody fragment

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Thr Tyr Tyr Tyr Asp Ser Ser Ala Pro Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro
    450

<210> SEQ ID NO 75
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 75

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Glu Asp Asp
            20                  25                  30
Leu Ala Trp Tyr Gln Gln Lys Pro Gly Lys Ala Pro Lys Leu Leu Ile
        35                  40                  45
Tyr Glu Ala Ser Thr Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Asp Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 76
<211> LENGTH: 452
<212> TYPE: PRT
<213> ORGANISM: Artificial Sequence
<220> FEATURE:
<223> OTHER INFORMATION: Synthetic antibody fragment

<400> SEQUENCE: 76

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Gly Ser Gly Phe Asn Trp Gly Asn Tyr Ala Phe Asp
            100                 105                 110

Ile Trp Gly Gln Gly Phe Ser Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

```
Val Asn His Lys Pro Ser Asn Thr Lys Val Asp Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
    450

<210> SEQ ID NO 77
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Arg Tyr Pro Tyr
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210
```

<210> SEQ ID NO 78
<211> LENGTH: 449
<212> TYPE: PRT
<213> ORGANISM: Artificial Sequence
<220> FEATURE:
<223> OTHER INFORMATION: Synthetic antibody fragment

<400> SEQUENCE: 78

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Pro Gly Gly Gly Glu Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro
```

<210> SEQ ID NO 79
<211> LENGTH: 217
<212> TYPE: PRT
<213> ORGANISM: Artificial Sequence
<220> FEATURE:
<223> OTHER INFORMATION: Synthetic antibody fragment

<400> SEQUENCE: 79

```
Gln Ser Val Leu Thr Gln Pro Pro Ser Val Ser Gly Ala Pro Gly Gln
1               5                   10                  15

Arg Val Thr Ile Ser Cys Thr Gly Ser Arg Ser Asn Met Gly Ala Gly
            20                  25                  30

Tyr Asp Val His Trp Tyr Gln Leu Leu Pro Gly Ala Ala Pro Lys Leu
        35                  40                  45

Leu Ile Ser His Asn Thr His Arg Pro Ser Gly Val Pro Asp Arg Phe
    50                  55                  60

Ser Gly Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser His Asp Ser Ser
                85                  90                  95

Leu Ser Ala Val Val Phe Gly Gly Gly Thr Lys Leu Thr Val Leu Ser
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160
```

```
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Cys Ser
    210                 215

<210> SEQ ID NO 80
<211> LENGTH: 453
<212> TYPE: PRT
<213> ORGANISM: Artificial Sequence
<220> FEATURE:
<223> OTHER INFORMATION: Synthetic antibody fragment

<400> SEQUENCE: 80

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Arg Asp Tyr Tyr Asp Ser Ser Gly Tyr Tyr Asp Ala Phe
            100                 105                 110
Asp Ile Trp Gly Gln Gly Thr Met Val Thr Val Ser Ser Ala Ser Thr
        115                 120                 125
Lys Gly Pro Ser Val Phe Pro Leu Ala Pro Ser Ser Lys Ser Thr Ser
    130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
        195                 200                 205
Asn Val Asn His Lys Pro Ser Asn Thr Lys Val Asp Lys Lys Val Glu
    210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
```

```
Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro
    450

<210> SEQ ID NO 81
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 81

Glu Thr Thr Val Thr Gln Ser Pro Ser Phe Leu Ser Ala Ser Val Gly
1               5                   10                  15

Asp Arg Val Thr Ile Thr Cys Ile Thr Thr Asp Ile Asp Asp Asp
            20                  25                  30

Met Asn Trp Phe Gln Gln Glu Pro Gly Lys Ala Pro Lys Leu Leu Ile
        35                  40                  45

Ser Glu Gly Asn Ile Leu Arg Pro Gly Val Pro Ser Arg Phe Ser Ser
    50                  55                  60

Ser Gly Tyr Gly Thr Asp Phe Thr Leu Thr Ile Ser Lys Leu Gln Pro
65                  70                  75                  80

Glu Asp Phe Ala Thr Tyr Tyr Cys Leu Gln Ser Asp Asn Leu Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 82
<211> LENGTH: 447
<212> TYPE: PRT
<213> ORGANISM: Artificial Sequence
<220> FEATURE:
<223> OTHER INFORMATION: Synthetic antibody fragment

<400> SEQUENCE: 82

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

```
Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
        435                 440                 445
```

<210> SEQ ID NO 83
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 83

```
Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 84
<211> LENGTH: 106
<212> TYPE: PRT
<213> ORGANISM: Artificial Sequence
<220> FEATURE:
<223> OTHER INFORMATION: Synthetic antibody fragment

<400> SEQUENCE: 84

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Phe Asp Ala Ser Asn Arg Ala Ala Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Lys Trp Val Thr
                85                  90                  95

Phe Gly Gly Gly Thr Thr Val Glu Ile Arg
            100                 105
```

<210> SEQ ID NO 85
<211> LENGTH: 454
<212> TYPE: PRT
<213> ORGANISM: Artificial Sequence
<220> FEATURE:
<223> OTHER INFORMATION: Synthetic antibody fragment

<400> SEQUENCE: 85

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Asp Ser Ser Gly Tyr Thr Asp Ala
                100                 105                 110

Phe Asp Ile Trp Gly Gln Gly Thr Met Val Thr Val Ser Ser Ala Ser
            115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255
```

```
Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450

<210> SEQ ID NO 86
<211> LENGTH: 219
<212> TYPE: PRT
<213> ORGANISM: Artificial Sequence
<220> FEATURE:
<223> OTHER INFORMATION: Synthetic antibody fragment

<400> SEQUENCE: 86

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 87
<211> LENGTH: 454
<212> TYPE: PRT
<213> ORGANISM: Artificial Sequence
<220> FEATURE:
<223> OTHER INFORMATION: Synthetic antibody fragment

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Ala Ala Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Ala Pro Tyr Tyr Asp Ser Ser Gly Tyr Thr Asp Ala
            100                 105                 110

Phe Asp Ile Trp Gly Gln Gly Thr Met Val Thr Val Ser Ser Ala Ser
            115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
                355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro
            450

<210> SEQ ID NO 88
<211> LENGTH: 454
<212> TYPE: PRT
<213> ORGANISM: Artificial Sequence
<220> FEATURE:
<223> OTHER INFORMATION: Synthetic antibody fragment

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro
        450

<210> SEQ ID NO 89
<211> LENGTH: 454
<212> TYPE: PRT
<213> ORGANISM: Artificial Sequence
<220> FEATURE:
<223> OTHER INFORMATION: Synthetic antibody fragment

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Ala Pro Tyr Tyr Tyr Ala Ser Ser Gly Tyr Thr Asp Ala
            100                 105                 110

-continued

```
Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450
```

<210> SEQ ID NO 90
<211> LENGTH: 454
<212> TYPE: PRT
<213> ORGANISM: Artificial Sequence
<220> FEATURE:
<223> OTHER INFORMATION: Synthetic antibody fragment

<400> SEQUENCE: 90

```
Glu Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Asp Ser Ser Gly Tyr Thr Ala Ala
            100                 105                 110

Phe Asp Ile Trp Gly Gln Gly Thr Met Val Thr Val Ser Ser Ala Ser
            115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
    195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

```
Ser Cys Ser Val Met His Glu Ala Leu His Asn His Tyr Thr Gln Lys
        435                 440                 445

Ser Leu Ser Leu Ser Pro
        450

<210> SEQ ID NO 91
<211> LENGTH: 454
<212> TYPE: PRT
<213> ORGANISM: Artificial Sequence
<220> FEATURE:
<223> OTHER INFORMATION: Synthetic antibody fragment

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Ala Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335
```

```
Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro
                450

<210> SEQ ID NO 92
<211> LENGTH: 213
<212> TYPE: PRT
<213> ORGANISM: Artificial Sequence
<220> FEATURE:
<223> OTHER INFORMATION: Synthetic antibody fragment

<400> SEQUENCE: 92

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Phe Ala Ala Ser Asn Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Lys Trp Val Thr
                85                  90                  95

Phe Gly Gly Gly Thr Thr Val Glu Ile Arg Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 93
<211> LENGTH: 213
```

```
<212> TYPE: PRT
<213> ORGANISM: Artificial Sequence
<220> FEATURE:
<223> OTHER INFORMATION: Synthetic antibody fragment

<400> SEQUENCE: 93

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Phe Asp Ala Ser Asn Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ala Lys Trp Val Thr
                85                  90                  95

Phe Gly Gly Gly Thr Thr Val Glu Ile Arg Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 94
<211> LENGTH: 453
<212> TYPE: PRT
<213> ORGANISM: Artificial Sequence
<220> FEATURE:
<223> OTHER INFORMATION: Synthetic antibody fragment

<400> SEQUENCE: 94

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Tyr Tyr Asp Ser Ser Gly Tyr Tyr Asp Ala Phe
            100                 105                 110
```

-continued

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Trp His Tyr Thr Gln Lys Ser
        435                 440                 445

Leu Ser Leu Ser Pro
    450

<210> SEQ ID NO 95
<211> LENGTH: 449
<212> TYPE: PRT
<213> ORGANISM: Artificial Sequence
<220> FEATURE:
<223> OTHER INFORMATION: Synthetic antibody fragment

<400> SEQUENCE: 95

Gln Val Gln Leu Val Gln Ser Gly Ala Glu Val Lys Lys Pro Gly Ala
1               5                   10                  15

-continued

Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Asp Pro Gly Gly Gly Glu Tyr Tyr Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430

His Glu Ala Leu His Trp His Tyr Thr Gln Lys Ser Leu Ser Leu Ser
            435                 440                 445
Pro

<210> SEQ ID NO 96
<211> LENGTH: 447
<212> TYPE: PRT
<213> ORGANISM: Artificial Sequence
<220> FEATURE:
<223> OTHER INFORMATION: Synthetic antibody fragment

<400> SEQUENCE: 96

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr

```
            340                 345                 350
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Trp His Tyr Thr Gln Lys Ser Leu Ser Leu Ser Pro
            435                 440                 445

<210> SEQ ID NO 97
<211> LENGTH: 464
<212> TYPE: PRT
<213> ORGANISM: Artificial Sequence
<220> FEATURE:
<223> OTHER INFORMATION: Synthetic antibody fragment

<400> SEQUENCE: 97

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Pro Thr Ser Pro Lys Val Phe
        115                 120                 125

Pro Leu Ser Leu Cys Ser Thr Gln Pro Asp Gly Asn Val Val Ile Ala
    130                 135                 140

Cys Leu Val Gln Gly Phe Phe Pro Gln Glu Pro Leu Ser Val Thr Trp
145                 150                 155                 160

Ser Glu Ser Gly Gln Gly Val Thr Ala Arg Asn Phe Pro Pro Ser Gln
                165                 170                 175

Asp Ala Ser Gly Asp Leu Tyr Thr Thr Ser Ser Gln Leu Thr Leu Pro
            180                 185                 190

Ala Thr Gln Cys Leu Ala Gly Lys Ser Val Thr Cys His Val Lys His
        195                 200                 205

Tyr Thr Asn Pro Ser Gln Asp Val Thr Val Pro Cys Pro Val Pro Ser
    210                 215                 220

Thr Pro Pro Thr Pro Ser Pro Ser Thr Pro Pro Thr Pro Ser Pro Ser
225                 230                 235                 240

Cys Cys His Pro Arg Leu Ser Leu His Arg Pro Ala Leu Glu Asp Leu
                245                 250                 255

Leu Leu Gly Ser Glu Ala Asn Leu Thr Cys Thr Leu Thr Gly Leu Arg
```

```
                    260                 265                 270
Asp Ala Ser Gly Val Thr Phe Thr Trp Thr Pro Ser Ser Gly Lys Ser
                275                 280                 285

Ala Val Gln Gly Pro Pro Glu Arg Asp Leu Cys Gly Cys Tyr Ser Val
            290                 295                 300

Ser Ser Val Leu Pro Gly Cys Ala Glu Pro Trp Asn His Gly Lys Thr
305                 310                 315                 320

Phe Thr Cys Thr Ala Ala Tyr Pro Glu Ser Lys Thr Pro Leu Thr Ala
                325                 330                 335

Thr Leu Ser Lys Ser Gly Asn Thr Phe Arg Pro Glu Val His Leu Leu
                340                 345                 350

Pro Pro Pro Ser Glu Glu Leu Ala Leu Asn Glu Leu Val Thr Leu Thr
            355                 360                 365

Cys Leu Ala Arg Gly Phe Ser Pro Lys Asp Val Leu Val Arg Trp Leu
            370                 375                 380

Gln Gly Ser Gln Glu Leu Pro Arg Glu Lys Tyr Leu Thr Trp Ala Ser
385                 390                 395                 400

Arg Gln Glu Pro Ser Gln Gly Thr Thr Thr Phe Ala Val Thr Ser Ile
                405                 410                 415

Leu Arg Val Ala Ala Glu Asp Trp Lys Lys Gly Asp Thr Phe Ser Cys
                420                 425                 430

Met Val Gly His Glu Ala Leu Pro Leu Ala Phe Thr Gln Lys Thr Ile
                435                 440                 445

Asp Arg Leu Ala Gly Lys Glu Gln Lys Leu Ile Ser Glu Glu Asp Leu
            450                 455                 460

<210> SEQ ID NO 98
<211> LENGTH: 458
<212> TYPE: PRT
<213> ORGANISM: Artificial Sequence
<220> FEATURE:
<223> OTHER INFORMATION: Synthetic antibody fragment

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Pro Thr Ser Pro Lys Val Phe Pro Leu Ser Leu
            115                 120                 125

Cys Ser Thr Gln Pro Asp Gly Asn Val Val Ile Ala Cys Leu Val Gln
        130                 135                 140

Gly Phe Phe Pro Gln Glu Pro Leu Ser Val Thr Trp Ser Glu Ser Gly
145                 150                 155                 160

Gln Gly Val Thr Ala Arg Asn Phe Pro Pro Ser Gln Asp Ala Ser Gly
```

```
                165                 170                 175

Asp Leu Tyr Thr Thr Ser Ser Gln Leu Thr Leu Pro Ala Thr Gln Cys
            180                 185                 190

Leu Ala Gly Lys Ser Val Thr Cys His Val Lys His Tyr Thr Asn Pro
            195                 200                 205

Ser Gln Asp Val Thr Val Pro Cys Pro Val Pro Ser Thr Pro Pro Thr
    210                 215                 220

Pro Ser Pro Ser Thr Pro Pro Thr Pro Ser Pro Ser Cys Cys His Pro
225                 230                 235                 240

Arg Leu Ser Leu His Arg Pro Ala Leu Glu Asp Leu Leu Leu Gly Ser
                245                 250                 255

Glu Ala Asn Leu Thr Cys Thr Leu Thr Gly Leu Arg Asp Ala Ser Gly
            260                 265                 270

Val Thr Phe Thr Trp Thr Pro Ser Ser Gly Lys Ser Ala Val Gln Gly
            275                 280                 285

Pro Pro Glu Arg Asp Leu Cys Gly Cys Tyr Ser Val Ser Ser Val Leu
    290                 295                 300

Pro Gly Cys Ala Glu Pro Trp Asn His Gly Lys Thr Phe Thr Cys Thr
305                 310                 315                 320

Ala Ala Tyr Pro Glu Ser Lys Thr Pro Leu Thr Ala Thr Leu Ser Lys
                325                 330                 335

Ser Gly Asn Thr Phe Arg Pro Glu Val His Leu Leu Pro Pro Pro Ser
            340                 345                 350

Glu Glu Leu Ala Leu Asn Glu Leu Val Thr Leu Thr Cys Leu Ala Arg
            355                 360                 365

Gly Phe Ser Pro Lys Asp Val Leu Val Arg Trp Leu Gln Gly Ser Gln
    370                 375                 380

Glu Leu Pro Arg Glu Lys Tyr Leu Thr Trp Ala Ser Arg Gln Glu Pro
385                 390                 395                 400

Ser Gln Gly Thr Thr Thr Phe Ala Val Thr Ser Ile Leu Arg Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Thr Ile Asp Arg Leu Ala
            435                 440                 445

Gly Lys Asp Tyr Lys Asp Asp Asp Lys
    450                 455

<210> SEQ ID NO 99
<211> LENGTH: 219
<212> TYPE: PRT
<213> ORGANISM: Artificial Sequence
<220> FEATURE:
<223> OTHER INFORMATION: Synthetic antibody fragment

<400> SEQUENCE: 99

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
             65                  70                  75                  80
Ser Arg Val Glu Ala Glu Asp Val Gly Val Tyr Tyr Cys Ser Gln Asn
                    85                  90                  95

Thr His Val Pro Pro Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 100
<211> LENGTH: 233
<212> TYPE: PRT
<213> ORGANISM: Artificial Sequence
<220> FEATURE:
<223> OTHER INFORMATION: Synthetic antibody fragment

<400> SEQUENCE: 100

Cys His Pro Arg Leu Ser Leu His Arg Pro Ala Leu Glu Asp Leu Leu
1               5                   10                  15

Leu Gly Ser Glu Ala Asn Leu Thr Cys Thr Leu Thr Gly Leu Arg Asp
                20                  25                  30

Ala Ser Gly Val Thr Phe Thr Trp Thr Pro Ser Ser Gly Lys Ser Ala
            35                  40                  45

Val Gln Gly Pro Pro Glu Arg Asp Leu Cys Gly Cys Tyr Ser Val Ser
50                  55                  60

Ser Val Leu Pro Gly Cys Ala Glu Pro Trp Asn His Gly Lys Thr Phe
65                  70                  75                  80

Thr Cys Thr Ala Ala Tyr Pro Glu Ser Lys Thr Pro Leu Thr Ala Thr
                85                  90                  95

Leu Ser Lys Ser Gly Asn Thr Phe Arg Pro Glu Val His Leu Leu Pro
                100                 105                 110

Pro Pro Ser Glu Glu Leu Ala Leu Asn Glu Leu Val Thr Leu Thr Cys
                115                 120                 125

Leu Ala Arg Gly Phe Ser Pro Lys Asp Val Leu Val Arg Trp Leu Gln
            130                 135                 140

Gly Ser Gln Glu Leu Pro Arg Glu Lys Tyr Leu Thr Trp Ala Ser Arg
145                 150                 155                 160

Gln Glu Pro Ser Gln Gly Thr Thr Thr Phe Ala Val Thr Ser Ile Leu
                165                 170                 175

Arg Val Ala Ala Glu Asp Trp Lys Lys Gly Asp Thr Phe Ser Cys Met
                180                 185                 190

Val Gly His Glu Ala Leu Pro Leu Ala Phe Thr Gln Lys Thr Ile Asp
                195                 200                 205

Arg Leu Ala Gly Lys Gly Gly Gly Gly Ser Gly Leu Asn Asp Ile Phe
```

```
                210                 215                 220
Glu Ala Gln Lys Ile Glu Trp His Glu
225                 230

<210> SEQ ID NO 101
<211> LENGTH: 450
<212> TYPE: PRT
<213> ORGANISM: Artificial Sequence
<220> FEATURE:
<223> OTHER INFORMATION: Synthetic antibody fragment

<400> SEQUENCE: 101

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ala Pro Gly Asn Trp Gly Ser Pro Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
```

```
                340                 345                 350
Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro
    450

<210> SEQ ID NO 102
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 103
<211> LENGTH: 451
<212> TYPE: PRT
```

<213> ORGANISM: Artificial Sequence
<220> FEATURE:
<223> OTHER INFORMATION: Synthetic antibody fragment

<400> SEQUENCE: 103

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Arg Trp Glu Thr Ala Ile Ser Ser Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr

```
385                 390                 395                 400
Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro
        450

<210> SEQ ID NO 104
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
                20                  25                  30

Leu Asn Trp Tyr Gln Gln Lys Pro Gly Lys Ala Pro Lys Leu Leu Ile
            35                  40                  45

Tyr Glu Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Ser Ser Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 105
<211> LENGTH: 448
<212> TYPE: PRT
<213> ORGANISM: Artificial Sequence
<220> FEATURE:
<223> OTHER INFORMATION: Synthetic antibody fragment

<400> SEQUENCE: 105

Gln Val Gln Leu Val Gln Ser Gly Ala Glu Val Lys Lys Pro Gly Ser
1               5                   10                  15
```

-continued

Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Asn Gly Asp Tyr Leu Glu Tyr Phe Gln His Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro

<210> SEQ ID NO 106
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 107
<211> LENGTH: 452
<212> TYPE: PRT
<213> ORGANISM: Artificial Sequence
<220> FEATURE:
<223> OTHER INFORMATION: Synthetic antibody fragment

<400> SEQUENCE: 107

Gln Val Gln Leu Gln Gln Ser Gly Pro Gly Leu Val Lys Pro Ser Glu
1               5                   10                  15

Thr Leu Ser Leu Thr Cys Thr Ile Leu Gly Gly Ser Ile Ser Gly His
            20                  25                  30

Tyr Trp Ser Trp Ile Arg Gln Thr Pro Gly Lys Gly Leu Glu Trp Ile
        35                  40                  45

Gly Tyr Ile Asp Tyr Ser Gly Ser Thr His Tyr Asn Pro Ser Leu Lys
    50                  55                  60

Ser Arg Val Thr Met Ser Val Asp Thr Ser Lys Asn Gln Phe Ser Leu
65                  70                  75                  80

```
Lys Leu Ser Ser Val Thr Ala Ala Asp Thr Ala Met Tyr Tyr Cys Ala
                 85                  90                  95

Arg Asp Asn Trp Asp Phe Gly Ser Gly Ser Tyr Tyr Asn Trp Phe Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
    450

<210> SEQ ID NO 108
<211> LENGTH: 214
<212> TYPE: PRT
<213> ORGANISM: Artificial Sequence
<220> FEATURE:
<223> OTHER INFORMATION: Synthetic antibody fragment
```

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr His Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Asn Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 109
<211> LENGTH: 545
<212> TYPE: PRT
<213> ORGANISM: Artificial Sequence
<220> FEATURE:
<223> OTHER INFORMATION: Synthetic antibody fragment

<400> SEQUENCE: 109

Gln Pro Pro Pro Pro Pro Asp Ala Thr Cys His Gln Val Arg Ser
1               5                   10                  15

Phe Phe Gln Arg Leu Gln Pro Gly Leu Lys Trp Val Pro Glu Thr Pro
            20                  25                  30

Val Pro Gly Ser Asp Leu Gln Val Cys Leu Pro Lys Gly Pro Thr Cys
        35                  40                  45

Cys Ser Arg Lys Met Glu Glu Lys Tyr Gln Leu Thr Ala Arg Leu Asn
    50                  55                  60

Met Glu Gln Leu Leu Gln Ser Ala Ser Met Glu Leu Lys Phe Leu Ile
65                  70                  75                  80

Ile Gln Asn Ala Ala Val Phe Gln Glu Ala Phe Glu Ile Val Val Arg
                85                  90                  95

His Ala Lys Asn Tyr Thr Asn Ala Met Phe Lys Asn Asn Tyr Pro Ser
            100                 105                 110

Leu Thr Pro Gln Ala Phe Glu Phe Val Gly Glu Phe Phe Thr Asp Val
        115                 120                 125

```
Ser Leu Tyr Ile Leu Gly Ser Asp Ile Asn Val Asp Met Val Asn
    130                 135                 140

Glu Leu Phe Asp Ser Leu Phe Pro Val Ile Tyr Thr Gln Leu Met Asn
145                 150                 155                 160

Pro Gly Leu Pro Asp Ser Ala Leu Asp Ile Asn Glu Cys Leu Arg Gly
                165                 170                 175

Ala Arg Arg Asp Leu Lys Val Phe Gly Asn Phe Pro Lys Leu Ile Met
            180                 185                 190

Thr Gln Val Ser Lys Ser Leu Gln Val Thr Arg Ile Phe Leu Gln Ala
        195                 200                 205

Leu Asn Leu Gly Ile Glu Val Ile Asn Thr Thr Asp His Leu Lys Phe
210                 215                 220

Ser Lys Asp Cys Gly Arg Met Leu Thr Arg Met Trp Tyr Cys Ser Tyr
225                 230                 235                 240

Cys Gln Gly Leu Met Met Val Lys Pro Cys Gly Gly Tyr Cys Asn Val
                245                 250                 255

Val Met Gln Gly Cys Met Ala Gly Val Val Glu Ile Asp Lys Tyr Trp
            260                 265                 270

Arg Glu Tyr Ile Leu Ser Leu Glu Glu Leu Val Asn Gly Met Tyr Arg
        275                 280                 285

Ile Tyr Asp Met Glu Asn Val Leu Leu Gly Leu Phe Ser Thr Ile His
290                 295                 300

Asp Ser Ile Gln Tyr Val Gln Lys Asn Ala Gly Lys Leu Thr Thr Thr
305                 310                 315                 320

Ile Gly Lys Leu Cys Ala His Ser Gln Gln Arg Gln Tyr Arg Ser Ala
                325                 330                 335

Tyr Tyr Pro Glu Asp Leu Phe Ile Asp Lys Lys Val Leu Lys Val Ala
            340                 345                 350

His Val Glu His Glu Thr Leu Ser Ser Arg Arg Glu Leu Ile
        355                 360                 365

Gln Lys Leu Lys Ser Phe Ile Ser Phe Tyr Ser Ala Leu Pro Gly Tyr
370                 375                 380

Ile Cys Ser His Ser Pro Val Ala Glu Asn Asp Thr Leu Cys Trp Asn
385                 390                 395                 400

Gly Gln Glu Leu Val Glu Arg Tyr Ser Gln Lys Ala Ala Arg Asn Gly
                405                 410                 415

Met Lys Asn Gln Phe Asn Leu His Glu Leu Lys Met Lys Gly Pro Glu
            420                 425                 430

Pro Val Val Ser Gln Ile Ile Asp Lys Leu Lys His Ile Asn Gln Leu
        435                 440                 445

Leu Arg Thr Met Ser Met Pro Lys Gly Arg Val Leu Asp Lys Asn Leu
450                 455                 460

Asp Glu Glu Gly Phe Glu Ala Gly Asp Cys Gly Asp Asp Glu Asp
465                 470                 475                 480

Cys Ile Gly Gly Ala Gly Asp Gly Met Ile Lys Val Lys Asn Gln Leu
                485                 490                 495

Arg Phe Leu Ala Glu Leu Ala Tyr Asp Leu Asp Val Asp Asp Ala Pro
            500                 505                 510

Gly Asn Ser Gln Gln Ala Thr Pro Lys Asp Asn Glu Ile Ser Thr Phe
        515                 520                 525

His Asn Leu Gly Asn Val His Ser Pro Leu Lys His His His His
530                 535                 540

His
```

<210> SEQ ID NO 110
<211> LENGTH: 443
<212> TYPE: PRT
<213> ORGANISM: Artificial Sequence
<220> FEATURE:
<223> OTHER INFORMATION: Synthetic antibody fragment

<400> SEQUENCE: 110

```
Glu Val Gln Leu Val Glu Thr Gly Gly Gly Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
```

```
               355                 360                 365
Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 111
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 112
<211> LENGTH: 459
<212> TYPE: PRT
<213> ORGANISM: Artificial Sequence
<220> FEATURE:
<223> OTHER INFORMATION: Synthetic antibody fragment

<400> SEQUENCE: 112
```

-continued

```
Gln Val Gln Leu Val Gln Ser Gly Gly Val Gln Pro Gly Arg
1               5                   10              15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Ala Gly Arg His Tyr Tyr Asp Ser Ser Gly Tyr Tyr
            100                 105                 110

Asp Tyr Tyr Tyr Gly Met Asp Val Trp Gly Gln Gly Thr Met Val Thr
                115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
            195                 200                 205

Thr Gln Thr Tyr Ile Cys Asn Val Asn His Lys Pro Ser Asn Thr Lys
        210                 215                 220

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
            290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Asp Glu Leu Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
```

```
                420             425             430
Gln Gly Asn Val Phe Ser Cys Ser Val Met His Glu Ala Leu His Asn
            435                 440                 445

His Tyr Thr Gln Lys Ser Leu Ser Leu Ser Pro
    450                 455

<210> SEQ ID NO 113
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
            20                  25                  30

Leu Asn Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 114
<211> LENGTH: 451
<212> TYPE: PRT
<213> ORGANISM: Artificial Sequence
<220> FEATURE:
<223> OTHER INFORMATION: Synthetic antibody fragment

<400> SEQUENCE: 114

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50              55              60
Lys Gly Arg Phe Thr Ile Ser Arg Asp Asn Ser Lys Asn Thr Leu Tyr
 65              70              75              80
Leu Gln Met Asn Ser Leu Arg Ala Glu Asp Thr Ala Val Tyr Tyr Cys
                 85              90              95
Ala Lys Asp Arg Thr Pro Tyr Asp Phe Trp Ser Gly Tyr Leu Asp Tyr
            100             105             110
Trp Gly Gln Gly Thr Leu Val Thr Val Ser Ser Ala Ser Thr Lys Gly
            115             120             125
Pro Ser Val Phe Pro Leu Ala Pro Ser Ser Lys Ser Thr Ser Gly Gly
    130             135             140
Thr Ala Ala Leu Gly Cys Leu Val Lys Asp Tyr Phe Pro Glu Pro Val
145             150             155             160
Thr Val Ser Trp Asn Ser Gly Ala Leu Thr Ser Gly Val His Thr Phe
                165             170             175
Pro Ala Val Leu Gln Ser Ser Gly Leu Tyr Ser Leu Ser Ser Val Val
            180             185             190
Thr Val Pro Ser Ser Ser Leu Gly Thr Gln Thr Tyr Ile Cys Asn Val
            195             200             205
Asn His Lys Pro Ser Asn Thr Lys Val Asp Lys Val Glu Pro Lys
    210             215             220
Ser Cys Asp Lys Thr His Thr Cys Pro Pro Cys Pro Ala Pro Glu Leu
225             230             235             240
Leu Gly Gly Pro Ser Val Phe Leu Phe Pro Pro Lys Pro Lys Asp Thr
                245             250             255
Leu Met Ile Ser Arg Thr Pro Glu Val Thr Cys Val Val Val Asp Val
            260             265             270
Ser His Glu Asp Pro Glu Val Lys Phe Asn Trp Tyr Val Asp Gly Val
            275             280             285
Glu Val His Asn Ala Lys Thr Lys Pro Arg Glu Glu Gln Tyr Asn Ser
            290             295             300
Thr Tyr Arg Val Val Ser Val Leu Thr Val Leu His Gln Asp Trp Leu
305             310             315             320
Asn Gly Lys Glu Tyr Lys Cys Lys Val Ser Asn Lys Ala Leu Pro Ala
                325             330             335
Pro Ile Glu Lys Thr Ile Ser Lys Ala Lys Gly Gln Pro Arg Glu Pro
            340             345             350
Gln Val Tyr Thr Leu Pro Pro Ser Arg Asp Glu Leu Thr Lys Asn Gln
            355             360             365
Val Ser Leu Thr Cys Leu Val Lys Gly Phe Tyr Pro Ser Asp Ile Ala
    370             375             380
Val Glu Trp Glu Ser Asn Gly Gln Pro Glu Asn Asn Tyr Lys Thr Thr
385             390             395             400
Pro Pro Val Leu Asp Ser Asp Gly Ser Phe Phe Leu Tyr Ser Lys Leu
                405             410             415
Thr Val Asp Lys Ser Arg Trp Gln Gln Gly Asn Val Phe Ser Cys Ser
            420             425             430
Val Met His Glu Ala Leu His Asn His Tyr Thr Gln Lys Ser Leu Ser
            435             440             445
Leu Ser Pro
    450
```

<210> SEQ ID NO 115
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 115

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 116
<211> LENGTH: 451
<212> TYPE: PRT
<213> ORGANISM: Artificial Sequence
<220> FEATURE:
<223> OTHER INFORMATION: Synthetic antibody fragment

<400> SEQUENCE: 116

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

-continued

```
Ala Arg Asp Ser Pro Leu Leu Trp Phe Gly Glu Pro Phe Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro
    450

<210> SEQ ID NO 117
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 117
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
            35                  40                  45

Tyr His Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 118
<211> LENGTH: 445
<212> TYPE: PRT
<213> ORGANISM: Artificial Sequence
<220> FEATURE:
<223> OTHER INFORMATION: Synthetic antibody fragment

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 119
<211> LENGTH: 219
<212> TYPE: PRT
<213> ORGANISM: Artificial Sequence
<220> FEATURE:
<223> OTHER INFORMATION: Synthetic antibody fragment

<400> SEQUENCE: 119

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Leu Gln Lys Pro Gly Gln Ser
                35                  40                  45

Pro Gln Leu Leu Ile Tyr Lys Val Ser Asn Arg Phe Ser Gly Val Pro
                50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 120
<211> LENGTH: 449
<212> TYPE: PRT
<213> ORGANISM: Artificial Sequence
<220> FEATURE:
<223> OTHER INFORMATION: Synthetic antibody fragment

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Ala Arg Asn Pro Thr Ile Tyr Pro Leu Thr Leu
        115                 120                 125

Pro Pro Val Leu Cys Ser Asp Pro Val Ile Gly Cys Leu Ile His
    130                 135                 140

Asp Tyr Phe Pro Phe Gly Thr Met Asn Val Thr Trp Gly Lys Ser Gly
145                 150                 155                 160

Lys Asp Ile Thr Thr Val Asn Phe Pro Pro Ala Leu Ala Ser Gly Gly
                165                 170                 175

Arg Tyr Thr Met Ser Ser Gln Leu Thr Leu Pro Ala Val Glu Cys Pro
            180                 185                 190

Glu Gly Glu Ser Val Lys Cys Ser Val Gln His Asp Ser Asn Pro Val
        195                 200                 205
```

Gln Glu Leu Asp Val Asn Cys Ser Gly Pro Thr Pro Pro Pro Ile
210                 215                 220

Thr Ile Pro Ser Cys Gln Pro Ser Leu Ser Leu Gln Arg Pro Ala Leu
225                 230                 235                 240

Glu Asp Leu Leu Leu Gly Ser Asp Ala Ser Ile Thr Cys Thr Leu Asn
                245                 250                 255

Gly Leu Arg Asn Pro Glu Gly Ala Ala Phe Thr Trp Glu Pro Ser Thr
            260                 265                 270

Gly Lys Asp Ala Val Gln Lys Lys Ala Ala Gln Asn Ser Cys Gly Cys
        275                 280                 285

Tyr Ser Val Ser Ser Val Leu Pro Gly Cys Ala Glu Arg Trp Asn Ser
290                 295                 300

Gly Ala Ser Phe Lys Cys Thr Val Thr His Pro Glu Ser Gly Thr Leu
305                 310                 315                 320

Thr Gly Thr Ile Ala Lys Val Thr Val Asn Thr Phe Pro Pro Gln Val
                325                 330                 335

His Leu Leu Pro Pro Ser Glu Glu Leu Ala Leu Asn Glu Leu
            340                 345                 350

Ser Leu Thr Cys Leu Val Arg Ala Phe Asn Pro Lys Glu Val Leu Val
355                 360                 365

Arg Trp Leu His Gly Asn Glu Glu Leu Ser Pro Glu Ser Tyr Leu Val
370                 375                 380

Phe Glu Pro Leu Lys Glu Pro Gly Glu Gly Ala Thr Thr Tyr Leu Val
385                 390                 395                 400

Thr Ser Val Leu Arg Val Ser Ala Glu Thr Trp Lys Gln Gly Asp Gln
                405                 410                 415

Tyr Ser Cys Met Val Gly His Glu Ala Leu Pro Met Asn Phe Thr Gln
            420                 425                 430

Lys Thr Ile Asp Arg Leu Ser Gly Lys Asp Tyr Lys Asp Asp Asp
        435                 440                 445

Lys

<210> SEQ ID NO 121
<211> LENGTH: 219
<212> TYPE: PRT
<213> ORGANISM: Artificial Sequence
<220> FEATURE:
<223> OTHER INFORMATION: Synthetic antibody fragment

<400> SEQUENCE: 121

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Ala Asp Ala Ala Pro Thr Val Ser Ile Phe Pro Pro Ser Ser Glu

```
                  115                 120                 125
Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
                195                 200                 205

Pro Ile Val Lys Ser Phe Asn Arg Asn Glu Cys
                210                 215

<210> SEQ ID NO 122
<211> LENGTH: 233
<212> TYPE: PRT
<213> ORGANISM: Artificial Sequence
<220> FEATURE:
<223> OTHER INFORMATION: Synthetic antibody fragment

<400> SEQUENCE: 122

Cys Gln Pro Ser Leu Ser Leu Gln Arg Pro Ala Leu Glu Asp Leu Leu
1               5                   10                  15

Leu Gly Ser Asp Ala Ser Ile Thr Cys Thr Leu Asn Gly Leu Arg Asn
                20                  25                  30

Pro Glu Gly Ala Ala Phe Thr Trp Glu Pro Ser Thr Gly Lys Asp Ala
            35                  40                  45

Val Gln Lys Lys Ala Ala Gln Asn Ser Cys Gly Cys Tyr Ser Val Ser
        50                  55                  60

Ser Val Leu Pro Gly Cys Ala Glu Arg Trp Asn Ser Gly Ala Ser Phe
65                  70                  75                  80

Lys Cys Thr Val Thr His Pro Glu Ser Gly Thr Leu Thr Gly Thr Ile
                85                  90                  95

Ala Lys Val Thr Val Asn Thr Phe Pro Pro Gln Val His Leu Leu Pro
                100                 105                 110

Pro Pro Ser Glu Glu Leu Ala Leu Asn Glu Leu Leu Ser Leu Thr Cys
            115                 120                 125

Leu Val Arg Ala Phe Asn Pro Lys Glu Val Leu Val Arg Trp Leu His
        130                 135                 140

Gly Asn Glu Glu Leu Ser Pro Glu Ser Tyr Leu Val Phe Glu Pro Leu
145                 150                 155                 160

Lys Glu Pro Gly Glu Gly Ala Thr Thr Tyr Leu Val Thr Ser Val Leu
                165                 170                 175

Arg Val Ser Ala Glu Thr Trp Lys Gln Gly Asp Gln Tyr Ser Cys Met
                180                 185                 190

Val Gly His Glu Ala Leu Pro Met Asn Phe Thr Gln Lys Thr Ile Asp
            195                 200                 205

Arg Leu Ser Gly Lys Gly Gly Gly Ser Gly Leu Asn Asp Ile Phe
        210                 215                 220

Glu Ala Gln Lys Ile Glu Trp His Glu
225                 230

<210> SEQ ID NO 123
<211> LENGTH: 449
<212> TYPE: PRT
```

<213> ORGANISM: Artificial Sequence
<220> FEATURE:
<223> OTHER INFORMATION: Synthetic antibody fragment

<400> SEQUENCE: 123

```
Gln Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Ser Lys Thr
            20                  25                  30

Tyr Ser Tyr Trp Ala Trp Ile Arg Gln His Pro Val Lys Gly Leu Glu
        35                  40                  45

Trp Ile Gly Tyr Ile Ser Tyr Gly Gly Thr His Tyr Asn Pro Ser
    50                  55                  60

Leu Lys Ser Arg Val Thr Ile Ser Ser Asp Thr Ser Lys Asn His Phe
65                  70                  75                  80

Ser Leu Asn Leu Asn Ser Val Thr Ala Ala Asp Thr Ala Val Tyr Tyr
                85                  90                  95

Cys Ala Arg Ser Gly Phe Arg Val Phe Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
```

```
385                 390                 395                 400
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro

<210> SEQ ID NO 124
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45

Tyr Asp Ala Ser His Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Asn Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 125
<211> LENGTH: 450
<212> TYPE: PRT
<213> ORGANISM: Artificial Sequence
<220> FEATURE:
<223> OTHER INFORMATION: Synthetic antibody fragment

<400> SEQUENCE: 125

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
```

```
                 20                  25                  30
Ser Tyr Tyr Trp Gly Trp Ile Arg Gln Pro Pro Gly Lys Gly Leu Glu
                35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg His Gly Pro Ser Gly Ser Tyr Tyr Ala Phe Asp Ile Trp
                100                 105                 110

Gly Gln Gly Thr Met Val Thr Val Ser Ser Ala Ser Thr Lys Gly Pro
                115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
                210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
                290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445
```

Ser Pro
    450

<210> SEQ ID NO 126
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Lys Ala Ser His Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His His Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 127
<211> LENGTH: 452
<212> TYPE: PRT
<213> ORGANISM: Artificial Sequence
<220> FEATURE:
<223> OTHER INFORMATION: Synthetic antibody fragment

<400> SEQUENCE: 127

Gln Val Gln Leu Gln Gln Ser Gly Pro Gly Leu Val Lys Pro Ser Glu
1               5                   10                  15

Ser Leu Ser Leu Thr Cys Asn Val Ser Gly Tyr Tyr Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr Pro Ser Gly Thr Ser His Tyr Asn Pro Ser Leu
50                  55                  60

Lys Ser Arg Val Thr Ile Ser Leu Asp Thr Ser Lys Asn Gln Phe Ser

```
                65                  70                  75                  80
Leu Lys Leu Ser Ser Leu Ser Ala Ala Asp Thr Ala Val Tyr Tyr Cys
                    85                  90                  95

Ala Arg Ala Gly Val Ile Ala Gly Gly Pro Arg Thr Tyr Ala Phe Asp
                100                 105                 110

Ile Trp Gly Gln Gly Thr Thr Val Thr Val Ser Ser Ala Ser Thr Lys
                115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
        450

<210> SEQ ID NO 128
<211> LENGTH: 214
<212> TYPE: PRT
<213> ORGANISM: Artificial Sequence
```

<220> FEATURE:
<223> OTHER INFORMATION: Synthetic antibody fragment

<400> SEQUENCE: 128

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser His
            20                  25                  30

Leu Ala Trp Tyr Gln Gln Lys Pro Gly Lys Ala Pro Lys Leu Leu Ile
        35                  40                  45

Tyr Lys Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 129
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 129

```
Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr Lys Lys Lys Phe Lys Asp Pro Asn Ala Pro Lys Arg
                85                  90                  95

Pro Pro Ser Ala Phe Phe Leu Phe Cys Ser Glu Tyr Arg Pro Lys Ile
                100                 105                 110

Lys Gly Glu His Pro Gly Leu Ser Ile Gly Asp Val Ala Lys Lys Leu
```

```
            115                 120                 125
Gly Glu Met Trp Asn Asn Thr Ala Ala Asp Asp Lys Gln Pro Tyr Glu
    130                 135                 140

Lys Lys Ala Ala Lys Leu Lys Glu Lys Tyr Glu Lys Asp Ile Ala Ala
145                 150                 155                 160

Tyr Arg Ala Lys Gly Lys Pro Asp Ala Ala Lys Lys Gly Val Val Lys
                165                 170                 175

Ala Glu Lys Ser Lys Lys Lys Glu Glu Glu Asp Glu Glu Asp
                180                 185                 190

Glu Glu Asp Glu Glu Glu Glu Asp Glu Glu Asp Glu Asp Glu Glu
            195                 200                 205

Glu Asp Asp Asp Asp Glu
    210
```

```
<210> SEQ ID NO 130
<211> LENGTH: 234
<212> TYPE: PRT
<213> ORGANISM: Artificial Sequence
<220> FEATURE:
<223> OTHER INFORMATION: Synthetic antibody fragment

<400> SEQUENCE: 130

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr Lys Lys Phe Lys Asp Pro Asn Ala Pro Lys Arg
                85                  90                  95

Pro Pro Ser Ala Phe Phe Leu Phe Cys Ser Glu Tyr Arg Pro Lys Ile
            100                 105                 110

Lys Gly Glu His Pro Gly Leu Ser Ile Gly Asp Val Ala Lys Lys Leu
        115                 120                 125

Gly Glu Met Trp Asn Asn Thr Ala Ala Asp Asp Lys Gln Pro Tyr Glu
    130                 135                 140

Lys Lys Ala Ala Lys Leu Lys Glu Lys Tyr Glu Lys Asp Ile Ala Ala
145                 150                 155                 160

Tyr Arg Ala Lys Gly Lys Pro Asp Ala Ala Lys Lys Gly Val Val Lys
                165                 170                 175

Ala Glu Lys Ser Lys Lys Lys Glu Glu Glu Asp Glu Glu Asp
                180                 185                 190

Glu Glu Asp Glu Glu Glu Glu Asp Glu Glu Asp Glu Asp Glu Glu
            195                 200                 205

Glu Asp Asp Asp Asp Glu Gly Gly Gly Ser Gly Leu Asn Asp Ile
    210                 215                 220

Phe Glu Ala Gln Lys Ile Glu Trp His Glu
225                 230
```

```
<210> SEQ ID NO 131
<211> LENGTH: 449
<212> TYPE: PRT
```

<213> ORGANISM: Artificial Sequence
<220> FEATURE:
<223> OTHER INFORMATION: Synthetic antibody fragment

<400> SEQUENCE: 131

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Pro Ile Ser Ser Ser
            20                  25                  30

Gly Tyr Tyr Trp Gly Trp Ile Arg Gln Pro Pro Gly Lys Gly Leu Glu
        35                  40                  45

Trp Ile Gly Thr Val Tyr Phe Asn Gly Asp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Glu Glu Gly Tyr Tyr Tyr Tyr Met Asp Val Trp Gly
            100                 105                 110

Lys Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro

```
                385                 390                 395                 400
Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                    420                 425                 430

His Glu Ala Leu His Asn His Tyr Thr Gln Lys Ser Leu Ser Leu Ser
                    435                 440                 445

Pro

<210> SEQ ID NO 132
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser His
                20                  25                  30

Leu Asn Trp Tyr Gln Gln Lys Pro Gly Lys Ala Pro Lys Leu Leu Ile
            35                  40                  45

Tyr Gly Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 133
<211> LENGTH: 459
<212> TYPE: PRT
<213> ORGANISM: Artificial Sequence
<220> FEATURE:
<223> OTHER INFORMATION: Synthetic antibody fragment

<400> SEQUENCE: 133

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                    20              25              30
Ala Ile Ser Trp Val Arg Gln Ala Pro Gly Gln Gly Leu Glu Trp Met
            35              40              45
Gly Gly Ile Ile Pro Ile Phe Gly Thr Ala Asn Tyr Ala Gln Lys Phe
        50              55              60
Gln Gly Arg Val Thr Ile Thr Ala Asp Glu Ser Thr Ser Thr Ala Tyr
65              70              75              80
Met Glu Leu Ser Ser Leu Arg Ser Glu Asp Thr Ala Val Tyr Tyr Cys
                85              90              95
Ala Arg Asp Asn Arg Thr Leu Thr Tyr Tyr Asp Phe Trp Ser Gly Tyr
            100             105             110
Ser Phe Trp Asp Ala Phe Asp Ile Trp Gly Gln Gly Thr Met Val Thr
            115             120             125
Val Ser Ser Ala Ser Thr Lys Gly Pro Ser Val Phe Pro Leu Ala Pro
        130             135             140
Ser Ser Lys Ser Thr Ser Gly Gly Thr Ala Ala Leu Gly Cys Leu Val
145             150             155             160
Lys Asp Tyr Phe Pro Glu Pro Val Thr Val Ser Trp Asn Ser Gly Ala
                165             170             175
Leu Thr Ser Gly Val His Thr Phe Pro Ala Val Leu Gln Ser Ser Gly
            180             185             190
Leu Tyr Ser Leu Ser Ser Val Val Thr Val Pro Ser Ser Ser Leu Gly
            195             200             205
Thr Gln Thr Tyr Ile Cys Asn Val Asn His Lys Pro Ser Asn Thr Lys
        210             215             220
Val Asp Lys Lys Val Glu Pro Lys Ser Cys Asp Lys Thr His Thr Cys
225             230             235             240
Pro Pro Cys Pro Ala Pro Glu Leu Leu Gly Gly Pro Ser Val Phe Leu
                245             250             255
Phe Pro Pro Lys Pro Lys Asp Thr Leu Met Ile Ser Arg Thr Pro Glu
            260             265             270
Val Thr Cys Val Val Val Asp Val Ser His Glu Asp Pro Glu Val Lys
            275             280             285
Phe Asn Trp Tyr Val Asp Gly Val Glu Val His Asn Ala Lys Thr Lys
        290             295             300
Pro Arg Glu Glu Gln Tyr Asn Ser Thr Tyr Arg Val Val Ser Val Leu
305             310             315             320
Thr Val Leu His Gln Asp Trp Leu Asn Gly Lys Glu Tyr Lys Cys Lys
                325             330             335
Val Ser Asn Lys Ala Leu Pro Ala Pro Ile Glu Lys Thr Ile Ser Lys
            340             345             350
Ala Lys Gly Gln Pro Arg Glu Pro Gln Val Tyr Thr Leu Pro Pro Ser
            355             360             365
Arg Asp Glu Leu Thr Lys Asn Gln Val Ser Leu Thr Cys Leu Val Lys
        370             375             380
Gly Phe Tyr Pro Ser Asp Ile Ala Val Glu Trp Glu Ser Asn Gly Gln
385             390             395             400
Pro Glu Asn Asn Tyr Lys Thr Thr Pro Pro Val Leu Asp Ser Asp Gly
                405             410             415
Ser Phe Phe Leu Tyr Ser Lys Leu Thr Val Asp Lys Ser Arg Trp Gln
            420             425             430
Gln Gly Asn Val Phe Ser Cys Ser Val Met His Glu Ala Leu His Asn
            435             440             445
```

His Tyr Thr Gln Lys Ser Leu Ser Leu Ser Pro
    450                 455

<210> SEQ ID NO 134
<211> LENGTH: 214
<212> TYPE: PRT
<213> ORGANISM: Artificial Sequence
<220> FEATURE:
<223> OTHER INFORMATION: Synthetic antibody fragment

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile His Ser His
            20                  25                  30

Leu Ala Trp Tyr Gln Gln Lys Pro Gly Lys Ala Pro Lys Leu Leu Ile
        35                  40                  45

Tyr Gly Ala Ser His Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 135
<211> LENGTH: 452
<212> TYPE: PRT
<213> ORGANISM: Artificial Sequence
<220> FEATURE:
<223> OTHER INFORMATION: Synthetic antibody fragment

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Asn Trp Val Arg Gln Ala Pro Gly Lys Gly Leu Glu Trp Ile
        35                  40                  45

Ser Tyr Ile Ser Ser Ser Gly Arg Thr Phe Ser Tyr Ala Asp Ser Val
50                  55                  60

Lys Gly Arg Phe Thr Ile Ser Arg Asp Asn Ala Lys Asn Ser Leu Tyr

```
             65                  70                  75                  80
Leu Gln Met Asn Ser Leu Arg Ala Glu Asp Thr Ala Val Tyr Tyr Cys
                 85                  90                  95

Ala Arg Asp Ser Gly Tyr Ser Asp Gly Trp Tyr Pro Ser Trp Phe Asp
                100                 105                 110

Ser Trp Gly Gln Gly Thr Leu Val Thr Val Ser Ser Ala Ser Thr Lys
                115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro
    450

<210> SEQ ID NO 136
<211> LENGTH: 214
<212> TYPE: PRT
<213> ORGANISM: Artificial Sequence
```

```
<220> FEATURE:
<223> OTHER INFORMATION: Synthetic antibody fragment

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser His
                20                  25                  30

Leu Ala Trp Tyr Gln Gln Lys Pro Gly Lys Ala Pro Lys Leu Leu Ile
            35                  40                  45

Tyr His Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Ser Tyr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

ION CONCENTRATION-DEPENDENT BINDING MOLECULE LIBRARY

CROSS-REFERENCE TO RELATED APPLICATIONS

This application is a continuation of U.S. application Ser. No. 14/348,511, § 371(c) date Mar. 28, 2014, which is a U.S. National Phase of PCT Application No. PCT/JP2012/006254, filed Sep. 28, 2012, which claims the benefit of Japanese Patent Application No. 2011-218006, filed Sep. 30, 2011, and Japanese Patent Application No. 2012-123479, filed May 30, 2012, each of which is incorporated herein by reference in its entirety.

REFERENCE TO SEQUENCE LISTING SUBMITTED ELECTRONICALLY

The content of the electronically submitted sequence listing (Name: 6663_0079_sequence_listing.txt; Size: 347 kilobytes; and Date of Creation: Jun. 18, 2018) filed with the application is incorporated herein by reference in its entirety.

FIELD OF INVENTION

The present invention relates to a library of antigen-binding molecules whose antigen-binding activity is changed depending on ion concentration conditions, a method for producing the library, a method for selecting such an antigen-binding molecule, a method for producing such an antigen-binding molecule, and a pharmaceutical composition comprising such an antigen-binding molecule.

BACKGROUND ART

Antibodies have received attention as pharmaceutical agents because of their high stability in plasma and few adverse reactions. Among others, many IgG antibody drugs have already been launched, and a large number of antibody drugs are still under development (Non Patent Literatures 1 and 2). Meanwhile, various techniques applicable to second-generation antibody drugs have been developed. For example, techniques of improving effector functions, antigen-binding ability, pharmacokinetics, or stability or of reducing the risk of immunogenicity have been reported (Non Patent Literature 3). Possible problems of such antibody drugs are the difficult preparation of subcutaneous administration preparations (this is because the antibody drugs are generally administered at very high doses), high production cost, etc. Methods for improving the pharmacokinetics of antibodies and methods for improving the affinity of antibodies for their antigens may be used for reducing the doses of the antibody drugs.

The artificial substitution of amino acids in constant regions has been reported as a method for improving the pharmacokinetics of antibodies (Non Patent Literatures 4 and 5). Previously reported affinity maturation, a technique of enhancing antigen-binding ability and antigen-neutralizing ability (Non Patent Literature 6), involves mutating amino acids in, for example, CDR regions of variable regions, to thereby achieve enhanced antigen-binding activity. Such enhancement in antigen-binding ability can improve biological activity in vitro or reduce doses and can further improve drug efficacy in vivo (Non Patent Literature 7).

The amount of an antigen that can be neutralized by one antibody molecule depends on affinity. Stronger affinity allows the antibody in a smaller amount to neutralize the antigen. The antibody affinity can be enhanced by various methods (Non Patent Literature 6). An antibody capable of covalently binding to an antigen with infinite affinity would be able to neutralize, by one molecule, one antigen molecule (or two antigens in the case of a divalent antibody). Previous methods, however, have a stoichiometric limitation of neutralization reaction up to one antigen molecule (or two antigens in the case of a divalent antibody) per antibody molecule and are unable to completely neutralize an antigen using an antibody in an amount below the amount of the antigen. In short, there is a limitation of the effect of enhancing affinity. (Non Patent Literature 9). A given duration of the neutralizing effect of a neutralizing antibody requires administering the antibody in an amount above the amount of an antigen produced in vivo for the period. Only the above-mentioned technique for improvement in the pharmacokinetics of antibodies or affinity maturation is not sufficient for reducing the necessary antibody doses. In this respect, one antibody must neutralize a plurality of antigens in order to sustain its antigen-neutralizing effect for the period of interest in an amount below the amount of the antigen.

In order to attain this object, an antibody binding to an antigen in a pH-dependent manner has been reported recently as a novel approach (Patent Literature 1). This literature discloses that histidine residue is introduced to an antigen-binding molecule to prepare a pH-dependent antigen-binding antibody whose property is changed between neutral pH and acidic pH conditions. This pH-dependent antigen-binding antibody binds to the antigen strongly under the neutral condition in plasma and dissociated from the antigen under the acidic condition in endosome. Thus, the pH-dependent antigen-binding antibody can be dissociated from the antigen in endosome. The pH-dependent antigen-binding antibody thus dissociated from the antigen can bind to an antigen after being recycled back to plasma by FcRn. This allows one antibody to bind to a plurality of antigens repeatedly.

Antigens have very short plasma retention, compared with antibodies, which are recycled through binding to FcRn. Antibody-antigen complexes of antibodies having long half life in plasma (long plasma retention) and such antigens having short half life in plasma (short plasma retention) have plasma retention as long as that of the antibodies. The binding of an antigen to an antibody therefore rather prolongs its plasma retention and raises antigen concentration in plasma. In such a case, even improvement in the affinity of the antibody for the antigen cannot promote the clearance of the antigen from plasma. Reportedly, the pH-dependent antigen-binding antibody mentioned above is also more effective as an approach for promoting antigen clearance from plasma than conventional antibodies (Patent Literature 1).

Thus, the pH-dependent antigen-binding antibody can bind to a plurality of antigens by one antibody molecule to promote the clearance of the antigens from plasma, compared with the conventional antibodies, and as such, has effects that cannot be achieved by the conventional antibodies. An amino acid in an existing antibody sequence can be substituted to thereby impart thereto pH-dependent antigen-binding activity. Meanwhile, a method for obtaining antibodies from immunized animals or a method for obtaining antibodies from a human antibody library may be used for obtaining such a novel antibody, but has possible limitations as described below.

A method which involves immunizing non-human animals might produce the pH-dependent binding antibody, but may rarely yield pH-dependent antigen-binding antibodies against various types of antigens in a short time or selectively yield antibodies specifically binding to particular epitopes. Alternatively, an antibody may be enriched from a human antibody library with pH-dependent antigen-binding ability as an index. The frequency of appearance of histidine residues in the variable regions of a human antibody (registered in the Kabat database), however, is generally known to be not high, as seen from 5.9% for heavy chain CDR1, 1.4% for heavy chain CDR2, 1.6% for heavy chain CDR3, 1.5% for light chain CDR1, 0.5% for light chain CDR2, and 2.2% for light chain CDR3, suggesting that the human antibody library contains only a very small number of sequences that can have pH-dependent antigen-binding ability. Accordingly, there has been a demand for providing an antibody library that has the increased frequency of appearance of histidine in antigen-binding sites and is rich in sequences that can have pH-dependent antigen-binding ability.

Effects such as the promotion of antigen clearance from plasma may be achieved if the dependence of antigen-binding ability on a factor (other than pH) different between the environments of plasma and early endosome can be imparted to the antibody.

Citation lists of the present invention will be given below.

CITATION LIST

Patent Literature

Patent Literature 1: WO2009125825

Non Patent Literature

Non Patent Literature 1: Janice M Reichert, Clark J Rosensweig, Laura B Faden & Matthew C Dewitz, Monoclonal antibody successes in the clinic, Nat. Biotechnol. (2005) 23, 1073-1078

Non Patent Literature 2: Pavlou A K, Belsey M J., The therapeutic antibodies market to 2008, Eur J Pharm Biopharm. (2005) 59 (3), 389-396.

Non Patent Literature 3: Kim S J, Park Y, Hong H J., Antibody engineering for the development of therapeutic antibodies, Mol Cells. (2005) 20 (1), 17-29

Non Patent Literature 4: Hinton P R, Xiong J M, Johlfs M G, Tang M T, Keller S, Tsurushita N., An engineered human IgG1 antibody with longer serum half-life, J Immunol. (2006) 176 (1), 346-356

Non Patent Literature 5: Ghetie V, Popov S, Borvak J, Radu C, Matesoi D, Medesan C, Ober R J, Ward E S., Increasing the serum persistence of an IgG fragment by random mutagenesis, Nat. Biotechnol. (1997) 15 (7), 637-640

Non Patent Literature 6: Rajpal A, Beyaz N, Haber L, Cappuccilli G, Yee H, Bhatt R R, Takeuchi T, Lerner R A, Crea R., A general method for greatly improving the affinity of antibodies by using combinatorial libraries, Proc. Natl. Acad. Sci. USA. (2005) 102 (24), 8466-8471

Non Patent Literature 7: Wu H, Pfarr D S, Johnson S, Brewah Y A, Woods R M, Patel N K, White W I, Young J F, Kiener P A. Development of Motavizumab, an Ultra-potent Antibody for the Prevention of Respiratory Syncytial Virus Infection in the Upper and Lower Respiratory Tract, J. Mol. Biol. (2007) 368, 652-665

Non Patent Literature 8: Hanson C V, Nishiyama Y, Paul S. Catalytic antibodies and their applications. Curr Opin Biotechnol, (2005) 16 (6), 631-6

Non Patent Literature 9: Rathanaswami P, Roalstad S, Roskos L, Su Q J, Lackie S, Babcook J. Demonstration of an in vivo generated sub-picomolar affinity fully human monoclonal antibody to interleukin-8, Biochem. Biophys. Res. Commun. (2005) 334 (4), 1004-13.

SUMMARY OF INVENTION

Technical Problem

The present invention has been made in light of such a situation, and an object of the present invention is to provide a library consisting essentially of a plurality of antigen-binding molecules differing in sequence from each other, wherein an antigen-binding domain in each of the antigen-binding molecules comprises at least one amino acid residue that changes the antigen-binding activity of the antigen-binding molecule depending on ion concentration conditions, a composition comprising a plurality of polynucleotide molecules each encoding the antigen-binding molecules, a composition comprising a plurality of vectors each comprising the polynucleotide molecules, a method for selecting the antigen-binding molecules, a method for isolating the polynucleotide molecules, a method for producing the antigen-binding molecules, and a pharmaceutical composition comprising any of the antigen-binding molecules.

Solution to Problem

The present inventors have conducted diligent studies on a library comprising a plurality of antigen-binding molecules differing in sequence from each other, wherein an antigen-binding domain in each of the antigen-binding molecules comprises at least one amino acid residue that changes the antigen-binding activity of the antigen-binding molecule depending on the difference in in vivo environmental factor. As a result, the present inventors have focused on the difference in ion concentration, particularly, calcium ion concentration, between plasma and early endosome or on the pHs of these environments and found that use of antigen-binding molecules having calcium-dependent or pH-dependent antigen-binding activity enables promotion of cellular uptake of antigens by the antigen-binding molecules and preparation of a library consisting essentially of antigen-binding molecules that reduce antigen concentration in plasma.

Specifically, the present invention relates to a library consisting essentially of a plurality of antigen-binding molecules differing in sequence from each other, wherein an antigen-binding domain in each of the antigen-binding molecules comprises at least one amino acid residue that changes the antigen-binding activity of the antigen-binding molecule depending on ion concentration conditions, a composition comprising a plurality of polynucleotide molecules each encoding the antigen-binding molecules, a composition comprising a plurality of vectors each comprising the polynucleotide molecules, a method for selecting the antigen-binding molecules, a method for isolating the polynucleotide molecules, a method for producing the antigen-binding molecules, a pharmaceutical composition comprising any of the antigen-binding molecules, etc. More specifically, the present invention relates to the following:

[1] A library consisting essentially of a plurality of antigen-binding molecules differing in sequence from each other, wherein an antigen-binding domain in each of the antigen-binding molecules comprises at least one amino acid residue that changes the antigen-binding activity of the antigen-binding molecule depending on ion concentration conditions.

[2] The library according to [1], wherein the ion concentration is a calcium ion concentration.

[3] The library according to [2], wherein the amino acid residue is contained in the antigen-binding domain in a heavy chain of the antigen-binding molecule.

[4] The library according to [3], wherein the antigen-binding domain in a heavy chain is a heavy chain variable region.

[5] The library according to [4], wherein the amino acid residue is contained in CDR3 of the heavy chain variable region.

[6] The library according to any of [2] to [5], wherein the amino acid residue is located at any one or more of positions 95, 96, 100a, and 101 defined by the Kabat numbering in the heavy chain CDR3.

[7] The library according to any of [2] to [6], wherein an amino acid sequence except for the amino acid residue comprises the amino acid sequence of a naive sequence.

[8] The library according to any of [3] to [7], wherein a light chain variable region of the antigen-binding molecule comprises the amino acid sequence of a naive sequence.

[9] The library according to [2], wherein the amino acid residue is contained in the antigen-binding domain in a light chain of the antigen-binding molecule.

[10] The library according to [9], wherein the antigen-binding domain in a light chain is a light chain variable region.

[11] The library according to [10], wherein the amino acid residue is contained in CDR1 of the light chain variable region.

[12] The library according to [11], wherein the amino acid residue is located at any one or more of positions 30, 31, and 32 defined by the Kabat numbering in the CDR1.

[13] The library according to any of [10] to [12], wherein the amino acid residue is contained in CDR2 of the light chain variable region.

[14] The library according to [13], wherein the amino acid residue is located at position 50 defined by the Kabat numbering in the light chain CDR2.

[15] The library according to any of [10] to [14], wherein the amino acid residue is contained in light chain CDR3.

[16] The library according to [15], wherein the amino acid residue is located at position 92 defined by the Kabat numbering in the light chain CDR3.

[17] The library according to any of [2] and [9] to [16], wherein a light chain framework region in the antigen-binding molecule comprises a germline framework sequence.

[18] The library according to any of [2] and [9] to [17], wherein a heavy chain variable region of the antigen-binding molecule comprises the amino acid sequence of a naive sequence.

[19] The library according to any of [1] to [18], wherein the amino acid residue forms a calcium-binding motif.

[20] The library according to [19], wherein the calcium-binding motif is any calcium-binding motif selected from a cadherin domain, an EF hand, a C2 domain, a Gla domain, a C-type lectin, A domain, an annexin, a thrombospondin type 3 domain, an EGF-like domain, a domain of Vk5, a domain represented by SEQ ID NO: 10, and a domain represented by SEQ ID NO: 11.

[21] The library according to any of [2] to [20], wherein the amino acid residue is an amino acid having a metal-chelating effect.

[22] The library according to [21], wherein the amino acid having a metal-chelating effect is any one or more amino acids selected from serine, threonine, asparagine, glutamine, aspartic acid, and glutamic acid.

[23] The library according to [1], wherein the ion concentration conditions are pH conditions.

[24] The library according to [23], wherein the amino acid residue is contained in the antigen-binding domain in a heavy chain of the antigen-binding molecule.

[25] The library according to [24], wherein the antigen-binding domain in a heavy chain is a heavy chain variable region.

[26] The library according to [25], wherein the amino acid residue is located at any one or more of positions 27, 31, 32, 33, 35, 50, 52, 53, 55, 57, 58, 59, 61, 62, 95, 96, 97, 98, 99, 100a, 100b, 100d, 100f, 100h, 102, and 107 defined by the Kabat numbering in the heavy chain variable region.

[27] The library according to [26], wherein an amino acid sequence except for the amino acid residue at any one or more of positions 27, 31, 32, 33, 35, 50, 52, 53, 55, 57, 58, 59, 61, 62, 95, 96, 97, 98, 99, 100a, 100b, 100d, 100f, 100h, 102, and 107 defined by the Kabat numbering in the heavy chain variable region comprises the amino acid sequence of a naive sequence.

[28] The library according to any of [23] to [27], wherein a light chain variable region of the antigen-binding molecule comprises a germline sequence.

[29] The library according to [23], wherein the amino acid residue is contained in the antigen-binding domain in a light chain of the antigen-binding molecule.

[30] The library according to [29], wherein the antigen-binding domain in a light chain is a light chain variable region.

[31] The library according to [30], wherein the amino acid residue is located at any one or more of positions 24, 27, 28, 30, 31, 32, 34, 50, 51, 52, 53, 54, 55, 56, 89, 90, 91, 92, 93, 94, and 95a defined by the Kabat numbering in the light chain variable region.

[32] The library according to [30] or [31], wherein the amino acid residue is contained in CDR1 of the light chain variable region.

[33] The library according to [32], wherein the amino acid residue is located at any one or more of positions 24, 27, 28, 30, 31, 32, and 34 defined by the Kabat numbering in the light chain CDR1.

[34] The library according to any of [30] to [33], wherein the amino acid residue is contained in light chain CDR2.

[35] The library according to [34], wherein the amino acid residue is located at any one or more of positions 50, 51, 52, 53, 54, 55, and 56 defined by the Kabat numbering in the light chain CDR2.

[36] The library according to any of [30] to [35], wherein the amino acid residue is contained in light chain CDR3.

[37] The library according to [36], wherein the amino acid residue is located at any one or more of positions 89, 90, 91, 92, 93, 94, and 95a defined by the Kabat numbering in the light chain CDR3.

[38] The library according to any of [29] to [37], wherein a light chain framework region comprises a germline framework sequence.

[39] The library according to any of [29] to [38], wherein a heavy chain variable region has a naive sequence.

[40] The library according to any of [23] to [39], wherein the amino acid residue is an amino acid having a side chain pKa of 4.0 to 8.0.
[41] The library according to any of [23] to [40], wherein the amino acid residue is glutamic acid.
[42] The library according to any of [23] to [39], wherein the amino acid residue is an amino acid having a side chain pKa of 5.5 to 7.0.
[43] The library according to any of [23] to [40] and [42], wherein the amino acid residue is histidine.
[44] A library consisting essentially of a plurality of fusion polypeptides each comprising antigen-binding molecules according to any of [1] to [43], wherein each of the fusion polypeptides is a fusion product of a heavy chain variable region of the antigen-binding molecule and at least a portion of a viral coat protein.
[45] The library according to [44], wherein the viral coat protein is selected from the group consisting of protein pIII, major coat protein pVIII, pVII, pIX, Soc, Hoc, gpD, pv1, and variants thereof.
[46] A composition comprising a plurality of polynucleotide molecules each encoding antigen-binding molecules differing in sequence from each other according to any of [1] to [43] or fusion polypeptides differing in sequence from each other according to [44] or [45].
[47] A composition comprising a plurality of vectors each comprising a plurality of polynucleotide molecules according to [46] in an operably linked state.
[48] The composition according to [47], wherein the vectors are replicable expression vectors.
[49] The composition according to [48], wherein each of the replicable expression vectors is an expression vector in which the polynucleotide is operably linked to a promoter region selected from the group consisting of a lacZ promoter system, an alkaline phosphatase phoA promoter (Ap), a bacteriophage λPL promoter (temperature-sensitive promoter), a tac promoter, a tryptophan promoter, a pBAD promoter, and a bacteriophage T7 promoter.
[50] The composition according to [48] or [49], wherein each of the replicable expression vectors is an M13, fl, fd, or Pf3 phage or a derivative thereof, or a lambdoid phage or a derivative thereof
[51] A composition comprising a plurality of viruses each comprising vectors according to any of [47] to [50].
[52] A composition comprising a plurality of viruses each displaying on their surface antigen-binding molecules differing in sequence from each other according to any of [1] to [43] or fusion polypeptides differing in sequence from each other according to [44] or [45].
[53] A library comprising antigen-binding molecules differing in sequence from each other according to any of [1] to [43] or fusion polypeptides differing in sequence from each other according to [44] or [45], wherein the library has $1 \times 10^6$ to $1 \times 10^{14}$ distinct variable region sequences.
[54] The library according to [53], wherein the library has $1 \times 10^8$ or more distinct variable region sequences.
[55] A method for preparing a library consisting essentially of a plurality of antigen-binding molecules differing in sequence from each other, the method comprising producing a plurality of antigen-binding molecules designed so that an antigen-binding domain in each of the antigen-binding molecules comprises at least one amino acid residue that changes the antigen-binding activity of the antigen-binding molecule depending on ion concentration conditions.
[56] The preparation method according to [55], wherein the antigen-binding molecules are antigen-binding molecules according to any of [2] to [43].
[57] The preparation method according to [55] or [56], wherein a heavy chain variable region of each of the antigen-binding molecules is fused with at least a portion of a viral coat protein.
[58] The preparation method according to any of [55] to [57], wherein the viral coat protein is selected from the group consisting of protein pIII, major coat protein pVIII, pVII, pIX, Soc, Hoc, gpD, pv1, and variants thereof
[59] A method for selecting an antigen-binding molecule whose antigen-binding activity is changed depending on ion concentration conditions, the method comprising the steps of:
 a) preparing a library consisting essentially of antigen-binding molecules differing in sequence from each other according to any of [1] to [43] or fusion polypeptides differing in sequence from each other according to [44] or [45];
 b) contacting the library with antigens under two or more different ion concentration conditions;
 c) sorting, from the library, a subpopulation of antigen-binding molecules whose antigen-binding activity is changed depending on the ion concentration conditions; and
 d) isolating each antigen-binding molecule whose antigen-binding activity is changed depending on the ion concentration conditions from the subpopulation sorted in the step c).
[60] A method for isolating a polynucleotide encoding an antigen-binding molecule whose antigen-binding activity is changed depending on ion concentration conditions, the method comprising the steps of:
 a) preparing a library comprising a plurality of replicable expression vectors each comprising, in an operably linked state, a plurality of polynucleotides each encoding antigen-binding molecules differing in sequence from each other according to any of [1] to [43] or fusion polypeptides differing in sequence from each other according to [44] or [45];
 b) allowing a plurality of viruses each transformed with the expression vectors contained in the library to express on their surface the antigen-binding molecules or the fusion polypeptides differing in sequence from each other encoded by the polynucleotides;
 c) contacting the plurality of viruses with antigens under two or more different ion concentration conditions;
 d) sorting, from the library, a subpopulation of viruses whose antigen-binding activity is changed depending on the ion concentration conditions;
 e) isolating each virus whose antigen-binding activity is changed depending on the ion concentration conditions from the virus subpopulation sorted in the step d); and
 f) isolating the polynucleotides from the isolated virus.
[61] The method according to [60], wherein the steps c) and d) are additionally repeated at least once.
[62] The method according to any of [59] to [61], wherein the ion concentration is a calcium ion concentration.
[63] The method according to [62], wherein an antigen-binding molecule having lower antigen-binding activity under a low-calcium concentration condition than that under a high-calcium concentration condition is selected.
[64] The method according to [63], wherein the low-calcium concentration condition is 0.1 μM to 30 μM.

[65] The method according to [63] or [64], wherein the high-calcium concentration condition is 100 μM to 10 mM.
[66] The method according to any of [59] to [61], wherein the ion concentration conditions are pH conditions.
[67] The method according to [66], wherein an antigen-binding molecule having lower antigen-binding activity in an acidic pH condition than that in a neutral pH condition is selected.
[68] The method according to [66], wherein the acidic pH condition is pH 4.0 to 6.5.
[69] The method according to [67] or [68], wherein the neutral pH condition is pH 6.7 to 10.0.
[70] A method for producing an antigen-binding molecule whose antigen-binding activity is changed depending on ion concentration conditions, the method comprising the steps of:
  a) preparing a library comprising a plurality of replicable expression vectors each comprising, in an operably linked state, a plurality of polynucleotides each encoding antigen-binding molecules differing in sequence from each other according to any of [1] to [43] or fusion polypeptides differing in sequence from each other according to [44] or [45];
  b) allowing a plurality of viruses each transformed with the expression vectors contained in the library to express on their surface the antigen-binding molecules or the fusion polypeptides differing in sequence from each other encoded by the polynucleotides;
  c) contacting the plurality of viruses with antigens under two or more different ion concentration conditions;
  d) sorting, from the library, a subpopulation of viruses whose antigen-binding activity is changed depending on the ion concentration conditions;
  e) isolating each virus whose antigen-binding activity is changed depending on the ion concentration conditions from the virus subpopulation sorted in the step d);
  f) isolating the polynucleotides from the isolated virus;
  g) culturing a host cell transfected with a vector having an operably linked insert of the isolated polynucleotides; and
  h) collecting the antigen-binding molecules from the cultures of the cell cultured in the step g).
[71] A method for producing an antigen-binding molecule whose antigen-binding activity is changed depending on ion concentration conditions, the method comprising the steps of:
  a) preparing a library comprising a plurality of replicable expression vectors each comprising, in an operably linked state, a plurality of polynucleotides each encoding antigen-binding molecules differing in sequence from each other according to any of [1] to [43] or fusion polypeptides differing in sequence from each other according to [44] or [45];
  b) allowing a plurality of viruses each transformed with the expression vectors contained in the library to express on their surface the antigen-binding molecules or the fusion polypeptides differing in sequence from each other encoded by the polynucleotides;
  c) contacting the plurality of viruses with antigens under two or more different ion concentration conditions;
  d) sorting, from the library, a subpopulation of viruses whose antigen-binding activity is changed depending on the ion concentration conditions;
  e) isolating each virus whose antigen-binding activity is changed depending on the ion concentration conditions from the virus subpopulation sorted in the step d);
  f) isolating the polynucleotides from the isolated virus;
  g) linking the isolated polynucleotides in frame with a polynucleotide encoding an antibody constant region;
  h) culturing a host cell transfected with a vector having an operably linked insert of the polynucleotides linked in the step g); and
  i) recovering the antigen-binding molecules from the cultures of the cell cultured in the step h).
[72] The production method according to [70] or [71], wherein the steps c) and d) are additionally repeated at least once.
[73] The production method according to any of [70] to [72], wherein the ion concentration is a calcium ion concentration.
[74] The production method according to [73], wherein an antigen-binding molecule having lower antigen-binding activity under a low-calcium concentration condition than that under a high-calcium concentration condition is selected.
[75] The production method according to [74], wherein the low-calcium concentration condition is 0.1 μM to 30 μM.
[76] The production method according to [74] or [75], wherein the high-calcium concentration condition is 100 μM to 10 mM.
[77] The production method according to any of [70] to [72], wherein the ion concentration conditions are pH conditions.
[78] The production method according to [77], wherein an antigen-binding molecule having lower antigen-binding activity in an acidic pH condition than that in a neutral pH condition is selected.
[79] The production method according to [78], wherein the acidic pH condition is pH 4.0 to 6.5.
[80] The production method according to [78] or [79], wherein the neutral pH condition is pH 6.7 to 10.0.
[81] An antigen-binding molecule produced by a production method according to any of [70] to [80].
[82] A pharmaceutical composition comprising an antigen-binding molecule according to [81] or a modified form thereof.

BRIEF DESCRIPTION OF DRAWINGS

FIG. 4A is a diagram showing the pattern of the interaction between a pH-dependent binding antibody and its antigen in plasma (pH 7.4) and in endosome (pH 6.0).

FIG. 4B is a diagram showing the pattern of the interaction between a calcium-dependent binding antibody and its antigen in plasma (2 mM Ca2+) and in endosome (3 μM Ca2+).

FIG. 4C is a diagram showing the pattern of the interaction between a pH- and calcium-dependent binding antibody and its antigen in plasma (2 mM Ca') and in endosome (3 µM $Ca^{2+}$).

FIG. 7 shows the ion-exchange chromatograms of an antibody comprising a LfVk1_Ca sequence (heavy chain: GC_H (SEQ ID NO: 48) and light chain: LfVk1_Ca (SEQ ID NO: 43)) and an antibody comprising a LfVk1_Ca6 sequence (heavy chain: GC_H (SEQ ID NO: 48) and light chain: LfVk1_Ca6 (SEQ ID NO: 49)) modified from the LfVk1_Ca sequence by the replacement of an Asp (D) residue at position 30 (defined by the Kabat numbering) with a Ser (S) residue after storage at 5° C. (solid line) or after storage at 50° C. (dotted line). The highest peak in each ion-exchange chromatogram after storage at 5° C. is defined as a main peak. In the diagram, the y-axis was normalized with the main peak.

FIG. 11 shows the structure of heavy chain CDR3 in the Fab fragment of a 6RL #9 antibody determined by X-ray crystal structure analysis. FIG. 11(*i*) is a diagram showing heavy chain CDR3 with a crystal structure obtained under crystallization conditions in the presence of calcium ions. FIG. 11(*ii*) is a diagram showing heavy chain CDR3 with a crystal structure obtained under crystallization conditions in the absence of calcium ions.

FIG. 13 shows a diagram depicting the interaction between an anti-human glypican 3 antibody and recombinant human glypican 3 at 1.2 mM $Ca^{2+}$ and at 3 µM $Ca^{2+}$ using ELISA.

DESCRIPTION OF EMBODIMENTS

Figure 1:
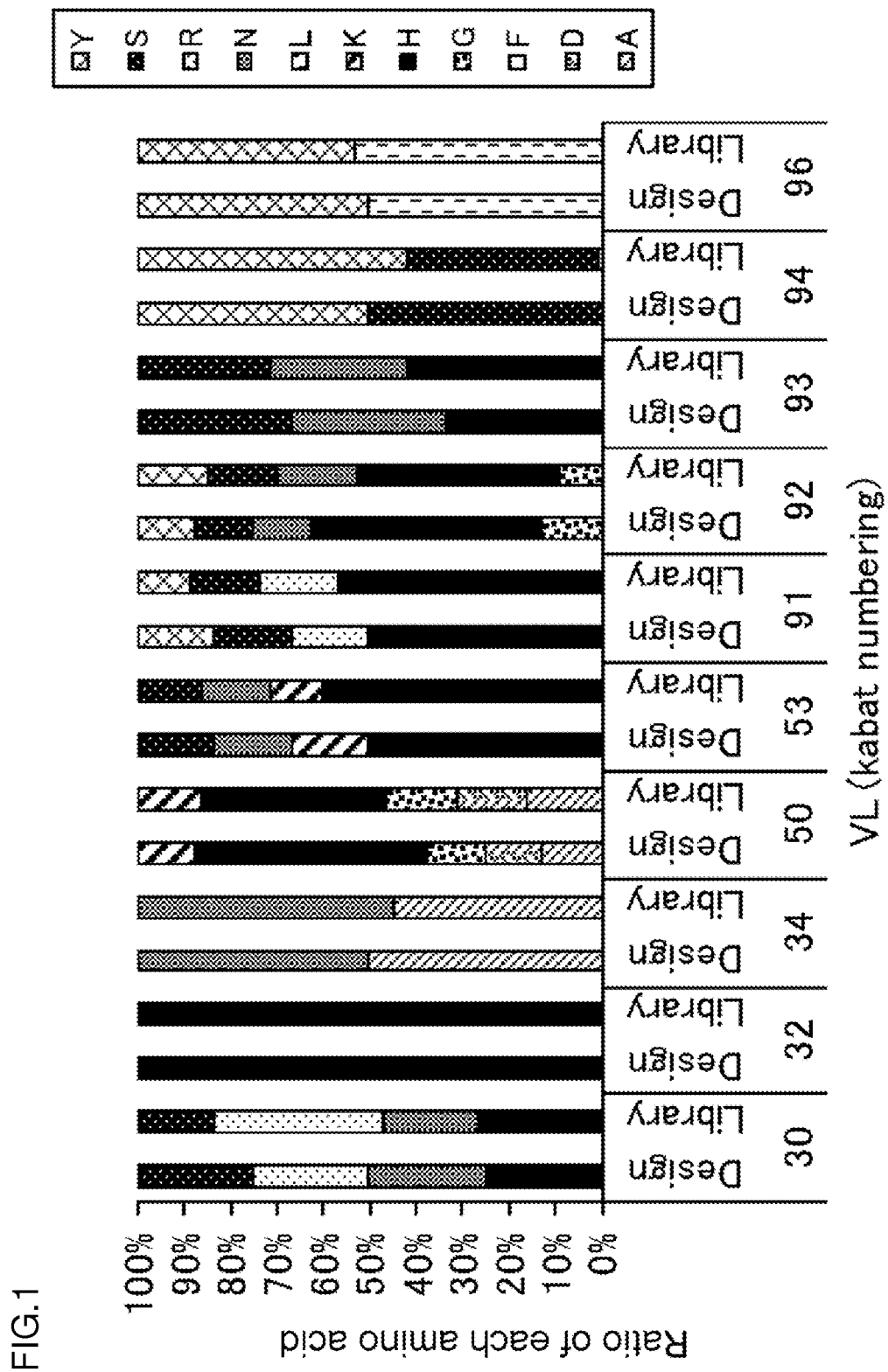
FIG. 1 is a graph showing the relationship between the amino acid distribution (indicated by Library) of sequence information about 132 clones isolated from *E. coli* transformed with a gene library of antibodies binding to antigens in a pH-dependent manner and a designed amino acid distribution (indicated by Design). The abscissa represents an amino acid position defined by the Kabat numbering. The ordinate represents the ratio of each amino acid in the distribution.

The disclosure of the present invention provides a library consisting essentially of a plurality of antigen-binding molecules differing in sequence from each other, wherein the antigen-binding activity of each antigen-binding molecule is changed depending on conditions of ion concentration or the like. The disclosure of the present invention also provides a novel systemic method for producing a library consisting essentially of a plurality of antigen-binding molecules differing in sequence from each other, wherein the antigen-binding activity of each antigen-binding molecule is changed depending on conditions of metal ion concentration and/or hydrogen ion concentration. Such a library can be used as a combinatorial library that helps select and/or screen for a synthetic antigen-binding molecule clone with desirable activity, for example, binding affinity and avidity, appropriate for, for example, conditions of metal ion concentration and/or hydrogen ion concentration.

These libraries are useful for identifying the polypeptide sequence of an antigen-binding molecule that can interact with any of target antigens of various types. For example, a library comprising the polypeptides of diversified antigen-binding molecules of the present invention expressed by phage display is particularly useful for selecting and/or screening for the antigen-binding molecule of interest. The present invention also provides an efficient high-throughput automatic system therefor. The method of the present invention can provide an antigen-binding molecule binding to a target antigen in a condition-dependent manner. The present invention further provides a pharmaceutical composition comprising the antigen-binding molecule as an active ingredient.

Definition

Amino acid: Each amino acid is indicated herein by single-letter code or three-letter code, or both, as represented by, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, and Val/V.

EU numbering and Kabat numbering: According to a method used in the present invention, amino acid positions assigned to antibody CDRs and FRs are defined according to the Kabat method (Sequences of Proteins of Immunological Interest, National Institute of Health, Bethesda, Md., 1987 and 1991). When the antigen-binding molecule described herein is an antibody or an antigen-binding fragment, amino acids in variable regions are indicated according to the Kabat numbering and amino acids in constant regions are indicated according to the EU numbering conforming to the Kabat amino acid positions.

Amino acid modification: Amino acids in the amino acid sequences of antigen-binding molecules can be modified by an appropriately adopted method known in the art such as site-directed mutagenesis (Kunkel et al., Proc. Natl. Acad. Sci. USA (1985) 82, 488-492) or overlap extension PCR. Also, the amino acids can be substituted by non-natural amino acids by use of a plurality of modification methods known in the art (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express, an R & D oriented company)) comprising a non-natural amino acid bound with an amber suppressor tRNA complementary to UAG codon (amber codon), which is a stop codon, is also preferably used. Also, expression in which the single-letter codes of amino acids before and after modification are used previous and next to a number representing a particular position may be appropriately used for representing amino acid modification. For example, a P238D modification used for adding an amino acid substitution to an Fc region contained in an antibody constant region represents the substitution of Pro at position 238 defined by the EU numbering by Asp. Specifically, the number represents an amino acid position defined by the EU numbering; the single-letter code of the amino acid previous to the number represents the amino acid before the substitution; and the single-letter code of the amino acid next to the number represents the amino acid after the substitution.

And/or: The term "and/or" described herein is meant to include every combination appropriately represented by "and" and "or". Specifically, for example, the phrase "amino acids 33, 55, and/or 96 are substituted" includes the following variations of amino acid modification:
(a) position 33, (b) position 55, (c) position 96, (d) positions 33 and 55, (e) positions 33 and 96, (f) positions 55 and 96, and (g) positions 33, 55, and 96.

Antigen-binding molecule: The term "antigen-binding molecule" described herein is used to mean a molecule comprising an antigen-binding domain in the broadest sense and specifically includes various molecular forms as long as these forms exhibit antigen-binding activity. Examples of a molecule comprising an antigen-binding domain bound with an FcRn-binding domain include antibodies. The antibodies can include single monoclonal antibodies (including agonistic and antagonistic antibodies), human antibodies, humanized antibodies, chimeric antibodies, and the like. Alternatively, a fragment of such an antibody may be used. Preferred examples of the fragment can include antigen-binding domains and antigen-binding fragments (e.g., Fab, F(ab')2, scFv, and Fv). The antigen-binding molecule of the present invention can also include scaffold molecules contained in a library for construction of antigen-binding domains comprising only partial structures of existing stable conformations (e.g., α/β barrel protein structure) used as scaffolds.

The "antigen-binding domain" described herein can be a domain having any structure as long as the domain used binds to the antigen of interest. Preferred examples of such a domain include variable regions of antibody heavy and light chains, an in-vivo membrane protein-derived module called A domain of approximately 35 amino acids contained in avimer (WO2004044011 and WO2005040229), Adnectin comprising a 10Fn3 domain as a protein-binding domain derived from a glycoprotein fibronectin expressed on cell membranes (WO2002032925), Affibody comprising an IgG-binding domain scaffold constituting a three-helix bundle composed of 58 amino acids of protein A (WO1995001937), DARPins (designed ankyrin repeat proteins) which are molecular surface-exposed regions of ankyrin repeats (AR) each having a 33-amino acid residue structure folded into a subunit of a turn, two antiparallel helices, and a loop (WO2002020565), anticalin having four loop regions connecting eight antiparallel strands bent toward the central axis in one end of a barrel structure highly conserved in lipocalin molecules such as neutrophil gelatinase-associated lipocalin (NGAL) (WO2003029462), and a depressed region in the internal parallel sheet structure of a horseshoe-shaped fold composed of repeated leucine-rich-repeat (LRR) modules of an immunoglobulin structure-free variable lymphocyte receptor (VLR) as seen in the acquired immune systems of jawless vertebrates such as lamprey or hagfish (WO2008016854). Preferred examples of the antigen-binding domain of the present invention include antigen-binding domains comprising variable regions of antibody heavy and light chains.

The term "antibody" described herein refers to a natural immunoglobulin or an immunoglobulin produced by partial or complete synthesis. The antibody may be isolated from natural resources (e.g., plasma or serum) where the antibody naturally occurs or from the culture supernatant of antibody-producing hybridoma cells. Alternatively, the antibody may be synthesized partially or completely by use of an approach such as gene recombination. Preferred examples of the antibody include immunoglobulin isotypes and subclasses of these isotypes. Human immunoglobulins are known to have 9 classes (isotypes): IgG1, IgG2, IgG3, IgG4, IgA1, IgA2, IgD, IgE, and IgM. The antibody of the present invention can include IgG1, IgG2, IgG3, and IgG4 of these isotypes. Sequences of proteins of immunological interest, NIH Publication No. 91-3242 describes a plurality of allotype sequences attributed to polymorphism as human IgG1, human IgG2, human IgG3, and human IgG4 constant regions, any of which may be used in the present invention. Particularly, human IgG1 may have a sequence with DEL or EEM as the amino acid sequence of positions 356 to 358 defined by the EU numbering. Sequences of proteins of immunological interest, NIH Publication No. 91-3242 describes a plurality of allotype sequences attributed to polymorphism as human IgK (kappa) and human IgL7 (lambda) constant regions, any of which may be used in the present invention. The antibody having desired binding activity is prepared by a method generally known to those skilled in the art.

The antibody can be obtained as a polyclonal or monoclonal antibody using means known in the art. A mammal-derived monoclonal antibody can be preferably prepared as the monoclonal antibody. The mammal-derived monoclonal antibody encompasses, for example, those produced by hybridomas and those produced by host cells transformed with expression vectors comprising antibody genes by a genetic engineering approach.

The monoclonal antibody-producing hybridomas can be prepared by use of a technique known in the art. Specifically, mammals are immunized with sensitizing antigens according to a usual immunization method. The obtained immunocytes are fused with parental cells known in the art by a usual cell fusion method. Next, these fused cells can be screened for monoclonal antibody-producing cells by a usual screening method to select hybridomas producing antibodies against the sensitizing antigens.

The mammals to be immunized with the sensitizing antigens are not limited to any particular animal and are preferably selected in consideration of compatibility with the parental cells for use in cell fusion. In general, rodents, for example, mice, rats, hamsters, or rabbits, or other mammals such as monkeys are preferably used.

These animals are immunized with the sensitizing antigens according to a method known in the art. For example, a general method can involve immunizing the mammals with the sensitizing antigens by administration through intraperitoneal or subcutaneous injection. Specifically, the sensitizing antigens diluted with PBS (phosphate-buffered saline), saline, or the like at an appropriate dilution ratio are mixed, if desired, with a usual adjuvant, for example, a Freund's complete adjuvant, and emulsified, and the resulting emulsion of the sensitizing antigens is then administered to the mammals several times at 4- to 21-day intervals. Also, an appropriate carrier may be used in the immunization with the sensitizing antigens. Particularly, in the case of using partial peptides having a small molecular weight as the sensitizing antigens, the sensitizing antigen peptides bound with carrier proteins such as albumin or keyhole limpet hemocyanin may be desirably used in the immunization.

The hybridomas producing antibodies against the desired polypeptide can also be prepared by DNA immunization as described below. The DNA immunization refers to an immunostimulation method which involves: immunizing animals by the administration of vector DNAs that have been constructed in a form capable of expressing antigenic protein-encoding genes in the immunized animals; and immunostimulating the animals by the in vivo expression of the sensitizing antigens. The DNA immunization can be expected to be superior in the following points to general immunization methods which involve immunizing animals by the administration of protein antigens:

when the antigen is membrane proteins, the DNA immunization can provide immunostimulation while the structures of membrane proteins are maintained; and
the DNA immunization eliminates the need of purifying immunizing antigens.

Mammalian myeloma cells are used in the cell fusion with the immunocytes. The myeloma cells preferably have an appropriate selection marker for screening. The selection marker refers to a character that can survive (or cannot survive) under particular culture conditions. For example, hypoxanthine-guanine phosphoribosyltransferase deficiency (hereinafter, abbreviated to HGPRT deficiency) or thymidine kinase deficiency (hereinafter, abbreviated to TK deficiency) is known in the art as the selection marker. Cells having the HGPRT or TK deficiency are sensitive to hypoxanthine-aminopterin-thymidine (hereinafter, abbreviated to HAT-sensitive). The HAT-sensitive cells are killed in a HAT selective medium because the cells fail to synthesize DNAs. By contrast, these cells, when fused with normal cells, become able to grow even in the HAT selective medium because the fused cells can continue DNA synthesis by use of the salvage pathway of the normal cells.

The cells having the HGPRT or TK deficiency can be selected in a medium containing 6-thioguanine or 8-azaguanine (hereinafter, abbreviated to 8AG), or 5'-bromodeoxyuridine, respectively. The normal cells are killed by incorporating these pyrimidine analogs into their DNAs. By contrast, the cells deficient in these enzymes can survive in the selective medium because the cells cannot incorporate the pyrimidine analogs therein. In addition, a selection marker called G418 resistance confers 2-deoxystreptamine antibiotic (gentamicin analog) resistance through a neomycin resistance gene. Various myeloma cells suitable for the cell fusion are known in the art.

For example, P3 (P3x63Ag8.653) (J. Immunol. (1979) 123 (4), 1548-1550), P3x63Ag8U.1 (Current Topics in Microbiology and Immunology (1978) 81, 1-7), NS-1 (C. Eur. J. Immunol. (1976) 6 (7), 511-519), MPC-11 (Cell (1976) 8 (3), 405-415), SP2/0 (Nature (1978) 276 (5685), 269-270), FO (J. Immunol. Methods (1980) 35 (1-2), 1-21), S194/5.XXO.BU.1 (J. Exp. Med. (1978) 148 (1), 313-323), or R210 (Nature (1979) 277 (5692), 131-133) can be preferably used as such myeloma cells.

Basically, the cell fusion of the immunocytes with the myeloma cells is performed according to a method known in the art, for example, the method of Kohler and Milstein et al. (Methods Enzymol. (1981) 73, 3-46).

More specifically, the cell fusion can be carried out, for example, in a usual nutrient culture medium in the presence of a cell fusion promoter. For example, polyethylene glycol (PEG) or hemagglutinating virus of Japan (HVJ) can be used as the fusion promoter. In addition, an auxiliary such as dimethyl sulfoxide is added thereto, if desired, and used for enhancing fusion efficiency.

The ratio between the immunocytes and the myeloma cells used can be arbitrarily set. For example, the amount of the immunocytes is preferably set to 1 to 10 times that of the myeloma cells. For example, an RPMI1640 or MEM medium suitable for the growth of the myeloma cell line or any other usual culture medium for use in this kind of cell culture can be used as the culture medium in the cell fusion and may be further supplemented with a solution supplemented with serum such as fetal calf serum (FCS).

For the cell fusion, the immunocytes and the myeloma cells are well mixed in the predetermined amounts in the culture medium, and a solution of PEG (e.g., having an average molecular weight on the order of 1000 to 6000) preheated to approximately 37° C. is usually added thereto at a concentration of 30 to 60% (w/v). The mixed solution is gently mixed to form the desired fusion cells (hybridomas) of interest. Subsequently, the appropriate culture medium exemplified above is sequentially added to the cell suspension, and its supernatant is removed by centrifugation. This procedure can be repeated to thereby remove the cell fusion agents or the like unfavorable for hybridoma growth.

The hybridomas thus obtained can be cultured for selection using a usual selective medium, for example, a HAT medium (culture medium containing hypoxanthine, aminopterin, and thymidine). The culture using the HAT medium can be continued for a time long enough (typically, for a few days to a few weeks) to kill cells (non-fused cells) other than the desired hybridomas. Subsequently, hybridomas producing the desired antibody are screened for and cloned as single clones by a usual limiting dilution method.

The hybridomas thus obtained can be selected by use of a selective medium appropriate for the selection marker carried by the myeloma cells used in the cell fusion. For example, the cells having the HGPRT or TK deficiency can be selected by culture in a HAT medium (culture medium containing hypoxanthine, aminopterin, and thymidine). Specifically, in the case of the HAT-sensitive myeloma cells used in the cell fusion, only cells successfully fused with normal cells are able to grow selectively in the HAT medium. The culture using the HAT medium is continued for a time long enough to kill cells (non-fused cells) other than the desired hybridomas. Specifically, the culture can generally be performed for a few days to a few weeks to select the desired hybridomas. Subsequently, hybridomas producing the desired antibody can be screened for and cloned as single clones by a usual limiting dilution method.

The screening of the desired antibody and the cloning as single clones thereof can be preferably carried out by a screening method based on antigen-antibody reaction known in the art. Such a monoclonal antibody can be screened for by, for example, FACS (fluorescence activated cell sorting). FACS refers to a system that can analyze cells contacted with fluorescent antibodies by means of laser light and measure fluorescence emitted by the individual cells to thereby assay the binding of the antibodies to the surface of the cells.

Alternatively, the antibody may be evaluated for its binding activity against immobilized antigens on the basis of the principles of ELISA. For example, antigens are immobilized on wells of an ELISA plate. The culture supernatant of the hybridomas is contacted with the antigens in the wells to detect an antigen-bound antibody. In the case of a mouse-derived monoclonal antibody, the antigen-bound antibody can be detected using an anti-mouse immunoglobulin antibody. These screening-selected hybridomas producing the desired antibody having antigen-binding ability can be cloned by a limiting dilution method or the like. The monoclonal antibody-producing hybridomas thus prepared can be subcloned in a usual culture medium. Also, the hybridomas can be stored over a long period in liquid nitrogen.

The hybridomas can be cultured according to a usual method. The desired monoclonal antibody can be obtained from the culture supernatant thereof. Alternatively, the hybridomas may be administered to mammals compatible therewith and grown, and the monoclonal antibody can be obtained from the ascitic fluids thereof. The former method is suitable for obtaining highly pure antibodies.

Antibodies encoded by antibody genes cloned from the antibody-producing cells such as hybridomas may also be preferably used. The cloned antibody genes are incorporated into appropriate vectors and transferred to hosts to express antibodies encoded by the genes. Methods for the antibody gene isolation, the introduction into vectors, and the transformation of host cells have already been established by, for example, Vandamme et al. (Eur. J. Biochem. (1990) 192 (3), 767-775). A method for producing recombinant antibodies is also known in the art, as mentioned below.

For example, cDNAs encoding the variable regions (V regions) of the antibody of interest are obtained from the hybridoma cells producing this antibody. For this purpose, usually, total RNAs are first extracted from the hybridomas. For example, the following methods can be used for mRNA extraction from the cells:

guanidine ultracentrifugation method (Biochemistry (1979) 18 (24), 5294-5299), and AGPC method (Anal. Biochem. (1987) 162 (1), 156-159).

The extracted mRNAs can be purified using mRNA Purification Kit (GE Healthcare Bio-Sciences Corp.) or the like. Alternatively, a kit for directly extracting total mRNAs from cells is also commercially available, such as QuickPrep mRNA Purification Kit (GE Healthcare Bio-Sciences Corp.). The mRNAs may be obtained from the hybridomas using such a kit. Antibody V region-encoding cDNAs can be synthesized from the obtained mRNAs using reverse transcriptase. The cDNAs can be synthesized using AMV Reverse Transcriptase First-strand cDNA Synthesis Kit (Seikagaku Corp.) or the like. Alternatively, SMART RACE cDNA amplification kit (Clontech Laboratories, Inc.) and 5'-RACE PCR (Proc. Natl. Acad. Sci. USA (1988) 85 (23), 8998-9002; and Nucleic Acids Res. (1989) 17 (8), 2919-2932) may be appropriately used for the cDNA synthesis and amplification. In the course of such cDNA synthesis, appropriate restriction sites described later can be further introduced into both ends of the cDNAs.

The cDNA fragments of interest are purified from the obtained PCR products and subsequently linked to vector DNAs. The recombinant vectors thus prepared are transferred to E. coli or the like, followed by colony selection. Then, the desired recombinant vector can be prepared from the E. coli that has formed the colony. Then, the presence or absence of the nucleotide sequence of the cDNA of interest in the recombinant vector is confirmed by a method known in the art, for example, a dideoxynucleotide chain termination method.

The variable region-encoding genes are conveniently obtained by the 5'-RACE method using primers for variable region gene amplification. First, cDNAs are synthesized with RNAs extracted from the hybridoma cells as a template to obtain a 5'-RACE cDNA library. A commercially available kit such as SMART RACE cDNA amplification kit is appropriately used in the synthesis of the 5'-RACE cDNA library.

Antibody genes are amplified by PCR using the obtained 5'-RACE cDNA library as a template. Primers for mouse antibody gene amplification can be designed on the basis of an antibody gene sequence known in the art. These primers have a nucleotide sequence that differs with respect to each immunoglobulin subclass. Thus, the subclass of the antibody of interest is desirably determined in advance using a commercially available kit such as Iso Strip mouse monoclonal antibody isotyping kit (Roche Diagnostics K.K.).

Specifically, primers capable of amplifying genes encoding γ1, γ2a, γ2b, and γ3 heavy chains and κ and λ light chains can be used, for example, for the purpose of obtaining mouse IgG-encoding genes. Primers annealing to portions corresponding to constant regions close to the variable regions are generally used as 3' primers for IgG variable region gene amplification. On the other hand, primers included in 5' RACE cDNA library preparation kit are used as 5' primers.

The PCR products thus amplified can be used to reshape immunoglobulins composed of heavy and light chains in combination. The reshaped immunoglobulins can be screened for the desired antibody with their antigen-binding activity as an index. For example, for the purpose of obtaining an antibody against an antigen, more preferably, the antibody specifically binds to the antigen. The antibody binding to the antigen can be screened for, for example, by the following steps:
(1) contacting antibodies comprising V regions encoded by the cDNAs obtained from the hybridomas, with antigens;
(2) detecting antigen-antibody binding; and
(3) selecting the antigen-binding antibody.

The antigen-antibody binding is detected by a method known in the art. Specifically, the antigen-antibody binding can be detected by the approach such as FACS or ELISA described above.

After obtainment of each cDNA encoding the antibody V region of interest, the cDNA is digested with restriction enzymes that recognize the restriction sites inserted in both ends of the cDNA. Preferably, the restriction enzymes recognize and digest a nucleotide sequence that appears at low frequency in nucleotide sequences constituting antibody genes. Further preferably, the restriction enzymes cleave the sites inserted therein to produce cohesive ends, in order to insert one copy of the digested fragment in the correct direction in a vector. The antibody V region-encoding cDNAs thus digested can be inserted to appropriate expression vectors to obtain antibody expression vectors. In this case, antibody constant region (C region)-encoding genes are fused in frame with the V region-encoding genes to obtain chimeric antibodies. In this context, the chimeric antibodies refer to antibodies comprising constant and variable regions of different origins. Thus, heterogeneous (e.g., mouse-human) chimeric antibodies as well as human-human homogeneous chimeric antibodies are also encompassed by the chimeric antibody according to the present invention. The V region genes may be inserted to expression vectors preliminarily having constant region genes to construct chimeric antibody expression vectors. Specifically, for example, recognition sequences for restriction enzymes that digest the V region genes can be appropriately located on the 5' side of expression vectors carrying the DNAs encoding the constant regions (C regions) of the desired antibody. The resulting expression vectors and the V region genes digested with the same combination of the restriction enzymes are fused in frame with each other to construct chimeric antibody expression vectors.

In order to produce the desired antibody, the antibody gene can be incorporated into expression vectors such that the gene is operably linked to control sequences. The control sequences for antibody expression encompass, for example, enhancers and promoters. Also, an appropriate signal sequence for extracellular secretion of the expressed antibody may be added to the amino terminus thereof. For example, a peptide having an amino acid sequence MGWSCIILFLVATATGVHS (SEQ ID NO: 13) can be used as the signal sequence. Any other suitable signal sequence may be added thereto. The expressed polypeptide is cleaved at the carboxyl end of the signal sequence, and the cleaved polypeptide can be extracellularly secreted as a mature polypeptide. Appropriate host cells can be transformed with these expression vectors to obtain recombinant cells expressing the DNA encoding the desired antibody.

For the antibody gene expression, the heavy chain (H chain)-encoding DNA and the light chain (L chain)-encoding DNA of the antibody are separately incorporated in different expression vectors. The same host cell can be co-transfected with the heavy chain-incorporated vector and the light chain-incorporated vector and thereby allowed to express antibody molecules comprising the H and L chains. Alternatively, the heavy chain- and light chain-encoding DNAs may be incorporated into a single expression vector, with which a host cell can then be transformed (see WO1994011523).

Many combinations of host cells and expression vectors are known in the art for antibody preparation by the transfer of the isolated antibody genes into appropriate hosts. All of these expression systems can be applied to the isolation of the antigen-binding molecule of the present invention. In the case of using eukaryotic cells as the host cells, animal, plant, or fungus cells can be appropriately used. Specifically, examples of the animal cells can include the following cells:
(1) mammalian cells such as CHO (Chinese hamster ovary cell line), COS (monkey kidney cell line), myeloma cells (Sp2/O, NS0, etc.), BHK (baby hamster kidney cell line), HEK293 (human embryonic kidney cell line with sheared adenovirus (Ad)5 DNA), PER.C6 cells (human embryonic retinal cell line transformed with the adenovirus type 5 (Ad5) E1A and E1B genes), Hela, and Vero (Current Protocols in Protein Science, May, 2001, Unit 5.9, Table 5.9.1);
(2) amphibian cells such as *Xenopus* oocytes; and
(3) insect cells such as sf9, sf21, and Tn5.

Alternatively, antibody gene expression systems using cells derived from the genus *Nicotiana* (e.g., *Nicotiana tabacum*) as the plant cells are known in the art. Cultured callus cells can be appropriately used for the plant cell transformation.

The following cells can be used as the fungus cells:
cells derived from yeasts of the genus *Saccharomyces* (e.g., *Saccharomyces cerevisiae*) and the genus *Pichia* (e.g., *Pichia pastoris*), and
cells derived from filamentous fungi of the genus *Aspergillus* (e.g., *Aspergillus niger*).

Also, antibody gene expression systems using prokaryotic cells are known in the art. In the case of using, for example, bacterial cells, cells of bacteria such as *E. coli* and *Bacillus subtilis* can be appropriately used. The expression vectors comprising the antibody gene of interest are transferred into these cells by transformation. The transformed cells are cultured in vitro, and the desired antibody can be obtained from the resulting cultures of the transformed cells.

In addition to the host cells, transgenic animals may be used for the recombinant antibody production. Specifically, the desired antibody can be obtained from animals transfected with the gene encoding this antibody. For example, the antibody genes can be inserted in frame into genes encoding proteins specifically produced in milk to construct fusion genes. For example, goat β casein can be used as the proteins secreted into milk. DNA fragments comprising the fusion genes having the antibody gene insert are injected into goat embryos, which are in turn introduced into female goats. From milk produced by transgenic goats (or progeny thereof) brought forth by the goats that have received the embryos, the desired antibody can be obtained as a fusion protein with the milk protein. In addition, hormone can be administered to the transgenic goats in order to increase the amount of milk containing the desired antibody produced from the transgenic goats (Bio/Technology (1994), 12 (7), 699-702).

In the case of administering the antigen-binding molecule described herein to humans, an antigen-binding domain derived from a genetically recombinant antibody that has been engineered artificially can be appropriately adopted as an antigen-binding domain for the molecule, for example, for the purpose of reducing heteroantigenicity in humans. The genetically recombinant antibody encompasses, for example, humanized antibodies. These engineered antibodies are appropriately produced using a method known in the art.

Each antibody variable region used for preparing the antigen-binding domain in the antigen-binding molecule described herein is typically composed of three complementarity-determining regions (CDRs) flanked by four framework regions (FRs). The CDRs are regions that substantially determine the binding specificity of the antibody. The CDRs have diverse amino acid sequences. On the other hand, the FRs are mostly constituted by amino acid sequences that are highly identical even among antibodies differing in binding specificity. Therefore, in general, the binding specificity of a certain antibody can be transplanted to other antibodies through CDR grafting.

The humanized antibodies are also called reshaped human antibodies. Specifically, for example, a humanized antibody consisting of a non-human animal (e.g., mouse) antibody CDR-grafted human antibody is known in the art. General gene recombination approaches are also known for obtaining the humanized antibodies. Specifically, for example, overlap extension PCR is known in the art as a method for grafting mouse antibody CDRs to human FRs. In the overlap extension PCR, a nucleotide sequence encoding each mouse antibody CDR to be grafted is added to primers for human antibody FR synthesis. The primers are prepared with respect to each of the four FRs. For grafting the mouse CDRs to the human FRs, it is generally regarded as advantageous to select human FRs highly identical to mouse FRs, in order to maintain the CDR functions. Specifically, in general, human FRs comprising amino acid sequences highly identical to those of FRs adjacent to the mouse CDRs to be grafted are preferably used.

The nucleotide sequences to be linked are designed so that the sequences are connected in frame with each other. The human FR-encoding nucleotide sequences are individually synthesized using their respective primers. The resulting products contain the mouse CDR-encoding DNA added to each human FR-encoding sequence. The mouse CDR-encoding nucleotide sequences are designed so that the nucleotide sequence in each product overlaps with another. Subsequently, the overlapping CDR portions in the products synthesized with human antibody genes as templates are annealed to each other for complementary strand synthesis reaction. Through this reaction, the human FR sequences are linked via the mouse CDR sequences.

Finally, the full-length sequence of the gene of the V region comprising three CDRs and four FRs linked is amplified using primers that each anneal to the 5' and 3' ends thereof and have an added recognition sequence for an appropriate restriction enzyme. The DNA thus obtained and a human antibody C region-encoding DNA can be inserted into expression vectors such that these DNAs are fused in frame to prepare vectors for humanized antibody expression. These vectors having the inserts are transferred to hosts to establish recombinant cells. Then, the recombinant cells are cultured for the expression of the humanized antibody-encoding DNA to produce the humanized antibodies into the cultures of the cultured cells (EP239400 and WO1996002576).

The humanized antibodies thus prepared can be evaluated for their antigen-binding activity by qualitative or quantitative assay to thereby select suitable human antibody FRs that allow CDRs to form a favorable antigen-binding site when linked via the CDRs. If necessary, FR amino acid residue(s) may be substituted such that the CDRs of the resulting reshaped human antibody form an appropriate antigen-binding site. For example, the amino acid sequence of FR can be mutated by the application of the PCR method used in the mouse CDR grafting to the human FRs. Specifically, a mutation of a partial nucleotide sequence can be introduced to the primers annealing to a FR nucleotide sequence. The FR nucleotide sequence synthesized using such primers contains the mutation thus introduced. Such variant antibodies having the substituted amino acid(s) can be evaluated for their antigen-binding activity by the same assay as above to thereby select variant FR sequences having the desired properties (Sato et al., Cancer Res (1993) 53, 851-856).

Alternatively, the desired human antibody can be obtained by DNA immunization using transgenic animals having all repertoires of human antibody genes (see WO1993012227, WO1992003918, WO1994002602, WO1994025585, WO1996034096, and WO1996033735) as immunized animals.

In addition, a technique of obtaining human antibodies by panning using human antibody libraries is also known. For example, human antibody V regions are expressed as a single-chain antibody (scFv) on the surface of phages by a phage display method. A phage expressing antigen-binding scFv can be selected. The gene of the selected phage can be analyzed to determine DNA sequences encoding the V regions of the antigen-binding human antibody. After the determination of the DNA sequence of the antigen-binding scFv, the V region sequences can be fused in frame with the sequences of the desired human antibody C regions and then inserted to appropriate expression vectors to prepare expression vectors. The expression vectors are transferred to the preferred expression cells as exemplified above. The human antibody-encoding genes are expressed by the cells to obtain the human antibodies. These methods are already known in the art (see WO1992001047, WO19992020791, WO1993006213, WO1993011236, WO1993019172, WO1995001438, and WO1995015388).

The "antigen-binding domain" described herein refers to a region that specifically binds to a portion or the whole of an antigen with complementarity. Examples of the antigen-binding domain can include domains having an antigen-binding domain of an antibody. Examples of the antigen-binding domain of an antibody can include CDRs and variable regions. In the case of using CDR(s) as the antigen-binding domain of an antibody, the antigen-binding domain may comprise all of 6 CDRs contained in the antibody or may comprise one or two or more of the CDRs. Each CDR contained as the binding region of an antibody may have, for example, amino acid deletion, substitution, addition, and/or insertion, or a portion of the CDR may be used, as long as the CDR contained has antigen-binding activity. The antibody directed against an antigen having a large molecular weight can bind only to a particular site in the antigen. The particular site is called epitope. The antigen-binding domain can be provided by one or more antibody variable domains. Preferably, the antigen-binding domain comprises an antibody light chain variable region (VL) and an antibody heavy chain variable region (VH). Preferred examples of such an antigen-binding domain include "scFv (single-chain Fv)", "single-chain antibody", "Fv", "scFv2 (single chain Fv2)", "Fab", "diabody", "linear antibody", and "F(ab')2".

The "antibody variable region" as used herein refers to a region that is contained in each of light and heavy chains of an antibody molecule and comprises the amino acid sequences of complementarity-determining regions (CDRs; i.e., CDR1, CDR2, and CDR3) and framework regions (FRs). VH represents a heavy chain variable region. VL represents a light chain variable region. According to a method used in the present invention, amino acid positions assigned to CDRs and FRs are defined according to the Kabat method (Sequences of Proteins of Immunological Interest, National Institute of Health, Bethesda, Md., 1987 and 1991). In the present specification, amino acids in an antibody or an antigen-binding fragment are also numbered according to the Kabat numbering conforming to the Kabat amino acid positions.

The term "complementarity-determining regions (CDRs; i.e., CDR1, CDR2, and CDR3)" as used herein refers to amino acid residues of the antibody variable region required to exist for antigen binding. Each variable region comprises three CDR regions generally indicated by CDR1, CDR2, and CDR3. Each complementarity-determining region may comprise amino acid residues from a "complementarity-determining region" as described by Kabat (i.e., residues 24 to 34 (CDR1), 50 to 56 (CDR2), and 89 to 97 (CDR3) in the light chain variable region and residues 31 to 35 (CDR1), 50 to 65 (CDR2), and 95 to 102 (CDR3) in the heavy chain variable region; Kabat et al., Sequences of Proteins of Immunological Interest, 5th edition, Public Health Service, National Institute of Health, Bethesda, Md. (1991)) and/or residues from a "hypervariable loop" (i.e., residues 26 to 32 (CDR1), 50 to 52 (CDR2), and 91 to 96 (CDR3) in the light chain variable region and residues 26 to 32 (CDR1), 53 to 55 (CDR2), and 96 to 101 (CDR3) in the heavy chain variable region; Chothia and Lesk, J. Mol. Biol. (1987) 196, 901-917). In some case, each complementarity-determining region may comprise amino acids from both of the CDR region and the hypervariable loop defined by the Kabat method.

The term "Fab" fragment comprises variable and constant regions of a light chain and a variable region and the first constant region (CH1) of a heavy chain. The F(ab')2 antibody fragment comprises a pair of Fab fragments typically linked covalently at sites close to their carboxy termini by cysteine in a hinge region therebetween. Other chemical bonds for antibody fragments are also known in the art to which the present invention belongs.

The term "single-chain Fv" or "scFv" antibody fragment comprises antibody VH and VL regions, which in turn constitute a single polypeptide chain. Usually, the Fv polypeptide further comprises a polypeptide linker between the VH and VL regions. This linker permits formation of a structure desirable for the antigen binding of scFv. The scFv is reviewed in, for example, Pluckthun, The Pharmacology of Monoclonal Antibodies (1994) Vol. 113, 269-315 (Rosenburg and Moore ed., Springer-Verlag, New York).

The term "diabody" refers to a small antibody fragment having two antigen-binding sites. This antibody fragment comprises a heavy chain variable region (VH) linked to a light chain variable region (VL) in one polypeptide chain (VH and VL). A linker that is too short to pair these two regions on the same polypeptide chain is used to forcedly pair these regions with their complementary regions on another polypeptide chain so that two antigen-binding sites are formed. The diabody is described in detail in, for example, patent literatures such as European Patent No. 404097 and WO1993011161 and non patent literatures such as Holliger et al., Proc. Natl. Acad. Sci. USA (1993) 90, 6444-6448.

The term "linear antibody" refers to an antibody described in Zapata et al., Protein Eng. (1995) 8 (10), 1057-1062. In short, this antibody comprises a pair of tandem Fd segments (VH-CH1-VH-CH1) that form a pair of antigen-binding domains with a complementary light chain polypeptide. The linear antibody may be bispecific or monospecific.

Antigen

The "antigen" described herein is not limited by a particular structure as long as the antigen comprises an epitope to which the antigen-binding domain binds. In another sense, the antigen may be inorganic matter or may be organic matter. Examples of the antigen can include the following molecules: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic factor, av/b3 integrin, Ax1, b2M, B7-1, B7-2, B7-H, B-lymphocyte stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), cancer-associated antigens, cathepsin A, cathepsin B, cathepsin C/DPPI, cathepsin D, cathepsin E, cathepsin H, cathepsin L, cathepsin O, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, botulinum toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigens, DAN, DCC, DcR3, DC-SIGN, decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast-activating protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle-stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP- 12, CDMP-3), GDF-8 (myostatin), GDF-9, GDF-15 (MIC-1), GDNF, GDNF, GFAP, GFRa-1, GFR-alpha 1, GFR-alpha 2, GFR-alpha 3, GITR, glucagon, Glut4, glycoprotein (GPIIb/IIIa), GM-CSF, gp130, gp72, GRO, growth hormone-releasing factor, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high-molecular-weight melanoma-associated antigen (HMW-MAA), HIV gp120, HIV IIIB gp120 V3 loop, HLA, HLA-DR, HM1.24, HMFG PEM, HRG, Hrk, human heart myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF-binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin chain A, insulin chain B, insulin-like growth factor 1, integrin alpha 2, integrin alpha 3, integrin alpha 4, integrin alpha 4/beta 1, integrin alpha 4/beta 7, integrin alpha 5 (alpha V), integrin alpha 5/beta 1, integrin alpha 5/beta 3, integrin alpha 6, integrin beta 1, integrin beta 2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y-related antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, metalloproteases, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), PlGF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, rheumatoid factor, RLIP76, RPA2, RSK, 5100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T cell receptor (e.g., T cell receptor alpha/beta), TdT, TECK, TEM1, TEMS, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta 1, TGF-beta 2, TGF-beta 3, TGF-beta 4, TGF-beta 5, thrombin, thymus Ck-1, thyroid stimulating hormone, Tie, TIMP, TIQ, tissue factor, TMEFF2, Tmpo, TMPRSS2, TNF, TNF-alpha, TNF-alpha/beta, TNF-beta 2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCER), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TSG, TSLP, tumor-associated antigen CA125, tumor-associated antigen-expressing Lewis-Y-related carbohydrate, TWEAK, TXB2, Ung, uPAR, uPAR-1, urokinase, VCAM, VCAM-1, VECAD, VE-cadherin, VE-cadherin-2, VEFGR-1 (flt-1), VEGF, VEGFR, VEGFR-3 (flt-4), VEGI, VIM, viral antigens, VLA, VLA-1, VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, Aβ, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, chromogranin A, chromogranin B, tau, VAP1, high-molecular-weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, syndecan-1, syndecan-2, syndecan-3, syndecan-4, LPA, S1P, acetylcholine receptor, AdipoR1, AdipoR2, ADP ribosyl cyclase-1, alpha-4/beta-7 integrin, alpha-5/beta-1 integrin, alpha-v/beta-6 integrin, alpha-v/beta-1 integrin, angiopoietin ligand-2, Angpt12, Anthrax, cadherin, carbonic anhydrase-IX, CD105, CD155, CD158a, CD37, CD49b, CD51, CD70, CD72, Claudin 18, *Clostridium difficile* toxin, CS1, delta-like protein ligand 4, DHICA oxidase, Dickkopf-1 ligand, dipeptidyl peptidase IV, EPOR, F protein of RSV, factor Ia, FasL, folate receptor alpha, glucagon receptor, glucagon-like peptide 1 receptor, glutamate carboxypeptidase II, GMCSFR, hepatitis C virus E2 glycoprotein, hepcidin, IL-17 receptor, IL-22 receptor, IL-23 receptor, IL-3 receptor, Kit tyrosine kinase, leucine rich alpha-2-glycoprotein 1 (LRG1), lysosphingolipid receptor, membrane glycoprotein OX2, mesothelin, MET, MICA, MUC-16, myelin associated glycoprotein, neuropilin-1, neuropilin-2, Nogo receptor, PLXNA1, PLXNA2, PLXNA3, PLXNA4A, PLXNA4B, PLXNB1, PLXNB2, PLXNB3, PLXNC1, PLXND1, programmed cell death ligand 1, proprotein convertase PC9, P-selectin glycoprotein ligand-1, RAGE, reticulon 4, RF, RON-8, SEMA3A, SEMA3B, SEMA3C, SEMA3D, SEMA3E, SEMA3F, SEMA3G, SEMA4A, SEMA4B, SEMA4C, SEMA4D, SEMA4F, SEMA4G, SEMA5A, SEMA5B, SEMA6A, SEMA6B, SEMA6C, SEMA6D, SEMA7A, Shiga like toxin II, sphingosine-1-phosphate receptor-1, ST2, Staphylococcal lipoteichoic acid, tenascin, TG2, thymic stromal lymphopoietin receptor, TNF superfamily receptor 12A, transmembrane glycoprotein NMB, TREM-1, TREM-2, trophoblast glycoprotein, TSH receptor, TTR, tubulin, ULBP2, and receptors for hormones or growth factors. Other examples of the antigen can include soluble molecules of the receptors described above that reside without being anchored on cells in body fluids in vivo.

The epitope, which means an antigenic determinant, contained in the antigen means a site on the antigen to which the antigen-binding domain in the antigen-binding molecule disclosed herein binds. Accordingly, for example, the epitope can be defined by its structure. Alternatively, the epitope may be defined by the antigen-binding activity of the antigen-binding molecule that recognizes the epitope. The epitope in an antigenic peptide or polypeptide may be determined by amino acid residues constituting the epitope. Alternatively, the epitope composed of a sugar chain may be determined by a particular sugar chain structure.

A linear epitope refers to an epitope comprising an epitope that is recognized via its primary sequence of amino acids. The linear epitope comprises typically at least 3 and most commonly at least 5, for example, approximately 8 to approximately 10 or 6 to 20 amino acids, in a unique sequence.

In contrast to the linear epitope, a conformational epitope refers to an epitope that is contained in a primary sequence of amino acids comprising a component other than the single defined component of the epitope to be recognized (e.g., an epitope whose primary sequence of amino acids may not be recognized by an antibody that determines the epitope). The conformational epitope may contain an increased number of amino acids, compared with the linear epitope. An antibody recognizes the conformational epitope by recognizing the three-dimensional structure of the antigenic peptide or protein. For example, the protein molecule may be folded to form a three-dimensional structure. In such a case, certain amino acids and/or polypeptide backbone constituting the conformational epitope are arranged in parallel to allow the antibody to recognize the epitope. The conformation of the epitope is determined by a method including, for example, but not limited to, X-ray crystallography, two-dimensional nuclear magnetic resonance spectroscopy, and site-specific spin labeling and electron paramagnetic resonance spectroscopy. See, for example, Epitope Mapping Protocols in Methods in Molecular Biology (1996), Vol. 66, Morris ed. Gene recombination approach The term "codon set" refers to a set of different nucleotide triplet sequences that are used for encoding a desired amino acid. One set of oligonucleotides includes sequences that represent every possible combination of nucleotide triplets provided by the codon set and encode a desired amino acid group. Such a set of oligonucleotides can be synthesized by, for example, a solid-phase method. The standard system of codon designation is provided by the IUB code. This code is known in the art. The codon set is generally indicated by three capitals, for example, NNK, NNS, DVK, or DVD.

IUB Code
G: guanine
A: adenine
T: thymine
C: cytosine
R (A or G)
Y (C or T)
M (A or C)
K (G or T)
S (C or G)
W (A or T)
H (A, C, or T)
B (C, G, or T)
V (A, C, or G)
D (A, G, or T)
N (A, C, G, or T)

For example, in a codon set DVK, D represents a nucleotide A, G, or T; V represents A, G, or C; and K represents G or T. This codon set represents 18 different codons and can encode amino acids Ala, Trp, Tyr, Lys, Thr, Asn, Lys, Ser, Arg, Asp, Glu, Gly, and Cys.

An oligonucleotide having a "degenerate" nucleotide at a particular position is designed by a method known in the art to which the present invention belongs (e.g., Garrard and Henner, Gene (1993) 128, 103-109). A set of oligonucleotides having such a certain kind of codon set can be synthesized using a commercially available nucleic acid synthesizer (available from, for example, Applied Biosystems, Inc., Foster City, Calif.), or can be obtained as commercially available products (e.g., Life Technologies, Rockville, Md.). Thus, a synthetic oligonucleotide set having a particular codon set generally comprises a plurality of oligonucleotides differing in sequence. In a non-limiting aspect of the present invention, the oligonucleotides may comprise, for example, restriction enzymes sites useful in cloning.

The terms "cell", "cell system", and "cell culture" are synonymously used herein. Such designations can include every progeny of cells or cell systems. Thus, for example, the terms "transformant" and "transformed cell" include primary target cells and cultures derived therefrom, regardless of passage number. It should also be understood that every progeny may not have accurately identical DNA contents, due to deliberate or inadvertent mutation. These terms may include the progeny of a variant having substantially the same functions or biological activity as screened for in the originally transformed cells. If a distinct designation is intended, this will be apparent from the context.

The term "control sequence" used to mention the expression of a coding sequence refers to a DNA nucleotide sequence necessary for the expression of an operably linked coding sequence in a particular host organism. Control sequences suitable for, for example, prokaryotes include promoters, optional operator sequences, ribosomal binding sites, and, probably, other sequences that still remain to be well understood. Use of a promoter, a polyadenylation signal, and an enhancer is known in the art for the expression of the coding sequence in eukaryotic cells.

The phrase "operably linked" as to a nucleic acid means that the nucleic acid has a functional relationship with another nucleic acid sequence. For example, a presequence or secretory leader DNA is operably bound with a DNA of a polypeptide, when expressed as a precursor protein involved in the secretion of the polypeptide. A promoter or an enhancer, when influencing the transcription of a coding sequence, is operably linked to the sequence. Alternatively, a ribosomal binding site, when positioned to facilitate translation, is operably linked to the coding sequence. Usually, the phrase "operably linked" means that the sequence of bound DNAs is consecutive and that a secretory leader sequence, for example, is consecutively present within a reading frame. The enhancer, however, does not have to be consecutive. Such linkage is achieved by ligation at appropriate restriction sites. In the absence of such sites, a synthetic oligonucleotide adaptor or linker is used according to conventional practice. Alternatively, the linked nucleic acids may be prepared by the overlap extension PCR approach described above.

The "ligation" refers to a method for forming a phosphodiester bond between two nucleic acid fragments. For the ligation of two fragments, the ends of these fragments must be compatible with each other. In some cases, these ends have compatibility immediately after endonuclease digestion. The compatibility for the ligation, however, requires first blunt-ending a cohesive end generally formed by endonuclease digestion. For the blunt-ending, each DNA is treated with approximately 10 unites of a Klenow fragment of DNA polymerase I or T4 DNA polymerase at 15° C. for at least 15 minutes, in the presence of four deoxyribonucleotide triphosphates in an appropriate buffer solution. Next, the DNA is purified by phenol-chloroform extraction and ethanol precipitation or silica purification. The DNA fragments to be linked are added in equimolar amounts to a solution. This solution contains ATP and a ligase buffer as well as approximately 10 units of ligase (e.g., T4 DNA ligase) per 0.5 µg of DNA. In the case of linking a DNA to a vector, the vector is first linearized by the digestive action of appropriate restriction endonuclease. The linearized fragment is then treated with bacterial alkaline phosphatase or calf intestinal phosphatase to thereby prevent self-ligation of the fragment during the ligation step.

The term "coat protein" refers to a protein, at least a portion of which is present on the surface of a viral particle. From a functional standpoint, the coat protein is an arbitrary protein that binds to viral particles in the course of construction of viruses in host cells and maintains its bound state until viral infection of other host cells. The coat protein may be a major coat protein or may be a minor coat protein. The minor coat protein is usually a coat protein present in viral capsid at preferably at least approximately 5, more preferably at least approximately 7, further preferably at least approximately 10 or more protein copies per virion. The major coat protein can be present at tens, hundreds, or thousands of copies per virion. Examples of the major coat protein include filamentous phage p8 protein.

The term "detection limit" for a chemical object such as an inorganic body, an organic body, or an organism in particular assay refers to the minimum concentration of the object detected above a background level for the assay. For example, in phage ELISA, the "detection limit" for a particular phage displaying a particular antigen-binding fragment refers to the phage concentration at which the particular phage produces more ELISA signals than those produced by a control phage that does not display the antigen-binding fragment.

The term "phage display" refers to an approach by which variant polypeptides are displayed as fusion proteins with at least a portion of coat proteins on the particle surface of phages, e.g., filamentous phages. The phage display is useful because a large library of randomized protein variants can be rapidly and efficiently screened for a sequence binding to a target antigen with high affinity. The display of peptide and protein libraries on the phages has been used for screening millions of polypeptides for ones with specific binding properties. A polyvalent phage display method has been used for displaying small random peptides and small proteins through fusions with filamentous phage gene III or gene VIII (Wells and Lowman, Curr. Opin. Struct. Biol. (1992) 3, 355-362; and references cited therein). Monovalent phage display involves fusing a protein or peptide library to gene III or a portion thereof, and expressing fusion proteins at low levels in the presence of wild-type gene III protein so that each phage particle displays one copy or none of the fusion proteins. The monovalent phages have a lower avidity effect than that of the polyvalent phages and are therefore screened on the basis of endogenous ligand affinity using phagemid vectors, which simplify DNA manipulation (Lowman and Wells, Methods: A Companion to Methods in Enzymology (1991) 3, 205-216).

The "phagemid" refers to a plasmid vector having a bacterial replication origin, for example, ColE1, and a copy of an intergenic region of a bacteriophage. Any bacteriophage known in the art, including, for example, filamentous bacteriophages and lambdoid bacteriophages can be appropriately used as the phagemid. Usually, the plasmid further contains a selective marker for antibiotic resistance. DNA fragments cloned into these vectors can be grown as plasmids. When cells transformed with these vectors possess all genes necessary for the production of phage particles, the replication pattern of plasmids is shifted to rolling circle replication to form copies of one plasmid DNA strand and package phage particles. The phagemid can form infectious or non-infectious phage particles. This term includes phagemids comprising a phage coat protein gene or fragment thereof bound with a heterologous polypeptide gene by gene fusion such that the heterologous polypeptide is displayed on the surface of the phage particle.

The term "phage vector" means a double-stranded replicative bacteriophage that comprises a heterologous gene and is capable of replicating. The phage vector has a phage replication origin that permits phage replication and phage particle formation. The phage is preferably a filamentous bacteriophage, for example, an M13, fl, fd, or Pf3 phage or a derivative thereof, or a lambdoid phage, for example, lambda, 21, phi80, phi81, 82, 424, 434, or any other phage or a derivative thereof.

The term "oligonucleotide" refers to a short single- or double-stranded polydeoxynucleotide that is chemically synthesized by a method known in the art (e.g., phosphotriester, phosphite, or phosphoramidite chemistry using a solid-phase approach such as an approach described in EP266032; or a method via deoxynucleotide H-phosphonate intermediate described in Froeshler et al., Nucl. Acids. Res. (1986) 14, 5399-5407). Other methods for oligonucleotide synthesis include the polymerase chain reaction described below and other autoprimer methods and oligonucleotide syntheses on solid supports. All of these methods are described in Engels et al., Agnew. Chem. Int. Ed. Engl. (1989) 28, 716-734. These methods are used provided that the whole nucleic acid sequence of the gene is known or provided that a nucleic acid sequence complementary to the coding strand is available. Alternatively, possible nucleic acid sequences may be appropriately predicted using known and preferred residues encoding each amino acid residue, if the target amino acid sequence is known. The oligonucleotide can be purified using polyacrylamide gels or molecular sizing columns or by precipitation.

The terms "fusion protein" and "fusion polypeptide" refer to a polypeptide having two segments covalently linked to each other. This polypeptide has different characters derived from these segments. These characters may each be, for example, a biological property such as in vitro or in vivo activity. Alternatively, these characters may each be a single chemical or physical property, for example, binding to a target antigen or catalysis of reaction. These two segments may be linked either directly through a single peptide bond or via a peptide linker comprising one or more amino acid residues. Usually, these two segments and the linker are present in the same reading frame. Preferably, the two segments of the polypeptide are obtained from heterologous or different polypeptides.

The term "heterologous DNA" refers to an arbitrary DNA that is transferred to host cells. The DNA may be derived from various sources including genomic DNAs, cDNAs, synthetic DNAs, and fusions or combinations thereof. The DNA may include DNAs from the same cells or cell type as host or recipient cells or DNAs from a different cell type, for example, from a mammal or a plant. The DNA may optionally comprise a marker or selective gene, for example, an antibiotic resistance gene or a temperature resistance gene, and the like.

The term "highly diverse position" as used herein refers to an amino acid position on light and heavy chain variable regions having several different amino acids presented at the position, when the amino acid sequences of known and/or natural antibodies or antigen-binding fragments are compared. The highly diverse position is generally located in CDR regions. In one aspect, the highly diverse position in known and/or natural antibodies is effectively determined on the basis of data provided by Kabat, Sequences of Proteins of Immunological Interest (National Institutes of Health, Bethesda, Md., 1987 and 1991). A plurality of databases (vbase.mrc-cpe.cam.ac.uk/and www.bioinf.org.uk/abs/index.html) on the internet provide an extensive collection of many human light and heavy chain sequences and their alignments. Information on these sequences and their alignments is useful in determining the highly diverse position according to the present invention. According to the present invention, an amino acid position is regarded as being highly diverse if the amino acid has a diversity of preferably approximately 2 to approximately 20, preferably approximately 3 to approximately 19, preferably approximately 4 to approximately 18, preferably 5 to 17, preferably 6 to 16, preferably 7 to 15, preferably 8 to 14, preferably 9 to 13, or preferably 10 to 12 possible different amino acid residues at the position. In some embodiments, an amino acid position may have a diversity of preferably at least approximately 2, preferably at least approximately 4, preferably at least approximately 6, preferably at least approximately 8, preferably approximately 10, preferably approximately 12 possible different amino acid residues. In the present specification, such amino acid residues are also referred to as flexible residues. The term "non-random codon set" refers to a codon set encoding a selected amino acid that partially (preferably, completely) satisfies the criteria for amino acid selection described herein. The term "random codon set" as used herein refers to a codon set having a combination of codons encoding an arbitrary amino acid selected from among 20 amino acids (Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, and Val/V).

Library

According to one aspect, the present invention provides a library consisting essentially of a plurality of antigen-binding molecules differing in sequence from each other, wherein an antigen-binding domain in each of the antigen-binding molecules comprises at least one amino acid residue that changes the antigen-binding activity of the antigen-binding molecule depending on ion concentration conditions. Preferred examples of the ion concentration include metal ion concentration and hydrogen ion concentration.

The term "library" described herein refers to a plurality of antigen-binding molecules, a plurality of fusion polypeptides each comprising the antigen-binding molecules, or nucleic acids or polynucleotides each encoding their sequences. The plurality of antigen-binding molecules contained in the library or the plurality of fusion polypeptides each comprising the antigen-binding molecules do not have single sequences and are antigen-binding molecules differing in sequence from each other or fusion polypeptides each comprising these antigen-binding molecules.

The term "metal ion" described herein refers to an ion of an element belonging to any of group I including alkali metals except for hydrogen and the copper family, group II including alkaline earth metals and the zinc family, group III except for boron, group IV except for carbon and silicon, group VIII including the iron family and the platinum family, and subgroups A of groups V, VI, and VII, or a metallic element such as antimony, bismuth, or polonium. Metallic atoms have the property of releasing valence electrons to become cations. This property is called ionization tendency. Metals having large ionization tendency are reportedly rich in chemical activity.

Examples of the metal ion preferred for the present invention include calcium ions. The calcium ions are involved in the regulation of many vital phenomena including the contraction of muscles such as skeletal muscle, smooth muscle, and cardiac muscle, the activation (e.g., movement and phagocytosis) of leucocytes, the activation (e.g., deformation and secretion) of platelets, the activation of lymphocytes, the activation (e.g., histamine secretion) of mast cells, cellular response mediated by catecholamine a receptor or acetylcholine receptor, exocytosis, the release of transmitters from neuronal ending, and the axonal flow of neurons. For example, troponin C, calmodulin, parvalbumin, and myosin light chain, which have several calcium ion-binding sites and are probably derived from a common origin in terms of molecular evolution, are known as intracellular calcium ion receptors. A large number of their binding motifs are also known. Well known binding motifs are, for example, a cadherin domain, an EF hand contained in calmodulin, a C2 domain contained in protein kinase C, a Gla domain contained in a blood-clotting protein factor IX, a C-type lectin contained in asialoglycoprotein receptor or mannose-binding receptor, an A domain contained in LDL receptor, an annexin, a thrombospondin type 3 domain, and an EGF-like domain.

When the metal ion according to the present invention is a calcium ion, examples of the calcium ion concentration conditions include a low-calcium ion concentration condition and a high-calcium ion concentration condition. The phrase "binding activity is changed depending on calcium ion concentration conditions" means that the antigen-binding activity of each antigen-binding molecule is changed depending on the difference between the low-calcium ion concentration condition and the high-calcium ion concentration condition. Examples of this case include higher antigen-binding activity of the antigen-binding molecule under the high-calcium ion concentration condition than that under the low-calcium ion concentration condition. Another example thereof includes higher antigen-binding activity of the antigen-binding molecule under the low-calcium ion concentration condition than that under the high-calcium ion concentration condition.

In the present specification, the high calcium ion concentration is not particularly limited to a univocal numeric value and can be preferably a concentration selected from the range of 100 µM to 10 mM. In another aspect, the high calcium ion concentration may be a concentration selected from the range of 200 µM to 5 mM. In a different aspect, the high calcium ion concentration may also be a concentration selected from the range of 500 µM to 2.5 mM. In an alternative aspect, the high calcium ion concentration may also be a concentration selected from the range of 200 µM to 2 mM. In addition, this concentration may also be a concentration selected from the range of 400 µM to 1.5 mM. Particularly preferred examples thereof include concentrations selected from the range of 500 µM to 2.5 mM, which are close to in vivo calcium ion concentrations in plasma (blood).

In the present specification, the low calcium ion concentration is not particularly limited to a univocal numeric value and can be preferably a concentration selected from the range of 0.1 µM to 30 µM. In another aspect, the low calcium ion concentration may be a concentration selected from the range of 0.2 µM to 20 µM. In a different aspect, the low calcium ion concentration may also be a concentration selected from the range of 0.5 µM to 10 µM. In an alternative aspect, the low calcium ion concentration may also be a concentration selected from the range of 1 µM to 5 µM. In addition, this concentration may also be a concentration selected from the range of 2 µM to 4 µM. Particularly preferred examples thereof include concentrations selected from the range of 1 µM to 5 µM, which are close to in vivo ionized calcium concentrations in early endosome.

In the present invention, the phrase "antigen-binding activity of the antigen-binding molecule is lower under the low-calcium ion concentration condition than that under the high-calcium ion concentration condition" means that the antigen-binding activity of the antigen-binding molecule at a calcium ion concentration selected from the range of 0.1 µM to 30 µM is weaker than that at a calcium ion concentration selected from the range of 100 µM to 10 mM. This phrase preferably means that the antigen-binding activity of the antigen-binding molecule at a calcium ion concentration selected from the range of 0.5 µM to 10 µM is weaker than that at a calcium ion concentration selected from the range of 200 µM to 5 mM. The phrase particularly preferably means that the antigen-binding activity at an in vivo calcium ion concentration in early endosome is weaker than that at an in vivo calcium ion concentration in plasma. This specifically means that the antigen-binding activity of the antigen-binding molecule at a calcium ion concentration selected from the range of 1 µM to 5 µM is weaker than that at a calcium ion concentration selected from the range of 500 µM to 2.5 mM.

Whether or not the antigen-binding activity of the antigen-binding molecule is changed depending on the metal ion concentration conditions can be determined by use of an assay method known in the art. For example, the antigen-binding activity of the antigen-binding molecule is compared between the low calcium ion concentration condition and the high-calcium ion concentration condition in order to confirm that the antigen-binding activity of the antigen-binding molecule is changed to a higher level under the high-calcium ion concentration condition than that under the low-calcium ion concentration condition.

In the present invention, the phrase "antigen-binding activity of the antigen-binding molecule is lower under the low-calcium ion concentration condition than that under the high-calcium ion concentration condition" may be expressed as "antigen-binding activity of the antigen-binding molecule is higher under the high-calcium ion concentration condition than that under the low-calcium ion concentration condition". In the present invention, the phrase "antigen-binding activity is lower under the low-calcium ion concentration condition than that under the high-calcium ion concentration condition" is also described as "antigen-binding ability is weaker under the low-calcium ion concentration condition than that under the high-calcium ion concentration condition". In addition, the phrase "antigen-binding activity under the low-calcium ion concentration condition is lowered with respect to that under the high-calcium ion concentration condition" is also described as "antigen-binding ability under the low-calcium ion concentration condition is weakened with respect to that under the high-calcium ion concentration condition".

Conditions other than the calcium ion concentration for assaying the antigen-binding activity may be appropriately selected by those skilled in the art without particular limitations. The antigen-binding activity can be assayed under conditions of, for example, a HEPES buffer and 37° C. Also, the antigen-binding activity can be assayed using, for example, Biacore (GE Healthcare Bio-Sciences Corp.). In the antigen-binding activity assay, the antigen-binding molecule can be evaluated for its binding ability against, for example, soluble antigens, by the injection of the antigens as an analyte to an antigen-binding molecule-immobilized chip. Alternatively, the antigen-binding molecule can be evaluated for its binding ability against, for example, membrane antigens, by the injection of the antigen-binding molecule as an analyte to an antigen-immobilized chip.

In the antigen-binding molecule of the present invention, the ratio between the antigen-binding activity under the low-calcium ion concentration condition and the antigen-binding activity under the high-calcium ion concentration condition is not particularly limited as long as the antigen-binding activity under the low-calcium ion concentration condition is weaker than that under the high-calcium ion concentration condition. The ratio of a dissociation constant KD under the low-calcium ion concentration condition to KD under the high-calcium ion concentration condition (KD (3 µM Ca)/KD (2 mM Ca)) for antigens is preferably 2 or higher, more preferably 10 or higher, further preferably 40 or higher. The upper limit of the KD (3 µM Ca)/KD (2 mM Ca) ratio is not particularly limited and can be any value including 400, 1000, 10000, etc. as long as the resulting antigen-binding molecule can be technically prepared by those skilled in the art. Alternatively, the ratio may be defined by a value of KD (3 µM Ca)/KD (1.2 mM Ca). Specifically, the KD (3 µM Ca)/KD (1.2 mM Ca) ratio is 2 or higher, more preferably 10 or higher, further preferably 40 or higher. The upper limit of the KD (3 µM Ca)/KD (1.2 mM Ca) ratio is not particularly limited and can be any value including 400, 1000, 10000, etc. as long as the resulting antigen-binding molecule can be technically prepared by those skilled in the art.

The dissociation constant KD may be used as the value of the antigen-binding activity for soluble antigens. Alternatively, apparent KD (apparent dissociation constant) may be used for membrane antigens. The KD (dissociation constant) and the apparent KD (apparent dissociation constant) can be measured by a method generally known to those skilled in the art, for example, using Biacore (GE Healthcare Bio-Sciences Corp.), a Scatchard plot, or a flow cytometer.

Alternatively, for example, a dissociation rate constant kd may be preferably used as a different index that indicates the ratio between the antigen-binding activity under the low-calcium concentration condition and the antigen-binding activity under the high-calcium concentration condition for the antigen-binding molecule of the present invention. In the case of using kd (dissociation rate constant) instead of KD (dissociation constant) as an index for the binding activity ratio, the ratio of kd (dissociation rate constant) under the low-calcium concentration condition to kd (dissociation rate constant) under the high-calcium concentration condition (kd (under the low-calcium concentration condition)/kd (under the high-calcium concentration condition)) for antigens is preferably 2 or higher, more preferably 5 or higher, further preferably 10 or higher, still further preferably 30 or higher. The upper limit of the kd (under the low-calcium concentration condition)/kd (under the high-calcium concentration condition) ratio is not particularly limited and can be any value including 50, 100, 200, etc. as long as the resulting antigen-binding molecule can be prepared according to the technical common sense of those skilled in the art.

The dissociation rate constant kd may be used as the value of the antigen-binding activity for soluble antigens. Alternatively, apparent kd (apparent dissociation rate constant) may be used for membrane antigens. The kd (dissociation rate constant) and the apparent kd (apparent dissociation rate constant) can be measured by a method generally known to those skilled in the art, for example, using Biacore (GE Healthcare Bio-Sciences Corp.) or a flow cytometer. In the present invention, the antigen-binding activity of the antigen-binding molecule at different calcium ion concentrations is preferably assayed with conditions other than the calcium concentration kept constant.

In the present invention, concentration conditions for a proton, i.e., a hydrogen atomic nucleus, are treated synonymously with hydrogen exponent (pH) conditions. When the active mass of hydrogen ions in an aqueous solution is indicated by $a_{H^+}$, the pH is defined as $-\log 10 a_{H^+}$. In an aqueous solution having low ionic strength (e.g., lower than $10^{-3}$), $a_{H^+}$ is almost equal to hydrogen ionic strength. For example, the ion product of water at 25° C. and 1 atmospheric pressure is $K_W = a_{H^+} \cdot a_{OH^-} = 10^{-14}$ and is therefore $a_{H^+} = a_{OH^-} = 10^{-7}$ for pure water. In this case, pH 7 represents a neutral aqueous solution; a pH smaller than 7 represents an acidic aqueous solution; and a pH larger than 7 represents an alkaline aqueous solution.

In the case of using pH conditions as the hydrogen ion concentration conditions according to the present invention, examples of the pH conditions include an acidic pH condition and a neutral pH condition. The phrase "binding activity is changed depending on pH conditions" means that the antigen-binding activity of each antigen-binding molecule is changed depending on the difference between the acidic pH condition and the neutral pH condition. Examples of this case include higher antigen-binding activity of the antigen-binding molecule under the neutral pH condition than that under the acidic pH condition. Another example thereof includes higher antigen-binding activity of the antigen-binding molecule under the acidic pH condition than that under the neutral pH condition.

In the present specification, the neutral pH is not particularly limited to a univocal numeric value and can be preferably selected from the range of pH 6.7 to pH 10.0. In another aspect, the neutral pH may be selected from the range of pH 6.7 to pH 9.5. In a different aspect, the neutral pH may be selected from the range of pH 7.0 to pH 9.0. In an alternative aspect, this pH may be selected from the range of pH 7.0 to pH 8.0. Particularly preferred examples thereof include pH 7.4, which is close to in vivo pH in plasma (blood).

In the present specification, the acidic pH is not particularly limited to a univocal numeric value and can be preferably selected from the range of pH 4.0 to pH 6.5. In another aspect, the acidic pH may be selected from the range of pH 4.5 to pH 6.5. In a different aspect, the acidic pH may be selected from the range of pH 5.0 to pH 6.5. In an alternative aspect, this pH may be selected from the range of pH 5.5 to pH 6.5. Particularly preferred examples thereof include pH 5.8, which is close to in vivo pH in early endosome.

In the present invention, the phrase "antigen-binding activity of the antigen-binding molecule is lower under the acidic pH condition than that under the neutral pH condition" means that the antigen-binding activity of the antigen-binding molecule at a pH selected from the range of pH 4.0 to pH 6.5 is weaker than that at a pH selected from the range of pH 6.7 to pH 10.0. This phrase preferably means that the antigen-binding activity of the antigen-binding molecule at a pH selected from the range of pH 4.5 to pH 6.5 is weaker than that at a pH selected from the range of pH 6.7 to pH 9.5. The phrase more preferably means that the antigen-binding activity of the antigen-binding molecule at a pH selected from the range of pH 5.0 to pH 6.5 is weaker than that at a pH selected from the range of pH 7.0 to pH 9.0. The phrase further preferably means that the antigen-binding activity of the antigen-binding molecule at a pH selected from the range of pH 5.5 to pH 6.5 is weaker than that at a pH selected from the range of pH 7.0 to pH 8.0. The phrase particularly preferably means that the antigen-binding activity at in vivo pH in early endosome is weaker than that at in vivo pH in plasma. This specifically means that the antigen-binding activity of the antigen-binding molecule at pH 5.8 is weaker than that at pH 7.4.

Whether or not the antigen-binding activity of the antigen-binding molecule is changed depending on the pH conditions can be determined, for example, according to a binding activity assay method under the different pH conditions described above. For example, the antigen-binding activity of the antigen-binding molecule is compared between the acidic pH condition and the neutral pH condition in order to confirm that the antigen-binding activity of the antigen-binding molecule is changed to a higher level under the neutral pH condition than that under the acidic pH condition.

In the present invention, the phrase "antigen-binding activity of the antigen-binding molecule is lower under the acidic pH condition than that under the neutral pH condition" may be expressed as "antigen-binding activity of the antigen-binding molecule is higher under the neutral pH condition than that under the acidic pH condition". In the present invention, the phrase "antigen-binding activity is lower under the acidic pH condition than that under the neutral pH condition" is also described as "antigen-binding ability is weaker under the acidic pH condition than that under the neutral pH condition". In addition, the phrase "antigen-binding activity under the acidic pH condition is lowered with respect to that under the neutral pH condition" is also described as "antigen-binding ability under the acidic pH condition is weakened with respect to that under the neutral pH condition".

When the metal ion is, for example, a calcium ion, the amino acid residue that changes the antigen-binding activity of the antigen-binding molecule depending on ion concentration conditions as described above is not limited by its type as long as the amino acid forms a calcium-binding motif. The calcium-binding motif is well known to those skilled in the art and is described in detail (e.g., Springer et al., Cell (2000) 102, 275-277; Kawasaki and Kretsinger, Protein Prof (1995) 2, 305-490; Moncrief et al., J. Mol. Evol. (1990) 30, 522-562; Chauvaux et al., Biochem. J. (1990) 265, 261-265; Bairoch and Cox, FEBS Lett. (1990) 269, 454-456; Davis, New Biol. (1990) 2, 410-419; Schaefer et al., Genomics (1995) 25, 638-643; Economou et al., EMBO J. (1990) 9, 349-354; and Wurzburg et al., Structure. (2006) 14, 6, 1049-1058). Specifically, the antigen-binding molecule of the present invention can comprise any calcium-binding motif known in the art, including C-type lectins such as ASGPR, CD23, MBR, and DC-SIGN. Other preferred examples of such a calcium-binding motif can include a calcium-binding motif contained in a domain of Vk5 present in an antibody light chain variable region having a germline sequence such as Vk5-2 as described later.

As an alternative example, an amino acid having a metal-chelating effect may be preferably used as the amino acid residue that changes the antigen-binding activity of the antigen-binding molecule depending on calcium ion concentration conditions. Preferred examples of the amino acid having a metal-chelating effect include serine (Ser (S)), threonine (Thr (T)), asparagine (Asn (N)), glutamine (Gln (Q)), aspartic acid (Asp (D)), and glutamic acid (Glu (E)).

The position of the amino acid residue contained in the antigen-binding domain is not limited to a particular position and can be any position in a heavy or light chain variable region constituting the antigen-binding domain as long as the resulting amino acid residue changes the antigen-binding activity of the antigen-binding molecule depending on calcium ion concentration conditions. In one aspect, the present invention provides the library consisting essentially of antigen-binding molecules differing in sequence from each other, wherein the amino acid residue that changes the antigen-binding activity of the antigen-binding molecule depending on calcium ion concentration conditions is contained in the antigen-binding domain in a heavy chain. In another aspect, the present invention provides the library consisting essentially of antigen-binding molecules differing in sequence from each other, wherein the amino acid residue is contained in heavy chain CDR3. In an alternative aspect, the present invention provides the library consisting essentially of antigen-binding molecules differing in sequence from each other, wherein the amino acid residue is located at any one or more of positions 95, 96, 100a, and 101 defined by the Kabat numbering in the heavy chain CDR3.

In one aspect, the present invention provides the library consisting essentially of antigen-binding molecules differing in sequence from each other, wherein the amino acid residue that changes the antigen-binding activity of the antigen-binding molecule depending on calcium ion concentration conditions is contained in the antigen-binding domain in a light chain. In another aspect, the present invention provides the library consisting essentially of antigen-binding molecules differing in sequence from each other, wherein the amino acid residue is contained in light chain CDR1. In an alternative aspect, the present invention provides the library consisting essentially of antigen-binding molecules differing in sequence from each other, wherein the amino acid residue is located at any one or more of positions 30, 31, and 32 defined by the Kabat numbering in the light chain CDR1.

In an alternative aspect, the present invention provides the library consisting essentially of antigen-binding molecules differing in sequence from each other, wherein the amino acid residue is contained in light chain CDR2. In a further alternative aspect, the present invention provides the library consisting essentially of antigen-binding molecules differing in sequence from each other, wherein the amino acid residue is located at position 50 defined by the Kabat numbering in the light chain CDR2.

In an alternative aspect, the present invention provides the library consisting essentially of antigen-binding molecules differing in sequence from each other, wherein the amino acid residue is contained in light chain CDR3. In a further alternative aspect, the present invention provides the library consisting essentially of antigen-binding molecules differing in sequence from each other, wherein the amino acid residue is located at position 92 defined by the Kabat numbering in the light chain CDR3.

In a different aspect, the present invention also provides the library consisting essentially of antigen-binding molecules differing in sequence from each other, wherein the amino acid residue is contained in two or three CDRs selected from the light chain CDR1, CDR2, and CDR3 described above. The present invention further provides the library consisting essentially of antigen-binding molecules differing in sequence from each other, wherein the amino acid residue is located at any one or more of positions 30, 31, 32, 50, and 92 defined by the Kabat numbering in the light chain.

In a particularly preferred embodiment, desirably, a framework sequence in the light chain and/or heavy chain variable regions of each antigen-binding molecule has a human germline framework sequence. Thus, in one aspect of the present invention, the antigen-binding molecule of the present invention having framework sequences, all of which are completely human sequences, probably causes little or no immunogenic response when administered to humans (e.g., for the treatment of a disease). In this context, the phrase "comprising a germline sequence" according to the present invention means that at least a portion of the framework sequence of the present invention is identical to a portion of any human germline framework sequence. For example, the sequence of heavy chain FR2 in the antigen-binding molecule of the present invention may be a sequence composed of a combination of heavy chain FR2 sequences from a plurality of different human germline framework sequences. Such an antigen-binding molecule is also included in the antigen-binding molecule "comprising a germline sequence" of the present invention.

Preferred examples of the framework region include the sequences of currently known completely human-derived framework regions listed in a website such as V-Base (vbase.mrc-cpe.cam.ac.uk/). Any of the sequences of these framework regions can be appropriately used as the germline sequence contained in the antigen-binding molecule of the present invention. The germline sequences can be classified on the basis of their analogy (Tomlinson et al., J. Mol. Biol. (1992) 227, 776-798; Williams and Winter, Eur. J. Immunol. (1993) 23, 1456-1461; and Cox et al., Nat. Genetics (1994) 7, 162-168). A preferred germline sequence can be appropriately selected from Vκ classified into 7 subgroups, Vλ classified into 10 subgroups and VH classified into 7 subgroups.

Preferred examples of completely human-derived VH sequences include, but not limited to, VH sequences of the VH1 subgroup (e.g., VH1-2, VH1-3, VH1-8, VH1-18, VH1-24, VH1-45, VH1-46, VH1-58, and VH1-69), the VH2 subgroup (e.g., VH2-5, VH2-26, and VH2-70), the VH3 subgroup (VH3-7, VH3-9, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-72, VH3-73, and VH3-74), the VH4 subgroup (VH4-4, VH4-28, VH4-31, VH4-34, VH4-39, VH4-59, and VH4-61), the VH5 subgroup (VH5-51), the VH6 subgroup (VH6-1), and the VH7 subgroup (VH7-4 and VH7-81). These sequences are also described in a public literature (Matsuda et al., J. Exp. Med. (1998) 188, 1973-1975), etc. Those skilled in the art can appropriately design the antigen-binding molecule of the present invention on the basis of the sequence information. Any other completely human-derived framework region or framework subregion may be preferably used.

Preferred examples of completely human-derived VK sequences include, but not limited to, A20, A30, L1, L4, L5, L8, L9, L11, L12, L14, L15, L18, L19, L22, L23, L24, O2, O4, O8, O12, O14, and O18 belonging to the Vk1 subgroup, A1, A2, A3, A5, A7, A17, A18, A19, A23, O1, and O11 belonging to the Vk2 subgroup, A11, A27, L2, L6, L10, L16, L20, and L25 belonging to the Vk3 subgroup, B3 belonging to the Vk4 subgroup, B2 belonging to the Vk5 subgroup (also referred to as Vk5-2 herein), and A10, A14, and A26 belonging to the VK6 subgroup (Kawasaki et al., Eur. J. Immunol. (2001) 31, 1017-1028; Schable and Zachau, Biol. Chem. Hoppe Seyler (1993) 374, 1001-1022; and Brensing-Kuppers et al., Gene (1997) 191, 173-181).

Preferred examples of completely human-derived VL sequences include, but not limited to, V1-2, V1-3, V1-4, V1-5, V1-7, V1-9, V1-11, V1-13, V1-16, V1-17, V1-18, V1-19, V1-20, and V1-22 belonging to the VL1 subgroup, V2-1, V2-6, V2-7, V2-8, V2-11, V2-13, V2-14, V2-15, V2-17, and V2-19 belonging to the VL2 subgroup, V3-2, V3-3, and V3-4 belonging to the VL3 subgroup, V4-1, V4-2, V4-3, V4-4, and V4-6 belonging to the VL4 subgroup, and V5-1, V5-2, V5-4, and V5-6 belonging to the VL5 subgroup (Kawasaki et al., Genome Res. (1997) 7, 250-261).

These framework sequences usually differ from each other by one or more amino acid residues. These framework sequences can be used together with "at least one amino acid residue that changes the antigen-binding activity of the antigen-binding molecule depending on ion concentration conditions" of the present invention. Examples of the completely human-derived framework regions used together with "at least one amino acid residue that changes the antigen-binding activity of the antigen-binding molecule depending on ion concentration conditions" of the present invention include, but not limited to, KOL, NEWM, REI, EU, TUR, TEI, LAY, and POM (e.g., Kabat et al., (1991); and Wu et al., J. Exp. Med. (1970) 132, 211-250).

Although the present invention is not bound to any particular theory, use of the germline sequence is expected to preclude adverse immune response in almost all of persons, probably in part because of the following: somatic mutations frequently occur in immunoglobulin variable regions as a result of an affinity maturation step that takes place during normal immune response. These mutations occur mainly around CDRs having a hypervariable sequence, but also influence residues in framework regions. These mutations in the framework regions are absent in germline genes and are not unlikely to be immunogenic to patients. On the other hand, ordinary human populations are exposed to a large number of framework sequences expressed by germline genes. As a result of immunological tolerance, these germline framework regions are presumed to be low immunogenic or non-immunogenic to patients. In order to maximize the possibility of immunological tolerance, the germline sequence can be selected from functional germline gene clusters where variable region-encoding genes are commonly present.

An antigen-binding molecule comprising "at least one amino acid residue that changes the antigen-binding activity of the antigen-binding molecule depending on ion concentration conditions" of the present invention in the framework sequence can be prepared by an appropriately adopted method known in the art such as site-directed mutagenesis (Kunkel et al., Proc. Natl. Acad. Sci. USA (1985) 82, 488-492) or overlap extension PCR.

For example, light chain variable regions selected as framework sequences preliminarily comprising "at least one amino acid residue that changes the antigen-binding activity of the antigen-binding molecule depending on ion concentration conditions" can be combined with heavy chain variable regions prepared as a randomized variable region sequence library to prepare the library of the present invention comprising a plurality of antigen-binding molecules differing in sequence from each other. When the ion concentration is a calcium ion concentration, non-limiting examples of such a library preferably include a library comprising in combination a light chain variable region sequence described in SEQ ID NO: 1 (Vk5-2) and heavy chain variable regions prepared as a randomized variable region sequence library. As a preferred example, the light chain variable region sequence described in SEQ ID NO: 1 (Vk5-2) as well as Vk5-2 variant 1 represented by SEQ ID NO: 2 or Vk5-2 variant 2 represented by SEQ ID NO: 3 described later is appropriately used as the light chain variable region sequence comprising a domain of Vk5 present in an antibody light chain variable region having a germline sequence such as Vk5-2. The domain of Vk5-2 comprising "at least one amino acid residue that changes the antigen-binding activity of the antigen-binding molecule depending on ion concentration conditions" contained in these molecules can be used as a domain comprising the calcium-binding motif of the present invention. In a non-limiting aspect of the present invention, at least one amino acid that forms a calcium-binding motif can be used as "at least one amino acid residue that changes the antigen-binding activity of the antigen-binding molecule depending on ion concentration conditions" of the present invention.

Also, the sequences of the light chain variable regions selected as framework sequences preliminarily comprising "at least one amino acid residue that changes the antigen-binding activity of the antigen-binding molecule depending on ion concentration conditions" may be designed so as to comprise diverse amino acids as residues other than the amino acid residue. In the present invention, such residues are referred to as flexible residues. The number and positions of the flexible residues are not limited to any particular aspect as long as the antigen-binding activity of the antigen-binding molecule of the present invention is changed depending on the ion concentration conditions. Specifically, the heavy chain and/or light chain CDR and/or FR sequences may each comprise one or more flexible residues. When the ion concentration is, for example, a calcium ion concentration, non-limiting examples of the flexible residues introduced to the light chain variable region sequence described in SEQ ID NO: 1 (Vk5-2) include amino acid residues described in Tables 13, 14, 17, and 18.

Alternatively, light chain variable regions in which "at least one amino acid residue that changes the antigen-binding activity of the antigen-binding molecule depending on ion concentration conditions" has been introduced may be combined with heavy chain variable regions prepared as a randomized variable region sequence library to prepare the library of the present invention comprising a plurality of antigen-binding molecules differing in sequence from each other. When the ion concentration is a calcium ion concentration, non-limiting examples of such a library preferably include a library comprising in combination light chain variable region sequences derived from a germline sequence of SEQ ID NO: 6 (Vk1), SEQ ID NO: 7 (Vk2), SEQ ID NO: 8 (Vk3), SEQ ID NO: 9 (Vk4), or the like by the substitution of a particular residue by "at least one amino acid residue that changes the antigen-binding activity of the antigen-binding molecule depending on calcium ion concentration conditions" and heavy chain variable regions prepared as a randomized variable region sequence library. Non-limiting examples of the amino acid residue include amino acid residues contained in light chain CDR1. Other non-limiting examples of the amino acid residue include amino acid residues contained in light chain CDR2. Further non-limiting examples of the amino acid residue include amino acid residues contained in light chain CDR3.

Non-limiting examples of the amino acid residue contained in the light chain CDR1 as described above include amino acid residues 30, 31, and/or 32 defined by the Kabat numbering in the light chain variable region CDR1. Non-limiting examples of the amino acid residue contained in the light chain CDR2 include amino acid residue 50 defined by the Kabat numbering in the light chain variable region CDR2. Non-limiting examples of the amino acid residue contained in the light chain CDR3 include amino acid residue 92 defined by the Kabat numbering in the light chain variable region CDR3. These amino acid residues may be contained alone or in combination of two or more of these amino acids as long as these amino acid residues form calcium-binding motifs and/or the antigen-binding activity of the antigen-binding molecule is changed depending on the calcium ion concentration conditions. For example, troponin C, calmodulin, parvalbumin, and myosin light chain, which have several calcium ion-binding sites and are probably derived from a common origin in terms of molecular evolution, are known. The light chain CDR1, CDR2, and/or CDR3 may be designed so as to comprise any of their binding motifs. For example, a cadherin domain, an EF hand contained in calmodulin, a C2 domain contained in protein kinase C, a Gla domain contained in a blood-clotting protein factor IX, a C-type lectin contained in asialoglycoprotein receptor or mannose-binding receptor, an A domain contained in LDL receptor, an annexin, a thrombospondin type 3 domain, and an EGF-like domain can be appropriately used for these purposes.

In the case of combining the light chain variable regions in which "at least one amino acid residue that changes the antigen-binding activity of the antigen-binding molecule depending on ion concentration conditions" has been introduced with the heavy chain variable regions prepared as a randomized variable region sequence library, the sequences of the light chain variable regions may be designed so as to comprise flexible residues, as in the above case. The number and positions of the flexible residues are not limited to any particular aspect as long as the antigen-binding activity of the antigen-binding molecule of the present invention is changed depending on the ion concentration conditions. Specifically, the heavy chain and/or light chain CDR and/or FR sequences may each comprise one or more flexible residues. When the ion concentration is, for example, a calcium ion concentration, non-limiting examples of the flexible residues introduced to the light chain variable region sequences include amino acid residues described in Tables 13, 14, 17, and 18.

Preferred examples of the heavy chain variable regions to be combined therewith include a randomized variable region library. The randomized variable region library is prepared by appropriately combined methods known in the art. In a non-limiting aspect of the present invention, an immune library constructed on the basis of antibody genes derived from the lymphocytes of animals immunized with particular antigens, patients with infectious disease, humans having an increased antibody titer in blood as a result of vaccination, cancer patients, or autoimmune diseases can be preferably used as the randomized variable region library.

In a non-limiting aspect of the present invention, a synthetic library obtained by the substitution of CDR sequences of genomic DNA V genes or reshaped functional V genes by a synthetic oligonucleotide set comprising sequences encoding a codon set having an appropriate length can also be preferably used as the randomized variable region library. In this case, only CDR3 sequences may be substituted thereby because diversity is observed in the gene sequence of heavy chain CDR3. Amino acid diversity yielded in the variable regions of the antigen-binding molecules is based on diversity imparted to amino acid residues at positions exposed on the surface of the antigen-binding molecules. The positions exposed on the surface refer to positions that are judged as being exposable on the surface and/or being accessible to antigens on the basis of the structures, structure ensemble, and/or modeled structures of the antigen-binding molecules, and are generally located in CDRs thereof. Preferably, the positions exposed on the surface are determined using a computer program such as Insight II program (Accelrys Inc.) and coordinates from three-dimensional models of the antigen-binding molecules. The positions exposed on the surface can be determined using an algorithm known in the art (e.g., Lee and Richards, J. Mol. Biol. (1971) 55, 379-400; and Connolly, J. Appl. Cryst. (1983) 16, 548-558). The positions exposed on the surface may be determined using software suitable for protein modeling and three-dimensional structure information obtained from antibodies. Preferred examples of the software that may be used for such a purpose include SYBYL biopolymer module software (Tripos Associates Inc.). Generally and preferably, the "size" of probes used in calculation is set to approximately 1.4 angstroms or lower in terms of radius, when the algorithm requires a user to input size parameters. The method for determining surface-exposed regions and areas using personal computer software is described in Pacios, Comput. Chem. (1994) 18 (4), 377-386, and J. Mol. Model. (1995) 1, 46-53.

In a further non-limiting aspect of the present invention, a naive library consisting of naive sequences which are bias-free antibody sequence repertoires constructed from antibody genes derived from the lymphocytes of healthy persons may also be particularly preferably used as the randomized variable region library (Gejima et al., Human Antibodies (2002) 11, 121-129; and Cardoso et al., Scand. J. Immunol. (2000) 51, 337-344). The amino acid sequence comprising a naive sequence as described in the present invention refers to an amino acid sequence obtained from such a naive library.

In one aspect of the present invention, heavy chain variable regions selected as framework sequences preliminarily comprising "at least one amino acid residue that changes the antigen-binding activity of the antigen-binding molecule depending on ion concentration conditions" can be combined with light chain variable regions prepared as a randomized variable region sequence library to prepare the library of the present invention comprising a plurality of antigen-binding molecules differing in sequence from each other. When the ion concentration is a calcium ion concentration, non-limiting examples of such a library preferably include a library comprising in combination a heavy chain variable region sequence described in SEQ ID NO: 10 (6RL #9H-IgG1) or SEQ ID NO: 11 (6KC4-1 #85H-IgG1) and light chain variable regions prepared as a randomized variable region sequence library. Alternatively, the library may be prepared using appropriately selected light chain variable regions having a germline sequence, instead of the light chain variable regions prepared as a randomized variable region sequence library. Preferred examples thereof include a library comprising in combination a heavy chain variable region sequence described in SEQ ID NO: 10 (6RL #9H-IgG1) or SEQ ID NO: 11 (6KC4-1 #85H-IgG1) and light chain variable regions having a germline sequence.

Also, the sequences of the heavy chain variable regions selected as framework sequences preliminarily comprising "at least one amino acid residue that changes the antigen-binding activity of the antigen-binding molecule depending on ion concentration conditions" may be designed so as to comprise flexible residues. The number and positions of the flexible residues are not limited to any particular aspect as long as the antigen-binding activity of the antigen-binding molecule of the present invention is changed depending on the ion concentration conditions. Specifically, the heavy chain and/or light chain CDR and/or FR sequences may each comprise one or more flexible residues. When the ion concentration is, for example, a calcium ion concentration, non-limiting examples of the flexible residues introduced to the heavy chain variable region sequence described in SEQ ID NO: 10 (6RL #9H-IgG1) include all amino acid residues of heavy chain CDR1 and CDR2 as well as amino acid residues of heavy chain CDR3 except for positions 95, 96, and/or 100a. Alternatively, non-limiting examples of the flexible residues introduced to the heavy chain variable region sequence described in SEQ ID NO: 11 (6KC4-1 #85H-IgG1) include all amino acid residues of heavy chain CDR1 and CDR2 as well as amino acid residues of heavy chain CDR3 except for positions 95 and/or 101.

Alternatively, heavy chain variable regions in which "at least one amino acid residue that changes the antigen-binding activity of the antigen-binding molecule depending on ion concentration conditions" has been introduced may be combined with light chain variable regions prepared as a randomized variable region sequence library or light chain variable regions having a germline sequence to prepare the library of the present invention comprising a plurality of antigen-binding molecules differing in sequence from each other. When the ion concentration is a calcium ion concentration, non-limiting examples of such a library preferably include a library comprising in combination heavy chain variable region sequences derived from the heavy chain variable regions by the substitution of a particular residue by "at least one amino acid residue that changes the antigen-binding activity of the antigen-binding molecule depending on calcium ion concentration conditions" and light chain variable regions prepared as a randomized variable region sequence library or light chain variable regions having a germline sequence. Non-limiting examples of the amino acid residue include amino acid residues contained in heavy chain CDR1. Other non-limiting examples of the amino acid residue include amino acid residues contained in heavy chain CDR2. Further non-limiting examples of the amino acid residue include amino acid residues contained in heavy chain CDR3. Non-limiting examples of the amino acid residue contained in the heavy chain CDR3 include amino acids at positions 95, 96, 100a, and/or 101 defined by the Kabat numbering in the heavy chain variable region CDR3. These amino acid residues may be contained alone or in combination of two or more of these amino acids as long as these amino acid residues form calcium-binding motifs and/or the antigen-binding activity of the antigen-binding molecule is changed depending on the calcium ion concentration conditions.

In the case of combining the heavy chain variable regions in which "at least one amino acid residue that changes the antigen-binding activity of the antigen-binding molecule depending on ion concentration conditions" has been introduced with the light chain variable regions prepared as a randomized variable region sequence library or the light chain variable regions having a germline sequence, the sequences of the heavy chain variable regions may be designed so as to comprise flexible residues, as in the above case. The number and positions of the flexible residues are not limited to any particular aspect as long as the antigen-binding activity of the antigen-binding molecule of the present invention is changed depending on the ion concentration conditions. Specifically, the heavy chain CDR and/or FR sequences may each comprise one or more flexible residues. Also, a randomized variable region library can be preferably used as the amino acid sequences of heavy chain variable region CDR1, CDR2, and/or CDR3 except for the "amino acid residue that changes the antigen-binding activity of the antigen-binding molecule depending on ion concentration conditions". In the case of using germline sequences as the light chain variable regions, non-limiting examples thereof can include germline sequences of SEQ ID NO: 6 (Vk1), SEQ ID NO: 7 (Vk2), SEQ ID NO: 8 (Vk3), and SEQ ID NO: 9 (Vk4).

Any amino acid residue can be preferably used as the amino acid residue that changes the antigen-binding activity of the antigen-binding molecule depending on calcium ion concentration conditions as long as the amino acid residue forms a calcium-binding motif. Specific examples of such an amino acid residue include amino acids having electron-donating properties. Preferred examples of the amino acids having such electron-donating properties include serine, threonine, asparagine, glutamine, aspartic acid, and glutamic acid.

In one aspect of the present invention, light chain variable regions in which "at least one amino acid residue that changes the antigen-binding activity of the antigen-binding molecule depending on hydrogen ion concentration conditions" has been introduced can also be combined with heavy chain variable regions prepared as a randomized variable region sequence library to prepare the library of the present invention comprising a plurality of antigen-binding molecules differing in sequence from each other.

Non-limiting examples of the amino acid residue include amino acid residues contained in light chain CDR1. Other non-limiting examples of the amino acid residue include amino acid residues contained in light chain CDR2. Further non-limiting examples of the amino acid residue include amino acid residues contained in light chain CDR3.

Non-limiting examples of the amino acid residue contained in the light chain CDR1 as described above include amino acid residues 24, 27, 28, 30, 31, 32, and/or 34 defined by the Kabat numbering in the light chain variable region CDR1. Non-limiting examples of the amino acid residue contained in the light chain CDR2 include amino acid residues 50, 51, 52, 53, 54, 55, and/or 56 defined by the Kabat numbering in the light chain variable region CDR2. Non-limiting examples of the amino acid residue contained in the light chain CDR3 include amino acid residues 89, 90, 91, 92, 93, 94, and/or 95a defined by the Kabat numbering in the light chain variable region CDR3. These amino acid residues may be contained alone or in combination of two or more of these amino acids as long as the antigen-binding activity of the antigen-binding molecule comprising the amino acid residue(s) is changed depending on the hydrogen ion concentration conditions.

In the case of combining the light chain variable regions in which "at least one amino acid residue that changes the antigen-binding activity of the antigen-binding molecule depending on hydrogen ion concentration conditions" has been introduced with the heavy chain variable regions prepared as a randomized variable region sequence library, the sequences of the light chain variable regions may be designed so as to comprise flexible residues, as in the above case. The number and positions of the flexible residues are not limited to any particular aspect as long as the antigen-binding activity of the antigen-binding molecule of the present invention is changed depending on the ion concentration conditions. Specifically, the heavy chain and/or light chain CDR and/or FR sequences may each comprise one or more flexible residues. Non-limiting examples of the flexible residues introduced to the light chain variable region sequences include amino acid residues described in Tables 4 and 5. As a non-limiting example, a germline sequence of Vk1 (SEQ ID NO: 6), Vk2 (SEQ ID NO: 7), Vk3 (SEQ ID NO: 8), Vk4 (SEQ ID NO: 9), or the like can be preferably used as the amino acid sequences of the light chain variable regions except for the amino acid residue that changes the antigen-binding activity of the antigen-binding molecule depending on hydrogen ion concentration conditions or the flexible residues.

Preferred examples of the heavy chain variable regions to be combined therewith include a randomized variable region library. The randomized variable region library is prepared by appropriately combined methods known in the art. In a non-limiting aspect of the present invention, an immune library constructed on the basis of antibody genes derived from the lymphocytes of animals immunized with particular antigens, patients with infectious disease, humans having an increased antibody titer in blood as a result of vaccination, cancer patients, or autoimmune diseases can be preferably used as the randomized variable region library.

In a non-limiting aspect of the present invention, a synthetic library obtained by the substitution of CDR sequences of genomic DNA V genes or reshaped functional V genes by a synthetic oligonucleotide set comprising sequences encoding a codon set having an appropriate length can also be preferably used as the randomized variable region library, as in the above case.

In a further non-limiting aspect of the present invention, a naive library consisting of naive sequences which are bias-free antibody sequence repertoires constructed from antibody genes derived from the lymphocytes of healthy persons may also be particularly preferably used as the randomized variable region library (Gejima et al., Human Antibodies (2002) 11, 121-129; and Cardoso et al., Scand. J. Immunol. (2000) 51, 337-344).

In an alternative aspect of the present invention, heavy chain variable regions in which "at least one amino acid residue that changes the antigen-binding activity of the antigen-binding molecule depending on hydrogen ion concentration conditions" has been introduced may be combined with light chain variable regions prepared as a randomized variable region sequence library or light chain variable regions having a germline sequence to prepare the library of the present invention comprising a plurality of antigen-binding molecules differing in sequence from each other. Non-limiting examples of such a library preferably include a library comprising in combination heavy chain variable region sequences derived from the heavy chain variable regions by the substitution of a particular residue by "at least one amino acid residue that changes the antigen-binding activity of the antigen-binding molecule depending on hydrogen ion concentration conditions" and light chain variable regions prepared as a randomized variable region sequence library or light chain variable regions having a germline sequence. Non-limiting examples of the amino acid residue include amino acid residues contained in heavy chain CDR1. Other non-limiting examples of the amino acid residue include amino acid residues contained in heavy chain CDR2. Further non-limiting examples of the amino acid residue include amino acid residues contained in heavy chain CDR3.

Non-limiting examples of the amino acid residue contained in the heavy chain CDR1 include amino acid residues 27, 31, 32, 33, and/or 35 defined by the Kabat numbering in the heavy chain variable region CDR1. Non-limiting examples of the amino acid residue contained in the heavy chain CDR2 include amino acid residues 50, 52, 53, 55, 57, 58, 59, 61, and/or 62 defined by the Kabat numbering in the heavy chain variable region CDR2. Non-limiting examples of the amino acid residue contained in the heavy chain CDR3 include amino acid residues 95, 96, 97, 98, 99, 100a, 100b, 100d, 100f, 100h, 102, and/or 107 defined by the Kabat numbering in the heavy chain variable region CDR3. These amino acid residues may be contained alone or in combination of two or more of these amino acids as long as the antigen-binding activity of the antigen-binding molecule comprising the amino acid residue(s) is changed depending on the hydrogen ion concentration conditions.

In the case of combining the heavy chain variable regions in which "at least one amino acid residue that changes the antigen-binding activity of the antigen-binding molecule depending on hydrogen ion concentration conditions" has been introduced with the light chain variable regions prepared as a randomized variable region sequence library or the light chain variable regions having a germline sequence, the sequences of the heavy chain variable regions may be designed so as to comprise flexible residues, as in the above case. The number and positions of the flexible residues are not limited to any particular aspect as long as the antigen-binding activity of the antigen-binding molecule of the present invention is changed depending on the hydrogen ion concentration conditions. Specifically, the heavy chain CDR and/or FR sequences may each comprise one or more flexible residues. Also, a randomized variable region library can be preferably used as the amino acid sequences of heavy chain variable region CDR1, CDR2, and/or CDR3 except for the "amino acid residue that changes the antigen-binding activity of the antigen-binding molecule depending on hydrogen ion concentration conditions". In the case of using germline sequences as the light chain variable regions, non-limiting examples thereof can include germline sequences of SEQ ID NO: 6 (Vk1), SEQ ID NO: 7 (Vk2), SEQ ID NO: 8 (Vk3), and SEQ ID NO: 9 (Vk4).

Any amino acid residue can be preferably used as the amino acid residue that changes the antigen-binding activity of the antigen-binding molecule depending on hydrogen ion concentration conditions. Specific examples of such an amino acid residue include amino acids having a side chain pKa of 4.0 to 8.0. Preferred examples of the amino acids having such electron-donating properties include natural amino acids such as histidine and glutamic acid as well as non-natural amino acids such as histidine analogs (US20090035836), m-NO2-Tyr (pKa: 7.45), 3,5-Br2-Tyr (pKa: 7.21), and 3,5-I2-Tyr (pKa: 7.38) (Bioorg. Med. Chem. (2003) 11 (17), 3761-2768). Particularly preferred examples of the amino acid residue include amino acids having a side chain pKa of 5.5 to 7.0. Preferred examples of the amino acids having such electron-donating properties include histidine.

Amino acids in antigen-binding domains can be modified by an appropriately adopted method known in the art such as site-directed mutagenesis (Kunkel et al., Proc. Natl. Acad. Sci. USA (1985) 82, 488-492) or overlap extension PCR. Also, the amino acids can be substituted by non-natural amino acids by use of a plurality of modification methods known in the art (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express, an R & D oriented company)) comprising a non-natural amino acid bound with an amber suppressor tRNA complementary to UAG codon (amber codon), which is a stop codon, is also preferably used.

Preferred examples of the light chain variable regions to be combined therewith include a randomized variable region library. The randomized variable region library is prepared by appropriately combined methods known in the art. In a non-limiting aspect of the present invention, an immune library constructed on the basis of antibody genes derived from the lymphocytes of animals immunized with particular antigens, patients with infectious disease, humans having an increased antibody titer in blood as a result of vaccination, cancer patients, or autoimmune diseases can be preferably used as the randomized variable region library.

In a non-limiting aspect of the present invention, a synthetic library obtained by the substitution of CDR sequences of genomic DNA V genes or reshaped functional V genes by a synthetic oligonucleotide set comprising sequences encoding a codon set having an appropriate length can also be preferably used as the randomized variable region library. In this case, only CDR3 sequences may be substituted thereby because diversity is observed in the gene sequence of heavy chain CDR3. Amino acid diversity yielded in the variable regions of the antigen-binding molecules is based on diversity imparted to amino acid residues at positions exposed on the surface of the antigen-binding molecules. The positions exposed on the surface refer to positions that are judged as being exposable on the surface and/or being accessible to antigens on the basis of the structures, structure ensemble, and/or modeled structures of the antigen-binding molecules, and are generally located in CDRs thereof. Preferably, the positions exposed on the surface are determined using a computer program such as Insight II program (Accelrys Inc.) and coordinates from three-dimensional models of the antigen-binding molecules. The positions exposed on the surface can be determined using an algorithm known in the art (e.g., Lee and Richards, J. Mol. Biol. (1971) 55, 379-400; and Connolly, J. Appl. Cryst. (1983) 16, 548-558). The positions exposed on the surface may be determined using software suitable for protein modeling and three-dimensional structure information obtained from antibodies. Preferred examples of the software that may be used for such a purpose include SYBYL biopolymer module software (Tripos Associates Inc.). Generally and preferably, the "size" of probes used in calculation is set to approximately 1.4 angstroms or lower in terms of radius, when the algorithm requires a user to input size parameters. The method for determining surface-exposed regions and areas using personal computer software is described in Pacios, Comput. Chem. (1994) 18 (4), 377-386, and J. Mol. Model. (1995) 1, 46-53.

In a further non-limiting aspect of the present invention, a naive library consisting of naive sequences which are bias-free antibody sequence repertoires constructed from antibody genes derived from the lymphocytes of healthy persons may also be particularly preferably used as the randomized variable region library (Gejima et al., Human Antibodies (2002) 11, 121-129; and Cardoso et al., Scand. J. Immunol. (2000) 51, 337-344).

Any amino acid can be used as amino acids other than the amino acid residue that changes the antigen-binding activity of the antigen-binding molecule depending on ion concentration conditions as long as the antigen-binding molecule of the present invention binds to antigens. As a preferred example, an antibody phage display library technique known in the art (e.g., J. D. Marks et al., J. Mol. Biol. (1991) 222, 581-597) can be appropriately applied thereto. Specifically, amino acid sequences except for the amino acid residue that changes the antigen-binding activity of the antigen-binding molecule depending on ion concentration conditions are adopted by the antibody phage library.

The term "differing in sequence from each other" in a plurality of antigen-binding molecules differing in sequence from each other as described in the present invention means that the individual antigen-binding molecules in the library have distinct sequences. Specifically, the number of the distinct sequences in the library reflects the number of independent clones differing in sequences in the library and is also referred to as a "library size". The library size of a usual phage display library is $10^6$ to $10^{12}$ and can be expanded to $10^{14}$ by the application of a technique known in the art such as a ribosome display method. The actual number of phage particles used in panning selection for the phage library, however, is usually 10 to 10,000 times larger than the library size. This excessive multiple, also called the "number of equivalents of the library", represents that 10 to 10,000 individual clones may have the same amino acid sequence. Accordingly, the term "differing in sequence from each other" described in the present invention means that the individual antigen-binding molecules in the library excluding the number of equivalents of the library have distinct sequences and more specifically means that the library has $10^6$ to $10^{14}$, preferably $10^7$ to $10^{12}$, more preferably $10^8$ to $10^{11}$, particularly preferably $10^8$ to $10^{10}$ antigen-binding molecules differing in sequence from each other.

The term "plurality of" in the library consisting essentially of a plurality of antigen-binding molecules as described in the present invention usually refers to a set of two or more types of substances as to, for example, the antigen-binding molecule, fusion polypeptide, polynucleotide molecule, vector, or virus of the present invention. For example, if two or more substances differ from each other in particular trait, the substances exist as two or more types.

Examples thereof can include variant amino acids observed at a particular amino acid position in an amino acid sequence. For example, two or more antigen-binding molecules of the present invention having substantially the same, preferably identical sequences except for flexible residues or except for particular variant amino acids at surface-exposed, highly diverse amino acid positions are regarded as a plurality of antigen-binding molecules of the present invention. In another example, two or more polynucleotide molecules of the present invention having substantially the same, preferably identical sequences except for bases encoding flexible residues or except for bases encoding particular variant amino acids at surface-exposed, highly diverse amino acid positions are regarded as a plurality of polynucleotide molecules of the present invention.

The term "consisting essentially of" in the library consisting essentially of a plurality of antigen-binding molecules as described in the present invention reflects the number of antigen-binding molecules that differ in antigen-binding activity depending on ion concentration conditions, among the independent clones differing in sequence in the library. Specifically, the library preferably has at least $10^4$ antigen-binding molecules that exhibit such binding activity. More preferably, the present invention provides the library having at least $10^5$ antigen-binding molecules that exhibit such binding activity. Further preferably, the present invention provides the library having at least $10^6$ antigen-binding molecules that exhibit such binding activity. Particularly preferably, the present invention provides the library having at least $10^7$ antigen-binding molecules that exhibit such binding activity. Also preferably, the present invention provides the library having at least $10^8$ antigen-binding molecules that exhibit such binding activity. In other words, the term may be preferably indicated by the ratio of the antigen-binding molecules that differ in antigen-binding activity depending on ion concentration conditions to the number of the independent clones differing in sequence in the library. Specifically, the present invention provides the library comprising antigen-binding molecules that exhibit such binding activity at a ratio of 0.1% to 80%, preferably 0.5% to 60%, more preferably 1% to 40%, further preferably 2% to 20%, particularly preferably 4% to 10% to the number of the independent clones differing in sequence in the library. Fusion polypeptides, polynucleotide molecules, or vectors can also be indicated by the number of molecules or the ratio to all molecules, as in the above case. Also, viruses can also be indicated by the number of virus individuals or the ratio to all individuals, as in the above case.

Fusion Polypeptide Comprising Antigen-Binding Molecule

In one embodiment of the present invention, a fusion molecule of the antigen-binding molecule of the present invention and a heterologous polypeptide can be prepared. In one embodiment, the antigen-binding molecule of the present invention can be fused with at least a portion of a viral coat protein selected from the group consisting of, for example, viral coat proteins pIll, pVIII, pVII, pIX, Soc, Hoc, gpD, and pVI, and variants thereof to form a fusion polypeptide.

In one embodiment, the antigen-binding molecule of the present invention can be ScFv, a Fab fragment, F(ab)2, or F(ab')2. In another embodiment, the present invention provides a library consisting essentially of a plurality of fusion molecules differing in sequence from each other, the fusion molecules each comprising any of these antigen-binding molecules and a heterologous polypeptide. Specifically, the present invention provides a library consisting essentially of a plurality of fusion molecules differing in sequence from each other, the fusion proteins each comprising any of these antigen-binding molecules and at least a portion of a viral coat protein selected from the group consisting of, for example, viral coat proteins pIII, pVIII, pVII, pIX, Soc, Hoc, gpD, and pVI, and variants thereof. The antigen-binding molecule of the present invention may further comprise a dimerization domain. In one embodiment, the dimerization domain can be located between the heavy or light chain variable region of the antibody and at least a portion of the viral coat protein. This dimerization domain may comprise at least one dimerization sequence and/or a sequence comprising one or more cysteine residues. This dimerization domain can be preferably linked to the C terminus of the heavy chain variable region or constant region. The dimerization domain can assume various structures, depending on whether the antibody variable region is prepared as a fusion protein component with the viral coat protein component (an amber stop codon following the dimerization domain is absent) or depending on whether the antibody variable region is prepared predominantly without comprising the viral coat protein component (e.g., an amber stop codon following the dimerization domain is present). When the antibody variable region is prepared predominantly as a fusion protein with the viral coat protein component, bivalent display is brought about by one or more disulfide bonds and/or a single dimerization sequence. The antigen-binding molecule of the present invention preferably has a dimerization domain comprising both of a cysteine residue and a dimerization sequence, when being the antibody variable region prepared predominantly without being fused with the viral coat protein component (e.g., an amber stop codon is present). In one embodiment, F(ab)2 heavy chains are dimerized at a dimerization domain comprising no hinge region. This dimerization domain may comprise, for example, a leucine zipper sequence known in the art such as a GCN4 sequence: GRMKQLEDKVEELLSKNYHL ENEVARLKKLVGERG (SEQ ID NO: 12).

Polynucleotide Encoding Antigen-Binding Molecule

An oligonucleotide or primer set for use in the preparation of a polynucleotide encoding each antigen-binding molecule can be synthesized using a standard method. For example, one set of oligonucleotides comprising sequences that include every possible combination of nucleotide triplets provided by the codon set and encode a desired amino acid group can be synthesized by a solid-phase method. Thus, a synthetic oligonucleotide set having a particular codon set generally comprises a plurality of oligonucleotides differing in sequence. This difference is attributed to the codon set in the whole sequence. The synthesis of oligonucleotides having selected "degenerate" nucleotides at certain positions is known in that art. Such a set of nucleotides having such a certain kind of codon set may be synthesized using a commercially available nucleic acid synthesizer (Applied Biosystems, Inc.) or may be obtained as commercially available products (e.g., Life Technologies). As used in the present invention, the oligonucleotides have a sequence that permits hybridization to a variable domain nucleic acid template and may also comprise restriction enzymes sites useful in cloning.

The library can be formed by use of upstream and downstream oligonucleotide sets. Each oligonucleotide set has a plurality of oligonucleotides having different sequences established by the codon set provided within the oligonucleotide sequence. The upstream and downstream oligonucleotide sets can be used, together with variable domain template nucleic acid sequences, for preparing a "library" of PCR products. The PCR products can be fused with other related or unrelated nucleic acid sequences, for example, nucleic acid sequences encoding viral coat protein constituents and dimerization domains, using an established molecular biological approach. Such an oligonucleotide set may therefore be referred to as a "nucleic acid cassette".

The sequence of each PCR primer comprises one or more codon sets designed for highly diverse flexible residues exposed on the surface of the antigen-binding molecule. As described above, each codon set is a set of different nucleotide triplet sequences that are used for encoding desired variant amino acids. Also, the oligonucleotide set has a sequence of sufficient length to be hybridized to a template nucleic acid and may optionally restriction sites. DNA templates are formed by vectors derived from bacteriophage M13 vectors or vectors containing a replication origin of a single-stranded phage described by Viera et al. (Meth. Enzymol. (1987) 153, 3). Thus, the DNA to be mutated is inserted into one of these vectors in order to form a single-stranded template. The production of the single-stranded template is described in the textbook of Sambrook et al.

Methods for introducing selected amino acids into antigen-binding molecules as described in a non-limiting embodiment of the present invention has already been established in the art. Some of these methods are described herein. For example, "at least one amino acid residue that changes the antigen-binding activity of the antigen-binding molecule depending on ion concentration conditions" or highly diverse flexible residues can be exposed on the surface of at least one antigen-binding molecule and/or introduced thereto using a Kunkel method provided by Kunkel et al. (Methods Enzymol. (1987) 154, 367-382) to prepare a library. Such a method may be appropriately adopted in the case of preparing, for example, the library of the present invention comprising a plurality of antigen-binding molecules differing in sequence from each other by the combination of light chain variable regions in which "at least one amino acid residue that changes the antigen-binding activity of the antigen-binding molecule depending on ion concentration conditions" of the present invention has been introduced with heavy chain variable regions prepared as a randomized variable region sequence library. When the metal ion is a calcium ion, non-limiting examples of such a case include the preparation of light chain variable region sequences derived from a germline sequence of SEQ ID NO: 6 (Vk1), SEQ ID NO: 7 (Vk2), SEQ ID NO: 8 (Vk3), SEQ ID NO: 9 (Vk4), or the like by the substitution of a particular residue by "at least one amino acid residue that changes the antigen-binding activity of the antigen-binding molecule depending on calcium ion concentration conditions". The method as described above can be adopted for the preparation of such light chain variable regions.

In this case, oligonucleotide sets can be used as primers in PCR reaction using variable region nucleic acid template sequences as templates for preparing nucleic acid cassettes. Each variable region nucleic acid template sequence used is preferably a sequence that encodes any site in an immunoglobulin light or heavy chain and comprises the target nucleic acid sequence (i.e., a nucleic acid sequence encoding an amino acid to be substituted). Referring to the above example, a nucleic acid encoding a variable region in a germline sequence of SEQ ID NO: 6 (Vk1), SEQ ID NO: 7 (Vk2), SEQ ID NO: 8 (Vk3), SEQ ID NO: 9 (Vk4), or the like can be used as the template sequence. The variable region nucleic acid template sequence encodes at least a portion of a variable region and encodes at least one CDR. In some cases, the variable region nucleic acid template sequence encodes a plurality of CDRs. The upstream and downstream sites of the variable region nucleic acid template sequence can be targets to be hybridized by members constituting the upstream and downstream oligonucleotide sets. A first oligonucleotide of the upstream primer set can be hybridized to the first nucleic acid strand while a second oligonucleotide of the downstream primer set can be hybridized to the second nucleic acid strand. The oligonucleotide primers can be designed so as to comprise one or more codon sets and to be hybridized to a portion of the variable region nucleic acid template sequence. Use of these oligonucleotides in PCR can introduce two or more codon sets into the PCR product (i.e., the nucleic acid cassette). The oligonucleotide primers that are hybridized to regions in the antibody variable region-encoding nucleic acid sequence can include sites encoding CDR residues to be substituted by other amino acids.

As described herein, overlap extension PCR can also be appropriately adopted as a method for introducing selected amino acids into antigen-binding molecules as described in a non-limiting embodiment of the present invention (WO1993003151). "At least one amino acid residue that changes the antigen-binding activity of the antigen-binding molecule depending on ion concentration conditions" or highly diverse flexible residues can be exposed on the surface of at least one antigen-binding molecule and/or introduced thereto to prepare a library. Upstream and downstream oligonucleotide sets used in overlap extension PCR can comprise a framework sequence of sufficient length to be hybridized to the variable region nucleic acid template sequence, together with a sequence encoding "at least one amino acid residue that changes the antigen-binding activity of the antigen-binding molecule depending on ion concentration conditions" or highly diverse flexible residues.

For example, oligonucleotide sets encoding codon sets for "at least one amino acid residue that changes the antigen-binding activity of the antigen-binding molecule depending on ion concentration conditions" and additional flexible residues are prepared in order to prepare polynucleotide molecules each encoding light chain variable regions in which the amino acid residue has been introduced as described in a non-limiting embodiment of the present invention. A framework sequence of sufficient length to be hybridized to the variable region nucleic acid template sequence is linked upstream or downstream in frame with the oligonucleotide sets.

In the case of introducing the amino acid residue or the additional flexible residues into, for example, light chain variable region CDR2 and CDR3, a sufficient-length oligonucleotide encoding the amino acid sequence of FR2 adjacent to CDR2 is linked to the 5' ends of an oligonucleotide set, while an oligonucleotide encoding the amino acid sequence of FR3 adjacent to CDR2 is linked to the 3' ends thereof to prepare primers. In addition, a sufficient-length oligonucleotide encoding the amino acid sequence of FR4 adjacent to CDR3 is linked to the 5' ends of an oligonucleotide set complementary to the above oligonucleotide set, while an oligonucleotide encoding the amino acid sequence of FR3 adjacent to CDR3 is linked to the 3' ends thereof to prepare complementary primers. When the FR3 amino acid-encoding oligonucleotide in the primers and the FR3 amino acid-encoding oligonucleotide in the complementary primers comprise overlapping sequences of sufficient length to be hybridizable to each other, light chain variable regions comprising the amino acid residue or the additional flexible residues introduced in CDR2 and CDR3 can be prepared through PCR reaction under conditions involving no template sequence. When these oligonucleotides comprise no such overlapping sequences, light chain variable regions comprising the amino acid residue or the additional flexible residues introduced in CDR2 and CDR3 can be similarly prepared through PCR reaction using, for example, a variable region nucleic acid of a germline sequence of SEQ ID NO: 6 (Vk1), SEQ ID NO: 7 (Vk2), SEQ ID NO: 8 (Vk3), SEQ ID NO: 9 (Vk4), or the like as a template sequence.

In the case of preparing, for example, a library comprising light chain variable regions having CDR3 with the amino acid residue or the additional flexible residues introduced therein and randomized CDR1 and CDR2, a sufficient-length oligonucleotide encoding the amino acid sequence of FR4 adjacent to CDR3 is linked to the 5' ends of an oligonucleotide set complementary to the oligonucleotide set, while an oligonucleotide encoding the amino acid sequence of FR3 adjacent to CDR3 is linked to the 3' ends thereof to prepare primers. A library of polynucleotides encoding light chain variable regions having CDR3 with the amino acid residue or the additional flexible residues introduced therein and randomized CDR1 and CDR2 can be similarly prepared by PCR using the prepared primers, primers having an FR1-encoding nucleotide sequence, and a library comprising randomized variable region (e.g., naive sequence) nucleic acids as template sequences. These methods for preparing a polynucleotide library of light chains in which "at least one amino acid residue that changes the antigen-binding activity of the antigen-binding molecule depending on ion concentration conditions" and/or flexible residues have been introduced are also appropriately adopted in order to prepare a polynucleotide library of heavy chains in which the amino acid residue and the additional flexible residues have been introduced.

Alternatively, the upstream and downstream oligonucleotide sets may be synthesized so that each oligonucleotide sequence comprises restriction sites. These restriction sites facilitate the insertion of the nucleic acid cassette (i.e., the PCR reaction product) into expression vectors having additional antibody sequences. Preferably, the restriction sites are designed so as to facilitate the cloning of the nucleic acid cassette without introducing foreign nucleic acid sequences or without removing the original nucleic acid sequences of CDRs or framework regions.

The prepared nucleic acid cassette can be cloned into an appropriate vector for expression of a partial or whole light or heavy chain sequence constituting the antigen-binding molecule of the present invention. According to a method described in detail in the present invention, the nucleic acid cassette is cloned into a vector that permits production of a partial or whole light or heavy chain sequence fused with the whole or a portion of a viral coat protein (i.e., formation of a fusion protein). Such a vector, as described later, can be an expression vector designed so that particles or cells display the fusion protein on their surface. For such a purpose, several types of vectors are obtained and used to carry out the present invention. Phagemid vectors are vectors preferably used herein. As generally known to those skilled in the art, the phagemid vectors can usually comprise various constituents including control sequences (e.g., promoters and signal sequences), phenotypic selective genes, replication origin sites, and other necessary constituents.

In a non-limiting embodiment for expression of particular variant amino acids in combination, the nucleic acid cassette can encode a whole or partial heavy or light chain variable region. For example, in the case of designing the nucleic acid cassette so that heavy chain CDR3 comprises "at least one amino acid residue that changes the antigen-binding activity of the antigen-binding molecule depending on ion concentration conditions" and/or flexible residues as described in a non-limiting aspect of the present invention, nucleic acid cassettes having the sequence diversity of heavy chain CDR3 can be prepared and then linked to nucleic acid cassettes encoding randomized variable regions such as naive sequences. As in the library, the nucleic acid cassettes can be inserted to expression vectors comprising additional antibody sequences, for example, whole or partial light and heavy chain variable or constant regions, in order to prepare antigen-binding molecules comprising these variant amino acids or variant amino acid combinations. These additional sequences in the antigen-binding molecules can be fused with other nucleic acid sequences, for example, sequences encoding a viral coat protein constituent. As a result, fusion proteins can be produced.

Vector

One non-limiting aspect of the present invention includes a replicable expression vector comprising a nucleic acid sequence encoding a fusion gene, wherein the fusion gene encodes a fusion protein comprising one variable region of the antigen-binding molecule or one variable region of the antigen-binding molecule and one constant region, fused with the whole or a portion of a viral coat protein. One non-limiting aspect of the present invention also includes a library of diverse replicable expression vectors each comprising a plurality of fusion genes each encoding a plurality of different fusion proteins comprising the variable regions with diverse sequences formed as described above in the plurality of antigen-binding molecules differing in sequence from each other. The vectors may comprise various constituents and are preferably constructed so that the variable region genes of the antigen-binding molecules can be transferred between different vectors and/or the fusion proteins can be displayed in different formats.

Preferred examples of the vectors include phage vectors. The phage vectors have a phage replication origin that permits phage replication and phage particle formation. Preferred examples of the phage can include filamentous bacteriophages including M13, fl, fd, and Pf3 phages and derivatives thereof, and lambdoid phages including lambda, 21, phi80, phi81, 82, 424, 434, and other phages and derivatives thereof.

Examples of the viral coat protein include infectious protein PIII, major coat protein PVIII, pVII, pIX, Soc (T4), Hoc (T4), gpD (bacteriophage λ), and minor bacteriophage coat protein 6 (pVI) (filamentous phage (J. Immunol. Methods. (1999) 231 (1-2), 39-51); and M13 bacteriophage major coat protein variant (P8) (Protein Sci. (2000) 9 (4), 647-654)). The fusion protein is displayed on phage surface. Appropriate phage systems include M13KO7 helper phage, M13R408, M13-VCS, and Phi X 174, pJuFo phage system (J. Virol. (2001) 75 (15), 7107-7113), hyper phage (Nat. Biotechnol. (2001) 19 (1), 75-78), and KM13 (Fold Des. (1998) 3 (5), 321-328). A preferred helper phage is M13KO7. A preferred coat protein is M13 phage gene III coat protein. A preferred host is *E. coli*, and a protease-deficient strain of *E. coli*. For example, vectors such as fth1 vectors (Nucleic Acids Res. (2001) 29 (10) e50) can be useful in the expression of the fusion protein.

The expression vector may also comprise a secretory signal sequence fused with a DNA encoding the heavy or light chain variable region of the antigen-binding molecule or a fragment thereof. This sequence is typically located at the 5'-flank of the gene encoding the fusion protein and thus transcribed at the amino terminus of the fusion protein. In some case, however, the signal sequence has been demonstrated to be located at a position other than the 5'-flank of the gene encoding the protein to be secreted. This sequence targets the protein to which the sequence is bound across the inner membrane of a bacterial cell. The DNA encoding the signal sequence is obtained as a restriction endonuclease fragment from any gene encoding a protein having the signal sequence. For example, a gene encoding LamB or OmpF (Wong et al., Gene (1983), 68 (2), 193-203), MalE, or PhoA and other genes may be used as appropriate prokaryotic signal sequences. A preferred prokaryotic signal sequence for carrying out the present invention is *E. coli* heat-stable enterotoxin II (STII) signal sequence described by Chang et al. (Gene (1987) 55 (2-3), 189-196), pelB, or malE.

The vector generally comprises a promoter as a control sequence that promotes the expression of the fusion protein. Promoters generally used in prokaryotic vectors include a lacZ promoter system, an alkaline phosphatase phoA promoter (Ap), a bacteriophage λPL promoter (temperature-sensitive promoter), a tac promoter (hybrid trp-lac promoter that is regulated by lac repressor), a tryptophan promoter, a pBAD promoter, and a bacteriophage T7 promoter. The promoters are reviewed in the textbook of Sambrook et al. (supra). Although these promoters are most commonly used, other appropriate microbial promoters may be similarly used.

The vector can also comprise other nucleic acid sequences, for example, sequences encoding gD tags, c-Myc epitopes, polyhistidine tags, fluorescent proteins (e.g., GFP), or β-galactosidase protein useful in the detection or purification of the fusion protein expressed on the phage or cell surface. For example, the gD tag-encoding nucleic acid sequence also enables positive or negative selection of cells or viruses expressing the fusion protein. In some embodiments, the gD tag is preferably fused with an antigen-binding molecule variable region unfused with the viral coat protein constituent. For example, the polyhistidine tag-encoding nucleic acid sequence is useful for identifying a fusion protein comprising an antigen-binding molecule variable region that binds to a specific antigen using an immunohistochemical approach. Such a tag useful in the detection of antigen binding can be fused with an antigen-binding molecule variable region unfused with the viral coat protein constituent or an antigen-binding molecule variable region fused with the viral coat protein constituent.

Preferred examples of other useful constituents in the vector used to carry out the present invention include phenotypic selective genes. A typical phenotypic selective gene is a gene encoding a protein that imparts antibiotic resistance to host cells. As such an example, an ampicillin resistance gene (ampr) and a tetracycline resistance gene (tetr) can be preferably used.

The vector may also comprise a nucleic acid sequence containing unique restriction sites and a suppressible stop codon. The unique restriction sites are useful for transferring the variable region gene of the antigen-binding molecule between different vectors and expression systems and particularly useful for producing the full-length antigen-binding molecule or antigen-binding fragment by cell culture. The suppressible stop codon is useful for regulating the expression level of the fusion protein and facilitates the purification of a soluble fragment of the antigen-binding molecule. For example, an amber stop codon can be translated into Gln in a supE host capable of phage display, whereas the codon is interpreted in a non-supE host as a stop codon to produce a soluble fragment of the antigen-binding molecule unfused with the phage coat protein. These synthetic sequences can be fused with genes encoding one or more variable regions of the antigen-binding molecule in the vector.

A vector can be preferably used, which allows the nucleic acid encoding the sequence of the antigen-binding molecule of interest to be easily retrieved from the vector and placed in another vector. For example, appropriate restriction sites can be incorporated into the vector in order to facilitate the retrieval of the nucleic acid sequence encoding the antigen-binding molecule of the present invention or its variable region. The restriction sequences are usually selected as unique ones in the vector in order to facilitate efficient excision and ligation into fresh vectors. The antigen-binding molecule or its variable region can then be expressed from the vectors as a molecule having a structure free from the fused foreign sequences, for example, the viral coat protein or other sequence tags.

A DNA encoding a termination or stop codon can be inserted between the nucleic acid encoding the variable region or constant region of the antigen-binding molecule (gene 1) and the nucleic acid encoding the viral coat protein constituent (gene 2). Such a termination codon includes UAG (amber), UAA (ocher), and UGA (opel) (Davis et al., Microbiology (1980), p. 237, 245-247, and 374, Harper & Row, New York). The termination or stop codon expressed in wild-type host cells results in the synthesis of the gene 1 protein product unbound with the gene 2 protein. The fusion protein, however, is synthesized in a detectable amount by growth in suppressor host cells. Such suppressor host cells are known in the art and described as *E. coli* suppressor gene strains (Bullock et al., BioTechniques (1987) 5, 376-379), etc. Such a termination codon can be inserted into an mRNA encoding the fusion polypeptide.

The suppressible codon can be inserted between the first gene encoding the variable or constant region of the antigen-binding molecule and a second gene encoding at least a portion of a phage coat protein. Alternatively, the suppressible termination codon may be inserted adjacent to the fusion site by the replacement of a triplet for the last amino acid in the variable region of the antigen-binding molecule or a triplet for the first amino acid in the phage coat protein. The suppressible termination codon may be inserted at or following a position corresponding to the C terminus of a dimerization domain. The replication of a plasmid containing the suppressible codon in suppressor host cells yields the fusion polypeptide comprising the polypeptide and the coat protein in a detectable amount. The replication of the plasmid in non-suppressor host cells terminates the translation at the inserted suppressible triplet UAG, UAA, or UGA and therefore results in the synthesis of the antigen-binding molecule variable region substantially without being fused with the phage coat protein. Accordingly, the antigen-binding molecule variable region expressed in non-suppressor cells is secreted from the host cells after synthesis, due to the absence of the fused phage coat protein to be anchored to the host membrane.

The light chain and/or heavy chain variable or constant regions of the antigen-binding molecule can be further fused with a peptide sequence that permits the interaction of one or more fusion polypeptides on viral particle or cell surface. This peptide sequence is referred to as a "dimerization domain" herein. The dimerization domain can comprise at least one or more dimerization sequences or at least one sequence comprising a cysteine residue, or both. Appropriate dimerization sequences include those of proteins having amphipathic α-helices that contain regularly spaced hydrophobic residues and permit dimer formation by the interaction of the hydrophobic residues of each protein. Such proteins and portions of the proteins comprise, for example, leucine zipper regions. The dimerization domain can also comprise one or more cysteine residues (e.g., provided by an antibody hinge sequence contained in the dimerization domain). The cysteine residues provide for dimerization by the formation of one or more disulfide bonds. In one embodiment wherein a stop codon is located downstream from a sequence encoding the dimerization domain, the dimerization domain comprises at least one cysteine residue. The dimerization domain is preferably located between the antibody variable or constant domain and the viral coat protein constituent.

In some cases, the vector encodes, for example, a phage polypeptide of a single antigen-binding molecule in a single-chain form comprising heavy and light chain variable regions fused with a coat protein. In these cases, the vector is considered "monocistronic" so that one transcript is expressed under the control of a certain promoter. Examples of such a vector include vectors that employ alkaline phosphatase (AP) or Tac promoter to promote the expression of a monocistronic sequence encoding the light chain variable region (VL domain) and the heavy chain variable region (VH domain) between which a linker peptide is located. Such a cistronic sequence is linked at its 5' end to an *E. coli* malE or heat-stable enterotoxin II (STII) signal sequence and at its 3' end to the whole or a portion of a viral coat protein (e.g., pIII protein). In some embodiments, the vector may further comprise a sequence encoding a dimerization domain (e.g., a leucine zipper), as shown in SEQ ID NO: 12, at its 3' end between the second variable region sequence and the viral coat protein sequence.

In other cases, the heavy and light chain variable regions can be expressed as separate polypeptides. Such a vector is "bicistronic" and permits the expression of separate transcripts. In this vector, an appropriate promoter, for example, tac or PhoA promoter, can be used for promoting the expression of a bicistronic mRNA. The first cistron encoding, for example, light chain variable and constant regions is linked at its 5' end to an *E. coli* malE, pelB, or heat-stable enterotoxin II (STII) signal sequence and at its 3' end to a gD tag-encoding nucleic acid sequence. The second cistron encoding, for example, a heavy chain variable region and constant region CH1, is linked at its 5' end to an *E. coli* malE or heat-stable enterotoxin II (STII) signal sequence and at its 3' end to the whole or a portion of a viral coat protein.

In a vector that generates a bicistronic mRNA and permits display of F(ab')2-pIII, an appropriate promoter, for example tac or PhoA (AP) promoter, promotes the expression of the first cistron that encodes light chain variable and constant regions and is operably linked at its 5' end to an *E. coli* malE or heat-stable enterotoxin II (STII) signal sequence and at its 3' end to a gD tag-encoding nucleic acid sequence. The second cistron encodes, for example, heavy chain variable and constant regions and is operably linked at its 5' end to an *E. coli* malE or heat-stable enterotoxin II (STII) signal sequence and at its 3' end to a sequence encoding a dimerization domain comprising an IgG hinge sequence and a leucine zipper sequence followed by at least a portion of a viral coat protein.

Display of Fusion Polypeptide

The fusion polypeptide of the variable region of the antigen-binding molecule can be displayed in various forms on cell, virus, or phagemid particle surface. These forms include single-chain Fv fragments (scFv), F(ab) fragments, and multivalent forms of these fragments. The multivalent forms are preferably a dimer of ScFv, Fab, or F(ab'), which are referred to as (ScFv)2, F(ab)2, and F(ab')2, respectively, herein. The display of the multivalent forms is preferred, probably in part because the displayed multivalent forms usually permit identification of low-affinity clones and/or have a plurality of antigen-binding sites that permit more efficient selection of rare clones in the course of selection.

Methods for displaying fusion polypeptides comprising antibody fragments on the surface of bacteriophages are known in the art and described in, for example, WO1992001047 and the present specification. Other related methods are described in WO1992020791, WO1993006213, WO1993011236, and 1993019172. Those skilled in the art can appropriately use these methods. Other public literatures (H. R. Hoogenboom & G. Winter (1992) J. Mol. Biol. 227, 381-388, WO1993006213, and WO1993011236) disclose the identification of antibodies using artificially rearranged variable region gene repertoires against various antigens displayed on the surface of phages.

In the case of constructing a vector for display in the form of scFv, this vector comprises nucleic acid sequences encoding the light and heavy chain variable regions of the antigen-binding molecule. In general, the nucleic acid sequence encoding the heavy chain variable region of the antigen-binding molecule is fused with a nucleic acid sequence encoding a viral coat protein constituent. The nucleic acid sequence encoding the light chain variable region of the antigen-binding molecule is linked to the heavy chain variable region nucleic acid of the antigen-binding molecule through a nucleic acid sequence encoding a peptide linker. The peptide linker generally contains approximately 5 to 15 amino acids. Optionally, an additional sequence encoding, for example, a tag useful in purification or detection, may be fused with the 3' end of the nucleic acid sequence encoding the light chain variable region of the antigen-binding molecule or the nucleic acid sequence encoding the heavy chain variable region of the antigen-binding molecule, or both.

In the case of constructing a vector for display in the form of F(ab), this vector comprises nucleic acid sequences encoding the variable and constant regions of the antigen-binding molecule. The nucleic acid sequence encoding the light chain variable region is fused with the nucleic acid sequence encoding the light chain constant region. The nucleic acid sequence encoding the heavy chain variable region of the antigen-binding molecule is fused with the nucleic acid sequence encoding the heavy chain constant CH1 region. In general, the nucleic acid sequence encoding the heavy chain variable and constant regions is fused with a nucleic acid sequence encoding the whole or a portion of a viral coat protein. The heavy chain variable and constant regions are preferably expressed as a fusion product with at least a portion of the viral coat protein, while the light chain variable and constant regions are expressed separately from the heavy chain-viral coat fusion protein. The heavy and light chains may be associated with each other through a covalent bond or a non-covalent bond. Optionally, an additional sequence encoding, for example, a polypeptide tag useful in purification or detection, may be fused with the 3' end of the nucleic acid sequence encoding the light chain constant region of the antigen-binding molecule or the nucleic acid sequence encoding the heavy chain constant region of the antigen-binding molecule, or both.

Transfer of Vector to Host Cell

The vectors thus constructed are transferred to host cells for amplification and/or expression. The vectors can be transferred to host cells by transformation methods known in the art, including electroporation, calcium phosphate precipitation and the like. When the vectors are infectious particles such as viruses, the vectors themselves invade the host cells. Fusion proteins are displayed on the surface of phage particles by the transfection of host cells with replicable expression vectors having the inserts of the fusion protein-encoding polynucleotides and the production of the phage particles by an approach known in the art.

The replicable expression vectors can be transferred to host cells by use of various methods. In a non-limiting embodiment, the vectors can be transferred to the cells by electroporation as described in WO2000106717. The cells are cultured at 37° C., optionally for approximately 6 to 48 hours (or until OD at 600 nm reaches 0.6 to 0.8) in a standard culture medium. Next, the culture medium is centrifuged, and the culture supernatant is removed (e.g., by decantation). At the initial stage of purification, the cell pellet is preferably resuspended in a buffer solution (e.g., 1.0 mM HEPES (pH 7.4)). Next, the suspension is centrifuged again to remove the supernatant. The obtained cell pellet is resuspended in glycerin diluted to, for example, 5 to 20% V/V. The suspension is centrifuged again to remove the supernatant, thereby obtaining a cell pellet. The obtained cell pellet is resuspended in water or diluted glycerin. On the basis of the measurement value of the obtained cell concentration, the final cell concentration is adjusted to a desired concentration using water or diluted glycerin.

Examples of preferred receptor cells include an *E. coli* strain SS320 capable of responding to electroporation (Sidhu et al., Methods Enzymol. (2000) 328, 333-363). The *E. coli* strain SS320 has been prepared by the coupling of MC1061 cells with XL1-BLUE cells under conditions sufficient for transferring fertility episome (F' plasmid) or XL1-BLUE into the MC1061 cells. The *E. coli* strain SS320 has been deposited with ATCC (10801 University Boulevard, Manassas, Va.) under deposition No. 98795. Any F' episome that permits phage replication in this strain can be used in the present invention. Appropriate episome may be obtained from strains deposited with ATCC or may be obtained as commercially available products (TG1, CJ236, CSH18, DHF', ER2738, JM101, JM103, JM105, JM107, JM109, JM110, KS1000, XL1-BLUE, 71-18, etc.).

Use of higher DNA concentrations (approximately 10 times) in electroporation improves transformation frequency and increases the amount of DNAs transforming the host cells. Use of high cell concentrations also improves the efficiency (approximately 10 times). The increased amount of transferred DNAs can yield a library having greater diversity and a larger number of independent clones differing in sequence. The transformed cells are usually selected on the basis of the presence or absence of growth on an antibiotic-containing medium.

Method for Selecting Antigen-Binding Molecule Whose Binding Activity is Changed Depending on Conditions and Method for Isolating Polynucleotide Encoding the Molecule Methods for using phage display for identifying antigen-binding molecules that exhibit desired binding activity against antigens have already been established in the art, also including methods variously modified therefrom. In one non-limiting aspect, appropriate host cells are transformed with a library of replicable vectors constructed so as to comprise transcriptional regulatory elements operably linked to fusion genes encoding fusion polypeptides. The transformed cells are cultured to form phage particles displaying the fusion polypeptides on their surface. Then, the step of "selecting binding molecules" which entails selection and sorting by contacting the recombinant phage particles with target antigens so that at least a portion of the particle subpopulation binds to the antigens is carried out for the purpose of increasing antigen-bound particles in the subpopulation with respect to antigen-unbound particles in the course of selection. For another round of screening under different or the same reaction conditions, the sorted subpopulation is amplified, for example, by the infection of fresh host cells such as XL1-Blue cells with the subpopulation. Next, the step of contacting the thus-amplified subpopulation of the obtained antigen-binding molecules with antigens under different ion concentrations is carried out to screen for antigen-binding molecules that bind to the antigens under the desired condition. This step of contacting the subpopulation with antigens under different ion concentrations may be carried out as the initial step of the selection method. The combination of the step of "selecting binding molecules" and the step of selecting binding molecules whose binding activity is changed under different ion concentration conditions may be appropriately changed. Also, the step of selection and sorting can be performed as many times as desired. These antigen-binding molecules that bind to the antigens under the different ion concentration conditions are useful as therapeutic drugs capable of rapidly removing pathogenic antigens from organisms when administered to the organisms.

Fusion polypeptides of variable regions or portions thereof comprising the amino acid that changes the antigen-binding activity of the antigen-binding molecule depending on ion concentration conditions and/or flexible residues according to the present invention are expressed on the surface of phages, phagemid particles, or cells. Next, the members constituting the fusion polypeptide subpopulation can be selected and/or sorted for their ability to bind to antigens under different ion concentrations. The method of selection, sorting, and screening for the fusion polypeptides also include a method of selection, sorting, and screening on general proteins having affinity for the variable regions of the antigen-binding molecules, such as protein L or labeled antibodies capable of binding to the antigen-binding molecules or their fragments displayed on phages. Such a method can be used to enrich the library size or the number of equivalents of a library that displays fragments of correctly folded antigen-binding molecules (or fusion polypeptides comprising the molecules).

Two main strategies can be used for the above selection, sorting, and screening. The first strategy is a solid-support method, plate screening, or immobilized antigen screening. The second strategy is a solution binding method.

In the "solid-support method", antigens can be attached to an appropriate solid or semisolid matrix known in the art, for example, agarose beads, acrylamide beads, glass beads, cellulose, various acrylic copolymers, hydroxyalkyl methacrylate gels, polyacrylic and polymethacrylic copolymers, nylon, and neutral and ionic carriers. The attachment of the antigens to the matrix can be achieved by a method described in Methods in Enzymology (1976) 44 or by other means known in the art.

After the antigen attachment to the matrix, the immobilized antigens are contacted with the library expressing the fusion polypeptides under conditions suitable for the binding of at least one subset of a subpopulation of phage particles with the immobilized antigens. Usually, the conditions, including pH, ionic strength, temperature and the like, are selected to mimic physiological conditions. Bound particles ("binders") with the immobilized antigens are separated from particles unbound with the target by washing with water. The washing conditions can be adjusted so as to remove all but high-affinity binders. The binders can be dissociated from the immobilized target by various methods. These methods include, for example, competitive dissociation using wild-type ligands (e.g., excessive antigens), change of pH and/or ionic strength, and methods known in the art. In general, the binders can be eluted from the affinity matrix with an appropriate elution material such as an acid (e.g., 0.1 M HCl) or ligands. Elution at increased ligand concentrations may elute displayed binding molecules with higher affinity.

Appropriate host cells can be infected with the isolated binders, i.e., viral particles (and, if necessary, helper phages, for example, when the viral particles are phagemid particles) to re-amplify the binders in the cells. The host cells thus obtained are cultured under conditions suitable for the amplification of the particles that display the desired fusion polypeptide. Next, the phage particles are collected, and the selection step is repeated one or more times until the binders of the antigens are enriched to account for a considerable proportion. Selection or screening may be performed as many times as desired. One of the selection or screening methods may involve isolating binders that bind to general affinity proteins such as protein L or antibodies against polypeptide tags present in the displayed polypeptides, for example, antibodies against gD protein or polyhistidine tags.

In one aspect of the present invention, a solution-phase screening method called "solution binding method" may be appropriately used. The solution binding method can be used for finding improved binders from a random library or from a library aimed at improving the binding activity of a desired binding clone or clone group. This method involves contacting a plurality of polypeptides, for example, polypeptides displayed on phage or phagemid particles (library), with antigens labeled or fused with tag molecules. Biotin or other specific binders can be used as the tag. The stringency of the solution phase can be varied using gradually decreased concentrations of labeled or fused antigens in the first solution binding phase. In order to further increase the stringency, the binding to the first antigens labeled with tag molecules or fused with labeled tag molecules in the first solution phase may be appropriately followed by additional contact with a second solution phase having a high concentration of antigens unlabeled with tag molecules or unfused with labeled tag molecules. In this case, the antigens unlabeled with tag molecules or unfused with labeled tag molecules are usually used in an amount of 100 to 1000 times the amount of the labeled target in the second phase. The incubation time of the first solution phase ranges from a few minutes to 1 to 2 hours or longer until reaching equilibrium. Since binders having a fast associate rate tend to have the property of binding to the target in a short time in this first phase, contact conditions for shortening the binding time may be adopted. The incubation time and temperature of the second phase can be varied in order to increase the stringency. Such variations in incubation conditions produce a selection bias for binders that come off the target at a slow rate (dissociation rate). After the contact of the plurality of polypeptides displayed on the phage or phagemid particles with the antigens, the phage or phagemid particles bound with the antigens labeled with tag molecules or fused with labeled tag molecules are separated from the unbound phage or phagemid particles. The phage or phagemid particle-antigen mixtures are isolated from the solution phase by the contact of the phage or phagemid particles with the antigens for a short time (e.g., 2 to 5 minutes) that allows for binding with the antigens labeled with tag molecules or fused with labeled tag molecules. The initial concentration of the antigens labeled with tag molecules or fused with labeled tag molecules ranges from approximately 0.1 nM to approximately 1000 nM. The particles can be eluted from the mixtures and then grown for the next round of screening. Multiple rounds of screening are preferably repeated using a lower concentration of the antigens labeled with tag molecules or fused with labeled tag molecules in each round of screening. As described later in Examples, for example, streptavidin-coated magnetic beads can be appropriately used in the solution binding method using biotin as the labeled tag molecule.

The solid-support method and the solution binding method may be appropriately performed alone or in combination in order to isolate binders having the desired character. After two, three, or four repetitive rounds of selection and screening for the antigens, the subpopulation selected for identifying specific binders having the desired property or character is usually screened for individual clones. Preferably, the screening process can be carried out using an automation system that enables high-throughput screening of the library.

After the identification of the binders on the basis of antigen binding, nucleic acids can be extracted from the binders. The extracted DNAs are then used for directly transforming E. coli host cells. Alternatively, the coding sequences thereof can be amplified, for example, by PCR using appropriate primers, and then sequenced by a typical sequencing method. Next, the variable region-encoding DNAs of the binders can be inserted to vectors digested with restriction enzymes for expression of the encoded antigen-binding molecules.

In order to select and screen phage particles expressing the antigen-binding molecule of the present invention whose antigen-binding activity is changed depending on ion concentration conditions, or the fusion polypeptide thereof, a subpopulation of phage particles whose antigen-binding activity is changed is sorted by varying conditions for contacting immobilized antigens with a library comprising phage particles expressing antigen-binding molecules or fusion polypeptides.

Taking a calcium ion as a preferred example of the metal ion, examples of the calcium ion concentration conditions include a low-calcium ion concentration condition and a high-calcium ion concentration condition. The phrase "binding activity is changed depending on calcium ion concentration conditions" means that the antigen-binding activity of each antigen-binding molecule is changed depending on the difference between the low-calcium ion concentration condition and the high-calcium ion concentration condition. Examples of this case include higher antigen-binding activity of the antigen-binding molecule under the high-calcium ion concentration condition than that under the low-calcium ion concentration condition. Another example thereof includes higher antigen-binding activity of the antigen-binding molecule under the low-calcium ion concentration condition than that under the high-calcium ion concentration condition.

In the present specification, the high calcium ion concentration is not particularly limited to a univocal numeric value and can be preferably a concentration selected from the range of 100 µM to 10 mM. In another aspect, the high calcium ion concentration may be a concentration selected from the range of 200 µM to 5 mM. In a different aspect, the high calcium ion concentration may also be a concentration selected from the range of 500 µM to 2.5 mM. In an alternative aspect, the high calcium ion concentration may also be a concentration selected from the range of 200 µM to 2 mM. In addition, this concentration may also be a concentration selected from the range of 400 µM to 1.5 mM. Particularly preferred examples thereof include concentrations selected from the range of 500 µM to 2.5 mM, which are close to in vivo calcium ion concentrations in plasma (blood).

In the present specification, the low calcium ion concentration is not particularly limited to a univocal numeric value and can be preferably a concentration selected from the range of 0.1 µM to 30 µM. In another aspect, the low calcium ion concentration may be a concentration selected from the range of 0.2 µM to 20 µM. In a different aspect, the low calcium ion concentration may also be a concentration selected from the range of 0.5 µM to 10 µM. In an alternative aspect, the low calcium ion concentration may also be a concentration selected from the range of 1 µM to 5 µM. In addition, this concentration may also be a concentration selected from the range of 2 µM to 4 µM. Particularly preferred examples thereof include concentrations selected from the range of 1 µM to 5 µM, which are close to in vivo ionized calcium concentrations in early endosome.

In the present invention, the phrase "antigen-binding activity of the antigen-binding molecule is lower under the low-calcium ion concentration condition than that under the high-calcium ion concentration condition" means that the antigen-binding activity of the antigen-binding molecule at a calcium ion concentration selected from the range of 0.1 µM to 30 µM is weaker than that at a calcium ion concentration selected from the range of 100 µM to 10 mM. This phrase preferably means that the antigen-binding activity of the antigen-binding molecule at a calcium ion concentration selected from the range of 0.5 µM to 10 µM is weaker than that at a calcium ion concentration selected from the range of 200 µM to 5 mM. The phrase particularly preferably means that the antigen-binding activity at an in vivo calcium ion concentration in early endosome is weaker than that at an in vivo calcium ion concentration in plasma. This specifically means that the antigen-binding activity of the antigen-binding molecule at a calcium ion concentration selected from the range of 1 µM to 5 µM is weaker than that at a calcium ion concentration selected from the range of 500 µM to 2.5 mM.

In order to select and screen, for example, phage particles expressing antigen-binding molecules whose antigen-binding activity is higher under the high-calcium ion concentration condition than that under the low-calcium ion concentration condition or fusion polypeptides thereof, a subpopulation of phage particles binding to immobilized antigens under the high-calcium concentration condition is first sorted. Then, the sorted subpopulation (library comprising phage particles expressing antigen-binding molecules or fusion polypeptides) is contacted with immobilized antigens under the low-calcium concentration condition. Phage particles that do not bind to the immobilized antigens under the low-calcium concentration condition are sorted and separated into a supernatant or subsequent washes. The high calcium concentration condition and the low-calcium concentration condition can be appropriately adopted within the ranges described above. In a non-limiting aspect, the subpopulation can be sorted on the basis of the difference between the antigen-binding activity at a calcium ion concentration selected from the range of 0.1 µM to 30 µM and the antigen-binding activity at a calcium ion concentration selected from the range of 100 µM to 10 mM. In another non-limiting aspect, the subpopulation may be sorted on the basis of the difference between the antigen-binding activity at a calcium ion concentration selected from the range of 0.5 µM to 10 µM and the antigen-binding activity at a calcium ion concentration selected from the range of 200 µM to 5 mM. In an alternative non-limiting aspect, the subpopulation may be sorted on the basis of the difference between the antigen-binding activity at an in vivo calcium ion concentration in early endosome and the antigen-binding activity at an in vivo calcium ion concentration in plasma, specifically, the difference between the antigen-binding activity at a calcium ion concentration selected from the range of 1 µM to 5 µM and the antigen-binding activity at a calcium ion concentration selected from the range of 500 µM to 2.5 mM.

Taking a hydrogen ion concentration as a preferred example of the ion concentration, examples of the hydrogen ion concentration conditions include an acidic pH condition and a neutral pH condition. The phrase "binding activity is changed depending on pH conditions" means that the antigen-binding activity of each antigen-binding molecule is changed depending on the difference between the acidic pH and the neutral pH. Examples of this case include higher antigen-binding activity of the antigen-binding molecule at the neutral pH than that at the acidic pH. Another example thereof includes higher antigen-binding activity of the antigen-binding molecule at the acidic pH than that at the neutral pH.

In the present specification, the neutral pH is not particularly limited to a univocal numeric value and can be preferably selected from the range of pH 6.7 to pH 10.0. In another aspect, the neutral pH may be selected from the range of pH 6.7 to pH 9.5. In a different aspect, the neutral pH may be selected from the range of pH 7.0 to pH 9.0. In an alternative aspect, this pH may be selected from the range of pH 7.0 to pH 8.0. Particularly preferred examples thereof include pH 7.4, which is close to in vivo pH in plasma (blood).

In the present specification, the acidic pH is not particularly limited to a univocal numeric value and can be preferably selected from the range of pH 4.0 to pH 6.5. In another aspect, the acidic pH may be selected from the range of pH 4.5 to pH 6.5. In a different aspect, the acidic pH may be selected from the range of pH 5.0 to pH 6.5. In an alternative aspect, this pH may be selected from the range of pH 5.5 to pH 6.5. Particularly preferred examples thereof include pH 5.8, which is close to in vivo ionized calcium concentration in early endosome.

In the present invention, the phrase "antigen-binding activity of the antigen-binding molecule is lower under the neutral pH condition than that under the acidic pH condition" means that the antigen-binding activity of the antigen-binding molecule at a pH selected from the range of pH 4.0 to pH 6.5 is weaker than that at a pH selected from the range of pH 6.7 to pH 10.0. This phrase preferably means that the antigen-binding activity of the antigen-binding molecule at a pH selected from the range of pH 4.5 to pH 6.5 is weaker than that at a pH selected from the range of pH 6.7 to pH 9.5. The phrase more preferably means that the antigen-binding activity of the antigen-binding molecule at a pH selected from the range of pH 5.0 to pH 6.5 is weaker than that at a pH selected from the range of pH 7.0 to pH 9.0. The phrase further preferably means that the antigen-binding activity of the antigen-binding molecule at a pH selected from the range of pH 5.5 to pH 6.5 is weaker than that at a pH selected from the range of pH 7.0 to pH 8.0. The phrase particularly preferably means that the antigen-binding activity at in vivo pH in early endosome is weaker than that at an in vivo pH in plasma. This specifically means that the antigen-binding activity of the antigen-binding molecule at pH 5.8 is weaker than that at pH 7.4.

Whether or not the antigen-binding activity of the antigen-binding molecule is changed depending on the pH conditions can be determined, for example, according to a binding activity assay method under the different pH conditions described above. For example, the antigen-binding activity of the antigen-binding molecule is compared between the acidic pH condition and the neutral pH condition in order to confirm that the antigen-binding activity of the antigen-binding molecule is changed to a higher level under the neutral pH condition than that under the acidic pH condition.

In order to select and screen, for example, phage particles expressing antigen-binding molecules whose antigen-binding activity is higher under the neutral pH condition than that under the acidic pH condition or fusion polypeptides thereof, a subpopulation of phage particles binding to immobilized antigens under the neutral pH condition is first sorted. Then, the sorted subpopulation (library comprising phage particles expressing antigen-binding molecules or fusion polypeptides) is contacted with immobilized antigens under the acidic pH condition. Phage particles that do not bind to the immobilized antigens under the acidic pH condition are sorted and separated into a supernatant or subsequent washes. The neutral pH condition and the acidic pH condition can be appropriately adopted within the ranges described above. In a non-limiting aspect, the subpopulation can be sorted on the basis of the difference between the antigen-binding activity at a pH selected from the range of pH 4.0 to pH 6.5 and the antigen-binding activity at a pH selected from the range of pH 6.7 to pH 10.0. In another non-limiting aspect, the subpopulation may be sorted on the basis of the difference between the antigen-binding activity at a pH selected from the range of pH 4.5 to pH 6.5 and the antigen-binding activity at a pH selected from the range of pH 6.7 to pH 9.5. In an alternative non-limiting aspect, the subpopulation may be sorted on the basis of the difference between the antigen-binding activity at a pH selected from the range of pH 5.0 to pH 6.5 and the antigen-binding activity at a pH selected from the range of pH 7.0 to pH 9.0. In addition, the subpopulation may be sorted on the basis of the difference between the antigen-binding activity at a pH selected from the range of pH 5.5 to pH 6.5 and the antigen-binding activity at a pH selected from the range of pH 7.0 to pH 8.0. In a further alternative non-limiting aspect, the subpopulation may be sorted on the basis of the difference between the antigen-binding activity at in vivo pH in early endosome and the antigen-binding activity at in vivo pH in plasma, specifically, the difference between the antigen-binding activity at pH 5.8 and the antigen-binding activity at pH 7.4.

Method for Producing Antigen-Binding Molecule Whose Binding Activity is Changed Depending on Conditions In a non-limiting aspect of the present invention, a polynucleotide encoding the thus-selected antigen-binding molecule whose binding activity is changed depending on conditions is isolated and then inserted to an appropriate expression vector. Specifically, after obtainment of each cDNA encoding the variable region of the antigen-binding molecule of interest, the cDNA is digested with restriction enzymes that recognize the restriction sites inserted in both ends of the cDNA. Preferably, the restriction enzymes recognize and digest a nucleotide sequence that appears at low frequency in nucleotide sequences constituting genes of antigen-binding molecules. Further preferably, the restriction enzymes cleave the sites inserted therein to produce cohesive ends, in order to insert one copy of the digested fragment in the correct direction in a vector. The antibody-binding molecule variable region-encoding cDNAs thus digested can be inserted to appropriate expression vectors to obtain expression vectors for the antigen-binding molecule of the present invention. In this case, antibody constant region (C region)-encoding genes can be fused in frame with the variable region-encoding genes.

In order to produce the desired antigen-binding molecule, the polynucleotide encoding the antigen-binding molecule is incorporated into expression vectors in a form operably linked to control sequences. The control sequences encompass, for example, enhancers and promoters. Also, an appropriate signal sequence for extracellular secretion of the expressed antigen-binding molecule may be linked to the amino terminus thereof. For example, a peptide having an amino acid sequence MGWSCIILFLVATATGVHS (SEQ ID NO: 13) can be used as the signal sequence. Any other suitable signal sequence may be linked thereto. The expressed polypeptide is cleaved at the carboxyl end of the signal sequence, and the cleaved polypeptide can be extracellularly secreted as a mature polypeptide. Appropriate host cells can be transformed with these expression vectors to obtain recombinant cells expressing the polynucleotide encoding the desired antigen-binding molecule.

For the expression of the antigen-binding molecule-encoding polynucleotide, the heavy chain-encoding polynucleotide and the light chain-encoding polynucleotide of the antigen-binding molecule are separately incorporated in different expression vectors. The same host cell can be co-transfected with the heavy chain-incorporated vector and the light chain-incorporated vector and thereby allowed to express antigen-binding molecules comprising the heavy and light chains. Alternatively, the heavy chain- and light chain-encoding polynucleotides may be incorporated into a single expression vector, with which a host cell can then be transformed (see WO1994011523).

Many combinations of host cells and expression vectors are known in the art for preparation of the antigen-binding molecule by the transfer of the isolated polynucleotide encoding the antigen-binding molecule into appropriate hosts. All of these expression systems can be applied to the isolation of the antigen-binding molecule of the present invention. In the case of using eukaryotic cells as the host cells, animal, plant, or fungus cells can be appropriately used. Specifically, examples of the animal cells can include the following cells:

(1) mammalian cells such as CHO (Chinese hamster ovary cell line), COS (monkey kidney cell line), myeloma cells (Sp2/O, NS0, etc.), BHK (baby hamster kidney cell line), HEK293 (human embryonic kidney cell line with sheared adenovirus (Ad)5 DNA), PER.C6 cells (human embryonic retinal cell line transformed with the adenovirus type 5 (Ad5) E1A and E1B genes), Hela, and Vero (Current Protocols in Protein Science (May, 2001, Unit 5.9, Table 5.9.1));

(2) amphibian cells such as *Xenopus* oocytes; and (3) insect cells such as sf9, sf21, and Tn5.

Alternatively, antibody gene expression systems using cells derived from the genus *Nicotiana* (e.g., *Nicotiana tabacum*) as the plant cells are known in the art. Cultured callus cells can be appropriately used for the plant cell transformation.

The following cells can be used as the fungus cells:
cells derived from yeasts of the genus *Saccharomyces* (e.g., *Saccharomyces cerevisiae*) and the genus *Pichia* (e.g., *Pichia pastoris*), and
cells derived from filamentous fungi of the genus *Aspergillus* (e.g., *Aspergillus niger*).

Also, expression systems for antigen-binding molecule-encoding polynucleotides using prokaryotic cells are known in the art. In the case of using, for example, bacterial cells, cells of bacteria such as *E. coli* and *Bacillus subtilis* can be appropriately used. The expression vectors comprising the antigen-binding molecule-encoding polynucleotide of interest are transferred into these cells by transformation. The transformed cells are cultured in vitro, and the desired antigen-binding molecule can be obtained from the resulting cultures of the transformed cells.

In addition to the host cells, transgenic animals may be used for the recombinant antigen-binding molecule production. Specifically, the desired antigen-binding molecule can be obtained from animals transfected with the polynucleotide encoding this antigen-binding molecule. For example, the antigen-binding molecule-encoding polynucleotide can be inserted in frame into genes encoding proteins specifically produced in milk to construct fusion genes. For example, goat β casein can be used as the proteins secreted into milk. DNA fragments comprising the fusion genes having the antigen-binding molecule-encoding polynucleotide insert are injected into goat embryos, which are in turn introduced into female goats. From milk produced by transgenic goats (or progeny thereof) brought forth by the goats that have received the embryos, the desired antigen-binding molecule can be obtained as a fusion protein with the milk protein. In addition, hormone can be administered to the transgenic goats in order to increase the amount of milk containing the desired antigen-binding molecule produced from the transgenic goats (Bio/Technology (1994), 12 (7), 699-702).

In the case of administering the antigen-binding molecule described herein to humans, an antigen-binding domain derived from a genetically recombinant antibody that has been engineered artificially can be appropriately adopted as an antigen-binding domain for the molecule, for example, for the purpose of reducing heteroantigenicity in humans. The genetically recombinant antibody encompasses, for example, humanized antibodies. These engineered antigen-binding molecules are appropriately produced using a method known in the art.

Each antigen-binding molecule variable region used for preparing the antigen-binding domain in the antigen-binding molecule described herein is typically composed of three complementarity-determining regions (CDRs) flanked by four framework regions (FRs). The CDRs are regions that substantially determine the binding specificity of the antigen-binding molecule. The CDRs have diverse amino acid sequences. On the other hand, the FRs are mostly constituted by amino acid sequences that are highly identical even among antigen-binding molecules differing in binding specificity. Therefore, in general, the binding specificity of a certain antigen-binding molecule can be transplanted to other antigen-binding molecules through CDR grafting.

The humanized antibodies are also called reshaped human antibodies. Specifically, for example, a humanized antibody consisting of a non-human animal (e.g., mouse) antibody CDR-grafted human antibody is known in the art. General gene recombination approaches are also known for obtaining the humanized antibodies. Specifically, for example, overlap extension PCR is known in the art as a method for grafting mouse antibody CDRs to human FRs. In the overlap extension PCR, a nucleotide sequence encoding each mouse antibody CDR to be grafted is added to primers for human antibody FR synthesis. The primers are prepared with respect to each of the four FRs. For grafting the mouse CDRs to the human FRs, it is generally regarded as advantageous to select human FRs highly identical to mouse FRs, in order to maintain the CDR functions. Specifically, in general, human FRs comprising amino acid sequences highly identical to those of FRs adjacent to the mouse CDRs to be grafted are preferably used.

The nucleotide sequences to be linked are designed so that the sequences are connected in frame with each other. The human FR-encoding nucleotide sequences are individually synthesized using their respective primers. The resulting products contain the mouse CDR-encoding DNA added to each human FR-encoding sequence. The mouse CDR-encoding nucleotide sequences are designed so that the nucleotide sequence in each product overlaps with another. Subsequently, the overlapping CDR portions in the products synthesized with human antibody genes as templates are annealed to each other for complementary strand synthesis reaction. Through this reaction, the human FR sequences are linked via the mouse CDR sequences.

Finally, the full-length sequence of the gene of the V region comprising three CDRs and four FRs linked is amplified using primers that each anneal to the 5' and 3' ends thereof and have an added recognition sequence for an appropriate restriction enzyme. The DNA thus obtained and a human antibody C region-encoding DNA can be inserted into expression vectors such that these DNAs are fused in frame to prepare vectors for humanized antibody expression. These vectors having the inserts are transferred to hosts to establish recombinant cells. Then, the recombinant cells are cultured for the expression of the humanized antibody-encoding DNA to produce the humanized antibodies into the cultures of the cultured cells (EP239400 and WO1996002576).

The humanized antibodies thus prepared can be evaluated for their antigen-binding activity by qualitative or quantitative assay to thereby select suitable human antibody FRs that allow CDRs to form a favorable antigen-binding site when linked via the CDRs. If necessary, FR amino acid residue(s) may be substituted such that the CDRs of the resulting reshaped human antibody form an appropriate antigen-binding site. For example, the amino acid sequence of FR can be mutated by the application of the PCR method used in the mouse CDR grafting to the human FRs. Specifically, a mutation of a partial nucleotide sequence can be introduced to the primers annealing to a FR nucleotide sequence. The FR nucleotide sequence synthesized using such primers contains the mutation thus introduced. Such variant antibodies having the substituted amino acid(s) can be evaluated for their antigen-binding activity by the same assay as above to thereby select variant FR sequences having the desired properties (Sato et al., Cancer Res (1993) 53, 851-856).

In a non-limiting aspect of the present invention, a modified form of the thus-isolated polynucleotide encoding the selected antigen-binding molecule whose binding activity is changed depending on conditions is then inserted to appropriate expression vectors. One preferred example of such a modified form includes a humanized form of a polynucleotide sequence encoding the antigen-binding molecule of the present invention screened for using, as the randomized variable region library, a synthetic library or an immune library prepared from non-human animals as a source. The humanized form of the antigen-binding molecule can be prepared by the adoption of a method similar to the humanized antibody preparation method described above.

In other aspects, preferred examples of the modified form include modified forms of the isolated polynucleotide sequence that has been modified so as to bring about enhancement in the antigen-binding affinity (affinity maturation) of the antigen-binding molecule of the present invention screened for using a synthetic library or a naive library as the randomized variable region library. Such modified forms can be obtained by various affinity maturation procedures known in the art, including CDR mutagenesis (Yang et al., J. Mol. Biol. (1995) 254, 392-403), chain shuffling (Marks et al., Bio/Technology (1992) 10, 779-783), use of mutator strains of *E. coli* (Low et al., J. Mol. Biol. (1996) 250, 359-368), DNA shuffling (Patten et al., Curr. Opin. Biotechnol. (1997) 8, 724-733), phage display (Thompson et al., J. Mol. Biol. (1996) 256, 77-88), and sexual PCR (Clameri et al., Nature (1998) 391, 288-291).

Examples of the antigen-binding molecule prepared by the production method of the present invention include antigen-binding molecules comprising an FcRn (particularly, human FcRn)-binding domain, as described above. The FcRn (particularly, human FcRn)-binding domain can be used in various modified forms. In one aspect, preferred examples of the modified form of the present invention also include a polynucleotide encoding an antigen-binding molecule having a heavy chain, wherein a polynucleotide encoding such a modified form of the FcRn (particularly, human FcRn)-binding domain is linked in frame with the polynucleotide encoding the selected antigen-binding molecule whose binding activity is changed depending on conditions.

In a non-limiting aspect of the present invention, preferred examples of the FcRn (particularly, human FcRn)-binding domain include constant regions of antibodies such as IgG1 represented by SEQ ID NO: 14 (AAC82527.1 with N-terminally added Ala), IgG2 represented by SEQ ID NO: 15 (AAB59393.1 with N-terminally added Ala), IgG3 represented by SEQ ID NO: 16 (CAA27268.1), and IgG4 represented by SEQ ID NO: 17 (AAB59394.1 with N-terminally added Ala). The relatively long plasma retention of IgG molecules (slow disappearance from plasma) is attributed to the functions of FcRn known as a salvage receptor in the IgG molecules. IgG molecules taken up into endosome through pinocytosis bind to FcRn expressed in the endosome under the acidic condition in the endosome. IgG molecules that have failed to bind to FcRn are moved to lysosome and then degraded therein, whereas the FcRn-bound IgG molecules are migrated to cell surface and dissociated from FcRn under the neutral condition in plasma to go back to the plasma.

The "antigen-binding molecule whose antigen-binding activity is changed depending on calcium ion concentration conditions" of the present invention is strongly associated with an antigen under the high-calcium concentration condition in plasma and dissociated from the antigen under the low-calcium concentration condition in endosome. Thus, this antigen-binding molecule can be dissociated from the antigen in endosome. The "antigen-binding molecule whose antigen-binding activity is changed depending on calcium ion concentration conditions" of the present invention, which is strongly associated with an antigen under the high-calcium concentration condition in plasma and dissociated from the antigen under the low-calcium concentration condition in endosome, is thus dissociated from the antigen and can be reassociated with an antigen after being recycled into plasma by FcRn. This allows one molecule of the antigen-binding molecule to bind to a plurality of antigens repeatedly. Also, the antigen bound with the antigen-binding molecule is dissociated therefrom in endosome and therefore, is not recycled into plasma. This promotes the cellular uptake of antigens by the antigen-binding molecule. The administration of the antigen-binding molecule can promote antigen disappearance and decrease antigen concentration in plasma.

The "antigen-binding molecule whose antigen-binding activity is changed depending on pH conditions" of the present invention is strongly associated with an antigen under the neutral pH condition in plasma and dissociated from the antigen under the acidic condition in endosome. Thus, this antigen-binding molecule can be dissociated from the antigen in endosome. The "antigen-binding molecule whose antigen-binding activity is changed depending on pH conditions" of the present invention, which is strongly associated with an antigen under the neutral pH condition in plasma and dissociated from the antigen under the acidic condition in endosome, is thus dissociated from the antigen and can be reassociated with an antigen after being recycled into plasma by FcRn. This allows one molecule of the antigen-binding molecule to bind to a plurality of antigens repeatedly. Also, the antigen bound with the antigen-binding molecule is dissociated therefrom in endosome and therefore, is not recycled into plasma. This promotes the cellular uptake of antigens by the antigen-binding molecule. The administration of the antigen-binding molecule can promote antigen disappearance and decrease antigen concentration in plasma.

The ability to bind to FcRn under the high-calcium concentration condition in plasma can be imparted to the "antigen-binding molecule whose antigen-binding activity is changed depending on calcium ion concentration conditions" of the present invention, which is strongly associated with an antigen under the high-calcium concentration condition in plasma and dissociated from the antigen under the low-calcium concentration condition in endosome. This promotes the cellular uptake of a complex of the antigen-binding molecule and the antigen. Thus, the administration of the antigen-binding molecule can promote antigen disappearance from plasma and decrease antigen concentration in plasma.

The ability to bind to FcRn under the neutral pH condition in plasma can be imparted to the "antigen-binding molecule whose antigen-binding activity is changed depending on pH conditions" of the present invention, which is strongly associated with an antigen under the neutral pH condition in plasma and dissociated from the antigen under the acidic pH condition in endosome. This promotes the cellular uptake of a complex of the antigen-binding molecule and the antigen. Thus, the administration of the antigen-binding molecule can promote antigen disappearance from plasma and decrease antigen concentration in plasma.

A conventional antibody comprising an Fc region has no FcRn-binding activity under the neutral pH condition in plasma. The conventional antibody and antibody-antigen complex are therefore taken up into cells through nonspecific endocytosis and transported to cell surface by binding to FcRn under the acidic pH condition in endosome. Since FcRn is responsible for the antibody transport from endosome to cell surface, some FcRn receptors are considered to also exist on cell surface. The antibody is dissociated from FcRn under the neutral pH condition on cell surface and therefore recycled into plasma.

In consideration of the in vivo kinetics of the antibody comprising an Fc region (FcRn-binding domain), the "antigen-binding molecule whose antigen-binding activity is changed depending on calcium ion concentration conditions" of the present invention, which is strongly associated with an antigen under the high-calcium concentration condition in plasma and dissociated from the antigen under the low-calcium concentration condition in endosome, is associated with the antigen in plasma and is dissociated from the bound antigen in endosome. Thus, the disappearance rate of the antigen is considered equal to the rate of cellular uptake through nonspecific endocytosis. In the case of insufficient calcium ion concentration dependence of antigen binding of the antigen-binding molecule, antigens undissociated in endosome are recycled into plasma. By contrast, in the case of sufficient calcium ion concentration dependence of antigen binding of the antigen-binding molecule, the disappearance rate of the antigen is determined by the rate of cellular uptake through nonspecific endocytosis.

The "antigen-binding molecule whose antigen-binding activity is changed depending on pH conditions" of the present invention, which is strongly associated with an antigen under the neutral pH condition in plasma and dissociated from the antigen under the acidic pH condition in endosome, is associated with the antigen in plasma and is dissociated from the bound antigen in endosome. Thus, the disappearance rate of the antigen is considered equal to the rate of cellular uptake through nonspecific endocytosis. In the case of insufficient pH dependence of antigen binding of the antigen-binding molecule, antigens undissociated in endosome are recycled into plasma. By contrast, in the case of sufficient pH dependence of antigen binding of the antigen-binding molecule, the disappearance rate of the antigen is determined by the rate of cellular uptake through nonspecific endocytosis.

Accordingly, the ability to bind to FcRn at neutral pH can be imparted to the antigen-binding molecule comprising an FcRn-binding domain. The resulting antigen-binding molecule is taken up into cells in an FcRn-dependent manner through binding to FcRn present on cell surface. The rate of FcRn-mediated cellular uptake is faster than the rate of cellular uptake through nonspecific endocytosis. In this regard, the imparting of the ability to bind to FcRn at neutral pH can further accelerate the disappearance rate of the antigen in plasma. Specifically, the antigen-binding molecule having the ability to bind to FcRn at neutral pH delivers an antigen more rapidly into cells than the conventional antigen-binding molecule comprising an Fc region (having no FcRn-binding activity under the neutral pH condition in plasma) and dissociates the antigen in endosome. The dissociated antigen-binding molecule is recycled to cell surface or plasma where the molecule is reassociated with an antigen, resulting in FcRn-mediated cellular uptake again. The higher ability to bind to FcRn at neutral pH can accelerate the rate of rotation of this cycle and therefore accelerates the disappearance rate of the antigen in plasma. The antigen-binding activity at acidic pH of the antigen-binding molecule can be lowered with respect to that at neutral pH to thereby further enhance the efficiency. The increased number of rotation of this cycle per antigen-binding molecule probably allows one antigen-binding molecule to bind to a larger number of antigens.

The antigen-binding molecule of the present invention can comprise an antigen-binding domain and an FcRn (particularly, human FcRn)-binding domain. The FcRn-binding domain neither influences antigen binding nor relies on antigen type, also as seen from the mechanism mentioned above. The antigen-binding activity (binding ability) of the antigen-binding molecule under the low-calcium ion concentration condition is lowered with respect to that under the high-calcium ion concentration condition, and/or the FcRn-binding activity of this molecule at neutral pH in plasma is enhanced. This may promote the cellular uptake of antigens by the antigen-binding molecule and accelerate the disappearance rate of the antigens.

As described above, the antigen-binding molecule of the present invention can comprise the antigen-binding domain and the FcRn-binding domain, which neither influences antigen binding nor relies on antigen type, also as seen from the mechanism mentioned above. The antigen-binding activity (binding ability) of the antigen-binding molecule under the acidic pH condition is lowered with respect to that under the neutral pH condition, and/or the FcRn-binding activity of this molecule at neutral pH in plasma is enhanced. This may promote the cellular uptake of antigens by the antigen-binding molecule and accelerate the disappearance rate of the antigens.

The FcRn-binding activity of the FcRn-binding domain (e.g., antibody constant region) can be assayed by a method generally known to those skilled in the art, as mentioned above in the paragraph about binding activity. Conditions other than the pH can be appropriately determined by those skilled in the art. The antigen-binding activity and human FcRn-binding activity of the antigen-binding molecule can be evaluated on the basis of, for example, KD (dissociation constant), apparent KD (apparent dissociation constant), kd (dissociation rate), or apparent kd (apparent dissociation rate). These indexes can be measured by a method generally known to those skilled in the art, for example, using Biacore (GE Healthcare Bio-Sciences Corp.), a Scatchard plot, or a flow cytometer.

Conditions other than the pH for assaying the human FcRn-binding activity of the FcRn-binding domain (e.g., antibody constant region) may be appropriately selected by those skilled in the art without particular limitations. The human FcRn-binding activity can be assayed under conditions of, for example, a MES buffer and 37° C., as described in WO2009125825. Also, the human FcRn-binding activity of the FcRn-binding domain (e.g., antibody constant region) can be assayed by a method generally known to those skilled in the art, for example, using Biacore (GE Healthcare Bio-Sciences Corp.). In the human FcRn-binding activity assay, the FcRn-binding domain (e.g., antibody constant region) can be evaluated for its binding ability by the injection of an analyte human FcRn to a chip with the immobilized FcRn-binding domain or antigen-binding molecule of the present invention comprising the FcRn-binding domain or by the injection of the analyte FcRn-binding domain or antigen-binding molecule of the present invention comprising the FcRn-binding domain to a human FcRn-immobilized chip.

The neutral pH as a condition under which the FcRn-binding domain (e.g., antibody constant region) or the antigen-binding molecule comprising the FcRn-binding domain has FcRn-binding activity usually means pH 6.7 to pH 10.0. The neutral pH is preferably a range indicated by any pH value of pH 7.0 to pH 8.0 and is preferably selected from pH 7.0, 7.1, 7.2, 7.3, 7.4, 7.5, 7.6, 7.7, 7.8, 7.9, and 8.0, particularly preferably pH 7.4, which is close to in vivo pH in plasma (blood). The binding affinity of the human FcRn-binding domain for human FcRn at pH 7.4 may be difficult to evaluate due to its low binding affinity. In such a case, pH 7.0 can be used instead of pH 7.4. In the present invention, the acidic pH as a condition under which the human FcRn-binding domain or the antigen-binding molecule comprising the human FcRn-binding domain has FcRn-binding activity usually means pH 4.0 to pH 6.5. The acidic pH preferably means pH 5.5 to pH 6.5 and particularly preferably means pH 5.8 to pH 6.0, which are close to in vivo pH in early endosome. The temperature used in assay conditions may be any temperature of 10° C. to 50° C. at which the human FcRn-binding domain or the antigen-binding molecule comprising the human FcRn-binding domain is evaluated for its human FcRn-binding affinity. Preferably, a temperature of 15° C. to 40° C. is used for determining the human FcRn-binding affinity of the human FcRn-binding domain or the antigen-binding molecule comprising the human FcRn-binding domain. More preferably, any temperature of 20° C. to 35° C., for example, any one of the temperatures 20, 21, 22, 23, 24, 25, 26, 27, 28, 29, 30, 31, 32, 33, 34, and 35° C., is also used for determining the human FcRn-binding affinity of the human FcRn-binding domain or the antigen-binding molecule comprising the human FcRn-binding domain. The temperature 25° C. is one non-limiting example in an aspect of the present invention.

According to The Journal of Immunology (2009) 182: 7663-7671, the human FcRn-binding activity of natural human IgG1 is KD 1.7 µM at acidic pH (pH 6.0), but is hardly detectable at neutral pH. Accordingly, in a preferred aspect, the antigen-binding molecule of the present invention having human FcRn-binding activity at acidic pH and at neutral pH can be screened for, which includes an antigen-binding molecule having human FcRn-binding activity of KD 20 µM or stronger at acidic pH and human FcRn-binding activity equivalent to or stronger than that of natural human IgG at neutral pH. In a more preferred aspect, an antigen-binding molecule having human FcRn-binding activity of KD 2.0 µM or stronger at acidic pH and human FcRn-binding activity of KD 40 µM or stronger at neutral pH can be screened for. In a further preferred aspect, an antigen-binding molecule having human FcRn-binding activity of KD 0.5 µM or stronger at acidic pH and human FcRn-binding activity of KD 15 µM or stronger at neutral pH can be screened for. These KD values are determined by a method described in The Journal of Immunology (2009) 182: 7663-7671 (which involves immobilizing antigen-binding molecules onto a chip and injecting thereto human FcRn as an analyte).

In the present invention, the FcRn-binding domain preferably has human FcRn-binding activity at acidic pH and at neutral pH. An FcRn-binding domain naturally having human FcRn-binding activity at acidic pH and at neutral pH can be directly used as the domain. When the domain has no or weak human FcRn-binding activity at acidic pH and/or at neutral pH, amino acid(s) in the antigen-binding molecule can be modified to obtain an FcRn-binding domain having the desired human FcRn-binding activity. Alternatively, amino acid(s) in the human FcRn-binding domain may be preferably modified to obtain an FcRn-binding domain having the desired human FcRn-binding activity at acidic pH and/or at neutral pH. Also, amino acid(s) in the FcRn-binding domain naturally having human FcRn-binding activity at acidic pH and/or at neutral pH may be modified to obtain an FcRn-binding domain having the desired human FcRn-binding activity. Such amino acid modification that confers the desired binding activity to the human FcRn-binding domain can be found by the comparison of human FcRn-binding activity at acidic pH and/or at neutral pH between before and after the amino acid modification. Those skilled in the art can appropriately carry out the amino acid modification using an approach known in the art.

In the present invention, the term "modification of amino acid(s)" or "amino acid modification" in the FcRn-binding domain includes modification to an amino acid sequence different from the amino acid sequence of a starting FcRn-binding domain. Any FcRn-binding domain can be used as the starting domain as long as the resulting modified form of the starting FcRn-binding domain can bind to human FcRn at acidic pH and/or at neutral pH (hence, the starting FcRn-binding domain is not necessarily required to have human FcRn-binding activity under the acidic pH and/or neutral pH conditions). Preferred examples of the starting FcRn-binding domain include IgG antibody constant regions, i.e., natural constant regions represented by any of SEQ ID NOs: 14 to 17. Alternatively, an FcRn-binding domain further modified from an already modified FcRn-binding domain as the starting FcRn-binding domain may be preferably used as the modified FcRn-binding domain of the present invention. The starting FcRn-binding domain may mean the polypeptide itself, a composition containing the starting FcRn-binding domain, or an amino acid sequence encoding the starting FcRn-binding domain. The starting FcRn-binding domain can include FcRn-binding domains of IgG antibodies known in the art produced by recombination reviewed in the paragraph about the antibody. The starting FcRn-binding domain is not limited by its origin and can be obtained from an arbitrary nonhuman animal organism or a human. Preferred examples of the arbitrary organism include an organism selected from mice, rats, guinea pigs, hamsters, gerbils, cats, rabbits, dogs, goats, sheep, cattle, horses, camels, and nonhuman primates. In another aspect, the starting FcRn-binding domain may be obtained from a cynomolgus monkey, a marmoset, a rhesus monkey, a chimpanzee, or a human. Preferably, the starting Fc region can be obtained from human IgG1, though the starting FcRn-binding domain of the present invention is not limited by a particular class of IgG. This means that the Fc region of human IgG1, IgG2, IgG3, or IgG4 can be appropriately used as the starting Fc region. Sequences of proteins of immunological interest, NIH Publication No. 91-3242 describes a plurality of allotype sequences attributed to polymorphism as human IgG1, human IgG2, human IgG3, and human IgG4 Fc regions, any of which may be used in the present invention. Particularly, human IgG1 may have a sequence with DEL or EEM as the amino acid sequence of positions 356 to 358 defined by the EU numbering. Likewise, this means herein that the FcRn-binding domain of arbitrary IgG class or subclass from the arbitrary organism can be preferably used as the starting FcRn-binding domain. Examples of variants of naturally occurring IgG or manipulated forms thereof are described in public literatures (Curr. Opin. Biotechnol. (2009) 20 (6), 685-91; Curr. Opin. Immunol. (2008) 20 (4), 460-470; Protein Eng. Des. Sel. (2010) 23 (4), 195-202; WO2009086320, WO2008092117, WO2007041635, and WO2006105338), though the variants or the manipulated forms of the present invention are not limited to those described therein.

Amino acid(s) in the FcRn-binding domain involved in FcRn binding is appropriately mutated in order to impart the ability to bind to FcRn (particularly, human FcRn) at neutral pH to the antigen-binding molecule comprising the FcRn (particularly, human FcRn)-binding domain. In the case of using an IgG antibody molecule constant region as the FcRn-binding domain, examples of such a modified FcRn-binding domain include constant regions derived from natural IgG constant regions by the modification of amino acids at positions 221 to 225, 227, 228, 230, 232, 233 to 241, 243 to 252, 254 to 260, 262 to 272, 274, 276, 278 to 289, 291 to 312, 315 to 320, 324, 325, 327 to 339, 341, 343, 345, 360, 362, 370, 375 to 378, 380, 382, 385 to 387, 389, 396, 414, 416, 423, 424, 426 to 438, 440, and 442 defined by the EU numbering to amino acids different from the corresponding naturally occurring ones. More specifically, examples thereof include modified forms of constant regions containing Pro at amino acid position 256, Lys at amino acid position 280, Thr at amino acid position 339, His at amino acid position 385, Leu at amino acid position 428, and/or Trp, Tyr, Phe, Ala, or His at amino acid position 434 (all defined by the EU numbering). Use of these modified forms can strengthen the human FcRn-binding activity of the IgG immunoglobulin Fc region at neutral pH.

Alternatively, a modified form capable of binding to human FcRn more strongly at acidic pH than a natural IgG constant region may be appropriately used. Such a modified form can be appropriately selected on the basis of its ability to also strongly bind to human FcRn at neutral pH and used in the present invention. Examples of such a modified form include constant regions derived from natural IgG constant regions by the modification of amino acids defined by the EU numbering to amino acids different from the corresponding naturally occurring ones. As an example of such amino acid modification, modified constant regions comprising amino acids listed in Table 1 can be preferably used.

Examples of particularly preferred amino acid modification include modification that substitutes amino acids at positions 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, and 436 defined by the EU numbering by amino acids different from the corresponding amino acids in the natural IgG constant region. At least one amino acid selected from these amino acids can be modified to another amino acid to thereby enhance the human FcRn-binding activity of the FcRn-binding domain at neutral pH.

TABLE 1

| Position | Amino acid modification |
|---|---|
| 221 | Y, K |
| 222 | Y |
| 223 | E, K |
| 224 | Y, E |
| 225 | E, K, W |
| 227 | K, E, G |
| 228 | Y, K, G |
| 230 | E, G |
| 232 | K |
| 233 | R, S, M, T, W, Y, G |
| 234 | H, R, E, I, V, F, D, Y, G |
| 235 | Y, V, N, S, T, Q, D |
| 236 | I, V, K, P, E, Q, H, W, Y, D, T, M, A, F, S, N, R |
| 237 | I, W, S, T, E, R, N, Q, K, H, D, P, L, M |
| 238 | A, L, D, S, T, H, W, V, I, G, M, F, E, K |
| 239 | M, R, T, G, V, E, D, L, A |
| 240 | I, M, T |
| 241 | E, W, L |
| 243 | E, W |
| 244 | L |
| 245 | R |
| 246 | Y, H |
| 247 | D |
| 248 | Y |
| 249 | P, Q, Y, H |
| 250 | I, E, Q |
| 251 | T, D |
| 252 | Y, W, Q |
| 254 | H |
| 255 | E, Y, H |
| 256 | A |
| 257 | A, I, M, N, S, V, T, L, Y, O |
| 258 | D, Y, H, A |
| 259 | I, F, N |
| 260 | S, D, E, H, Y |
| 262 | L, E |
| 263 | I |
| 264 | F, A, I, T, N, S, D |
| 265 | R, P, G, A |
| 266 | I |
| 267 | K, E, A |
| 268 | E, M |
| 269 | M, W, K, P, I, S, G, V, F, Y, A |

TABLE 1-continued

| Position | Amino acid modification |
|---|---|
| 270 | K, S, I, A |
| 271 | A, V, S, Y, I, T |
| 272 | A, L, R, I, D, H, V, W, Y, P, T |
| 274 | M, F, G, E, I, T, N |
| 276 | D, F, H, R, L, V, W, A |
| 278 | R, S, V, M, N, I, L, D |
| 279 | A, D, G, H, M, N, Q, R, S, T, W, Y, O, I |
| 281 | D, Y |
| 282 | G, K, E, Y |
| 283 | A, D, F, G, H, I, K, L, N, P, Q, R, S, T, W, Y |
| 284 | T, L, Q, E |
| 285 | N, Y, W, Q, K, E, D, Y |
| 286 | F, L, Y, E, P, D, K, A |
| 287 | S, H |
| 288 | N, P, Y, H, D, I, V, C, E, G, L, Q, R |
| 289 | H |
| 291 | Q, H |
| 292 | Y, E, D |
| 293 | V |
| 294 | I, K, G |
| 295 | V, T |
| 296 | E, I, L |
| 298 | F, E, T, H |
| 299 | W, F, H, Y |
| 300 | K, A, G, V, M, G, N, E |
| 301 | E |
| 302 | I |
| 303 | Y, E, A |
| 304 | N, T |
| 305 | A, H |
| 306 | Y |
| 307 | A, E, M, G, Q, H |
| 308 | A, R, F, C, Y, W, N, H |
| 311 | A, I, K, L, M, V, W, T, H |
| 312 | A, P, H |
| 315 | T, H |
| 316 | K |
| 317 | A, P, H |
| 318 | N, T, R, L, Y |
| 319 | L, I, W, H, M, V, A |
| 320 | L, W, H, N |
| 324 | T, D |
| 325 | F, M, D |
| 326 | A |
| 327 | D, K, M, Y, H, L |
| 328 | G, A, W, R, F |
| 329 | K, R, W |
| 330 | G, W, V, P, H, F |
| 331 | L, F, Y |
| 332 | F, H, K, L, M, R, S, W, T, Q, E, Y, D, N, V |
| 333 | L, F, M, A |
| 334 | A |
| 335 | H, F, N, V, M, W, I, S, P, L |
| 336 | E, K |
| 337 | A |
| 338 | A |
| 339 | N, W |
| 341 | P |
| 343 | E, H, K, Q, R, T, Y |
| 360 | H, A |
| 362 | A |
| 375 | R |
| 376 | A, G, I, M, P, T, V |
| 377 | K |
| 378 | Q, D, N, W |
| 380 | A, N, S, T, Q, R, H |
| 382 | A, F, H, I, K, L, M, N, Q, R, S, T, V, W, Y |
| 385 | N, E |
| 386 | H |
| 387 | H, Q |
| 414 | A |
| 423 | N |
| 424 | A |
| 426 | H, L, V, R |
| 427 | N |
| 428 | F |
| 429 | Q |
| 430 | A, F, G, H, I, K, L, M, N, Q, R, S, T, V, Y |

TABLE 1-continued

| Position | Amino acid modification |
|---|---|
| 431 | H, K |
| 432 | H |
| 433 | P |
| 434 | G, T, M, S, |
| 435 | K |
| 436 | I, L, T |
| 437 | H |
| 438 | K, L, T, W |
| 440 | K |
| 442 | K |

Examples of particularly preferred modification include modification of the natural IgG constant region that results in: Met at amino acid position 237, Ala at amino acid position 238, Lys at amino acid position 239, Ile at amino acid position 248, Ala, Phe, Ile, Met, Gln, Ser, Val, Trp, or Tyr at amino acid position 250, Phe, Trp, or Tyr at amino acid position 252, Thr at amino acid position 254, Glu at amino acid position 255, Asp, Glu, or Gln at amino acid position 256, Ala, Gly, Ile, Leu, Met, Asn, Ser, Thr, or Val at amino acid position 257, His at amino acid position 258, Ala at amino acid position 265, Phe at amino acid position 270, Ala or Glu at amino acid position 286, His at amino acid position 289, Ala at amino acid position 297, Gly at amino acid position 298, Ala at amino acid position 303, Ala at amino acid position 305, Ala, Asp, Phe, Gly, His, Ile, Lys, Leu, Met, Asn, Pro, Gln, Arg, Ser, Val, Trp, or Tyr at amino acid position 307, Ala, Phe, Ile, Leu, Met, Pro, Gln, or Thr at amino acid position 308, Ala, Asp, Glu, Pro, or Arg at amino acid position 309, Ala, His, or Ile at amino acid position 311, Ala or His at amino acid position 312, Lys or Arg at amino acid position 314, Ala or His at amino acid position 315, Ala at amino acid position 317, Gly at amino acid position 325, Val at amino acid position 332, Leu at amino acid position 334, His at amino acid position 360, Ala at amino acid position 376, Ala at amino acid position 380, Ala at amino acid position 382, Ala at amino acid position 384, Asp or His at amino acid position 385, Pro at amino acid position 386, Glu at amino acid position 387, Ala or Ser at amino acid position 389, Ala at amino acid position 424, Ala, Asp, Phe, Gly, His, Ile, Lys, Leu, Asn, Pro, Gln, Ser, Thr, Val, Trp, or Tyr at amino acid position 428, Lys at amino acid position 433, Ala, Phe, His, Ser, Trp, or Tyr at amino acid position 434, and His at amino acid position 436 (all defined by the EU numbering).

The number of amino acids to be modified is not particularly limited. Only one amino acid may be modified, or two or more amino acids may be modified. Examples of the combination of two or more amino acids to be modified include combinations as shown in Table 2.

TABLE 2

| Variant | KD (M) | Amino acid modification site |
|---|---|---|
| F1 | 8.10E−07 | N434W |
| F2 | 3.20E−06 | M252Y/S254T/T256E |
| F3 | 2.50E−06 | N434Y |
| F4 | 5.80E−06 | N434S |
| F5 | 6.80E−06 | N434A |
| F7 | 5.60E−06 | M252Y |
| F8 | 4.20E−06 | M252W |
| F9 | 1.40E−07 | M252Y/S254T/T256E/N434Y |
| F10 | 6.90E−08 | M252Y/S254T/T256E/N434W |
| F11 | 3.10E−07 | M252Y/N434Y |
| F12 | 1.70E−07 | M252Y/N434W |

TABLE 2-continued

| Variant | KD (M) | Amino acid modification site |
|---|---|---|
| F13 | 3.20E−07 | M252W/N434Y |
| F14 | 1.80E−07 | M252W/N434W |
| F19 | 4.60E−07 | P257L/N434Y |
| F20 | 4.60E−07 | V308F/N434Y |
| F21 | 3.00E−08 | M252Y/V308P/N434Y |
| F22 | 2.00E−06 | M428L/N434S |
| F25 | 9.20E−09 | M252Y/S254T/T256E/V308P/N434W |
| F26 | 1.00E−06 | I332V |
| F27 | 7.40E−06 | G237M |
| F29 | 1.40E−06 | I332V/N434Y |
| F31 | 2.80E−06 | G237M/V308F |
| F32 | 8.00E−07 | S254T/N434W |
| F33 | 2.30E−06 | S254T/N434Y |
| F34 | 2.80E−07 | T256E/N434W |
| F35 | 8.40E−07 | T256E/N434Y |
| F36 | 3.60E−07 | S254T/T256E/N434W |
| F37 | 1.10E−06 | S254T/T256E/N434Y |
| F38 | 1.00E−07 | M252Y/S254T/N434W |
| F39 | 3.00E−07 | M252Y/S254T/N434Y |
| F40 | 8.20E−08 | M252Y/T256E/N434W |
| F41 | 1.50E−07 | M252Y/T256E/N434Y |
| F42 | 1.00E−06 | M252Y/S254T/T256E/N434A |
| F43 | 1.70E−06 | M252Y/N434A |
| F44 | 1.10E−06 | M252W/N434A |
| F47 | 2.40E−07 | M252Y/T256Q/N434W |
| F48 | 3.20E−07 | M252Y/T256Q/N434Y |
| F49 | 5.10E−07 | M252F/T256D/N434W |
| F50 | 1.20E−06 | M252F/T256D/N434Y |
| F51 | 8.10E−06 | N434F/Y436H |
| F52 | 3.10E−06 | H433K/N434F/Y436H |
| F53 | 1.00E−06 | I332V/N434W |
| F54 | 8.40E−08 | V308P/N434W |
| F56 | 9.40E−07 | I332V/M428L/N434Y |
| F57 | 1.10E−05 | G385D/Q386P/N389S |
| F58 | 7.70E−07 | G385D/Q386P/N389S/N434W |
| F59 | 2.40E−06 | G385D/Q386P/N389S/N434Y |
| F60 | 1.10E−05 | G385H |
| F61 | 9.70E−07 | G385H/N434W |
| F62 | 1.90E−06 | G385H/N434Y |
| F63 | 2.50E−06 | N434F |
| F64 | 5.30E−06 | N434H |
| F65 | 2.90E−07 | M252Y/S254T/T256E/N434F |
| F66 | 4.30E−07 | M252Y/S254T/T256E/N434H |
| F67 | 6.30E−07 | M252Y/N434F |
| F68 | 9.30E−07 | M252Y/N434H |
| F69 | 5.10E−07 | M428L/N434W |
| F70 | 1.50E−06 | M428L/N434Y |
| F71 | 8.30E−08 | M252Y/S254T/T256E/M428L/N434W |
| F72 | 2.00E−07 | M252Y/S254T/T256E/M428L/N434Y |
| F73 | 1.70E−07 | M252Y/M428L/N434W |
| F74 | 4.60E−07 | M252Y/M428L/N434Y |
| F75 | 1.40E−06 | M252Y/M428L/N434A |
| F76 | 1.00E−06 | M252Y/S254T/T256E/M428L/N434A |
| F77 | 9.90E−07 | T256E/M428L/N434Y |
| F78 | 7.80E−07 | S254T/M428L/N434W |
| F79 | 5.90E−06 | S254T/T256E/N434A |
| F80 | 2.70E−06 | M252Y/T256Q/N434A |
| F81 | 1.60E−06 | M252Y/T256E/N434A |
| F82 | 1.10E−06 | T256Q/N434W |
| F83 | 2.60E−06 | T256Q/N434Y |
| F84 | 2.80E−07 | M252W/T256Q/N434W |
| F85 | 5.50E−07 | M252W/T256Q/N434Y |
| F86 | 1.50E−06 | S254T/T256Q/N434W |
| F87 | 4.30E−06 | S254T/T256Q/N434Y |
| F88 | 1.90E−07 | M252Y/S254T/T256Q/N434W |
| F89 | 3.60E−07 | M252Y/S254T/T256Q/N434Y |
| F90 | 1.90E−08 | M252Y/T256E/V308P/N434W |
| F91 | 4.80E−08 | M252Y/V308P/M428L/N434Y |
| F92 | 1.10E−08 | M252Y/S254T/T256E/V308P/M428L/N434W |
| F93 | 7.40E−07 | M252W/M428L/N434W |
| F94 | 3.70E−07 | P257L/M428L/N434Y |
| F95 | 2.60E−07 | M252Y/S254T/T256E/M428L/N434F |
| F99 | 6.20E−07 | M252Y/T256E/N434H |
| F101 | 1.10E−07 | M252W/T256Q/P257L/N434Y |
| F103 | 4.40E−08 | P238A/M252Y/V308P/N434Y |
| F104 | 3.70E−08 | M252Y/D265A/V308P/N434Y |
| F105 | 7.50E−08 | M252Y/T307A/V308P/N434Y |

TABLE 2-continued

| Variant | KD (M) | Amino acid modification site |
|---|---|---|
| F106 | 3.70E−08 | M252Y/V303A/V308P/N434Y |
| F107 | 3.40E−08 | M252Y/V308P/D376A/N434Y |
| F108 | 4.10E−08 | M252Y/V305A/V308P/N434Y |
| F109 | 3.20E−08 | M252Y/V308P/Q311A/N434Y |
| F111 | 3.20E−08 | M252Y/V308P/K317A/N434Y |
| F112 | 6.40E−08 | M252Y/V308P/E380A/N434Y |
| F113 | 3.20E−08 | M252Y/V308P/E382A/N434Y |
| F114 | 3.80E−08 | M252Y/V308P/S424A/N434Y |
| F115 | 6.60E−06 | T307A/N434A |
| F116 | 8.70E−06 | E380A/N434A |
| F118 | 1.40E−05 | M428L |
| F119 | 5.40E−06 | T250Q/M423L |
| F120 | 6.30E−08 | P257L/V308P/M428L/N434Y |
| F121 | 1.50E−08 | M252Y/T256E/V308P/M428L/N434W |
| F122 | 1.20E−07 | M252Y/T256E/M428L/N434W |
| F123 | 3.00E−07 | M252Y/T256E/V308P/N434Y |
| F124 | 2.90E−07 | M252Y/T256E/M428L/N434Y |
| F125 | 2.40E−08 | M252Y/S254T/T256E/V308P/M428L/N434Y |
| F128 | 1.70E−07 | P257L/M428L/N434W |
| F129 | 2.20E−07 | P257A/M428L/N434Y |
| F131 | 3.00E−06 | P257G/M428L/N434Y |
| F132 | 2.10E−07 | P257I/M428L/N434Y |
| F133 | 4.10E−07 | P257M/M428L/N434Y |
| F134 | 2.70E−07 | P257N/M428L/N434Y |
| F135 | 7.50E−07 | P257S/M428L/N434Y |
| F136 | 3.80E−07 | P257T/M428L/N434Y |
| F137 | 4.60E−07 | P257V/M428L/N434Y |
| F139 | 1.50E−08 | M252W/V308P/N434W |
| F140 | 3.60E−08 | S239K/M252Y/V308P/N434Y |
| F141 | 3.50E−08 | M252Y/S298G/V308P/N434Y |
| F142 | 3.70E−08 | M252Y/D270F/V308P/N434Y |
| F143 | 2.00E−07 | M252Y/V308A/N434Y |
| F145 | 5.30E−08 | M252Y/V308F/N434Y |
| F147 | 2.40E−07 | M252Y/V308I/N434Y |
| F149 | 1.90E−07 | M252Y/V308L/N434Y |
| F150 | 2.00E−07 | M252Y/V308M/N434Y |
| F152 | 2.70E−07 | M252Y/V308Q/N434Y |
| F154 | 1.80E−07 | M252Y/V308T/N434Y |
| F157 | 1.50E−07 | P257A/V308P/M428L/N434Y |
| F158 | 5.90E−08 | P257T/V308P/M428L/N434Y |
| F159 | 4.40E−08 | P257V/V308P/M428L/N434Y |
| F160 | 8.50E−07 | M252W/M428I/N434Y |
| F162 | 1.60E−07 | M252W/M428Y/N434Y |
| F163 | 4.20E−07 | M252W/M428F/N434Y |
| F164 | 3.70E−07 | P238A/M252W/N434Y |
| F165 | 2.90E−07 | M252W/D265A/N434Y |
| F166 | 1.50E−07 | M252W/T307Q/N434Y |
| F167 | 2.90E−07 | M252W/V303A/N434Y |
| F168 | 3.20E−07 | M252W/D376A/N434Y |
| F169 | 2.90E−07 | M252W/V305A/N434Y |
| F170 | 1.70E−07 | M252W/Q311A/N434Y |
| F171 | 1.90E−07 | M252W/D312A/N434Y |
| F172 | 2.20E−07 | M252W/K317A/N434Y |
| F173 | 7.70E−07 | M252W/E380A/N434Y |
| F174 | 3.40E−07 | M252W/E382A/N434Y |
| F175 | 2.70E−07 | M252W/S424A/N434Y |
| F176 | 2.90E−07 | S239K/M252W/N434Y |
| F177 | 2.80E−07 | M252W/S298G/N434Y |
| F178 | 2.70E−07 | M252W/D270F/N434Y |
| F179 | 3.10E−07 | M252W/N325G/N434Y |
| F182 | 6.60E−08 | P257A/M428L/N434W |
| F183 | 2.20E−07 | P257T/M428L/N434W |
| F184 | 2.70E−07 | P257V/M428L/N434W |
| F185 | 2.60E−07 | M252W/I332V/N434Y |
| F188 | 3.00E−06 | P257I/Q311I |
| F189 | 1.90E−07 | M252Y/T307A/N434Y |
| F190 | 1.10E−07 | M252Y/T307Q/N434Y |
| F191 | 1.60E−07 | P257L/T307A/M428L/N434Y |
| F192 | 1.10E−07 | P257A/T307A/M428L/N434Y |
| F193 | 8.50E−08 | P257T/T307A/M428L/N434Y |
| F194 | 1.20E−07 | P257V/T307A/M428L/N434Y |
| F195 | 5.60E−07 | P257L/T307Q/M428L/N434Y |
| F196 | 3.50E−08 | P257A/T307Q/M428L/N434Y |
| F197 | 3.30E−08 | P257T/T307Q/M428L/N434Y |
| F198 | 4.80E−08 | P257V/T307Q/M428L/N434Y |
| F201 | 2.10E−07 | M252Y/T307D/N434Y |
| F203 | 2.40E−07 | M252Y/T307F/N434Y |
| F204 | 2.10E−07 | M252Y/T307G/N434Y |
| F205 | 2.00E−07 | M252Y/T307H/N434Y |
| F206 | 2.30E−07 | M252Y/T307I/N434Y |
| F207 | 9.40E−07 | M252Y/T307K/N434Y |
| F208 | 3.90E−07 | M252Y/T307L/N434Y |
| F209 | 1.30E−07 | M252Y/T307M/N434Y |
| F210 | 2.90E−07 | M252Y/T307N/N434Y |
| F211 | 2.40E−07 | M252Y/T307P/N434Y |
| F212 | 6.80E−07 | M252Y/T307R/N434Y |
| F213 | 2.30E−07 | M252Y/T307S/N434Y |
| F214 | 1.70E−07 | M252Y/T307V/N434Y |
| F215 | 9.60E−08 | M252Y/T307W/N434Y |
| F216 | 2.30E−07 | M252Y/T307Y/N434Y |
| F217 | 2.30E−07 | M252Y/K334L/N434Y |
| F218 | 2.60E−07 | M252Y/G385H/N434Y |
| F219 | 2.50E−07 | M252Y/Q289H/N434Y |
| F220 | 2.50E−07 | M252Y/Q311H/N434Y |
| F221 | 3.10E−07 | M252Y/D312H/N434Y |
| F222 | 3.40E−07 | M252Y/N315H/N434Y |
| F223 | 2.70E−07 | M252Y/K360H/N434Y |
| F225 | 1.50E−06 | M252Y/L314R/N434Y |
| F226 | 5.40E−07 | M252Y/L314K/N434Y |
| F227 | 1.20E−07 | M252Y/N286E/N434Y |
| F228 | 2.30E−07 | M252Y/L309E/N434Y |
| F229 | 5.10E−07 | M252Y/R255E/N434Y |
| F230 | 2.50E−07 | M252Y/P387E/N434Y |
| F236 | 8.90E−07 | K248I/M428L/N434Y |
| F237 | 2.30E−07 | M252Y/M428A/N434Y |
| F238 | 7.40E−07 | M252Y/M428D/N434Y |
| F240 | 7.20E−07 | M252Y/M428F/N434Y |
| F241 | 1.50E−06 | M252Y/M428G/N434Y |
| F242 | 8.50E−07 | M252Y/M428H/N434Y |
| F243 | 1.80E−07 | M252Y/M428I/N434Y |
| F244 | 1.30E−06 | M252Y/M428K/N434Y |
| F245 | 4.70E−07 | M252Y/M428N/N434Y |
| F246 | 1.10E−06 | M252Y/M428P/N434Y |
| F247 | 4.40E−07 | M252Y/M428Q/N434Y |
| F249 | 6.40E−07 | M252Y/M428S/N434Y |
| F250 | 2.90E−07 | M252Y/M428T/N434Y |
| F251 | 1.90E−07 | M252Y/M428V/N434Y |
| F252 | 1.00E−06 | M252Y/M428W/N434Y |
| F253 | 7.10E−07 | M252Y/M428Y/N434Y |
| F254 | 7.50E−08 | M252W/T307Q/M428Y/N434Y |
| F255 | 1.10E−07 | M252W/Q311A/M428Y/N434Y |
| F256 | 5.40E−08 | M252W/T307Q/Q311A/M428Y/N434Y |
| F257 | 5.00E−07 | M252Y/T307A/M428Y/N434Y |
| F258 | 3.20E−07 | M252Y/T307Q/M428Y/N434Y |
| F259 | 2.80E−07 | M252Y/D270F/N434Y |
| F260 | 1.30E−07 | M252Y/T307A/Q311A/N434Y |
| F261 | 8.40E−08 | M252Y/T307Q/Q311A/N434Y |
| F262 | 1.90E−07 | M252Y/T307A/Q311H/N434Y |
| F263 | 1.10E−07 | M252Y/T307Q/Q311H/N434Y |
| F264 | 2.80E−07 | M252Y/E382A/N434Y |
| F265 | 6.80E−07 | M252Y/E382A/M428Y/N434Y |
| F266 | 4.70E−07 | M252Y/T307A/E382A/M428Y/N434Y |
| F267 | 3.20E−07 | M252Y/T307Q/E382A/M428Y/N434Y |
| F268 | 6.30E−07 | P238A/M252Y/M428F/N434Y |
| F269 | 5.20E−07 | M252Y/V305A/M428F/N434Y |
| F270 | 6.60E−07 | M252Y/N325G/M428F/N434Y |
| F271 | 6.90E−07 | M252Y/D376A/M428F/N434Y |
| F272 | 6.80E−07 | M252Y/E380A/M428F/N434Y |
| F273 | 6.50E−07 | M252Y/E382A/M428F/N434Y |
| F274 | 7.60E−07 | M252Y/E380A/E382A/M428F/N434Y |
| F275 | 4.20E−08 | S239K/M252Y/V308P/E382A/N434Y |
| F276 | 4.10E−08 | M252Y/D270F/V308P/E382A/N434Y |
| F277 | 1.30E−07 | S239K/M252Y/V308P/M428Y/N434Y |
| F278 | 3.00E−08 | M252Y/T307Q/V308P/E382A/N434Y |
| F279 | 6.10E−08 | M252Y/V308P/Q311H/E382A/N434Y |
| F280 | 4.10E−08 | S239K/M252Y/D270F/V308P/N434Y |
| F281 | 9.20E−08 | M252Y/V308P/E382A/M428F/N434Y |
| F282 | 2.90E−08 | M252Y/V308P/E382A/M428L/N434Y |
| F283 | 1.00E−07 | M252Y/V308P/E382A/M428Y/N434Y |
| F284 | 1.00E−07 | M252Y/V308P/M428Y/N434Y |
| F285 | 9.90E−08 | M252Y/V308P/M428F/N434Y |
| F286 | 1.20E−07 | S239K/M252Y/V308P/E382A/M428Y/N434Y |
| F287 | 1.00E−07 | M252Y/V308P/E380A/E382A/M428F/N434Y |
| F288 | 1.90E−07 | M252Y/T256E/E382A/N434Y |

TABLE 2-continued

| Variant | KD (M) | Amino acid modification site |
|---|---|---|
| F289 | 4.80E−07 | M252Y/T256E/M428Y/N434Y |
| F290 | 4.60E−07 | M252Y/T256E/E382A/M428Y/N434Y |
| F292 | 2.30E−08 | S239K/M252Y/V308P/E382A/M428I/N434Y |
| F293 | 5.30E−08 | M252Y/V308P/E380A/E382A/M428I/N434Y |
| F294 | 1.10E−07 | S239K/M252Y/V308P/M428F/N434Y |
| F295 | 6.80E−08 | S239K/M252Y/E380A/E382A/M428F/N434Y |
| F296 | 4.90E−07 | M252Y/Q311A/M428Y/N434Y |
| F297 | 5.10E−07 | M252Y/D312A/M428Y/N434Y |
| F298 | 4.80E−07 | M252Y/Q311A/D312A/M428Y/N434Y |
| F299 | 9.40E−08 | S239K/M252Y/V308P/Q311A/M428Y/N434Y |
| F300 | 8.30E−08 | S239K/M252Y/V308P/D312A/M428Y/N434Y |
| F301 | 7.20E−08 | S239K/M252Y/V308P/Q311A/D312A/M428Y/N434Y |
| F302 | 1.90E−08 | M252Y/T256E/T307P/N434Y |
| F303 | 6.70E−07 | M252Y/T307P/M428Y/N434Y |
| F304 | 1.60E−08 | M252W/V308P/M428Y/N434Y |
| F305 | 2.70E−08 | M252Y/T256E/V308P/E382A/N434Y |
| F306 | 3.60E−08 | M252W/V308P/E382A/N434Y |
| F307 | 3.60E−08 | S239K/M252W/V308P/E382A/N434Y |
| F308 | 1.90E−08 | S239K/M252W/V308P/E382A/M428Y/N434Y |
| F310 | 9.40E−08 | S239K/M252W/V308P/E382A/M428I/N434Y |
| F311 | 2.80E−08 | S239K/M252W/V308P/M428F/N434Y |
| F312 | 4.50E−07 | S239K/M252W/E380A/E382A/M428F/N434Y |
| F313 | 6.50E−07 | S239K/M252Y/T307P/M428Y/N434Y |
| F314 | 3.20E−07 | M252Y/T256E/Q311A/D312A/M428Y/N434Y |
| F315 | 6.80E−07 | S239K/M252Y/M428Y/N434Y |
| F316 | 7.00E−08 | S239K/M252Y/D270F/M428Y/N434Y |
| F317 | 1.10E−07 | S239K/M252Y/D270F/V308P/M428Y/N434Y |
| F318 | 1.80E−08 | S239K/M252Y/V308P/M428I/N434Y |
| F320 | 2.00E−08 | S239K/M252Y/V308P/N325G/E382A/M428I/N434Y |
| F321 | 3.20E−08 | S239K/M252Y/D270F/V308P/N325G/N434Y |
| F322 | 9.20E−08 | S239K/M252Y/D270F/T307P/V308P/N434Y |
| F323 | 2.70E−08 | S239K/M252Y/T256E/D270F/V308P/N434Y |
| F324 | 2.80E−08 | S239K/M252Y/D270F/T307Q/V308P/N434Y |
| F325 | 2.10E−08 | S239K/M252Y/D270F/T307Q/V308P/Q311A/N434Y |
| F326 | 7.50E−08 | S239K/M252Y/D270F/T307Q/Q311A/N434Y |
| F327 | 6.50E−08 | S239K/M252Y/T256E/D270F/T307Q/Q311A/N434Y |
| F328 | 1.90E−08 | S239K/M252Y/D270F/V308P/M428I/N434Y |
| F329 | 1.20E−08 | S239K/M252Y/D270F/N286E/V308P/N434Y |
| F330 | 3.60E−08 | S239K/M252Y/D270F/V308P/L309E/N434Y |
| F331 | 3.00E−08 | S239K/M252Y/D270F/V308P/P387E/N434Y |
| F333 | 7.40E−08 | S239K/M252Y/D270F/T307Q/L309E/Q311A/N434Y |
| F334 | 1.90E−08 | S239K/M252Y/D270F/V308P/N325G/M428I/N434Y |
| F335 | 1.50E−08 | S239K/M252Y/T256E/D270F/V308P/M428I/N434Y |
| F336 | 1.40E−08 | S239K/M252Y/D270F/T307Q/V308P/Q311A/M428I/N434Y |
| F337 | 5.60E−08 | S239K/M252Y/D270F/T307Q/Q311A/M428I/N434Y |
| F338 | 7.70E−09 | S239K/M252Y/D270F/N286E/V308P/M428I/N434Y |
| F339 | 1.90E−08 | S239K/M252Y/D270F/V308P/L309E/M428I/N434Y |
| F343 | 3.20E−08 | S239K/M252Y/D270F/V308P/M428L/N434Y |
| F344 | 3.00E−08 | S239K/M252Y/V308P/M428L/N434Y |
| F349 | 1.50E−08 | S239K/M252Y/V308P/L309P/M428L/N434Y |
| F350 | 1.70E−07 | S239K/M252Y/V308P/L309R/M428L/N434Y |
| F352 | 6.00E−07 | S239K/M252Y/L309P/M428L/N434Y |
| F353 | 1.10E−06 | S239K/M252Y/L309R/M428L/N434Y |
| F354 | 2.80E−08 | S239K/M252Y/T307Q/V308P/M428L/N434Y |
| F356 | 3.40E−08 | S239K/M252Y/D270F/V308P/L309E/P387E/N434Y |
| F357 | 1.60E−08 | S239K/M252Y/T256E/D270F/V308P/N325G/M428I/N434Y |
| F358 | 1.00E−08 | S239K/M252Y/T307Q/N434Y |
| F359 | 4.20E−07 | P257V/T307Q/M428I/N434Y |
| F360 | 1.30E−06 | P257V/T307Q/M428V/N434Y |
| F362 | 5.40E−08 | P257V/T307Q/N325G/M428L/N434Y |
| F363 | 4.10E−08 | P257V/T307Q/Q311A/M428L/N434Y |
| F364 | 3.50E−08 | P257V/T307Q/Q311A/N325G/M428L/N434Y |
| F365 | 5.10E−08 | P257V/V305A/T307Q/M428L/N434Y |
| F367 | 1.50E−08 | S239K/M252Y/E258H/D270F/T307Q/V308P/Q311A/N434Y |
| F368 | 2.00E−08 | S239K/M252Y/D270F/V308P/N325G/E382A/M428I/N434Y |
| F369 | 7.50E−08 | M252Y/P257V/T307Q/M428I/N434Y |
| F372 | 1.30E−08 | S239K/M252W/V308P/M428Y/N434Y |
| F373 | 1.10E−08 | S239K/M252W/V308P/Q311A/M428Y/N434Y |
| F374 | 1.20E−08 | S239K/M252W/T256E/V308P/M428Y/N434Y |
| F375 | 5.50E−09 | S239K/M252W/N286E/V308P/M428Y/N434Y |
| F376 | 9.60E−09 | S239K/M252Y/T256E/D270F/N286E/V308P/N434Y |
| F377 | 1.30E−07 | S239K/M252Y/T307P/M428Y/N434Y |
| F379 | 9.00E−09 | S239K/M252Y/T256E/V308P/Q311A/M428Y/N434Y |
| F380 | 5.60E−09 | S239K/M252W/T256E/N286E/V308P/M428Y/N434Y |
| F381 | 1.10E−07 | P257V/T307A/Q311A/M428L/N434Y |
| F382 | 8.70E−08 | P257V/V305A/T307A/M428L/N434Y |
| F386 | 3.20E−08 | M252Y/V308P/L309E/N434Y |
| F387 | 1.50E−07 | M252Y/V308P/L309D/N434Y |
| F388 | 7.00E−08 | M252Y/V308P/L309A/N434Y |
| F389 | 1.70E−08 | M252Y/V308P/L309E/M428Y/N434Y |
| F390 | 6.80E−08 | M252W/V308P/L309D/M428Y/N434Y |
| F391 | 3.60E−08 | M252W/V308P/L309A/M428Y/N434Y |
| F392 | 6.90E−09 | S239K/M252Y/N286E/V308P/M428I/N434Y |
| F393 | 1.20E−08 | S239K/M252Y/N286E/V308P/M428Y/N434Y |
| F394 | 5.30E−08 | S239K/M252Y/T307Q/Q311A/M428I/N434Y |
| F395 | 2.40E−08 | S239K/M252Y/T256E/V308P/N434Y |
| F396 | 2.00E−08 | S239K/M252Y/D270F/N286E/T307Q/Q311A/M428I/N434Y |
| F397 | 4.50E−08 | S239K/M252Y/D270F/T307Q/Q311A/P387E/M428I/N434Y |
| F398 | 4.40E−09 | S239K/M252Y/D270F/N286E/T307Q/V308P/Q311A/M428I/N434Y |
| F399 | 6.50E−09 | S239K/M252Y/D270F/N286E/T307Q/V308P/M428I/N434Y |
| F400 | 6.10E−09 | S239K/M252Y/D270F/N286E/V308P/Q311A/M428I/N434Y |
| F401 | 6.90E−09 | S239K/M252Y/D270F/N286E/V308P/P387E/M428I/N434Y |
| F402 | 2.30E−08 | P257V/T307Q/M428L/N434W |
| F403 | 5.10E−08 | P257V/T307A/M428L/N434W |
| F404 | 9.40E−08 | P257A/T307Q/L309P/M428L/N434Y |
| F405 | 1.70E−07 | P257A/T307Q/L309P/M428L/N434Y |
| F406 | 1.50E−07 | P257A/T307Q/L309R/M428L/N434Y |
| F407 | 1.60E−07 | P257V/T307Q/L309R/M428L/N434Y |
| F408 | 2.50E−07 | P257V/N286E/M428L/N434Y |
| F409 | 2.00E−07 | P257V/P387E/M428L/N434Y |
| F410 | 2.20E−07 | P257V/T307H/M428L/N434Y |
| F411 | 1.30E−07 | P257V/T307N/M428L/N434Y |
| F412 | 8.80E−08 | P257V/T307G/M428L/N434Y |
| F413 | 1.20E−07 | P257V/T307P/M428L/N434Y |
| F414 | 1.10E−07 | P257V/T307S/M428L/N434Y |
| F415 | 5.60E−08 | P257V/N286E/T307A/M428L/N434Y |
| F416 | 9.40E−08 | P257V/T307A/P387E/M428L/N434Y |
| F418 | 6.20E−08 | S239K/M252Y/T307P/N325G/M428Y/N434Y |
| F419 | 1.60E−07 | M252Y/T307A/Q311H/K360H/N434Y |
| F420 | 1.50E−07 | M252Y/T307A/Q311H/P387E/N434Y |
| F421 | 1.30E−07 | M252Y/T307A/Q311H/M428A/N434Y |
| F422 | 1.80E−07 | M252Y/T307A/Q311H/E382A/N434Y |
| F423 | 8.40E−08 | M252Y/T307W/Q311H/N434Y |
| F424 | 9.40E−08 | S239K/P257A/V308P/M428L/N434Y |
| F425 | 8.00E−08 | P257A/V308P/L309E/M428L/N434Y |
| F426 | 8.40E−08 | P257V/T307Q/N434Y |
| F427 | 1.10E−07 | M252Y/P257V/T307Q/M428V/N434Y |
| F428 | 8.00E−08 | M252Y/P257V/T307Q/M428L/N434Y |
| F429 | 3.70E−08 | M252Y/P257V/T307Q/N434Y |
| F430 | 8.10E−08 | M252Y/P257V/T307Q/M428Y/N434Y |
| F431 | 6.50E−08 | M252Y/P257V/T307Q/M428F/N434Y |
| F432 | 9.20E−07 | P257V/T307Q/Q311A/N325G/M428V/N434Y |
| F433 | 6.00E−08 | P257V/T307Q/Q311A/N325G/N434Y |
| F434 | 2.00E−08 | P257V/T307Q/Q311A/N325G/M428Y/N434Y |
| F435 | 2.50E−08 | P257V/T307Q/Q311A/N325G/M428F/N434Y |
| F436 | 2.50E−07 | P257A/T307Q/M428V/N434Y |
| F437 | 5.70E−08 | P257A/T307Q/N434Y |
| F438 | 3.60E−08 | P257A/T307Q/M428Y/N434Y |
| F439 | 4.00E−08 | P257A/T307Q/M428F/N434Y |

TABLE 2-continued

| Variant | KD (M) | Amino acid modification site |
|---|---|---|
| F440 | 1.50E−08 | P257V/N286E/T307Q/Q311A/N325G/M428L/N434Y |
| F441 | 1.80E−07 | P257A/Q311A/M428L/N434Y |
| F442 | 2.00E−07 | P257A/Q311H/M428L/N434Y |
| F443 | 5.50E−08 | P257A/T307Q/Q311A/M428L/N434Y |
| F444 | 1.40E−07 | P257A/T307A/Q311A/M428L/N434Y |
| F445 | 6.20E−08 | P257A/T307Q/Q311H/M428L/N434Y |
| F446 | 1.10E−08 | P257A/T307A/Q311H/M428L/N434Y |
| F447 | 1.40E−08 | P257A/N286E/T307Q/M428L/N434Y |
| F448 | 5.30E−08 | P257A/N286E/T307A/M428L/N434Y |
| F449 | 5.70E−07 | S239K/M252Y/D270F/T307P/N325G/M428Y/N434Y |
| F450 | 5.20E−07 | S239K/M252Y/T307P/L309E/N325G/M428Y/N434Y |
| F451 | 1.00E−07 | P257S/T307A/M428L/N434Y |
| F452 | 1.40E−07 | P257M/T307A/M428L/N434Y |
| F453 | 7.80E−08 | P257N/T307A/M428L/N434Y |
| F454 | 9.60E−08 | P257I/T307A/M428L/N434Y |
| F455 | 2.70E−08 | P257V/T307Q/M428Y/N434Y |
| F456 | 3.40E−08 | P257V/T307Q/M428F/N434Y |
| F457 | 4.00E−08 | S239K/P257V/V308P/M428L/N434Y |
| F458 | 1.50E−08 | P257V/T307Q/V308P/M428L/N434Y |
| F459 | 1.30E−08 | P257V/T307Q/V308P/Q311A/N325G/M428L/N434Y |
| F460 | 4.70E−08 | P257V/T307A/V308P/N325G/M428L/N434Y |
| F462 | 8.50E−08 | P257A/V308P/N325G/M428L/N434Y |
| F463 | 1.30E−07 | P257A/T307A/V308P/M428L/N434Y |
| F464 | 5.50E−08 | P257A/T307Q/V308P/M428L/N434Y |
| F465 | 2.10E−08 | P257V/N286E/T307Q/N325G/M428L/N434Y |
| F466 | 3.50E−07 | T256E/P257V/N434Y |
| F467 | 5.70E−07 | T256E/P257T/N434Y |
| F468 | 5.70E−08 | S239K/P257T/V308P/M428L/N434Y |
| F469 | 5.60E−08 | P257T/V308P/N325G/M428L/N434Y |
| F470 | 5.40E−08 | T258E/P257T/V308P/N325G/M428L/N434Y |
| F471 | 6.60E−08 | P257T/V308P/N325G/E382A/M428L/N434Y |
| F472 | 5.40E−08 | P257T/V308P/N325G/P387E/M428L/N434Y |
| F473 | 4.50E−08 | P257T/V308P/L309N/N325G/M428L/N434Y |
| F474 | 3.50E−07 | P257T/V308P/L309R/N325G/M428L/N434Y |
| F475 | 4.30E−08 | T256E/P257V/T307Q/M428L/N434Y |
| F476 | 5.50E−08 | P257V/T307Q/E382A/M428L/N434Y |
| F477 | 4.30E−08 | P257V/T307Q/P387E/M428L/N434Y |
| F480 | 3.90E−08 | P257L/V308P/N434Y |
| F481 | 5.60E−08 | P257T/T307Q/N434Y |
| F482 | 7.00E−08 | P257V/T307Q/N325G/N434Y |
| F483 | 5.70E−08 | P257V/T307Q/Q311A/N434Y |
| F484 | 6.20E−08 | P257V/V305A/T307Q/N434Y |
| F485 | 9.70E−08 | P257V/N286E/T307A/N434Y |
| F486 | 3.40E−07 | P257V/T307Q/L309R/Q311H/M428L/N434Y |
| F488 | 3.50E−08 | P257V/V308P/N325G/M428L/N434Y |
| F490 | 7.50E−08 | S239K/P257V/V308P/Q311H/M428L/N434Y |
| F492 | 9.80E−08 | P257V/V305A/T307A/N325G/M428L/N434Y |
| F493 | 4.90E−07 | S239K/D270F/T307P/N325G/M428Y/N434Y |
| F497 | 3.10E−06 | P257T/T307A/M428V/N434Y |
| F498 | 1.30E−06 | P257A/M428V/N434Y |
| F499 | 5.20E−07 | P257A/M428V/M434Y/N434Y |
| F500 | 4.30E−08 | P257S/T307Q/M428L/N434Y |
| F506 | 1.90E−08 | P257V/N297A/T307Q/M428L/N434Y |
| F507 | 5.10E−08 | P257V/N286A/T307Q/M428L/N434Y |
| F508 | 1.10E−08 | P257V/T307Q/N315A/M428L/N434Y |
| F509 | 5.80E−08 | P257V/T307Q/N384A/M428L/N434Y |
| F510 | 5.30E−08 | P257V/T307Q/N389A/M428L/N434Y |
| F511 | 4.20E−07 | P257V/N434Y |
| F512 | 5.80E−07 | P257T/N434Y |
| F517 | 3.10E−07 | P257V/N286E/N434Y |
| F518 | 4.20E−07 | P257T/N286E/N434Y |
| F519 | 2.60E−08 | P257V/N286E/T307Q/N434Y |
| F521 | 1.10E−08 | P257V/N286E/T307Q/M428Y/N434Y |
| F523 | 2.60E−08 | P257V/V305A/T307Q/M428Y/N434Y |
| F526 | 1.90E−08 | P257T/T307Q/M428Y/N434Y |
| F527 | 9.40E−09 | P257V/T307Q/V308P/N325G/M428Y/N434Y |
| F529 | 2.50E−08 | P257T/T307Q/M428F/N434Y |
| F533 | 1.20E−08 | P257A/N286E/T307A/M428F/N434Y |
| F534 | 1.20E−08 | P257A/N286E/T307Q/M428Y/N434Y |
| F535 | 3.90E−08 | T250A/P257V/T307Q/M428L/N434Y |
| F538 | 9.90E−08 | T250F/P257V/T307Q/M428L/N434Y |
| F541 | 6.00E−08 | T250I/P257V/T307Q/M428L/N434Y |
| F544 | 3.10E−08 | T250M/P257V/T307Q/M428L/N434Y |
| F549 | 5.40E−08 | T250S/P257V/T307Q/M428L/N434Y |
| F550 | 5.90E−08 | T250V/P257V/T307Q/M428L/N434Y |
| F551 | 1.20E−07 | T250W/P257V/T307Q/M428L/N434Y |
| F552 | 1.10E−07 | T250Y/P257V/T307Q/M428L/N434Y |
| F553 | 1.70E−07 | M252Y/Q311A/N434Y |
| F554 | 2.80E−07 | S239K/M252Y/S254T/V308P/N434Y |
| F556 | 1.50E−06 | M252Y/T307Q/Q311A |
| F559 | 8.00E−08 | M252Y/S254T/N286E/N434Y |
| F560 | 2.80E−08 | M252Y/S254T/V308P/N434Y |
| F561 | 1.40E−07 | M252Y/S254T/T307A/N434Y |
| F562 | 8.30E−08 | M252Y/S254T/T307Q/N434Y |
| F563 | 1.30E−07 | M252Y/S254T/Q311A/N434Y |
| F564 | 1.90E−07 | M252Y/S254T/Q311H/N434Y |
| F565 | 9.20E−08 | M252Y/S254T/T307A/Q311A/N434Y |
| F566 | 6.10E−08 | M252Y/S254T/T307Q/Q311A/N434Y |
| F567 | 2.20E−07 | M252Y/S254T/M428I/N434Y |
| F568 | 1.10E−07 | M252Y/T256E/T307A/Q311H/N434Y |
| F569 | 2.00E−07 | M252Y/T256Q/T307A/Q311H/N434Y |
| F570 | 1.30E−07 | M252Y/S254T/T307A/Q311H/N434Y |
| F571 | 8.10E−08 | M252Y/N286E/T307A/Q311H/N434Y |
| F572 | 1.00E−07 | M252Y/T307A/Q311H/M428I/N434Y |
| F576 | 1.60E−06 | M252Y/T256E/T307Q/Q311H |
| F577 | 1.30E−06 | M252Y/N286E/T307A/Q311A |
| F578 | 5.70E−07 | M252Y/N286E/T307Q/Q311A |
| F580 | 8.60E−07 | M252Y/N286E/T307Q/Q311H |
| F581 | 7.20E−08 | M252Y/T256E/N286E/N434Y |
| F582 | 7.50E−08 | S239K/M252Y/V308P |
| F583 | 7.80E−07 | S239K/M252Y/V308P/E382A |
| F584 | 6.30E−07 | S239K/M252Y/T256E/V308P |
| F585 | 2.90E−07 | S239K/M252Y/N286E/V308P |
| F586 | 1.40E−07 | S239K/M252Y/N286E/V308P/M428I |
| F587 | 1.90E−07 | M252Y/N286E/M428L/N434Y |
| F592 | 2.00E−07 | M252Y/S254T/E382A/N434Y |
| F593 | 3.10E−08 | S239K/M252Y/S254T/V308P/M428I/N434Y |
| F594 | 1.60E−07 | S239K/M252Y/T256E/V308P/M428I/N434Y |
| F595 | 1.80E−07 | S239K/M252Y/M428I/N434Y |
| F596 | 4.00E−08 | M252Y/D312A/E382A/M428Y/N434Y |
| F597 | 2.20E−07 | M252Y/E382A/P387E/N434Y |
| F598 | 1.40E−07 | M252Y/D312A/P387E/N434Y |
| F599 | 5.20E−07 | M252Y/P387E/M428Y/N434Y |
| F600 | 2.80E−07 | M252Y/T256Q/E382A/N434Y |
| F601 | 9.60E−09 | M252Y/N286E/V308P/N434Y |
| F608 | | G236A/S239D/I332E |
| F611 | 2.80E−07 | M252Y/V305T/T307P/V308I/L309A/N434Y |
| F612 | 3.60E−07 | M252Y/T307P/V308I/L309A/N434Y |
| F613 | | S239D/A330L/I332E |
| F616 | | S239D/K326D/L328Y |
| F617 | 7.40E−07 | S239K/N434W |
| F618 | 6.40E−07 | S239K/V308F/N434Y |
| F619 | 3.10E−07 | S239K/M252Y/N434Y |
| F620 | 2.10E−07 | S239K/M252Y/S254T/N434Y |
| F621 | 1.50E−07 | S239K/M252Y/T307A/Q311H/N434Y |
| F622 | 3.50E−07 | S239K/M252Y/T256Q/N434Y |
| F623 | 1.80E−07 | S239K/M252W/N434W |
| F624 | 1.40E−07 | S239K/P257A/N286E/T307Q/M428L/N434Y |
| F625 | 7.60E−08 | S239K/P257A/T307Q/M428L/N434Y |
| F626 | 1.30E−06 | V308P |
| F629 | 3.90E−08 | M252Y/V279L/V308P/N434Y |
| F630 | 3.70E−08 | S239K/M252Y/V279L/V308P/N434Y |
| F633 | 2.40E−07 | M252Y/V282D/V308P/N434Y |
| F634 | 3.20E−08 | S239K/M252Y/V282D/V308P/N434Y |
| F635 | 4.50E−08 | M252Y/V284K/V308P/N434Y |
| F636 | 4.80E−08 | S239K/M252Y/V284K/V308P/N434Y |
| F637 | 1.50E−07 | M252Y/K288S/V308P/N434Y |
| F638 | 1.40E−07 | S239K/M252Y/K288S/V308P/N434Y |
| F639 | 2.70E−08 | M252Y/V308P/G385R/N434Y |
| F640 | 3.60E−08 | S239K/M252Y/V308P/G385R/N434Y |
| F641 | 3.00E−08 | M252Y/V308P/Q386K/N434Y |
| F642 | 3.00E−08 | S239K/M252Y/V308P/Q386K/N434Y |
| F643 | 3.20E−08 | L235G/G236R/S239K/M252Y/V308P/N434Y |
| F644 | 3.00E−08 | G236R/S239K/M252Y/V308P/N434Y |
| F645 | 3.30E−08 | S239K/M252Y/V308P/L328R/N434Y |
| F646 | 3.80E−08 | S239K/M252Y/N297A/V308P/N434Y |
| F647 | 2.90E−08 | P238D/M252Y/V308P/N434Y |
| F648 | | P238D |
| F649 | 1.20E−08 | S239K/M252Y/N286E/N434Y |
| F650 | 1.70E−07 | S239K/M252Y/T256E/N434Y |

TABLE 2-continued

| Variant | KD (M) | Amino acid modification site |
|---|---|---|
| F651 | 1.80E−07 | S239K/M252Y/Q311A/N434Y |
| F652 | 2.40E−07 | P238D/M252Y/N434Y |
| F654 | 3.20E−08 | L235K/S239K/M252Y/V308P/N434Y |
| F655 | 3.40E−08 | L235R/S239K/M252Y/V308P/N434Y |
| F656 | 3.30E−08 | G237K/S239K/M252Y/V308P/N434Y |
| F657 | 3.20E−08 | G237R/S239K/M252Y/V308P/N434Y |
| F658 | 3.20E−08 | P238K/S239K/M252Y/V308P/N434Y |
| F659 | 3.00E−08 | P238R/S239K/M252Y/V308P/N434Y |
| F660 | 3.10E−08 | S239K/M252Y/V308P/P329K/N434Y |
| F661 | 3.40E−08 | S239K/M252Y/V308P/P329R/N434Y |
| F663 | 6.40E−09 | S239K/M252Y/N286E/T307Q/V308P/Q311A/N434Y |
| F664 | 3.90E−08 | M252Y/N286A/V308P/N434Y |
| F665 | 2.00E−08 | M252Y/N286D/V308P/N434Y |
| F666 | 2.10E−08 | M252Y/N286F/V308P/N434Y |
| F667 | 3.00E−08 | M252Y/N286G/V308P/N434Y |
| F668 | 4.00E−08 | M252Y/N286H/V308P/N434Y |
| F669 | 3.50E−08 | M252Y/N286I/V308P/N434Y |
| F670 | 2.10E−07 | M252Y/N286K/V308P/N434Y |
| F671 | 2.20E−08 | M252Y/N286L/V308P/N434Y |
| F672 | 2.40E−08 | M252Y/N286M/V308P/N434Y |
| F673 | 2.30E−08 | M252Y/N286P/V308P/N434Y |
| F674 | 3.20E−08 | M252Y/N286Q/V308P/N434Y |
| F675 | 5.10E−08 | M252Y/N286R/V308P/N434Y |
| F676 | 3.20E−08 | M252Y/N286S/V308P/N434Y |
| F677 | 4.70E−08 | M252Y/N286T/V308P/N434Y |
| F678 | 3.30E−08 | M252Y/N286V/V308P/N434Y |
| F679 | 1.70E−08 | M252Y/N286W/V308P/N434Y |
| F680 | 1.50E−08 | M252Y/N286Y/V308P/N434Y |
| F681 | 4.90E−08 | M252Y/K288A/V308P/N434Y |
| F682 | 8.20E−08 | M252Y/K288D/V308P/N434Y |
| F683 | 5.00E−08 | M252Y/K288E/V308P/N434Y |
| F684 | 5.10E−08 | M252Y/K288F/V308P/N434Y |
| F685 | 5.30E−08 | M252Y/K288G/V308P/N434Y |
| F686 | 4.60E−08 | M252Y/K288H/V308P/N434Y |
| F687 | 4.90E−08 | M252Y/K288I/V308P/N434Y |
| F688 | 2.80E−08 | M252Y/K288L/V308P/N434Y |
| F689 | 4.10E−08 | M252Y/K288M/V308P/N434Y |
| F690 | 1.00E−07 | M252Y/K288N/V308P/N434Y |
| F691 | 3.20E−07 | M252Y/K288P/V308P/N434Y |
| F692 | 3.90E−08 | M252Y/K298Q/V308P/N434Y |
| F693 | 3.60E−08 | M252Y/K288R/V308P/N434Y |
| F694 | 4.70E−08 | M252Y/K288V/V308P/N434Y |
| F695 | 4.00E−08 | M252Y/K288W/V308P/N434Y |
| F696 | 4.40E−08 | M252Y/K288Y/V308P/N434Y |
| F697 | 3.10E−08 | S239K/M252Y/V308P/N325G/N434Y |
| F698 | 2.20E−08 | M252Y/N286E/T307Q/Q311A/N434Y |
| F699 | 2.30E−08 | S239K/M252Y/N286E/T307Q/Q311A/N434Y |
| F700 | 5.20E−08 | M252Y/V308P/L328E/N434Y |
| F705 | 7.10E−09 | M252Y/N286E/V308P/M428I/N434Y |
| F706 | 1.80E−08 | M252Y/N286E/T307Q/V308P/Q311A/N434Y |
| F707 | 5.90E−09 | M252Y/N286E/T307Q/V308P/Q311A/N434Y |
| F708 | 4.10E−09 | M252Y/N286E/T307Q/V308P/Q311A/M428I/N434Y |
| F709 | 2.00E−08 | S239K/M252Y/N286E/T307Q/Q311A/M428I/N434Y |
| F710 | 1.50E−08 | P238D/M252Y/N286E/T307Q/Q311A/M428I/N434Y |
| F711 | 6.50E−08 | S239K/M252Y/T307Q/Q311A/N434Y |
| F712 | 6.00E−08 | P238D/M252Y/T307Q/Q311A/N434Y |
| F713 | 2.00E−08 | P238D/M252Y/N286E/T307Q/Q311A/N434Y |
| F714 | 2.30E−07 | P238D/M252Y/N325S/N434Y |
| F715 | 2.30E−07 | P238D/M252Y/N325M/N434Y |
| F716 | 2.70E−07 | P238D/M252Y/N325L/N434Y |
| F717 | 2.60E−07 | P238D/M252Y/N325I/N434Y |
| F718 | 2.80E−07 | P238D/M252Y/Q295M/N434Y |
| F719 | 7.40E−08 | P238D/M252Y/N325G/N434Y |
| F720 | 2.40E−08 | M252Y/T307Q/V308P/Q311A/N434Y |
| F721 | 1.50E−08 | M252Y/T307Q/V308P/Q311A/M428I/N434Y |
| F722 | 2.70E−08 | P238D/M252Y/A327G/N434Y |
| F723 | 2.80E−07 | P238D/M252Y/L328D/N434Y |
| F724 | 2.50E−07 | P238D/M252Y/L328E/N434Y |
| F725 | 4.20E−08 | L235K/G237R/S239K/M252Y/V308P/N434Y |
| F726 | 3.70E−08 | L235K/P238D/S239K/M252Y/V308P/N434Y |
| F729 | 9.20E−07 | T307A/Q311A/N434Y |
| F730 | 6.00E−07 | T307Q/Q311A/N434Y |
| F731 | 8.50E−07 | T307A/Q311H/N434Y |
| F732 | 6.80E−07 | T307Q/Q311H/N434Y |
| F733 | 3.20E−07 | M252Y/L328E/N434Y |
| F734 | 3.10E−07 | G236D/M252Y/L328E/N434Y |
| F736 | 3.10E−07 | M252Y/S267M/L328E/N434Y |
| F737 | 3.10E−07 | M252Y/S267L/L328E/N434Y |
| F738 | 3.50E−07 | P238D/M252Y/T307P/N434Y |
| F739 | 2.20E−07 | M252Y/T307P/Q311A/N434Y |
| F740 | 2.90E−07 | M252Y/T307P/Q311H/N434Y |
| F741 | 3.10E−07 | P238D/T250A/M252Y/N434Y |
| F744 | 9.90E−07 | P238D/T250F/M252Y/N434Y |
| F745 | 6.60E−07 | P238D/T250G/M252Y/N434Y |
| F746 | 6.00E−07 | P238D/T250H/M252Y/N434Y |
| F747 | 2.80E−07 | P238D/T250I/M252Y/N434Y |
| F749 | 5.10E−07 | P238D/T250L/M252Y/N434Y |
| F750 | 3.00E−07 | P238D/T250M/M252Y/N434Y |
| F751 | 5.30E−07 | P238D/T250N/M252Y/N434Y |
| F753 | 1.80E−07 | P238D/T250Q/M252Y/N434Y |
| F755 | 3.50E−07 | P238D/T250S/M252Y/N434Y |
| F756 | 3.70E−07 | P238D/T250V/M252Y/N434Y |
| F757 | 1.20E−06 | P238D/T250W/M252Y/N434Y |
| F758 | 1.40E−06 | P238D/T250Y/M252Y/N434Y |
| F759 |  | L235K/S239K |
| F760 |  | L235R/S239K |
| F761 | 1.10E−06 | P238D/N434Y |
| F762 | 3.60E−08 | L235K/S239K/M252Y/N286E/T307Q/Q311A/N434Y |
| F763 | 3.50E−08 | L235R/S239K/M252Y/N286E/T307Q/Q311A/N434Y |
| F764 | 6.30E−07 | P238D/T307Q/Q311A/N434Y |
| F765 | 8.50E−08 | P238D/M252Y/T307Q/L309E/Q311A/N434Y |
| F766 | 6.00E−07 | T307A/L309E/Q311A/N434Y |
| F767 | 4.30E−07 | T307Q/L309E/Q311A/N434Y |
| F768 | 6.40E−07 | T307A/L309E/Q311H/N434Y |
| F769 | 4.60E−07 | T307Q/L309E/Q311H/N434Y |
| F770 | 3.00E−07 | M252Y/T256A/N434Y |
| F771 | 4.00E−07 | M252Y/E272A/N434Y |
| F772 | 3.80E−07 | M252Y/K274A/N434Y |
| F773 | 3.90E−07 | M252Y/V282A/N434Y |
| F774 | 4.00E−07 | M252Y/N286A/N434Y |
| F775 | 6.20E−07 | M252Y/K338A/N434Y |
| F776 | 3.90E−07 | M252Y/K340A/N434Y |
| F777 | 3.90E−07 | M252Y/E345A/N434Y |
| F779 | 3.90E−07 | M252Y/N361A/N434Y |
| F780 | 3.90E−07 | M252Y/Q362A/N434Y |
| F781 | 3.70E−07 | M252Y/S375A/N434Y |
| F782 | 3.50E−07 | M252Y/Y391A/N434Y |
| F783 | 4.00E−07 | M252Y/D413A/N434Y |
| F784 | 5.00E−07 | M252Y/L309A/N434Y |
| F785 | 7.40E−07 | M252Y/L309H/N434Y |
| F786 | 2.80E−08 | M252Y/S254T/N286E/T307Q/Q311A/N434Y |
| F787 | 8.80E−08 | M252Y/S254T/T307Q/L309E/Q311A/N434Y |
| F788 | 4.10E−07 | M252Y/N315A/N434Y |
| F789 | 1.50E−07 | M252Y/N315D/N434Y |
| F790 | 2.70E−07 | M252Y/N315E/N434Y |
| F791 | 4.40E−07 | M252Y/N315F/N434Y |
| F792 | 4.40E−07 | M252Y/N315G/N434Y |
| F793 | 3.30E−07 | M252Y/N315I/N434Y |
| F794 | 4.10E−07 | M252Y/N315K/N434Y |
| F795 | 3.10E−07 | M252Y/N315L/N434Y |
| F796 | 3.40E−07 | M252Y/N315M/N434Y |
| F798 | 3.50E−07 | M252Y/N315Q/N434Y |
| F799 | 4.10E−07 | M252Y/N315R/N434Y |
| F800 | 3.80E−07 | M252Y/N315S/N434Y |
| F801 | 4.40E−07 | M252Y/N315T/N434Y |
| F802 | 3.30E−07 | M252Y/N315V/N434Y |
| F803 | 3.60E−07 | M252Y/N315W/N434Y |
| F804 | 4.00E−07 | M252Y/N315Y/N434Y |
| F805 | 3.00E−07 | M252Y/N325A/N434Y |
| F806 | 3.10E−07 | M252Y/N384A/N434Y |
| F807 | 3.20E−07 | M252Y/N389A/N434Y |
| F808 | 3.20E−07 | M252Y/N389A/N390A/N434Y |
| F809 | 2.20E−07 | M252Y/S254T/T256S/N434Y |
| F810 | 2.20E−07 | M252Y/A378V/N434Y |
| F811 | 4.90E−07 | M252Y/E380S/N434Y |
| F812 | 2.70E−07 | M252Y/E382V/N434Y |
| F813 | 2.80E−07 | M252Y/S424E/N434Y |
| F814 | 1.20E−07 | M252Y/N434Y/Y436I |

TABLE 2-continued

| Variant | KD (M) | Amino acid modification site |
|---|---|---|
| F815 | 5.50E−07 | M252Y/N434Y/T437R |
| F816 | 3.60E−07 | P238D/T250V/M252Y/T307P/N434Y |
| F817 | 9.80E−08 | P238D/T250V/M252Y/T307Q/Q311A/N434Y |
| F819 | 1.40E−07 | P238D/M252Y/N286E/N434Y |
| F820 | 3.40E−07 | L235K/S239K/M252Y/N434Y |
| F821 | 3.10E−07 | L235R/S239K/M252Y/N434Y |
| F822 | 1.10E−06 | P238D/T250V/M252Y/W313Y/N434Y |
| F823 | 1.10E−06 | P238D/T250Y/M252Y/W313F/N434Y |
| F828 | 2.50E−06 | P238D/T250V/M252Y/I253V/N434Y |
| F831 | 1.60E−06 | P238D/T250V/M252Y/R255A/N434Y |
| F832 | 2.60E−06 | P238D/T250V/M252Y/R255D/N434Y |
| F833 | 8.00E−07 | P238D/T250V/M252Y/R255E/N434Y |
| F834 | 8.10E−07 | P238D/T250V/M252Y/R255F/N434Y |
| F836 | 5.00E−07 | P238D/T250V/M252Y/R255H/N434Y |
| F837 | 5.60E−07 | P238D/T250V/M252Y/R255I/N434Y |
| F838 | 4.30E−07 | P238D/T250V/M252Y/R255K/N434Y |
| F839 | 3.40E−07 | P238D/T250V/M252Y/R255L/N434Y |
| F840 | 4.20E−07 | P238D/T250V/M252Y/R255M/N434Y |
| F841 | 1.10E−06 | P238D/T250V/M252Y/R255N/N434Y |
| F843 | 6.60E−07 | P238D/T250V/M252Y/R255Q/N434Y |
| F844 | 1.30E−06 | P238D/T250V/M252Y/R255S/N434Y |
| F847 | 3.40E−07 | P238D/T250V/M252Y/R255W/N434Y |
| F848 | 8.30E−07 | P238D/T250V/M252Y/R255Y/N434Y |
| F849 | 3.30E−07 | M252Y/D280A/N434Y |
| F850 | 2.90E−07 | M252Y/D280E/N434Y |
| F852 | 3.30E−07 | M252Y/D280G/N434Y |
| F853 | 3.20E−07 | M252Y/D280H/N434Y |
| F855 | 3.20E−07 | M252Y/D280K/N434Y |
| F858 | 3.20E−07 | M252Y/D280N/N434Y |
| F860 | 3.30E−07 | M252Y/D280Q/N434Y |
| F861 | 3.20E−07 | M252Y/D280R/N434Y |
| F862 | 3.00E−07 | M252Y/D280S/N434Y |
| F863 | 2.70E−07 | M252Y/D280T/N434Y |
| F867 | 2.80E−07 | M252Y/N384A/N389A/N434Y |
| F868 | 2.00E−08 | G236A/S239D/M252Y/N286E/T307Q/Q311A/N434Y |
| F869 |  | G236A/S239D |
| F870 | 7.30E−08 | L235K/S239K/M252Y/T307Q/Q311A/N434Y |
| F871 | 7.10E−08 | L235R/S239K/M252Y/T307Q/Q311A/N434Y |
| F872 | 1.30E−07 | L235K/S239K/M252Y/N286E/N434Y |
| F873 | 1.20E−07 | L235R/S239K/M252Y/N286E/N434Y |
| F875 | 4.80E−07 | M252Y/N434Y/Y436A |
| F877 | 8.30E−07 | M252Y/N434Y/Y436E |
| F878 | 1.90E−07 | M252Y/N434Y/Y436F |
| F879 | 9.20E−07 | M252Y/N434Y/Y436G |
| F880 | 3.90E−07 | M252Y/N434Y/Y436H |
| F881 | 3.10E−07 | M252Y/N434Y/Y436K |
| F882 | 1.30E−07 | M252Y/N434Y/Y436L |
| F883 | 2.10E−07 | M252Y/N434Y/Y436M |
| F884 | 4.00E−07 | M252Y/N434Y/Y436N |
| F888 | 4.80E−07 | M252Y/N434Y/Y436S |
| F889 | 2.20E−07 | M252Y/N434Y/Y436T |
| F890 | 1.10E−07 | M252Y/N434Y/Y436V |
| F891 | 1.70E−07 | M252Y/N434Y/Y436W |
| F892 | 7.10E−08 | M252Y/S254T/N434Y/Y436I |
| F893 | 9.80E−08 | L235K/S239K/M252Y/N434Y/Y436I |
| F894 | 9.20E−08 | L235R/S239K/M252Y/N434Y/Y436I |
| F895 | 2.10E−08 | L235K/S239K/M252Y/N286E/T307Q/Q311A/N315E/N434Y |
| F896 | 2.00E−08 | L235R/S239K/M252Y/N286E/T307Q/Q311A/N315E/N434Y |
| F897 | 9.70E−08 | M252Y/N315D/N384A/N389A/N434Y |
| F898 | 1.70E−07 | M252Y/N315E/N384A/N389A/N434Y |
| F899 | 1.10E−07 | M252Y/N315D/G316A/N434Y |
| F900 | 1.70E−07 | M252Y/N315D/G316D/N434Y |
| F901 | 1.30E−07 | M252Y/N315D/G316E/N434Y |
| F902 | 2.20E−07 | M252Y/N315D/G316F/N434Y |
| F903 | 2.30E−07 | M252Y/N315D/G316H/N434Y |
| F904 | 1.00E−07 | M252Y/N315D/G316I/N434Y |
| F905 | 1.30E−07 | M252Y/N315D/G316K/N434Y |
| F906 | 1.50E−07 | M252Y/N315D/G316L/N434Y |
| F907 | 1.30E−07 | M252Y/N315D/G316M/N434Y |
| F908 | 1.50E−07 | M252Y/N315D/G316N/N434Y |
| F909 | 1.30E−07 | M252Y/N315D/G316P/N434Y |
| F910 | 1.40E−07 | M252Y/N315D/G316Q/N434Y |
| F911 | 1.30E−07 | M252Y/N315D/G316R/N434Y |
| F912 | 1.20E−07 | M252Y/N315D/G316S/N434Y |
| F913 | 1.10E−07 | M252Y/N315D/G316T/N434Y |
| F914 | 1.50E−07 | M252Y/N315D/G316V/N434Y |
| F915 | 2.30E−07 | M252Y/N315D/G316W/N434Y |
| F917 | 2.50E−07 | M252Y/N286S/N434Y |
| F918 | 2.80E−07 | M252Y/D280E/N384A/N389A/N434Y |
| F919 | 3.30E−07 | M252Y/D280G/N384A/N389A/N434Y |
| F920 | 2.50E−07 | M252Y/N286S/N384A/N389A/N434Y |
| F921 | 1.20E−07 | M252Y/N286E/N384A/N389A/N434Y |
| F922 | 5.90E−08 | L235K/S239K/M252Y/N286E/N434Y/Y436I |
| F923 | 6.00E−08 | L235R/S239K/M252Y/N286E/N434Y/Y436I |
| F924 | 3.40E−08 | L235K/S239K/M252Y/T307Q/Q311A/N434Y/Y436I |
| F925 | 3.20E−08 | L235R/S239K/M252Y/T307Q/Q311A/N434Y/Y436I |
| F926 | 1.10E−07 | L235K/S239K/M252Y/S254T/N434Y/Y436I |
| F927 | 1.00E−07 | L235R/S239K/M252Y/S254T/N434Y/Y436I |
| F928 | 2.90E−08 | M252Y/T307Q/Q311A/N434Y/Y436I |
| F929 | 2.90E−08 | M252Y/S254T/T307Q/Q311A/N434Y/Y436I |
| F930 | 1.40E−07 | P238D/T250V/M252Y/N286E/N434Y |
| F931 | 1.20E−07 | P238D/T250V/M252Y/N434Y/Y436I |
| F932 | 3.20E−07 | T250V/M252Y/N434Y |
| F933 | 3.00E−07 | L234R/P238D/T250V/M252Y/N434Y |
| F934 | 3.10E−07 | G236K/P238D/T250V/M252Y/N434Y |
| F935 | 3.20E−07 | G237K/P238D/T250V/M252Y/N434Y |
| F936 | 3.20E−07 | G237R/P238D/T250V/M252Y/N434Y |
| F937 | 3.10E−07 | P238D/S239K/T250V/M252Y/N434Y |
| F938 | 1.60E−07 | L235K/S239K/M252Y/N434Y/Y436V |
| F939 | 1.50E−07 | L235R/S239K/M252Y/N434Y/Y436V |
| F940 | 1.50E−07 | P238D/T250V/M252Y/N434Y/Y436V |
| F941 | 1.20E−08 | M252Y/N286E/T307Q/Q311A/N434Y/Y436V |
| F942 | 4.20E−08 | L235K/S239K/M252Y/T307Q/Q311A/N434Y/Y436V |
| F943 | 4.00E−08 | L235R/S239K/M252Y/T307Q/Q311A/N434Y/Y436V |
| F944 | 1.70E−07 | T250V/M252Y/N434Y/Y436V |
| F945 | 1.70E−07 | T250V/M252Y/V308P/N434Y/Y436V |
| F946 | 4.30E−08 | T250V/M252Y/T307Q/Q311A/N434Y/Y436V |
| F947 | 1.10E−08 | T250V/M252Y/T307Q/V308P/Q311A/N434Y/Y436V |
| F954 | 5.30E−07 | M252Y/N434Y/H435K/Y436V |
| F957 | 7.70E−07 | M252Y/N434Y/H435N/Y436V |
| F960 | 8.00E−07 | M252Y/N434Y/H435R/Y436V |
| F966 | 3.10E−07 | M252Y/S254A/N434Y |
| F970 | 2.50E−06 | M252Y/S254G/N434Y |
| F971 | 2.60E−06 | M252Y/S254H/N434Y |
| F972 | 2.60E−07 | M252Y/S254I/N434Y |
| F978 | 1.30E−06 | M252Y/S254Q/N434Y |
| F980 | 1.80E−07 | M252Y/S254V/N434Y |
| F987 | 4.00E−08 | P238D/T250V/M252Y/T307Q/Q311A/N434Y/Y436V |
| F988 | 6.90E−08 | P238D/T250V/M252Y/N286E/N434Y/Y436V |
| F989 | 1.40E−07 | L235R/S239K/M252Y/V308P/N434Y/Y436V |
| F990 | 9.40E−09 | L235R/S239K/M252Y/T307Q/V308P/Q311A/N434Y/Y436V |
| F991 | 1.30E−08 | L235R/S239K/M252Y/N286E/T307Q/Q311A/N434Y/Y436V |
| F992 | 5.10E−08 | L235R/S239K/M252Y/T307Q/Q311A/M428I/N434Y/Y436V |
| F993 | 3.80E−08 | M252Y/T307Q/Q311A/N434Y/Y436V |
| F994 | 2.80E−07 | M252Y/N325G/N434Y |
| F995 | 2.90E−07 | L235R/P238D/S239K/M252Y/N434Y |
| F996 | 1.30E−07 | L235R/P238D/S239K/M252Y/N434Y/Y436V |
| F997 | 3.80E−07 | K248I/T250V/M252Y/N434Y/Y436V |
| F998 | 8.50E−07 | K248Y/T250V/M252Y/N434Y/Y436V |
| F999 | 2.10E−07 | T250V/M252Y/E258H/N434Y/Y436V |
| F1005 |  | N325G |
| F1008 | 1.70E−07 | L235R/S239K/T250V/M252Y/N434Y/Y436V |
| F1009 | 1.20E−08 | L235R/S239K/T250V/M252Y/T307Q/V308P/Q311A/N434Y/Y436V |
| F1010 | 1.90E−07 | L235R/S239K/M252Y/T307A/Q311H/N434Y |
| F1011 | 4.50E−08 | T250V/M252Y/V308P/N434Y |
| F1012 | 4.70E−08 | L235R/S239K/T250V/M252Y/V308P/N434Y |
| F1013 | 3.00E−08 | T250V/M252Y/T307Q/V308P/Q311A/N434Y |
| F1014 | 3.20E−08 | L235R/S239K/T250V/M252Y/T307Q/V308P/Q311A/N434Y |
| F1015 | 2.20E−08 | L235R/S239K/M252Y/T307Q/V308P/Q311A/N434Y |

TABLE 2-continued

| Variant | KD (M) | Amino acid modification site |
|---|---|---|
| F1016 | 3.80E−09 | T250V/M252Y/N286E/T307Q/V308P/Q311A/N434Y/Y436V |
| F1017 | 4.20E−09 | L235R/S239K/T250V/M252Y/N286E/T307Q/V308P/Q311A/N434Y/Y436V |
| F1018 | 3.20E−09 | L235R/S239K/M252Y/N286E/T307Q/V308P/Q311A/N434Y/Y436V |
| F1019 | 3.40E−07 | P238D/T250V/M252Y/N325G/N434Y |
| F1020 | 8.50E−08 | P238D/T250V/M252Y/T307Q/Q311A/N325G/N434Y |
| F1021 | 3.30E−07 | P238D/T250V/M252Y/N325A/N434Y |
| F1022 | | K326D/L328Y |
| F1023 | 4.40E−08 | S239D/T250V/M252Y/T307Q/Q311A/N434Y/Y436V |
| F1024 | 4.00E−08 | T250V/M252Y/T307Q/Q311A/K326D/L328Y/N434Y/Y436V |
| F1025 | 3.60E−08 | S239D/T250V/M252Y/T307Q/Q311A/K326D/L328Y/N434Y/Y436V |
| F1026 | 8.40E−08 | M252Y/T307A/Q311H/N434Y/Y436V |
| F1027 | 8.60E−08 | L235/S239K/M252Y/T307A/Q311H/N434Y/Y436V |
| F1028 | 4.60E−08 | G236A/S239D/T250V/M252Y/T307Q/Q311A/N434Y/Y436V |
| F1029 | 5.10E−08 | T250V/M252Y/T307Q/Q311A/I332E/N434Y/Y436V |
| F1030 | | I332E |
| F1031 | 5.30E−08 | G236A/S239D/T250V/M252Y/T307Q/Q311A/I332E/N434Y/Y436V |
| F1032 | 4.30E−08 | P238D/T250V/M252Y/T307Q/Q311A/N325G/N434Y/Y436V |
| F1033 | 1.00E−06 | P238D/N434W |
| F1034 | 1.50E−08 | L235K/S239K/M252Y/V308P/N434Y/Y436V |
| F1035 | 1.00E−08 | L235K/S239K/M252Y/T307Q/V308P/Q311A/N434Y/Y436V |
| F1036 | 1.40E−08 | L235K/S239K/M252Y/N286E/T307Q/Q311A/N434Y/Y436V |
| F1037 | 6.10E−08 | L235K/S239K/M252Y/T307Q/Q311A/M428I/N434Y/Y436V |
| F1038 | 2.80E−07 | L235K/P238D/S239K/M252Y/N434Y |
| F1039 | 1.30E−07 | L235K/P238D/S239K/M252Y/N434Y/Y436V |
| F1040 | 2.00E−07 | L235K/S239K/T250V/M252Y/N434Y/Y436V |
| F1041 | 1.40E−08 | L235K/S239K/T250V/M252Y/T307Q/V308P/Q311A/N434Y/Y436V |
| F1042 | 2.00E−07 | L235K/S239K/M252Y/T307A/Q311H/N434Y |
| F1043 | 5.20E−08 | L235K/S239K/T250V/M252Y/V308P/N434Y |
| F1044 | 3.50E−08 | L235K/S239K/T250V/M252Y/T307Q/V308P/Q311A/N434Y |
| F1045 | 2.50E−08 | L235K/S239K/M252Y/T307Q/V308P/Q311A/N434Y |
| F1046 | 4.50E−09 | L235K/S239K/T250V/M252Y/N286E/T307Q/V308P/Q311A/N434Y/Y436V |
| F1047 | 3.40E−09 | L235K/S239K/M252Y/N286E/T307Q/V308P/Q311A/N434Y/Y436V |
| F1048 | 9.90E−08 | L235K/S239K/M252Y/T307A/Q311H/N434Y/Y436V |
| F1050 | 3.50E−09 | T250V/M252Y/N286E/T307Q/V308P/Q311A/M428I/N434Y/Y436V |
| F1051 | 3.90E−09 | L235R/S239K/T250V/M252Y/N286E/T307Q/V308P/Q311A/M428I/N434Y/Y436V |
| F1052 | 3.20E−09 | L235R/S239K/M252Y/N286E/T307Q/V308P/Q311A/M428I/N434Y/Y436V |
| F1053 | 4.23E−08 | L235R/S239K/T250V/M252Y/T307Q/Q311A/N434Y/Y436V |
| F1058 | 1.31E−07 | M252Y/Q386E/N434Y/Y436V |
| F1059 | 1.39E−07 | M252Y/Q386R/N434Y/Y436V |
| F1060 | 1.43E−07 | M252Y/Q386S/N434Y/Y436V |
| F1061 | 1.19E−07 | M252Y/P387E/N434Y/Y436V |
| F1062 | 1.2E−07 | M252Y/P387R/N434Y/Y436V |
| F1063 | 1.43E−07 | M252Y/P387S/N434Y/Y436V |
| F1064 | 1.32E−07 | M252Y/V422E/N434Y/Y436V |
| F1065 | 1.38E−07 | M252Y/V422R/N434Y/Y436V |
| F1066 | 1.45E−07 | M252Y/V422S/N434Y/Y436V |
| F1067 | 1.26E−07 | M252Y/S424E/N434Y/Y436V |
| F1068 | 1.69E−07 | M252Y/S424R/N434Y/Y436V |
| F1069 | 1.39E−07 | M252Y/N434Y/Y436V/Q438E |
| F1070 | 1.73E−07 | M252Y/N434Y/Y436V/Q438R |
| F1071 | 1.24E−07 | M252Y/N434Y/Y436V/Q438S |
| F1072 | 1.35E−07 | M252Y/N434Y/Y436V/S440E |
| F1073 | 1.34E−07 | M252Y/N434Y/Y436V/S440R |
| F1074 | 1.32E−07 | S239D/M252Y/N434Y/Y436V |
| F1075 | 1.4E−07 | M252Y/K326D/L328Y/N434Y/Y436V |
| F1076 | 1.27E−07 | S239D/M252Y/K326D/L328Y/N434Y/Y436V |
| F1077 | 2.03E−06 | K248N/M252Y/N434Y |
| F1078 | 4.7E−07 | M252Y/E380N/E382S/N434Y |
| F1079 | 3.44E−07 | M252Y/E382N/N384S/N434Y |
| F1080 | 3.19E−07 | M252Y/S424N/N434Y |
| F1081 | 6.2E−07 | M252Y/N434Y/Y436N/Q438T |
| F1082 | 2.76E−07 | M252Y/N434Y/Q438N |
| F1083 | 3.45E−07 | M252Y/N434Y/S440N |
| F1094 | 2.6E−07 | M252Y/N434Y/S442N |
| F1095 | 2.86E−07 | M252Y/S383N/G385S/N434Y |
| F1096 | 2.72E−07 | M252Y/Q386T/N434Y |
| F1097 | 2.82E−07 | M252Y/G385N/P387S/N434Y |
| F1098 | 2.58E−07 | S239D/M252Y/N434Y |
| F1099 | 2.57E−07 | M252Y/K326D/L328Y/N434Y |
| F1100 | 2.41E−07 | S239D/M252Y/K326D/L328Y/N434Y |
| F1101 | 6.59E−08 | S239D/M252Y/T307Q/Q311A/N434Y |
| F1102 | 6.46E−08 | M252Y/T307Q/Q311A/K326D/L328Y/N434Y |
| F1103 | 6.11E−08 | S239D/M252Y/T307Q/Q311A/K326D/L328Y/N434Y |
| F1104 | 1.77E−07 | M252Y/V422E/S424R/N434Y/Y436V |
| F1105 | 1.54E−07 | M252Y/V422S/S424R/N434Y/Y436V |
| F1106 | 1.42E−07 | M252Y/N434Y/Y436V/Q438R/S440E |
| F1107 | 1.23E−07 | M252Y/V422D/N434Y/Y436V |
| F1108 | 1.26E−07 | M252Y/V422K/N434Y/Y436V |
| F1109 | 1.27E−07 | M252Y/V422T/N434Y/Y436V |
| F1110 | 1.33E−07 | M252Y/V422Q/N434Y/Y436V |
| F1111 | 1.65E−07 | M252Y/S424K/N434Y/Y436V |
| F1112 | 1.23E−07 | M252Y/N434Y/Y436V/Q438K |
| F1113 | 1.18E−07 | M252Y/N434Y/Y436V/S440D |
| F1114 | 1.31E−07 | M252Y/N434Y/Y436V/S440Q |
| F1115 | 1.35E−07 | M252Y/S424N/N434Y/Y436V |
| F1116 | 7.44E−08 | M252Y/T307Q/Q311A/S424N/N434Y |
| F1117 | 4.87E−08 | T250V/M252Y/T307Q/Q311A/S424N/N434Y/Y436V |
| F1118 | 1.32E−08 | T250V/M252Y/T307Q/V308P/Q311A/S424N/N434Y/Y436V |
| F1119 | 1.03E−08 | T250V/M252Y/T307Q/V308P/Q311A/V422E/N434Y/Y436V |
| F1120 | 1.04E−08 | T250V/M252Y/T307Q/V308P/Q311A/S424R/N434Y/Y436V |
| F1121 | 1.04E−08 | T250V/M252Y/T307Q/V308P/Q311A/V422E/S424R/N434Y/Y436V |
| F1122 | 1.37E−08 | T250V/M252Y/T307Q/V308P/Q311A/N434Y/Y436V/Q438R |
| F1123 | 9.55E−09 | T250V/M252Y/T307Q/V308P/Q311A/N434Y/Y436V/S440E |
| F1124 | 1.22E−08 | T250V/M252Y/T307Q/V308P/Q311A/N434Y/Y436V/Q438R/S440E |
| F1125 | 5.18E−08 | M252Y/T307Q/N434Y/Y436V |
| F1126 | 8.95E−08 | M252Y/T307A/N434Y/Y436V |
| F1127 | 7.94E−08 | M252Y/Q311A/N434Y/Y436V |
| F1128 | 1.17E−07 | M252Y/Q311H/N434Y/Y436V |
| F1129 | 4.48E−08 | M252Y/T307Q/Q311H/N434Y/Y436V |
| F1130 | 5.54E−08 | M252Y/T307A/Q311A/N434Y/Y436V |
| F1131 | 1.29E−07 | L235R/S239K/M252Y/V422E/N434Y/Y436V |
| F1132 | 1.4E−07 | L235R/S239K/M252Y/V422S/N434Y/Y436V |
| F1133 | 1.58E−07 | L235R/S239K/M252Y/S424R/N434Y/Y436V |
| F1134 | 1.66E−07 | L235R/S239K/M252Y/N434Y/Y436V/Q438R |
| F1135 | 1.26E−07 | L235R/S239K/M252Y/N434Y/Y436V/S440E |
| F1136 | 1.63E−07 | L235R/S239K/M252Y/V422E/S424R/N434Y/Y436V |
| F1137 | 1.58E−07 | L235R/S239K/M252Y/V422S/S424R/N434Y/Y436V |
| F1138 | 1.65E−07 | L235R/S239K/M252Y/N434Y/Y436V/Q438R/S440E |
| F1139 | 1.52E−07 | L235R/S239K/M252Y/S424N/N434Y/Y436V |
| F1140 | 1.62E−07 | M252Y/V422E/S424R/N434Y/Y436V/Q438R/S440E |
| F1141 | 1.77E−07 | M252Y/V422S/S424R/N434Y/Y436V/Q438R/S440E |
| F1142 | 1.87E−07 | L235R/S239K/M252Y/V422E/S424R/N434Y/Y436V/Q438R/S440E |
| F1143 | 1.98E−07 | L235R/S239K/M252Y/V422S/S424R/N434Y/Y436V/Q438R/S440E |

TABLE 2-continued

| Variant | KD (M) | Amino acid modification site |
|---|---|---|
| F1144 | 1.44E−08 | L235R/S239K/T250V/M252Y/T307Q/V308P/Q311A/N434Y/Y436V/Q438R/S440E |
| F1145 | 5.23E−08 | T250V/M252Y/T307Q/Q311A/N434Y/Y436V/Q438R/S440E |
| F1146 | 6.24E−08 | L235R/S239K/T250V/M252Y/T307Q/Q311A/N434Y/Y436V/Q438R/S440E |
| F1147 | 7.19E−08 | M252Y/T307Q/Q311A/N434Y/Q438R/S440E |
| F1148 | 7.63E−08 | L235R/S239K/M252Y/T307Q/Q311A/N434Y/Q438R/S440E |
| F1151 | 2.51E−07 | L235R/S239K/M252Y/S424N/N434Y |
| F1152 | 7.38E−08 | L235R/S239K/M252Y/T307Q/Q311A/S424N/N434Y |
| F1153 | 4.85E−08 | L235R/S239K/T250V/M252Y/T307Q/Q311A/S424N/N434Y/Y436V |
| F1154 | 1.34E−08 | L235R/S239K/T250V/M252Y/T307Q/V308P/Q311A/S424N/N434Y/Y436V |
| F1157 | 2.09E−07 | M252Y/N434Y/Q438R/S440E |
| F1158 | 2.44E−07 | L235R/S239K/M252Y/N434Y/Q438R/S440E |
| F1159 | 4.79E−07 | S424N/N434W |
| F1160 | 2.88E−07 | V308F/S424N/N434Y |
| F1161 | 1.07E−06 | I332V/S424N/N434Y |
| F1162 | 3.43E−07 | P238D/T250Y/M252Y/N434Y/Y436V |
| F1163 | 1.54E−07 | P238D/T250Y/M252Y/T307Q/Q311A/N434Y |
| F1164 | 6.96E−08 | P238D/T250Y/M252Y/T307Q/Q311A/N434Y/Y436V |
| F1165 | 1.63E−08 | P238D/T250Y/M252Y/T307Q/V308P/Q311A/N434Y/Y436V |
| F1174 | 4.9E−07 | P257I/N434H |
| F1176 | 1.98E−06 | V308F |
| F1178 | 8.72E−07 | V259I/V308F/M128L |
| F1183 | 1.28E−06 | E380A/M428L/N434S |
| F1184 | 1E−06 | T307A/M428L/N434S |
| F1185 | 9.17E−07 | T307A/E380A/M428L/N434S |
| F1188 | 1.72E−06 | T307A/E380A/N434H |
| F1189 | 1.57E−07 | M252Y/H433D/N434Y/Y436V/Q438R/S440E |
| F1190 | 2.4E−07 | M252Y/H433E/N434Y/Y436V/Q438R/S440E |
| F1191 | 2.11E−07 | M252Y/N434Y/Y436V/T437A/Q438R/S440E |
| F1192 | 1.27E−07 | M252Y/N434Y/Y436V/T437G/Q438R/S440E |
| F1194 | 1.55E−07 | M252Y/N434Y/Y436V/Q438R/K439D/S440E |
| F1195 | 1.76E−07 | M252Y/N434Y/Y436V/Q438R/S440E/L441A |
| F1196 | 1.51E−07 | M252Y/N434Y/Y436V/Q438R/S440E/L441E |
| F1197 | 9.46E−08 | M252Y/S254T/N434Y/Y436V/Q438R/S440E |
| F1198 | 7.83E−08 | M252Y/T256E/N434Y/Y436V/Q438R/S440E |
| F1199 | 6.25E−08 | M252Y/S254T/T256E/N434Y/Y436V/Q438R/S440E |
| F1200 | 1.26E−07 | T250V/M252Y/S254T/N434Y/Y436V/Q438R/S440E |
| F1201 | 1.07E−07 | T250V/M252Y/T256E/N434Y/Y436V/Q438R/S440E |
| F1202 | 8.81E−08 | T250V/M252Y/S254T/T256E/N434Y/Y436V/Q438R/S440E |
| F1203 | 1.52E−07 | M252Y/T256Q/N434Y/Y436V/Q438R/S440E |
| F1204 | 1.18E−07 | M252Y/S254T/T256Q/N434Y/Y436V/Q438R/S440E |
| F1205 | 1.98E−07 | T250V/M252Y/T256Q/N434Y/Y436V/Q438R/S440E |
| F1206 | 1.69E−07 | T250V/M252Y/S254T/T256Q/N434Y/Y436V/Q438R/S440E |
| F1207 | 1.11E−06 | I332E/M428L/N434S |
| F1208 | 5.71E−07 | L251A/M252Y/N434Y/Y436V |
| F1211 | 1.23E−06 | L251H/M252Y/N434Y/Y436V |
| F1213 | 6.33E−07 | L251N/M252Y/N434Y/Y436V |
| F1216 | 1.16E−06 | L251S/M252Y/N434Y/Y436V |
| F1217 | 1.14E−06 | L251T/M252Y/N434Y/Y436V |
| F1218 | 2.51E−07 | L251V/M252Y/N434Y/Y436V |
| F1229 | 2.81E−06 | M252Y/I253V/N434Y/Y436V |
| F1230 | 1.12E−07 | M252Y/N434Y/Y436V/Q438R/S440D |
| F1231 | 9.73E−08 | M252Y/N434Y/Y436V/Q438K/S440E |
| F1232 | 9.79E−08 | M252Y/N434Y/Y436V/Q438K/S440D |
| F1243 | 1.25E−07 | L235R/S239K/M252Y/S254T/N434Y/Y436V/Q438R/S440E |
| F1244 | 1.02E−07 | L235R/S239K/M252Y/T256E/N434Y/Y436V/Q438R/S440E |
| F1245 | 8.2E−08 | L235R/S239K/M252Y/S254T/T256E/N434Y/Y436V/Q438R/S440E |
| F1246 | 1.73E−07 | L235R/S239K/T250V/M252Y/S254T/N434Y/Y436V/Q438R/S440E |
| F1247 | 1.45E−07 | L235R/S239K/T250V/M252Y/T256E/N434Y/Y436V/Q438R/S440E |
| F1248 | 1.2E−07 | L235R/S239K/T250V/M252Y/S254T/T256E/N434Y/Y436V/Q438R/S440E |
| F1249 | 2.06E−07 | L235R/S239K/M252Y/T256Q/N434Y/Y436V/Q438R/S440E |
| F1250 | 1.66E−07 | L235R/S239K/M252Y/S254T/T256Q/N434Y/Y436V/Q438R/S440E |
| F1251 | 2.77E−07 | L235R/S239K/T250V/M252Y/T256Q/N434Y/Y436V/Q438R/S440E |
| F1252 | 2.33E−07 | L235R/S239K/T250V/M252Y/S254T/T256Q/N434Y/Y436V/Q438R/S440E |
| F1253 | 1.12E−07 | L235R/S239K/M252Y/T307A/N434Y/Y436V/Q438R/S440E |
| F1254 | 6.42E−08 | L235R/S239K/M252Y/T307Q/N434Y/Y436V/Q438R/S440E |
| F1255 | 1.11E−07 | L235R/S239K/M252Y/Q311A/N434Y/Y436V/Q438R/S440E |
| F1256 | 1.56E−07 | L235R/S239K/M252Y/Q311H/N434Y/Y436V/Q438R/S440E |
| F1257 | 7.81E−08 | L235R/S239K/M252Y/T307A/Q311A/N434Y/Y436V/Q438R/S440E |
| F1258 | 1.05E−07 | L235R/S239K/M252Y/T307A/Q311H/N434Y/Y436V/Q438R/S440E |
| F1259 | 4.46E−08 | L235R/S239K/M252Y/T307Q/Q311A/N434Y/Y136V/Q438R/S440E |
| F1260 | 6.53E−08 | L235R/S239K/M252Y/T307Q/Q311H/N434Y/Y136V/Q438R/S440E |
| F1261 | 1.35E−07 | L235R/S239K/M252Y/N434Y/Y436V/Q438R/S440D |
| F1262 | 1.26E−07 | L235R/S239K/M252Y/N434Y/Y436V/Q438K/S440E |
| F1263 | 1.24E−07 | L235R/S239K/M252Y/N434Y/Y436V/Q438K/S440D |
| F1264 | 1.27E−07 | L235R/S239K/M252Y/T256A/N434Y/Y436V/Q438R/S440E |
| F1265 | 1.57E−07 | L235R/S239K/M252Y/T256G/N434Y/Y436V/Q438R/S440E |
| F1266 | 9.99E−08 | L235R/S239K/M252Y/T256N/N434Y/Y436V/Q438R/S440E |
| F1267 | 1.5E−07 | L235R/S239K/M252Y/S254A/N434Y/Y436V/Q438R/S440E |
| F1268 | 2E−07 | L235R/S239K/M252Y/H433D/N434Y/Y436V/Q438R/S440E |
| F1269 | 1.69E−07 | L235R/S239K/M252Y/H433D/N434Y/Y436V/Q438K/S440D |
| F1270 | 1.18E−07 | L235R/S239K/M252Y/S254A/N434Y/Y436V/Q438K/S440D |
| F1271 | 2.05E−07 | L235R/S239K/M252Y/S254A/H433D/N434Y/Y436V/Q438R/S440E |
| F1272 | 1.71E−07 | L235R/S239K/M252Y/S254A/H433D/N434Y/Y436V/Q438K/S440D |
| F1273 | 1.53E−07 | L235R/S239K/M252Y/T256Q/N434Y/Y436V/Q438K/S440D |
| F1274 | 2.48E−07 | L235R/S239K/M252Y/T256Q/H433D/N434Y/Y436V/Q438R/S440E |
| F1275 | 2.09E−07 | L235R/S239K/M252Y/T256Q/H433D/N434Y/Y436V/Q438K/S440D |
| F1276 | 1.02E−07 | L235R/S239K/M252Y/T256A/N434Y/Y436V/Q438K/S440D |
| F1277 | 1.69E−07 | L235R/S239K/M252Y/T256A/H433D/N434Y/Y436V/Q438R/S440E |
| F1278 | 1.4E−07 | L235R/S239K/M252Y/T256A/H433D/N434Y/Y436V/Q438K/S440D |
| F1279 | 1.23E−07 | L235R/S239K/M252Y/T256G/N434Y/Y436V/Q438K/S440D |
| F1280 | 2.09E−07 | L235R/S239K/M252Y/T256G/H433D/N434Y/Y436V/Q438R/S440E |
| F1281 | 1.74E−07 | L235R/S239K/M252Y/T256G/H433D/N434Y/Y436V/Q438K/S440D |
| F1282 | 7.69E−08 | L235R/S239K/M252Y/T256N/N434Y/Y436V/Q438K/S440D |
| F1283 | 1.34E−07 | L235R/S239K/M252Y/T256N/H433D/N434Y/Y436V/Q438R/S440E |
| F1284 | 1.12E−07 | L235R/S239K/M252Y/T256N/H433D/N434Y/Y436V/Q438K/S440D |
| F1285 | 9.36E−08 | L235R/S239K/M252Y/S254T/N434Y/Y436V/ |

TABLE 2-continued

| Variant | KD (M) | Amino acid modification site |
|---|---|---|
|  |  | Q438K/S440D |
| F1286 | 1.57E−07 | L235R/S239K/M252Y/S254T/H433D/N434Y/Y436V/Q438R/S440E |
| F1287 | 1.5E−07 | L235R/S239K/M252Y/S254T/H433D/N434Y/Y436V/Q438K/S440D |
| F1288 | 7.95E−08 | L235R/S239K/M252Y/T256E/N434Y/Y436V/Q438K/S440D |
| F1289 | 1.33E−07 | L235R/S239K/M252Y/T256E/H433D/N434Y/Y436V/Q438K/S440E |
| F1290 | 1.11E−07 | L235R/S239K/M252Y/T256E/H433D/N434Y/Y436V/Q438K/S440D |
| F1291 | 1.51E−07 | L235R/S239K/M252Y/H433D/N434Y/Y436V |
| F1292 | 4.24E−07 | L235R/S239K/H433D/N434W/Y436V/Q438R/S440E |
| F1293 | 1.61E−07 | L235R/S239K/M252Y/T256E/N434Y/Q438R/S440E |
| F1294 | 2E−07 | L235R/S239K/M252Y/T256E/N434Y/Y436T/Q438R/S440E |
| F1295 | 9.84E−08 | L235R/S239K/M252Y/T256E/N434Y/Y436F/Q438R/S440E |
| F1296 | 2.27E−07 | L235R/S239K/M252Y/T256E/H433D/N434Y/Q438R/S440E |
| F1297 | 2.5E−07 | L235R/S239K/M252Y/T256E/H433D/N434Y/Y436T/Q438R/S440E |
| F1298 | 1.47E−07 | L235R/S239K/M252Y/T256E/H433D/N434Y/Y436F/Q438R/S440E |
| F1299 | 1.5E−07 | L235R/S239K/M252Y/T256E/N434Y/Q438K/S440D |
| F1300 | 1.63E−07 | L235R/S239K/M252Y/T256E/N434Y/Y436T/Q438K/S440D |
| F1301 | 8.3E−08 | L235R/S239K/M252Y/T256E/N434Y/Y436F/Q438K/S440D |
| F1302 | 2.15E−07 | L235R/S239K/M252Y/T256E/H433D/N434Y/Q438K/S440D |
| F1303 | 2.1E−07 | L235R/S239K/M252Y/T256E/H433D/N434Y/Y436T/Q438K/S440D |
| F1304 | 1.24E−07 | L235R/S239K/M252Y/T256E/H433D/N434Y/Y436F/Q438K/S440D |
| F1305 | 2.05E−07 | L235R/S239K/M252Y/H433D/N434Y/Y436V/Q438K/S440D |
| F1306 | 1.92E−07 | L235R/S239K/M252Y/H433D/N434Y/Y436V/Q438K/S440E |
| F1307 | 1.44E−07 | L235R/S239K/M252Y/V422A/S424A/N434Y/Y436V |
| F1308 | 2.06E−07 | L235R/S239K/M252Y/V422L/S424L/N434Y/Y436V |
| F1309 | 1.26E−07 | L235R/S239K/M252Y/N434Y/Y436V/Q438A/S440A |
| F1310 | 2.28E−07 | L235R/S239K/M252Y/N434Y/Y436V/Q438L/S440L |
| F1311 | 1.69E−07 | L235R/S239K/M252Y/V422A/S424A/H433D/N434Y/Y436V |
| F1312 | 1.79E−07 | L235R/S239K/M252Y/V422L/S424L/H433D/N434Y/Y436V |
| F1313 | 1.77E−07 | L235R/S239K/M252Y/H433D/N434Y/Y436V/Q438A/S440A |
| F1314 | 2.27E−07 | L235R/S239K/M252Y/H433D/N434Y/Y436V/Q438L/S440L |
| F1315 | 1.52E−07 | G237K/S239K/M252Y/N434Y/Y436V |
| F1316 | 1.49E−07 | G237R/S239K/M252Y/N434Y/Y436V |
| F1317 | 1.38E−07 | S239K/M252Y/P329K/N434Y/Y436V |
| F1318 | 1.43E−07 | S239K/M252Y/P329R/N434Y/Y436V |
| F1319 | 2.67E−07 | M252Y/L328Y/N434Y |
| F1320 | 1.22E−07 | L235R/S239K/M252Y/S254T/N434Y/Y436V/Q438R/S440D |
| F1321 | 1.03E−07 | L235R/S239K/M252Y/S254T/N434Y/Y436V/Q438K/S440E |
| F1322 | 1.6E−07 | L235R/S239K/M252Y/S254T/H433D/N434Y/Y436V/Q438R/S440D |
| F1323 | 1.49E−07 | L235R/S239K/M252Y/S254T/H433D/N434Y/Y436V/Q438K/S440E |
| F1324 | 1.32E−07 | L234A/L235A/M252Y/N434Y/Y436V |
| F1325 | 2.13E−07 | L234A/L235A/M252Y/N297A/N434Y/Y436V |
| F1326 | 1.09E−08 | L234A/L235A/T250V/M252Y/T307Q/V308P/Q311A/N434Y/Y436V |
| F1327 | 1.41E−08 | L234A/L235A/T250V/M252Y/N297A/T307Q/V308P/Q311A/N434Y/Y436V |
| F1328 | 1.52E−07 | L235R/G236R/S239K/M252Y/N434Y/Y436V/Q438R/S440E |
| F1329 | 1.29E−07 | L235R/G236R/S239K/M252Y/S254T/N434Y/Y436V/Q438R/S440E |
| F1330 | 1.03E−07 | L235R/G236R/S239K/M252Y/T256E/N434Y/Y436V/Q438R/S440E |
| F1331 | 7.75E−08 | L235R/G236R/S239K/M252Y/S254T/T256E/N434Y/Y436V/Q438R/S440E |
| F1333 | 1.23E−07 | L235R/G236R/S239K/M252Y/N434Y/Y436V |
| F1334 | 1.04E−07 | L235R/G236R/S239K/M252Y/N434Y/Y436V/Q438K/S440D |
| F1335 | 8.78E−08 | L235R/G236R/S239K/M252Y/S254T/N434Y/Y436V/Q438K/S440D |
| F1336 | 7.18E−08 | L235R/G236R/S239K/M252Y/T256E/N434Y/Y436V/Q438K/S440D |
| F1337 | 7.41E−08 | L235R/S239K/M252Y/T256E/N434Y/Y436V/Q438K/S440E |
| F1338 | 1.04E−07 | L235R/S239K/M252Y/T256E/H433D/N434Y/Y436V/Q438K/S440E |
| F1339 | 2.51E−07 | L235R/S239K/M252Y/S254T/T256E/H433D/N434Y/Y436T/Q438K/S440E |
| F1340 | 5.58E−08 | L235R/S239K/M252Y/S254T/T256E/N434Y/Y436V/Q438K/S440E |
| F1341 | 3.22E−07 | L235R/S239K/M252Y/S254T/N434Y/Y436T/Q438K/S440E |
| F1342 | 2.51E−07 | L235R/S239K/M252Y/T256E/N434Y/Y436T/Q438K/S440E |
| F1343 | 2.01E−07 | L235R/S239K/M252Y/S254T/T256E/N434Y/Y436T/Q438K/S440E |
| F1344 | 3.96E−07 | L235R/S239K/M252Y/N434Y/Y436T/Q438K/S440E |
| F1345 | 1.05E−07 | L235R/G236R/S239K/M252Y/N434Y/Y436V/Q438K/S440E |
| F1346 | 8.59E−08 | L235R/G236R/S239K/M252Y/S254T/N434Y/Y436V/Q438K/S440E |
| F1347 | 7.14E−08 | L235R/G236R/S239K/M252Y/T256E/N434Y/Y436V/Q438K/S440E |
| F1348 | 5.52E−08 | L235R/G236R/S239K/M252Y/S254T/T256E/N434Y/Y436V/Q438K/S440E |
| F1349 | 3.36E−07 | L235R/S239K/M252Y/N434Y/Y436T/Q438R/S440E |
| F1350 | 1.18E−07 | L235R/S239K/M252Y/N434Y/Y436F/Q438K/S440E |
| F1351 | 1.62E−07 | L235R/S239K/M252Y/N434Y/Y436F/Q438R/S440E |
| F1352 | 3.93E−07 | L235R/S239K/M252Y/H433D/N434Y/Y436T/Q438K/S440E |
| F1353 | 4.33E−07 | L235R/S239K/M252Y/H433D/N434Y/Y436T/Q438R/S440E |
| F1354 | 2.29E−07 | L235R/S239K/M252Y/H433D/N434Y/Y436F/Q438K/S440E |
| F1355 | 2.47E−07 | L235R/S239K/M252Y/H433D/N434Y/Y436F/Q438K/S440E |
| F1356 | 1.58E−07 | G236R/M252Y/L328R/N434Y/Y436V |
| F1357 | 2.81E−07 | L235R/S239K/M252Y/S254T/N434Y/Y436T/Q438K/S440E |
| F1358 | 9.07E−08 | L235R/S239K/M292Y/S254T/N434Y/Y436F/Q438K/S440E |
| F1359 | 1.28E−07 | L235R/S239K/M252Y/S254T/N434Y/Y436F/Q438R/S440E |
| F1360 | 3.12E−07 | L235R/S239K/M252Y/S254T/H433D/N434Y/Y436T/Q438K/S440E |
| F1361 | 3.52E−07 | L235R/S239K/M252Y/S254T/H433D/N434Y/Y436T/Q438K/S440E |
| F1362 | 1.41E−07 | L235R/S239K/M252Y/S254T/H433D/N434Y/Y436F/Q438K/S440E |
| F1363 | 1.9E−07 | L235R/S239K/M252Y/S254T/H433D/N434Y/Y436F/Q438K/S440E |
| F1364 | 7.49E−08 | L235R/S239K/M252Y/T256E/N434Y/Y436F/Q438K/S440E |
| F1365 | 3.14E−07 | L235R/S239K/M252Y/T256E/H433D/N434Y/Y436T/Q438K/S440E |
| F1366 | 1.17E−07 | L235R/S239K/M252Y/T256E/H433D/N434Y/Y436F/Q438K/S440E |
| F1367 | 1.79E−07 | L235R/S239K/M252Y/S254T/T256E/N434Y/Y436T/Q438R/S440E |

TABLE 2-continued

| Variant | KD (M) | Amino acid modification site |
|---|---|---|
| F1368 | 5.49E−08 | L235R/S239K/M252Y/S254T/T256E/N434Y/Y436F/Q438K/S440E |
| F1369 | 7.6E−08 | L235R/S239K/M252Y/S254T/T256E/N434Y/Y436F/Q438R/S440E |
| F1370 | 9.14E−08 | L235R/S239K/M252Y/S254T/T256E/H433D/N434Y/Y436V/Q438K/S444E |
| F1371 | 1.09E−07 | L235R/S239K/M252Y/S254T/T256E/H433D/N434Y/Y436V/Q438R/S440E |
| F1372 | 2.28E−07 | L235R/S239K/M252Y/S254T/T256E/H433D/N434Y/Y436T/Q438R/S440E |
| F1373 | 8.67E−08 | L235R/S239K/M252Y/S254T/T256E/H433D/N434Y/Y436F/Q438K/S440E |
| F1374 | 1.2E−07 | L235R/S239K/M252Y/S254T/T256E/H433D/N434Y/Y436F/Q438R/S440E |
| F1375 | 1.03E−07 | L235R/S239K/M252Y/S254T/N434Y/Y436V |
| F1376 | 9.09E−08 | L235R/S239K/M252Y/S254T/T256E/N434Y/Y436V |
| F1377 | 8.27E−08 | L235R/S239K/M252Y/T256E/N434Y/Y436V |
| F1378 | 3.61E−07 | L235R/S239K/M252Y/N434Y/Y436T |
| F1379 | 2.85E−07 | L235R/S239K/M252Y/N434Y/Y436F |
| F1410 | 1.90E−06 | V308P/I332V |
| F1411 | 1.70E−07 | V308P/I332V/M428L/N434S |
| F1413 | 3.70E−08 | L235R/S239K/M252Y/S254T/T256E/T307Q/Q311A/H433D/N434Y/Y436V/Q438K/S440E |
| F1414 | 5.60E−08 | L235R/S239K/M252Y/S254T/T256E/T307Q/H433D/N434Y/Y436V/Q438R/S440E |
| F1415 | 5.90E−08 | L235R/S239K/M252Y/S254T/T256E/Q311A/H433D/N434Y/Y436V/Q438K/S440E |
| F1416 | 1.30E−08 | L235R/S239K/M252Y/S254T/T256E/V308P/H433D/N434Y/Y436V/Q438K/S440E |
| F1417 | 5.90E−08 | L235R/S239K/M252Y/S254T/T256E/H433D/N434W/Y436V/Q438K/S440E |
| F1418 | 7.50E−08 | L235R/S239K/M252Y/S254T/T256E/H433D/N434W/Y436V/Q438R/S440E |
| F1419 | 1.50E−07 | L235R/S239K/M252Y/H433D/N434W/Y436V/Q438E/S440E |
| F1420 | 1.30E−07 | L235R/S239K/M252Y/H433D/N434W/Y436V/Q438K/S440E |
| F1421 | 3.20E−08 | V308P/M428L/N434W |
| F1422 | 1.90E−08 | L235R/S239K/M252Y/T256E/V308P/H433D/N434Y/Y436V/Q438R/S440E |
| F1423 | 1.60E−08 | L235R/S239K/M252Y/T256E/V302D/V308P/H433D/N434Y/Y436V/Q438R/S440E |
| F1424 | 1.60E−08 | L235R/S239K/M252Y/T256E/V302E/V308P/H433D/N434Y/Y436V/Q438R/S440E |
| F1425 | 1.90E−08 | L235R/S239K/M252Y/T256E/V303D/V308P/H433D/N434Y/Y436V/Q438R/S440E |
| F1426 | 1.80E−08 | L235R/S239K/M252Y/T256E/V303E/V308P/H433D/N434Y/Y436V/Q438R/S440E |
| F1428 | 1.50E−08 | L235R/S239K/M252Y/T256E/S304E/V308P/H433D/N434Y/Y436V/Q438R/S440E |
| F1430 | 3.10E−08 | L235R/S239K/M252Y/T256E/V305E/V308P/H433D/N434Y/Y436V/Q438R/S440E |
| F1433 | 4.50E−08 | L235R/S239K/M252Y/T256E/T307D/V308P/H433D/N434Y/Y436V/Q438R/S440E |
| F1434 | 3.60E−08 | L235R/S239K/M252Y/T256E/T307E/V308P/H433D/N434Y/Y436V/Q438R/S440E |
| F1437 | 1.2E−07 | V308P/M428L/N434F |
| F1438 | 2.2E−07 | V308P/M428L/N434H |
| F1439 | 4.7E−08 | V308P/M428Y/N434W |
| F1440 | 2.6E−07 | V308P/M428I/N434W |
| F1441 | 2.5E−07 | L235R/S239K/M252Y/T256E/M428L/H433D/N434Y/Y436V/Q438R/S440E |
| F1442 | 2.4E−07 | V308P/M428L/N434S |
| F1443 | 5.0E−07 | T307A/V308P/M428L/N434S |
| F1444 | 2.6E−07 | T307Q/V308P/M428L/N434S |
| F1445 | 2.1E−07 | V308P/Q311A/M428L/N434S |
| F1446 | 2.1E−07 | T307Q/V308P/Q311A/M428L/N434S |
| F1447 | 6.7E−08 | L235R/S239K/M252Y/T256E/N286E/H433D/N434Y/Y436V/Q438R/S440E |
| F1448 | 4.3E−08 | L235R/S239K/M252Y/S254T/T256E/N286E/H433D/N434Y/Y436V/Q438R/S440E |
| F1449 | 1.2E−07 | L235R/S239K/M252W/T256E/H433D/N434Y/Y436V/Q438R/S440E |
| F1450 | 8.6E−08 | L235R/S239K/M252Y/S254T/T256E/H433D/N434Y/Y436V/Q438R/S440E |
| F1451 | 4.0E−07 | L235R/S239K/D249A/M252Y/S254T/T256E/H433D/N434Y/Y436V/Q438R/S440E |
| F1452 | 6.1E−07 | L235R/S239K/D249E/M252Y/S254T/T256E/H433D/N434Y/Y436V/Q438R/S440E |
| F1455 | 7.9E−07 | L235R/S239K/D249H/M252Y/S254T/T256E/H433D/N434Y/Y436V/Q438R/S440E |
| F1460 | 5.8E−07 | L235R/S239K/D249N/M252Y/S254T/T256E/H433D/N434Y/Y436V/Q438R/S440E |
| F1464 | 8.4E−07 | L235R/S239K/D249S/M252Y/S254T/T256E/H433D/N434Y/Y436V/Q438K/S440E |
| F1465 | 8.2E−07 | L235R/S239K/D249T/M252Y/S254T/T256E/H433D/N434Y/Y436V/Q438R/S440E |
| F1469 | 9.2E−08 | L235R/S239K/T250A/M252Y/S254T/T256E/H433D/N434Y/Y436V/Q438R/S440E |
| F1472 | 5.3E−07 | L235R/S239K/T250F/M252Y/S254T/T256E/H433D/N434Y/Y436V/Q438R/S440E |
| F1475 | 2.0E−07 | L235R/S239K/T250I/M252Y/S254T/T256E/H433D/N434Y/Y436V/Q438R/S440E |
| F1478 | 2.0E−07 | L235R/S239K/T250M/M252Y/S254T/T256E/H433D/N434Y/Y436V/Q438R/S440E |
| F1479 | 1.2E−06 | L235R/S239K/T250N/M252Y/S254T/T256E/H433D/N434Y/Y436V/Q438R/S440E |
| F1481 | 1.1E−07 | L235R/S239K/T250Q/M252Y/S254T/T256E/H433D/N434Y/Y436V/Q438R/S440E |
| F1483 | 1.8E−07 | L235R/S239K/T250S/M252Y/S254T/T256E/H433D/N434Y/Y436V/Q438R/S440E |
| F1484 | 1.5E−07 | L235R/S239K/T250V/M252Y/S254T/T256E/H433D/N434Y/Y436V/Q438R/S440E |
| F1486 | 3.1E−07 | L235R/S239K/T250Y/M252Y/S254T/T256E/H433D/N434Y/Y436V/Q438R/S440E |
| F1490 | 4.6E−07 | L235R/S239K/L251F/M252Y/S254T/T256E/H433D/N434Y/Y436V/Q438R/S440E |
| F1495 | 5.4E−07 | L235R/S239K/L251M/M252Y/S254T/T256E/H433D/N434Y/Y436V/Q438R/S440E |
| F1504 | 6.3E−07 | L235R/S239K/L251Y/M252Y/S254T/T256E/H433D/N434Y/Y436V/Q438R/S440E |
| F1520 | 1.3E−06 | L235R/S239K/M252Y/I253V/S254T/T256E/H433D/N434Y/Y436V/Q438R/S440E |
| F1523 | 1.8E−07 | L235R/S239K/M252Y/S254T/R255A/T256E/H433D/N434Y/Y436V/Q438R/S440E |
| F1524 | 1.4E−06 | L235R/S239K/M252Y/S254T/R255D/T256E/H433D/N434Y/Y436V/Q438R/S440E |
| F1525 | 4.2E−07 | L235R/S239K/M252Y/S254T/R255E/T256E/H433D/N434Y/Y436V/Q438R/S440E |
| F1526 | 1.7E−07 | L235R/S239K/M252Y/S254T/R255F/T256E/H433D/N434Y/Y436V/Q438R/S440E |
| F1527 | 1.9E−07 | L235R/S239K/M252Y/S254T/R255G/T256E/H433D/N434Y/Y436V/Q438R/S440E |
| F1528 | 1.6E−07 | L235R/S239K/M252Y/S254T/R255H/T256E/H433D/N434Y/Y436V/Q438R/S440E |
| F1529 | 1.5E−07 | L235R/S239K/M252Y/S254T/R255I/T256E/H433D/N434Y/Y436V/Q438R/S440E |
| F1530 | 1.5E−07 | L235R/S239K/M252Y/S254T/R255K/T256E/H433D/N434Y/Y436V/Q438R/S440E |
| F1531 | 6.5E−08 | L235R/S239K/M252Y/S254T/R255L/T256E/H433D/N434Y/Y436V/Q438R/S440E |
| F1532 | 1.1E−07 | L235R/S239K/M252Y/S254T/R255M/T256E/H433D/N434Y/Y436V/Q438R/S440E |
| F1533 | 3.2E−07 | L235R/S239K/M252Y/S254T/R255N/T256E/H433D/N434Y/Y436V/Q438R/S440E |
| F1535 | 2.7E−07 | L235R/S239K/M252Y/S254T/R255Q/T256E/H433D/N434Y/Y436V/Q438R/S440E |
| F1536 | 2.2E−07 | L235R/S239K/M252Y/S254T/R255S/T256E/H433D/N434Y/Y436V/Q438R/S440E |
| F1537 | 3.0E−07 | L235R/S239K/M252Y/S254T/R255T/T256E/H433D/N434Y/Y436V/Q438R/S440E |
| F1538 | 7.4E−07 | L235R/S239K/M252Y/S254T/R255V/T256E/H433D/N434Y/Y436V/Q438R/S440E |
| F1539 | 5.6E−07 | L235R/S239K/M252Y/S254T/R255W/T256E/H433D/N434Y/Y436V/Q438R/S440E |
| F1540 | 1.7E−07 | L235R/S239K/M252Y/S254T/R255Y/T256E/H433D/N434Y/Y436V/Q438R/S440E |
| F1541 | 1.2E−07 | L235R/S239K/M252Y/S254T/T256E/E258A/H433D/N434Y/Y436V/Q438R/S440E |
| F1542 | 5.7E−08 | L235R/S239K/M252Y/S254T/T256E/E258D/H433D/N434Y/Y436V/Q438R/S440E |

TABLE 2-continued

| Variant | KD (M) | Amino acid modification site |
|---|---|---|
| F1543 | 1.2E−07 | L235R/S239K/M252Y/S254T/T256E/E258F/H433D/N434Y/Y436V/Q438R/S440E |
| F1544 | 8.2E−08 | L235R/S239K/M252Y/S254T/T256E/E258G/H433D/N434Y/Y436V/Q438R/S440E |
| F1545 | 9.5E−08 | L235R/S239K/M252Y/S254T/T256E/E258H/H433D/N434Y/Y436V/Q438R/S440E |
| F1546 | 6.2E−08 | L235R/S239K/M252Y/S254T/T256E/E258I/H433D/N434Y/Y436V/Q438R/S440E |
| F1547 | 7.9E−08 | L235R/S239K/M252Y/S254T/T256E/E258K/H433D/N434Y/Y436V/Q438R/S440E |
| F1548 | 6.6E−08 | L235R/S239K/M252Y/S254T/T256E/E258L/H433D/N434Y/Y436V/Q438R/S440E |
| F1549 | 7.8E−08 | L235R/S239K/M252Y/S254T/T256E/E258M/H433D/N434Y/Y436V/Q438R/S440E |
| F1550 | 1.2E−07 | L235R/S239K/M252Y/S254T/T256E/E258N/H433N/N434Y/Y436V/Q438R/S440E |
| F1552 | 8.1E−08 | L235R/S239K/M252Y/S254T/T256E/E258Q/H433D/N434Y/Y436V/Q438R/S440E |
| F1553 | 6.9E−08 | L235R/S239K/M252Y/S254T/T256E/E258R/H433D/N434Y/Y436V/Q438R/S440E |
| F1554 | 1.1E−07 | L235R/S239K/M252Y/S254T/T256E/E258S/H433D/N434Y/Y436V/Q438R/S440E |
| F1555 | 9.6E−08 | L235R/S239K/M252Y/S254T/T256E/E258T/H433D/N434Y/Y436V/Q438R/S440E |
| F1556 | 7.4E−08 | L235R/S239K/M252Y/S254T/T256E/E258V/H433D/N434Y/Y436V/Q438R/S440E |
| F1557 | 8.9E−08 | L235R/S239K/M252Y/S254T/T256E/E258W/H433D/N434Y/Y436V/Q438R/S440E |
| F1558 | 1.3E−07 | L235R/S239K/M252Y/S254T/T256E/E258Y/H433D/N434Y/Y436V/Q438R/S440E |
| F1559 | 1.4E−07 | V308P/Q311A/I332V/M428L/N434S |
| F1560 | 2.4E−08 | V308P/Q311A/M428L/N434W |
| F1561 | 2.5E−08 | V308P/Q311A/M428Y/N434W |
| F1562 | 2.7E−07 | K288D/V308P/I332V/M428L/N434S |
| F1563 | 5.0E−08 | K288D/V308P/M428L/N434W |
| F1564 | 4.8E−08 | K288D/V308P/M428Y/N434W |
| F1565 | 3.1E−08 | V308P/I332V/M428Y/N434W |
| F1566 | 3.4E−08 | L235R/S239K/M252Y/S254T/T256E/N286E/H433D/N434Y/Y436V/Q438R/S440E |
| F1567 | 4.8E−08 | L235R/S239K/M252Y/S254T/T256E/H433A/N434Y/Y436V/Q438R/S440E |
| F1568 | 1.5E−07 | L235R/S239K/M252Y/S254T/T256E/H433E/N434Y/Y436V/Q438R/S440E |
| F1569 | 2.6E−07 | L235R/S239K/M252Y/S254T/T256E/H433F/N434Y/Y436V/Q438R/S440E |
| F1570 | 2.1E−07 | L235R/S239K/M252Y/S254T/T256E/H433G/N434Y/Y436V/Q438R/S440E |
| F1571 | 1.7E−07 | L235R/S239K/M252Y/S254T/T256E/H433I/N434Y/Y436V/Q438R/S440E |
| F1572 | 4.1E−08 | L235R/S239K/M252Y/S254T/T256E/H433K/N434Y/Y436V/Q438R/S440E |
| F1573 | 1.3E−07 | L235R/S239K/M252Y/S254T/T256E/H433L/N434Y/Y436V/Q438R/S440E |
| F1574 | 9.4E−08 | L235R/S239K/M252Y/S254T/T256E/H433M/N434Y/Y436V/Q438R/S440E |
| F1575 | 8.8E−08 | L235R/S239K/M252Y/S254T/T256E/H433N/N434Y/Y436V/Q438R/S440E |
| F1576 | 4.3E−08 | L235R/S239K/M252Y/S254T/T256E/H433P/N434Y/Y436V/Q438R/S440E |
| F1577 | 6.6E−08 | L235R/S239K/M252Y/S254T/T256E/H433Q/N434Y/Y436V/Q438R/S440E |
| F1578 | 4.6E−08 | L235R/S239K/M252Y/S254T/T256E/H433R/N434Y/Y436V/Q438R/S440E |
| F1579 | 5.4E−08 | L235R/S239K/M252Y/S254T/T256E/H433S/N434Y/Y436V/Q438R/S440E |
| F1580 | 9.8E−08 | L235R/S239K/M252Y/S254T/T256E/H433T/N434Y/Y436V/Q438R/S440E |
| F1581 | 1.4E−07 | L235R/S239K/M252Y/S254T/T256E/H433V/N434Y/Y436V/Q438R/S440E |
| F1582 | 1.9E−07 | L235R/S239K/M252Y/S254T/T256E/H433W/N434Y/Y436V/Q438R/S440E |
| F1583 | 2.7E−07 | L235R/S239K/M252Y/S254T/T256E/H433Y/N434Y/Y436V/Q438R/S440E |
| F1586 | 5.5E−08 | L235R/S239K/M252Y/S254T/R255L/T256E/E258D/H433D/N434Y/Y436V/Q438R/S440E |
| F1587 | 6.1E−08 | L235R/S239K/T250Q/M252Y/S254T/T256E/E258D/H433D/N434Y/Y436V/Q438R/S440E |
| F1588 | 3.4E−08 | L235R/G236R/S239K/M252Y/T307Q/Q311A/M428I/N434Y/Y436V |
| F1589 | 4.2E−08 | L235R/G236R/S239K/T250V/M252Y/V308P/N434Y |
| F1590 | 4.7E−08 | L235R/G236R/S239K/T250V/M252Y/T307Q/Q311A/N434Y/Y436V |
| F1591 | 4.3E−08 | L235R/G236R/S239K/M252Y/T307Q/Q311A/N434Y/Y436V/Q438R/S440E |
| F1592 | 5.5E−08 | L235R/S239K/M252Y/S254T/R255L/T256E/E258I/H433D/N434Y/Y436V/Q438R/S440E |
| F1593 | 5.9E−08 | L235R/S239K/M252Y/S254T/R255L/T256E/E258K/H433D/N434Y/Y436V/Q438R/S440E |
| F1594 | 5.7E−08 | L235R/S239K/M252Y/S254T/R255L/T256E/E258L/H433D/N434Y/Y436V/Q438R/S440E |
| F1595 | 6.3E−08 | L235R/S239K/M252Y/S254T/R255L/T256E/E258M/H433D/N434Y/Y436V/Q438R/S440E |
| F1596 | 5.7E−08 | L235R/S239K/M252Y/S254T/R255L/T256E/E258Q/H433D/N434Y/Y436V/Q438R/S440E |
| F1597 | 5.6E−08 | L235R/S239K/M252Y/S254T/R255L/T256E/E258R/H433D/N434Y/Y436V/Q438R/S440E |
| F1598 | 6.6E−08 | L235R/S239K/M252Y/S254T/R255L/T256E/E258V/H433D/N434Y/Y436V/Q438R/S440E |
| F1599 | 7.4E−08 | L235R/S239K/M252Y/S254T/T256E/H433D/N434Y/Y436V/Q438K/S440D |
| F1600 | 8.5E−08 | L235R/S239K/M252Y/S254T/T256E/H433D/N434Y/Y436V/Q438R/S440D |
| F1601 | 3.5E−08 | L235R/S239K/M252Y/S254T/T256E/N286E/H433D/N434Y/Y436V/Q438K/S440D |
| F1602 | 3.6E−08 | L235R/S239K/M252Y/S254T/T256E/N286E/H433D/N434Y/Y436V/Q438R/S440D |
| F1603 | 5.9E−08 | L235R/S239K/M252Y/S254T/R255L/T256E/H433D/N34Y/Y436V/Q438K/S440E |
| F1604 | 6.0E−08 | L235R/S239K/M252Y/S254T/R255L/T256E/H433D/N434Y/Y436V/Q438R/S440D |
| F1605 | 6.1E−08 | L235R/S239K/M252Y/S254T/R255L/T256E/H433D/N434Y/Y436V/Q438K/S440E |
| F1606 | 3.2E−08 | L235R/S239K/M252Y/T256E/V302D/V308P/H433D/N434Y/Y436T/Q438R/S440E |
| F1607 | 2.0E−08 | L235R/S239K/M252Y/T256E/V302D/V308P/H433D/N434Y/Y436F/Q438R/S440E |
| F1608 | 2.9E−08 | L235R/S239K/M252Y/T256E/V302D/V308P/H433D/N434Y/Q438R/S440E |
| F1610 | 4.8E−08 | L235R/S239K/M252Y/S254T/R255L/T256E/E258D/H433D/N434Y/Y436V/Q438K/S440E |
| F1611 | 5.2E−08 | L235R/S239K/M252Y/S254T/R255L/T256E/E258I/H433D/N434Y/Y436V/Q438K/S440E |
| F1612 | 4.9E−08 | L235R/S239K/M252Y/S254T/R255L/T256E/E258D/H433D/N434Y/Y436V/Q438K/S440D |
| F1613 | 5.2E−08 | L235R/S239K/M252Y/S254T/R255L/T256E/E258I/H433D/N434Y/Y436V/Q438K/S440D |
| F1614 | 5.1E−08 | L235R/S239K/M252Y/S254T/R255L/T256E/E258D/H433D/N434Y/Y436V/Q438R/S440D |
| F1615 | 6.0E−08 | L235R/S239K/M252Y/S254T/R255L/T256E/E258I/H433D/N434Y/Y436V/Q438R/S440E |
| F1616 | 8.2E−08 | L235R/S239K/T250Q/M252Y/S254T/R255L/T256E/H433D/N434Y/Y436V/Q438K/S440E |
| F1617 | 9.6E−08 | L235R/S239K/T250Q/M252Y/S254T/R255L/T256E/H433D/N434Y/Y436V/Q438R/S440E |
| F1618 | 8.6E−08 | L235R/S239K/T250Q/M252Y/S254T/R255L/T256E/H433D/N434Y/Y436V/Q438K/S440D |
| F1619 | 8.8E−08 | L235R/S239K/T250Q/M252Y/S254T/R255L/T256E/H433D/N434Y/Y436V/Q438R/S440D |
| F1620 | 6.4E−08 | L235R/S239K/M252Y/T256E/H433A/N434Y/Y436V/Q438K/S440E |
| F1621 | 5.8E−08 | L235R/S239K/M252Y/T256E/H433K/N434Y/Y436V/Q438K/S440E |
| F1622 | 6.1E−08 | L235R/S239K/M252Y/T256E/H433P/N434Y/Y436V/Q438K/S440E |
| F1623 | 5.9E−08 | L235R/S239K/M252Y/T256E/H433R/N434Y/Y436V/Q438K/S440E |
| F1624 | 7.3E−08 | L235R/S239K/M252Y/T256E/H433S/N434Y/Y436V/Q438K/S440E |
| F1625 | 6.5E−08 | L235R/S239K/M252Y/T256E/H433A/N434Y/Y436V/Q438K/S440D |
| F1626 | 5.4E−08 | L235R/S239K/M252Y/T256E/H433K/N434Y/Y436V/Q438K/S440D |

TABLE 2-continued

| Variant | KD (M) | Amino acid modification site |
|---|---|---|
| F1627 | 6.5E−08 | L235R/S239K/M252Y/T256E/H433P/N434Y/Y436V/Q438K/S440D |
| F1628 | 6.0E−08 | L235R/S239K/M252Y/T256E/H433R/N434Y/Y436V/Q438K/S440D |
| F1629 | 6.9E−08 | L235R/S239K/M252Y/T256E/H433S/N434Y/Y436V/Q438K/S440D |
| F1641 | 4.1E−08 | L235R/S239K/M254Y/S256T/T256E/H433A/N434Y/Y436V/Q438K/S440E |
| F1642 | 4.1E−08 | L235R/S239K/M252Y/S254T/T256E/H433A/N434Y/Y436V/Q438R/S440D |
| F1643 | 3.9E−08 | L235R/S239K/M252Y/S254T/T256E/H433A/N434Y/Y436V/Q438K/S440D |
| F1644 | 3.5E−08 | L235R/S239K/M252Y/S254T/T256E/H433K/N434Y/Y436V/Q438R/S440E |
| F1645 | 3.6E−08 | L235R/S239K/M252Y/S2S4T/T256E/H433K/N434Y/Y436V/Q438R/S440D |
| F1646 | 3.5E−08 | L235R/S239K/M252Y/S254T/T256E/H433K/N434Y/Y436V/Q438K/S440D |
| F1647 | 3.8E−08 | L235R/S239K/M252Y/S254T/T256E/H433P/N434Y/Y436V/Q438K/S440E |
| F1648 | 3.8E−08 | L235R/S239K/M252Y/S254T/T256E/H433P/N434Y/Y436V/Q438R/S440D |
| F1649 | 3.7E−08 | LS239R/S239K/M252Y/S254T/T256E/H433P/N434Y/Y436V/Q438K/S440D |
| F1650 | 4.0E−08 | L235R/S239K/M252Y/S254T/T256E/H433R/N434Y/Y436V/Q438R/S440E |
| F1651 | 4.4E−08 | L235R/S239K/M252Y/S254T/T256E/H433R/N434Y/Y436V/Q438R/S440D |
| F1652 | 4.0E−08 | L235R/S239K/M252Y/S254T/T256E/H433R/N434Y/Y436V/Q438K/S440D |
| F1653 | 4.5E−08 | L235R/S239K/M252Y/S254T/T256E/H433S/N434Y/Y436V/Q438K/S440E |
| F1654 | 4.5E−08 | L235R/S239K/M252Y/S254T/T256E/H433S/N434Y/Y436V/Q438R/S440D |
| F1655 | 4.4E−08 | L235R/S239K/M252Y/S254T/T256E/H433S/N434Y/Y436V/Q438K/S440D |
| F1656 | 6.5E−08 | L235R/S239K/M252Y/S254T/T256E/N434Y/Y436V/Q438R/S440D |
| F1657 | 6.1E−08 | L235R/S239K/M252Y/S254T/T256E/N434Y/Y436V/Q438K/S440D |
| F1659 | 3.0E−06 | L235R/S239K/M252Y/S254T/T256E |
| F1670 | 1.1E−06 | L235R/S239K/N434Y/Y436V/Q438R/S440E |
| F1671 | 2.0E−06 | L235R/S239K/N434Y/Y436V |
| F1672 | 2.3E−06 | L235R/S239K/M252Y/S254T/R255L/T256E |
| F1673 | 1.8E−06 | L235R/S239K/M252Y/S254T/R255L/T256E/E258D |
| F1674 | 2.0E−06 | L235R/S239K/M252Y/S254T/R255L/T256E/E258I |
| F1675 | 9.6E−07 | L235R/S239K/H433D/N434Y/Y436V |
| F1677 | 3.7E−06 | L235R/S239K/S254T/T256E/N434H |
| F1680 | 1.3E−06 | L235R/S239K/N434Y/Y436T |
| F1681 | 1.3E−06 | L235R/S239K/N434Y/Y436T/Q438R/S440E |
| F1683 | 1.1E−06 | L235R/S239K/N434Y/Y436F/Q438R/S440E |
| F1684 | 1.8E−06 | L235R/S239K/N434Y |
| F1686 | 4.0E−06 | L235R/S239K/N434A/Y436V/Q438R/S440E |
| F1689 | 1.5E−06 | L235R/S239K/N434F/Y436V/Q438R/S440E |
| E1703 | 8.5E−07 | L235R/S239K/N434W/Y436V/Q438R/S440E |
| F1705 | 2.0E−06 | L235R/S239K/M428L/N434S |
| F1706 | 2.1E−06 | L235R/G236R/S239K/M428L/N434S |
| F1708 | 2.4E−06 | L235R/S239K/M252Y/S254T/R255L/T256E/Q438R/S440E |
| F1709 | 1.7E−06 | L236R/S239K/M252Y/S254T/R255L/T256E/E258D/Q438R/S440E |
| F1710 | 2.1E−06 | L235R/S239K/M252Y/S254T/R255L/T256E/E258I/Q436R/S440E |
| F1711 | 1.8E−06 | L235R/S239K/N434Y/Y436V/Q438R/S440D |
| F1712 | 9.3E−07 | L235R/S239K/N434Y/Y436V/Q438K/S440E |
| F1713 | 9.6E−07 | L235R/S239K/N434Y/Y436V/Q438K/S440D |
| F1714 | 1.2E−06 | L235R/S239K/H433D/N434Y/Y436V/Q438R/S440E |
| F1715 | 1.0E−06 | L235R/S239K/H433D/N434Y/Y436V/Q438R/S440D |
| F1716 | 1.0E−06 | L235R/S239K/H433D/N434Y/Y436V/Q438K/S440E |
| F1717 | 9.6E−07 | L235R/S239K/H433D/N434Y/Y436V/Q438K/S440D |
| F1718 | 2.0E−06 | N434Y/Y436V/Q435R/S440E |
| F1719 | 1.8E−06 | N434Y/Y436V/Q438R/S440D |
| F1720 | 9.0E−07 | N434Y/Y436V/Q438K/S440E |
| F1721 | 9.0E−07 | N434Y/Y436V/Q438K/S440D |
| F1722 | 1.1E−06 | H433D/N434Y/Y436V/Q438R/S440E |
| F1723 | 9.9E−07 | H433D/N434Y/Y436V/Q438R/S440D |
| F1724 | 9.6E−07 | H433D/N434Y/Y436V/Q438K/S440E |
| F1725 | 9.1E−07 | H433D/N434Y/Y436V/Q438K/S440D |
| F1734 | 1.2E−06 | L235R/S239K/N434Y/Y436F/Q438R/S440D |
| F1735 | 8.1E−07 | L235R/S239K/N434Y/Y436F/Q438K/S440E |
| F1736 | 8.9E−07 | L235R/S239K/N434Y/Y436F/Q438K/S440D |
| F1737 | 1.3E−06 | L235R/S239K/H433D/N434Y/Y436F/Q438R/S440E |
| F1738 | 1.2E−06 | L235R/S239K/H433D/N434Y/Y436F/Q438R/S440D |
| F1739 | 9.7E−07 | L235R/S239K/H433D/N434Y/Y436F/Q438K/S440E |
| F1740 | 1.1E−06 | L235R/S239K/H433D/N434Y/Y436F/Q438K/S440D |
| F1741 | 1.1E−06 | N434Y/Y436F/Q438R/S440E |
| F1742 | 1.1E−06 | N434Y/Y436F/Q438R/S440D |
| F1743 | 8.2E−07 | N434Y/Y436F/Q438K/S440E |
| F1744 | 9.2E−07 | N434Y/Y436F/Q438K/S440D |
| F1745 | 1.1E−06 | H433D/N434Y/Y436F/Q438R/S440E |
| F1746 | 1.2E−06 | H433D/N434Y/Y436E/Q438R/S440D |
| F1747 | 9.6E−07 | H433D/N434Y/Y436F/Q438K/S440E |
| F1748 | 1.0E−06 | H433D/N434Y/Y436F/Q438K/S440D |
| F1749 | 1.3E−06 | L235R/S239K/N434Y/Y436T/Q438R/S440D |
| F1750 | 1.1E−06 | L235R/S239K/N434Y/Y436T/Q438K/S440E |
| F1751 | 1.1E−06 | L235R/S239K/N434Y/Y436T/Q438K/S440D |
| F1752 | 1.4E−06 | L235R/S239K/H433D/N434Y/Y436T/Q438R/S440E |
| F1753 | 1.3E−06 | L235R/S239K/H433D/N434Y/Y436T/Q438R/S440D |
| F1754 | 1.1E−06 | L235R/S239K/H433D/N434Y/Y436T/Q438K/S440E |
| F1755 | 1.3E−06 | L235R/S239K/H433D/N434Y/Y436T/Q438K/S440D |
| F1756 | 1.2E−06 | N434Y/Y436T/Q438R/S440E |
| F1757 | 1.1E−06 | N434Y/Y436T/Q438R/S440D |
| F1758 | 1.1E−06 | N434Y/Y436T/Q438K/S440E |
| F1759 | 1.0E−06 | N434Y/Y436T/Q438K/S440D |
| F1760 | 1.2E−06 | H433D/N434Y/Y436T/Q438R/S440E |
| F1761 | 1.3E−06 | H433D/N434Y/Y436T/Q438R/S440D |
| F1762 | 1.1E−06 | H433D/N434Y/Y436T/Q438K/S440E |
| F1763 | 1.1E−06 | H433D/N434Y/Y436T/Q438K/S440D |
| F1764 | 4.8E−06 | L235R/S239K/N434Y/Q438R/S440D |
| F1765 | 1.7E−06 | L235R/S239K/N434Y/Q438K/S440E |
| F1766 | 2.4E−06 | L235R/S239K/N434Y/Q438K/S440D |
| F1767 | 1.5E−06 | L235R/S239K/H433D/N434Y/Q438R/S440E |
| F1768 | 1.5E−06 | L235R/S239K/H433D/N434Y/Q438R/S440D |
| F1769 | 1.9E−06 | L235R/S239K/H433D/N434Y/Q438K/S440E |
| F1770 | 1.4E−06 | L235R/S239K/H433D/N434Y/Q438K/S440D |
| F1771 | 1.9E−06 | N434Y/Q438R/S440E |
| F1772 | 3.4E−06 | N434Y/Q438R/S440D |
| F1773 | 1.7E−06 | N434Y/Q438K/S440E |
| F1774 | 2.7E−06 | N434Y/Q438K/S440D |
| F1775 | 1.3E−06 | H433D/N434Y/Q438R/S440E |
| F1776 | 1.5E−06 | H433D/N434Y/Q438R/S440D |
| F1777 | 1.4E−06 | H433D/N434Y/Q438K/S440E |
| F1778 | 1.3E−06 | H433D/N434Y/Q438K/S440D |

Examples of the modification include one or more mutations, for example, a mutation that substitutes amino acid(s) in the starting Fc region by amino acid residue(s) different therefrom, the insertion of one or more amino acid residues into the amino acid sequence of the starting Fc region, and the deletion of one or more amino acids from the amino acid sequence of the starting Fc region. Preferably, the amino acid sequence of the Fc region thus modified comprises an amino acid sequence containing at least a non-natural portion of the Fc region. Such a variant inevitably has less than 100% sequence identity or similarity to the starting Fc region. In a preferred embodiment, the variant has an amino acid sequence with approximately 75% to less than 100% sequence identity or similarity, more preferably approximately 80% to less than 100%, further preferably approximately 85% to less than 100%, still further preferably approximately 90% to less than 100%, most preferably approximately 95% to less than 100% sequence identity or similarity to the amino acid sequence of the starting Fc region. In a non-limiting aspect of the present invention, the starting Fc region and the modified Fc region of the present invention differ by at least one amino acid. The difference in amino acid between the starting Fc region and the modified Fc region may be preferably determined by a difference in amino acid with the identified position of its amino acid residue defined particularly by the EU numbering.

The amino acid(s) in the Fc region can be modified by an appropriately adopted method known in the art such as site-directed mutagenesis (Kunkel et al., Proc. Natl. Acad. Sci. USA (1985) 82, 488-492) or overlap extension PCR. Also, the amino acid(s) can be substituted by non-natural amino acids by use of a plurality of modification methods known in the art (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express, an R & D oriented company)) comprising a non-natural amino acid bound with an amber suppressor tRNA complementary to UAG codon (amber codon), which is a stop codon, is also preferably used.

In one aspect of the modified form of the present invention, a polynucleotide encoding an antigen-binding molecule having a heavy chain is prepared, in which a polynucleotide encoding the modified FcRn-binding domain having the amino acid(s) thus mutated is linked in frame with the polynucleotide encoding the selected antigen-binding molecule whose binding activity is changed depending on conditions.

The present invention provides a method for producing an antigen-binding molecule, comprising recovering the antigen-binding molecule from cultures of a cell transfected with a vector having an operably linked insert in which a polynucleotide encoding an FcRn-binding domain is linked in frame with the polynucleotide isolated from the virus of the present invention. The present invention also provides a method for producing an antigen-binding molecule, comprising recovering the antigen-binding molecule from cultures of a cell transfected with a vector having an operably linked insert in which an FcRn-binding domain-encoding polynucleotide operably linked in advance in the vector is linked in frame with the polynucleotide isolated from the virus of the present invention.

Pharmaceutical Composition

Although the present invention is not bound to any particular theory, for example, the number of antigens that can be bound per antigen-binding molecule is increased and antigen disappearance from plasma is promoted, as a result of cellular uptake promoted in an organism that has received an antigen-binding molecule comprising an antigen-binding domain whose antigen-binding activity is changed depending on ion concentration conditions so that the antigen-binding activity is lower in an acidic pH condition than that in a neutral pH condition, and additionally comprising an FcRn-binding domain (e.g., antibody constant region) having human FcRn-binding activity under the neutral pH condition. This is probably because of the following:

When a membrane antigen-binding antibody, for example, is administered as the antigen-binding molecule to an organism, the antibody is associated with the antigen and then taken up, together with the antigen (while maintaining its antigen-bound state), into intracellular endosome through internalization. Then, the antibody is migrated to lysosome while maintaining its antigen-bound state, and the antigen-antibody complex is degraded by lysosome. The internalization-mediated disappearance from plasma is called antigen-dependent disappearance and has been reported as to many antibody molecules (Drug Discov Today (2006) 11 (1-2), 81-88). Once one IgG antibody molecule bivalently binds to antigens, this one antibody molecule in a state bound with two antigen molecules is internalized and degraded in this state in lysosome. Thus, one conventional IgG antibody molecule cannot bind to three or more antigen molecules. For example, one IgG antibody molecule having neutralizing activity cannot neutralize three or more antigen molecules.

The relatively long plasma retention of IgG molecules (slow disappearance) is attributed to the functions of human FcRn known as a salvage receptor in the IgG molecules. IgG molecules taken up into endosome through pinocytosis bind to human FcRn expressed in the endosome under the acidic condition in the endosome. IgG molecules that have failed to bind to human FcRn are then migrated to lysosome and degraded therein. On the other hand, the human FcRn-bound IgG molecules are migrated to cell surface. The IgG molecules are dissociated from human FcRn under the neutral condition in plasma and therefore recycled into the plasma.

When the antigen-binding molecule is a soluble antigen-binding antibody, the antibody administered to an organism is associated with the antigen and then taken up into cells while maintaining its antigen-bound state. Most of the antibodies thus taken up in cells are associated with FcRn in endosome and then migrated to cell surface. These antibodies are dissociated from human FcRn under the neutral condition in plasma and therefore released from the cells. However, the antibody comprising the conventional antigen-binding domain whose antigen-binding activity is not changed depending on ion concentration (e.g., pH) conditions is released from the cells while maintaining its antigen-bound state. Thus, this antibody cannot be reassociated with an antigen. Thus, as in the membrane antigen-binding antibody, one conventional IgG antibody molecule whose antigen-binding activity is not changed depending on ion concentration (e.g., pH) conditions cannot bind to three or more antigen molecules.

A pH-dependent antigen-binding antibody that is strongly associated with an antigen under the neutral pH condition in plasma and dissociated from the antigen under the acidic pH condition in endosome (antibody capable of binding to an antigen under the neutral pH condition and coming off the antigen under the acidic pH condition) or a calcium ion concentration-dependent antigen-binging antibody that is strongly associated with an antigen under the high-calcium ion concentration condition in plasma and dissociated from the antigen under the low-calcium ion concentration condition in endosome (antibody capable of binding to an antigen under the high-calcium ion concentration condition and coming off the antigen under the low-calcium ion concentration condition) can be dissociated from the antigen in endosome. The pH-dependent antigen-binding antibody or the calcium ion concentration-dependent antigen-binding antibody thus dissociated from the antigen can be reassociated with an antigen after being recycled into plasma by FcRn. This allows one antibody molecule to bind to a plurality of antigen molecules repeatedly. Also, the antigen bound with the antigen-binding molecule is dissociated from the antibody in endosome and is therefore degraded in lysosome without being recycled into plasma. The administration of such an antigen-binding molecule to an organism can promote the cellular uptake of antigens and decrease antigen concentration in plasma.

The ability to bind to human FcRn under the neutral pH condition (pH 7.4) can be imparted to the pH-dependent antigen-binding antibody that is strongly associated with an antigen under the neutral pH condition in plasma and dissociated from the antigen under the acidic pH condition in endosome (antibody capable of binding to an antigen under the neutral pH condition and coming off the antigen under the acidic pH condition) or the calcium ion concentration-dependent antigen-binging antibody that is strongly associated with an antigen under the high-calcium ion concentration condition in plasma and dissociated from the antigen under the low-calcium ion concentration condition in endosome (antibody capable of binding to an antigen under the high-calcium ion concentration condition and coming off the antigen under the low-calcium ion concentration condition). The resulting antigen-binding molecule further promotes cellular uptake of antigens bound thereto. The administration of such an antigen-binding molecule to an organism can promote antigen disappearance and decrease antigen concentration in plasma. A conventional antibody having neither pH-dependent antigen-binding ability nor calcium ion concentration-dependent antigen-binding ability and an antibody-antigen complex thereof is taken up into cells through nonspecific endocytosis and transported to cell surface by binding to FcRn under the acidic pH condition in endosome. The antibody is dissociated from FcRn under the neutral pH condition on cell surface and therefore recycled into plasma. When the antibody that binds to an antigen in a sufficiently pH-dependent manner (i.e., which is associated with an antigen under the neutral pH condition and dissociated therefrom under the acidic pH condition) or in a sufficiently calcium ion concentration-dependent manner (i.e., which is associated with an antigen under the high-calcium ion concentration condition and dissociated therefrom under the low-calcium ion concentration condition) is associated with the antigen in plasma and dissociated from the bound antigen in endosome, the disappearance rate of the antigen is considered equal to the rate of cellular uptake of the antibody and the antibody-antigen complex thereof through nonspecific endocytosis. In the case of insufficient pH dependence or calcium ion concentration dependence of antigen binding of the antibody, antigens undissociated in endosome are recycled into plasma, together with the antibody. By contrast, in the case of sufficient pH dependence of the antigen binding, the disappearance rate of the antigen is determined by the rate of cellular uptake through nonspecific endocytosis. Since FcRn is responsible for the antibody transport from endosome to cell surface, some FcRn receptors are considered to also exist on cell surface.

Usually, IgG immunoglobulin, which is one form of an antigen-binding molecule, hardly has FcRn-binding activity at neutral pH. The present inventors have hypothesized that IgG immunoglobulin having FcRn-binding activity at neutral pH is capable of binding to FcRn present on cell surface and is taken up into cells in an FcRn-dependent manner by binding to FcRn present on cell surface. The rate of FcRn-mediated cellular uptake is faster than the rate of cellular uptake through nonspecific endocytosis. This suggests that the imparting of the ability to bind to FcRn at neutral pH can further accelerate the disappearance rate of the antigen by the antigen-binding molecule. Specifically, the antigen-binding molecule having the ability to bind to FcRn at neutral pH delivers an antigen more rapidly into cells than the usual (natural human) IgG immunoglobulin and dissociates the antigen in endosome. The dissociated antigen-binding molecule is recycled to cell surface or plasma where the molecule is reassociated with an antigen, resulting in FcRn-mediated cellular uptake again. The higher ability to bind to FcRn at neutral pH can accelerate the rate of rotation of this cycle and therefore accelerates the disappearance rate of the antigen in plasma. The antigen-binding activity at acidic pH of the antigen-binding molecule can be lowered with respect to that at neutral pH to thereby further enhance the disappearance rate of the antigen in plasma. The increased rate of rotation of this cycle may result in the increased number of the cycle that probably allows one antigen-binding molecule to bind to a larger number of antigen molecules. The antigen-binding molecule of the present invention can comprise an antigen-binding domain and an FcRn-binding domain. The FcRn-binding domain neither influences antigen binding nor relies on antigen type, also as seen from the mechanism mentioned above. The antigen-binding activity (binding ability) of the antigen-binding molecule under the ion concentration condition such as the acidic pH or low-calcium ion concentration condition is lowered with respect to that under the ion concentration condition such as the neutral pH or high-calcium ion concentration condition, and/or the FcRn-binding activity of this molecule at pH in plasma is enhanced. This may promote the cellular uptake of antigens by the antigen-binding molecule and accelerate the disappearance rate of the antigens. Accordingly, the antigen-binding molecule of the present invention can be expected to exert superior effects to conventional therapeutic antibodies in, for example, reduction in adverse reaction caused by antigens, a rise in antibody dose, and improvement in in vivo antibody kinetics.

Specifically, the present invention relates to a pharmaceutical composition comprising the antigen-binding molecule of the present invention, the antigen-binding molecule isolated by the screening method of the present invention, or the antigen-binding molecule produced by the production method of the present invention. The antigen-binding molecule of the present invention or the antigen-binding molecule produced by the production method of the present invention is useful as a pharmaceutical composition because its administration produces the high effect of decreasing antigen concentration in plasma compared with conventional antigen-binding molecules. The pharmaceutical composition of the present invention may comprise a pharmaceutically acceptable carrier.

In the present invention, the pharmaceutical composition usually refers to an agent for treatment or prevention of a disease or for examination or diagnosis.

The pharmaceutical composition of the present invention can be formulated using a method generally known to those skilled in the art. For example, the pharmaceutical composition of the present invention can be parenterally used in the form of an injection in a sterile solution or suspension with water or any other pharmaceutically acceptable solution. For example, the active ingredient can be appropriately combined with pharmacologically acceptable carriers or media, specifically, sterile water or saline, a plant oil, an emulsifier, a suspending agent, a surfactant, a stabilizer, a flavor, an excipient, a vehicle, an antiseptic, a binder, and the like and mixed therewith in a unit dosage form required for generally accepted pharmaceutical practice to produce preparations. The amount of the active ingredient in these preparations is set to give an appropriate volume within a prescribed range.

Sterile compositions for injection can be formulated according to usual pharmaceutical practice using a vehicle such as injectable distilled water. Examples of injectable aqueous solutions include saline and isotonic solutions containing glucose or other adjuvants (e.g., D-sorbitol, D-mannose, D-mannitol, and sodium chloride). An appropriate solubilizer, for example, an alcohol (ethanol, etc.), a polyalcohol (propylene glycol, polyethylene glycol, etc.), or a nonionic surfactant (Polysorbate 80™, HCO-50, etc.) may be used in combination therewith.

Examples of oil solutions include sesame oil and soybean oil. Benzyl benzoate and/or benzyl alcohol may be used as a solubilizer in combination therewith. These injectable solutions may be mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The prepared injections are usually charged into appropriate ampules.

The pharmaceutical composition of the present invention is preferably administered through a parenteral route. For example, the composition is administered in a dosage form of an injection, a transnasal agent, a transpulmonary agent, or a percutaneous agent. The composition can be administered systemically or locally by, for example, intravenous injection, intramuscular injection, intraperitoneal injection, or subcutaneous injection.

The administration method can be appropriately selected according to the age and symptoms of the patient. The single dose of the pharmaceutical composition containing the antigen-binding molecule can be set within the range of, for example, 0.0001 mg to 1000 mg per kg body weight. Alternatively, the dose may be set to, for example, 0.001 to 100000 mg per patient, though the dose of the present invention is not necessarily limited to these numeric values. The dose and the administration method vary depending on the body weight, age, symptoms, etc. of the patient. Those skilled in the art can set an appropriate dose and administration method in consideration of these conditions.

Amino acids contained in the amino acid sequences described in the present invention may undergo posttranslational modification (e.g., the modification of N-terminal glutamine to pyroglutamic acid by pyroglutamylation, which is well known to those skilled in the art). Even such forms having the posttranslationally modified amino acids are also included in the amino acid sequences described in the present invention, as a matter of course.

All prior art documents cited herein are incorporated herein by reference.

As used herein, an aspect represented by expression with "comprising" encompasses an aspect represented by expression with "essentially consisting of" and an aspect represented by expression with "consisting of".

EXAMPLES

Hereinafter, the present invention will be described more specifically with reference to Examples. However, the present invention is not intended to be limited by these Examples.

[Example 1] Design of pH-Dependent Binding Antibody Library (1-1) Method for Obtaining pH-Dependent Binding Antibody WO2009125825 discloses that histidine is introduced to an antigen-binding molecule to prepare a pH-dependent antigen-binding antibody whose property is changed between neutral pH and acidic pH regions. The disclosed pH-dependent binding antibody is obtained by modification that substitutes a portion of the amino acid sequence of the desired antigen-binding molecule by histidine. A possible method for more efficiently obtaining the pH-dependent binding antibody without obtaining in advance the antigen-binding molecule to be modified involves introducing histidine to variable regions (more preferably, positions that may be involved in antigen binding) and obtaining an antigen-binding molecule binding to the desired antigen from the resulting pool of antigen-binding molecules (referred to as a His library). The antigen-binding molecule obtained from the His library has higher frequency of appearance of histidine than that of usual antibody libraries, suggesting that the antigen-binding molecules having the desired property can be obtained efficiently.

(1-2) Design of Pool (His Library) of Antibody Molecules Containing Histidine Residues in Variable Regions, which Permits Efficient Obtainment of Binding Antibody that Binds to Antigen in pH-Dependent Manner First, histidine introduction positions were selected for the His library. WO2009125825 discloses that pH-dependent antigen-binding antibodies were prepared by the substitution of amino acid residues in the sequences of an IL-6 receptor antibody, an IL-6 antibody, and an IL-31 receptor antibody by histidine. In addition, an anti-egg-white lysozyme antibody (FEBS Letter 11483, 309, 1, 85-88) and an anti-hepcidin antibody (WO2009139822) having pH-dependent antigen-binding ability have been prepared by the substitution of amino acids in the amino acid sequences of antigen-binding molecules by histidine. Table 3 shows histidine introduction positions in the IL-6 receptor antibody, the IL-6 antibody, the IL-31 receptor antibody, the egg-white lysozyme antibody, and the hepcidin antibody. The positions shown in Table 3 can serve as candidates of positions that can control antigen-antibody binding. In addition to the positions shown in Table 3, highly antigen-accessible positions were also considered appropriate as histidine introduction positions.

TABLE 3

| Antibody | Chain | Position (Kabat numbering) | | | | | | | | |
|---|---|---|---|---|---|---|---|---|---|---|
| IL-6 receptor antibody | H | 27 | 31 | 32 | 35 | 50 | 58 | 62 | 100B | 102 |
|  | L | 28 | 32 | 53 | 56 | 92 |  |  |  |  |
| IL-6 antibody | H | 32 | 59 | 61 | 99 |  |  |  |  |  |
|  | L | 53 | 54 | 90 | 94 |  |  |  |  |  |
| IL-31 receptor antibody | H | 33 |  |  |  |  |  |  |  |  |
|  | L |  |  |  |  |  |  |  |  |  |
| Egg-white lysozyme antibody | H | 33 | 98 |  |  |  |  |  |  |  |
|  | L | 54 |  |  |  |  |  |  |  |  |
| Hepcidin antibody | H | 52 | 56 | 95 | 100c |  |  |  |  |  |
|  | L | 28 | 90 |  |  |  |  |  |  |  |

In the His library constituted by heavy and light chain variable regions, the heavy chain variable regions used were human antibody sequences, while histidine was introduced to the light chain variable regions. The positions listed above and positions that might be involved in antigen binding, i.e., positions 30, 32, 50, 53, 91, 92, and 93 (defined by the Kabat numbering; Kabat E A et al., 1991. Sequence of Proteins of Immunological Interest. NIH) in the light chains were selected as the histidine introduction positions for the His library. Also, a Vk1 sequence was selected as a light chain variable region template sequence for histidine introduction.

A plurality of amino acids were allowed to appear at each given position in the template sequence to expand the diversity of the antigen-binding molecules constituting the library. Surface-exposed positions in the variable regions that were likely to interact with antigens were selected as the position at which the plurality of amino acids appeared. Specifically, positions 30, 31, 32, 34, 50, 53, 91, 92, 93, 94, and 96 (defined by the Kabat numbering; Kabat E A et al. 1991. Sequence of Proteins of Immunological Interest. NIH) in the light chains were selected as such flexible residues.

Next, the types and incidences of the amino acid residues to appear were set.

The amino acids at the flexible residues were analyzed for their frequency of appearance in the sequences of hVk1 and hVk3 registered in the Kabat database (KABAT, E. A. et al.: 'Sequences of proteins of immunological interest', vol. 91, 1991, NIH PUBLICATION). On the basis of the analysis results, the types of amino acids appearing in the His library were selected from among amino acids with high frequency of appearance at each position. In this procedure, amino acids confirmed to have low frequency of appearance from the analysis results were also selected so as to prevent amino acid properties from being unbalanced. The frequency of appearance of the selected amino acids was set with reference to the analysis results of the Kabat database.

In consideration of the amino acids thus selected and the frequency of appearance thereof, two His libraries were designed: His library 1 fixed on the condition that each CDR contained one histidine residue without exception; and His library 2 that placed more emphasis on sequence diversity than the His library 1. The detailed design of the His library 1 and the His library 2 is shown in Tables 4 and 5 ("Position" in each table represents the Kabat numbering). The frequency of amino acid appearance described in Tables 4 and 5 can exclude Ser (S) at position 94 defined by the Kabat numbering in the case of Asn (N) at position 92.

TABLE 5

| CDR | Position | Amino acid | | | |
|---|---|---|---|---|---|
| CDR1 | 28 | S: 100% | | | |
| | 29 | I: 100% | | | |
| | 30 | H: 30% | N: 10% | S: 50% | R: 10% |
| | 31 | N: 35% | S: 65% | | |
| | 32 | H: 40% | N: 20% | Y: 40% | |
| | 33 | L: 100% | | | |
| | 34 | A: 70% | N: 30% | | |
| CDR2 | 50 | A: 25% | D: 15% | G: 25% | H: 30% | K: 5% |
| | 51 | A: 100% | | | |
| | 52 | S: 100% | | | |
| | 53 | H: 30% | K: 10% | N: 15% | S: 45% |
| | 54 | L: 100% | | | |
| | 55 | Q: 100% | | | |
| | 56 | S: 100% | | | |
| CDR3 | 90 | Q: 100% | | | |
| | 91 | H: 30% | S: 15% | R: 10% | Y: 45% |
| | 92 | G: 20% | H: 30% | N: 20% | S: 15% | Y: 15% |
| | 93 | H: 30% | N: 25% | S: 45% | |
| | 94 | S: 50% | Y: 50% | | |
| | 95 | P: 100% | | | |
| | 96 | L: 50% | Y: 50% | | |

[Example 2] Preparation of Human Antibody Phage Display Library (His Library 1) for Obtaining Antibody Binding to Antigen in pH-Dependent Manner A gene library of antibody heavy chain variable regions was amplified by PCR using poly-A RNA prepared from human PBMC, commercially available human poly-A RNA, or the like as a template. A gene library of antibody light chain variable regions designed as the His library 1 described in Example 1 was amplified using PCR. Combinations of the sequences in the gene library of antibody heavy chain variable regions and the gene library of anti-

TABLE 4

| Position | Aminoacid | | | |
|---|---|---|---|---|
| CDR1 | | | | |
| 28 | S: 100% | | | |
| 29 | I: 100% | | | |
| 30 | N: 25% | S: 25% | R: 25% | H: 25% |
| 31 | S: 100% | | | |
| 32 | H: 100% | | | |
| 33 | L: 100% | | | |
| 34 | A: 50 % | N: 50% | | |
| CDR2 | | | | |
| 50 | H: 100% | | | or A: 25% D: 25% G: 25% K: 25% |
| 51 | A: 100% | | | A: 100% |
| 52 | S: 100% | | | S: 100% |
| 53 | K: 33.3% | N: 33.3% | S: 33.3% | H: 100% |
| 54 | L: 100% | | | L: 100% |
| 55 | Q: 100% | | | Q: 100% |
| 56 | S: 100% | | | S: 100% |
| CDR3 | | | | |
| 90 | Q: 100% | | | or Q: 100% |
| 91 | H: 100% | | | S: 33.3% R: 33.3% Y: 33.3% |
| 92 | G: 25% | N: 25% | S: 25% | Y: 25% H: 100% |
| 93 | H: 33.3% | N: 33.3% | S: 33.3% | H: 33.3% N: 33.3% S: 33.3% |
| 94 | S: 50% | Y: 50% | | S: 50% Y: 50% |
| 95 | P: 100% | | | P: 100% |
| 96 | L: 50% | Y: 50% | | L: 50% Y: 50% | body light chain variable regions thus prepared were inserted into phagemid vectors to construct a human antibody phage display library displaying Fab domains composed of human antibody sequences. The construction method was performed with reference to Methods Mol Biol. (2002) 178, 87-100. In this construction of the library, the sequence of a phage display library was used, which comprised a linker portion for linking phagemid Fab and phage pIII protein, and a tryptic cleavage sequence inserted between the N2 and CT domains of helper phage pIII protein. Antibody gene portions isolated from *E. coli* transformed with the antibody gene library were sequenced to obtain sequence information about 132 clones. FIG. 1 shows the designed amino acid distribution and an amino acid distribution in the confirmed sequence. A library comprising diverse sequences corresponding to the designed amino acid distribution was constructed.

[Example 3] Obtainment of Antibody Binding to IL-6R in pH-Dependent Manner (3-1) Obtainment of Antibody Fragment Binding to Antigen in pH-Dependent Manner from Library by Bead Panning The first round of screening of the constructed His library 1 was carried out by the enrichment of only antibody fragments having antigen (IL-6R)-binding ability.

Phages were produced from *E. coli* carrying the constructed phagemid for phage display. 2.5 M NaCl/10% PEG was added to cultures of *E. coli* that had produced phages, and a pool of the phages thus precipitated was diluted with TBS to obtain a phage library solution. BSA and $CaCl_2$ (final concentration: 4% BSA and 1.2 mM calcium ion) were added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of biotin-labeled antigens was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed three times with 1 mL of 1.2 mM $CaCl_2$/TBST (TBS containing 1.2 mM $CaCl_2$ and 0.1% Tween 20) and then further washed twice with 1 mL of 1.2 mM $CaCl_2$/TBS (pH 7.6). After addition of 0.5 mL of 1 mg/mL trypsin, the beads were suspended at room temperature for 15 minutes, immediately after which the beads were separated using a magnetic stand to recover a phage solution. The recovered phage solution was added to 10 mL of an *E. coli* strain ER2738 in a logarithmic growth phase (OD600: 0.4-0.7). The *E. coli* strain was infected by the phages through the gentle spinner culture of the strain at 37° C. for 1 hour. The infected *E. coli* was inoculated to a plate of 225 mm×225 mm. Next, phages were recovered from cultures of the inoculated *E. coli* to prepare a phage library solution.

In the second and subsequent rounds of panning, the phages were enriched with antigen-binding ability or pH-dependent binding ability as an index. Specifically, 40 pmol of biotin-labeled antigens was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed several times with 1 mL of 1.2 mM $CaCl_2$/TBST and 1.2 mM $CaCl_2$/TBS. For the enrichment with antigen-binding ability as an index, the beads supplemented with 0.5 mL of 1 mg/mL trypsin were suspended at room temperature for 15 minutes, immediately after which the beads were separated using a magnetic stand to recover a phage solution. For the enrichment with pH-dependent antigen-binding ability as an index, the beads supplemented with 0.1 mL of 50 mM MES/1.2 mM $CaCl_2$/150 mM NaCl (pH 5.5) were suspended at room temperature. Immediately thereafter, the beads were separated using a magnetic stand to recover a phage solution. The addition of 5 µL of 100 mg/mL trypsin to the recovered phage solution cleaved the pIII proteins (helper phage-derived pIII proteins) of non-Fab-displaying phages to cancel the ability of the non-Fab-displaying phages to infect *E. coli*. The recovered phages were added to 10 mL of an *E. coli* strain ER2738 in a logarithmic growth phase (OD600: 0.4-0.7). The *E. coli* strain was infected by the phages through the gentle spinner culture of the strain at 37° C. for 1 hour. The infected *E. coli* was inoculated to a plate of 225 mm×225 mm. Next, phages were recovered from cultures of the inoculated *E. coli* to recover a phage library solution. This panning with antigen-binding ability or pH-dependent binding ability as an index was performed 2 rounds in total.

(3-2) Evaluation by Phage ELISA

A phage-containing culture supernatant was recovered according to a conventional method (Methods Mol. Biol. (2002) 178, 133-145) from each single colony of the *E. coli* obtained by the above method.

After addition of BSA and $CaCl_2$ (final concentration: 4% BSA and 1.2 mM calcium ion), the phage-containing culture supernatant was subjected to ELISA by the following procedures: StreptaWell 96 microtiter plate (F. Hoffmann-La Roche Ltd.) was coated overnight with 100 µL of PBS containing biotin-labeled antigens. Each well of the plate was washed with PBST (PBS containing 0.1% Tween 20) to remove unbound antigens. Then, the well was blocked with 250 µL of 4% BSA-TBS for 1 hour or longer. After removal of 4% BSA-TBS, the prepared culture supernatant was added to each well, and the plate was left standing at 37° C. for 1 hour to associate phage-displayed antibodies with the antigens contained in each well. Each well was washed with 1.2 mM $CaCl_2$/TBST, and 1.2 mM $CaCl_2$/TBS (pH 7.6) or 1.2 mM $CaCl_2$/TBS (pH 5.5) was added thereto. The plate was left standing at 37° C. for 30 minutes for incubation. After washing with 1.2 mM $CaCl_2$/TBST, HRP-conjugated anti-M13 antibodies (Amersham Pharmacia Biotech Inc.) diluted with TBS having 4% BSA and an ionized calcium concentration of 1.2 mM were added to each well. The plate was incubated for 1 hour. After washing with 1.2 mM $CaCl_2$/TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm.

17 clones were antigen-specifically ELISA-positive as a result of the phage ELISA of 96 clones (after 2 rounds of panning) enriched with antigen-binding ability as an index. Thus, samples derived from 3 rounds of panning were analyzed. On the other hand, 70 clones were ELISA-positive as a result of the phage ELISA of 94 clones (after 2 rounds of panning) enriched with pH-dependent antigen-binding ability as an index. Thus, these samples derived from 2 rounds of panning were analyzed.

Genes of the clones subjected to the phage ELISA were amplified using specific primers and then analyzed for their nucleotide sequences.

The results of phage ELISA and sequence analysis are shown in the following Table 6.

TABLE 6

| Library | His library 1 | His library 1 |
|---|---|---|
| Enrichment index | Antigen-binding ability | pH-dependent antigen-binding ability |
| Number of panning campaign | 3 | 2 |
| Number of clones tested | 80 | 94 |
| ELISA-positive | 76 | 70 |
| Type of ELISA-positive clone sequence | 30 | 67 |
| Type of pH-dependent binding clone sequence | 22 | 47 |

Antibodies having pH-dependent antigen-binding ability were obtained by a similar method from a naive human antibody phage display library. 13 types of pH-dependent binding antibodies were obtained by the evaluation of 88 clones enriched with antigen-binding ability as an index. Also, 27 types of pH-dependent binding antibodies were obtained by the evaluation of 83 clones enriched with pH-dependent antigen-binding ability as an index.

These results demonstrated that the His library 1 produces more variations of clones having pH-dependent antigen-binding ability than those of the naive human antibody phage display library.

(3-3) Antibody Expression and Purification

The gene of each clone judged as having pH-dependent antigen-binding ability as a result of the phage ELISA was introduced to plasmids for expression in animal cells. Antibody expression was performed by the following method: a human embryonic kidney cell-derived FreeStyle 293-F line (Invitrogen Corp.) was suspended in FreeStyle 293 Expression Medium (Invitrogen Corp.). The suspension having a cell density of $1.33 \times 10^6$ cells/mL was inoculated at a concentration of 3 mL/well to a 6-well plate. The prepared plasmids were transferred to the cells by lipofection. The cells were cultured for 4 days in a $CO_2$ incubator (37° C., 8% $CO_2$, 90 rpm). Antibodies were purified from the obtained culture supernatant by a method generally known to those skilled in the art using rProtein A Sepharose™ Fast Flow (Amersham Biosciences, Inc.). The absorbance of the purified antibody solution was measured at 280 nm using a spectrophotometer. The antibody concentration was calculated from the obtained measurement value by use of an extinction coefficient calculated by PACE (Protein Science (1995) 4, 2411-2423).

(3-4) Evaluation of Obtained Antibody for its pH-Dependent Binding Ability Against Human IL-6 Receptor In order to judge the pH dependence of the human IL-6 receptor-binding activity of antibodies 6RpH #01 (heavy chain: SEQ ID NO: 18 and light chain: SEQ ID NO: 19), 6RpH #02 (heavy chain: SEQ ID NO: 20 and light chain: SEQ ID NO: 21), and 6RpH #03 (heavy chain: SEQ ID NO: 22 and light chain: SEQ ID NO: 23) obtained in the step (3-3), these antibodies were analyzed for their interaction with human IL-6 receptors using Biacore T100 (GE Healthcare Bio-Sciences Corp.). Tocilizumab (heavy chain: SEQ ID NO: 24 and light chain: SEQ ID NO: 25) was used as a control antibody having no pH-dependent binding activity against human IL-6 receptors. The interaction of antigen-antibody reaction was analyzed in solutions of pH 7.4 and pH 6.0 as neutral pH and acidic pH conditions, respectively. Approximately of 300 RU of each antibody of interest was captured onto Sensor chip CM5 (GE Healthcare Bio-Sciences Corp.) with protein A/G (Invitrogen Corp.) immobilized thereon in an appropriate amount by the amine coupling method. Two types of buffer solutions were used as running buffers: 20 mM ACES, 150 mM NaCl, 0.05% (w/v) Tween 20, and 1.2 mM $CaCl_2$) (pH 7.4); and 20 mM ACES, 150 mM NaCl, 0.05% (w/v) Tween 20, and 1.2 mM $CaCl_2$) (pH 6.0). The human IL-6 receptors were also diluted with each of these buffers. Assay was all carried out at 37° C.

In the analysis on the interaction of antigen-antibody reaction using the control antibody tocilizumab, the 6RpH #01 antibody, the 6RpH #02 antibody, and the 6RpH #03 antibody, the diluted IL-6 receptor solution or a blank running buffer was injected at a flow rate of 5 μL/min for 3 minutes to interact the IL-6 receptors with the tocilizumab antibody, the 6RpH #01 antibody, the 6RpH #02 antibody, or the 6RpH #03 antibody captured on the sensor chip. Then, 10 mM glycine-HCl (pH 1.5) was injected thereto at a flow rate of 30 μL/min for 30 seconds to regenerate the sensor chip.

Figure 2:
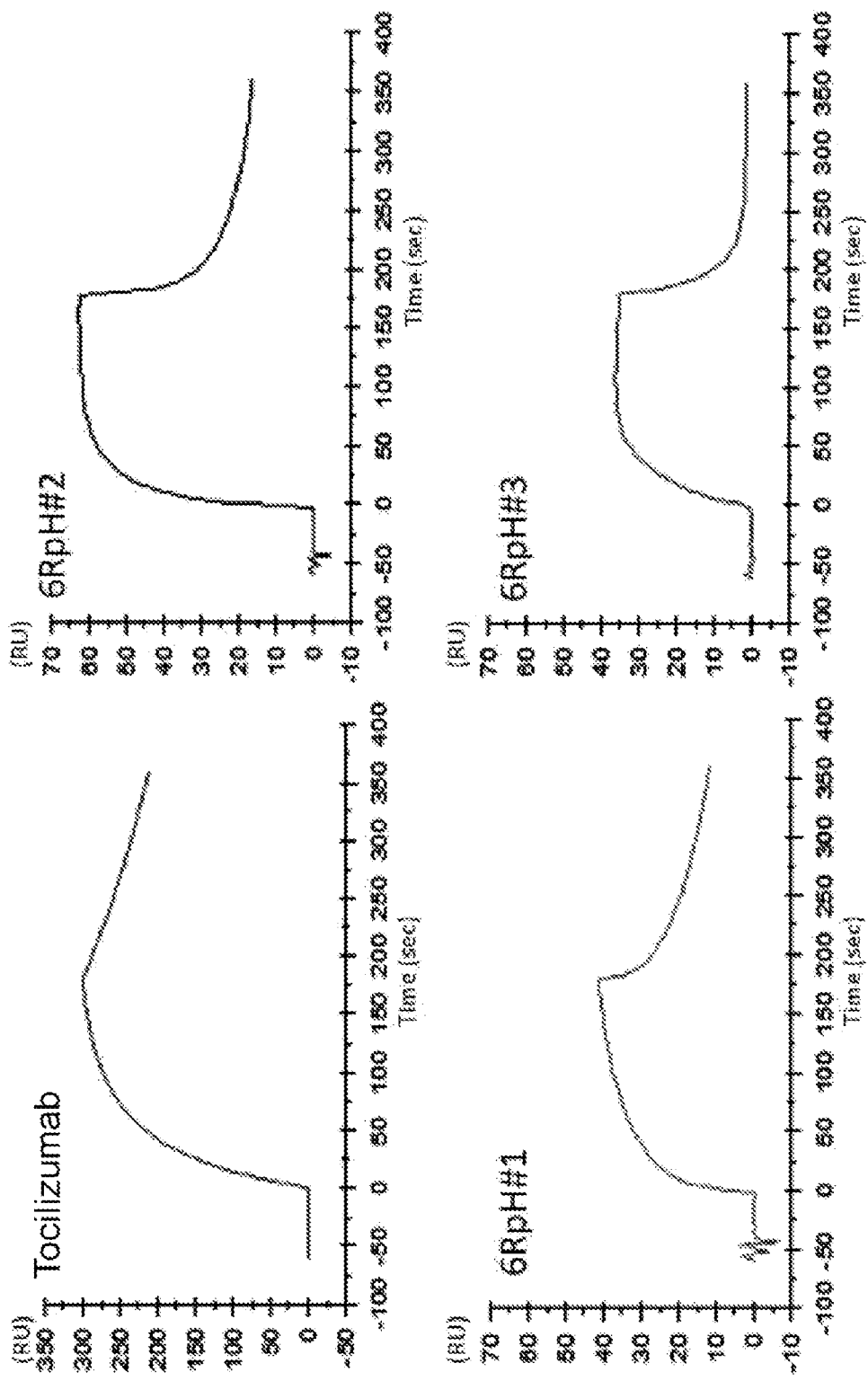
FIG. 2 shows the sensorgrams of an anti-IL-6R antibody (tocilizumab), a 6RpH #01 antibody, a 6RpH #02 antibody, and a 6RpH #03 antibody at pH 7.4. The abscissa represents time. The ordinate represents RU values.
Figure 3:
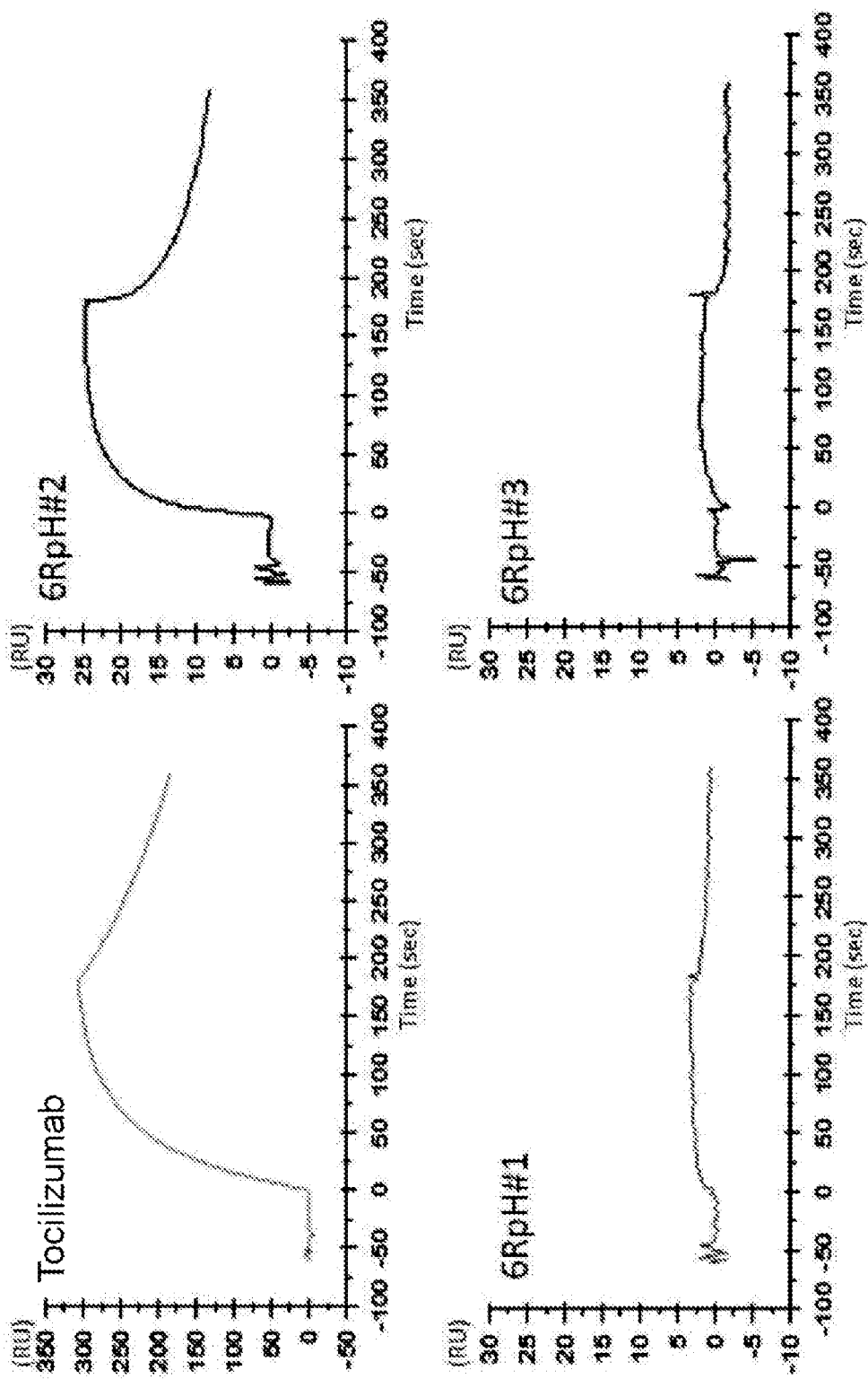
FIG. 3 shows the sensorgrams of the anti-IL-6R antibody (tocilizumab), the 6RpH #01 antibody, the 6RpH #02 antibody, and the 6RpH #03 antibody at pH 6.0. The abscissa represents time. The ordinate represents RU values.

FIG. 2 shows the sensorgrams of the antibodies assayed at pH 7.4 by the above method. FIG. 3 shows the sensorgrams of the antibodies under the condition of pH 6.0 obtained by a similar method.

As a result, the IL6 receptor-binding ability of the 6RpH #01 antibody, the 6RpH #02 antibody, and the 6RpH #03 antibody was observed to be drastically reduced by the change of the buffer pH from pH 7.4 to pH 6.0.

[Example 4] Preparation of Human Antibody Phage Display Library (His Library 2) for Obtaining Antibody Binding to Antigen in pH-Dependent Manner A gene library of antibody heavy chain variable regions was amplified by PCR using poly-A RNA prepared from human PBMC, commercially available human poly-A RNA, or the like as a template. In order to improve the frequency of appearance of antibodies having pH-dependent antigen-binding ability as described in Example 1, the light chain portions of antibody variable regions are designed so that the frequency of appearance of histidine residues at sites likely to serve as antigen contact sites is enhanced in these light chain portions. A library of antibody light chain variable regions is designed so that amino acids with high frequency of appearance determined from information about the frequency of appearance of amino acids in natural human antibodies are evenly distributed as amino acid residues other than the histidine-introduced residues among the flexible residues. The gene library of antibody light chain variable regions thus designed is synthesized. The library may be prepared by outsourcing its synthesis to a commercial entrusted company or the like. Combinations of the sequences in the gene library of antibody heavy chain variable regions and the gene library of antibody light chain variable regions thus prepared are inserted into phagemid vectors. A human antibody phage display library displaying Fab domains composed of human antibody sequences is constructed according to a method known in the art (Methods Mol Biol. (2002) 178, 87-100). Antibody gene portions isolated from *E. coli* transformed with the antibody gene library are sequenced according to the method described in Example 2.

[Example 5] Obtainment of Antibody Binding to IL-6R in pH-Dependent Manner (5-1) Obtainment of Antibody Fragment Binding to Antigen in pH-Dependent Manner from Library by Bead Panning The first round of screening of the constructed His library 2 is carried out by the enrichment of only antibody fragments having antigen (IL-6 receptor)-binding ability.

Phages are produced from *E. coli* carrying the constructed phagemid for phage display. 2.5 M NaCl/10% PEG is added to cultures of *E. coli* that has produced phages, and a pool of the phages thus precipitated is diluted with TBS to obtain a phage library solution. Subsequently, BSA or skim milk is added as a blocking agent to the phage library solution. The panning method is performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used are NeutrAvidin coated beads (Sera-Mag SpeedBeads NeutrAvidin-coated) or Streptavidin coated beads (Dynabeads M-280 Streptavidin).

Specifically, 250 pmol of biotin-labeled antigens is added to the prepared phage library solution and thereby contacted with the phage library solution at room temperature for 60 minutes. After addition of magnetic beads blocked with a blocking agent, the antigen-phage complexes are attached to the magnetic beads at room temperature for 15 minutes. The beads are washed three times with 1 mL of TBST and then further washed twice with 1 mL of TBS. After addition of 0.5 mL of 1 mg/mL trypsin, the beads are suspended at room temperature for 15 minutes, immediately after which the beads are separated using a magnetic stand to recover a phage solution. The collected phage solution is added to 10 mL of an *E. coli* strain ER2738 in a logarithmic growth phase (OD600: 0.4-0.7). The *E. coli* strain is infected by the phages through the gentle spinner culture of the strain at 37° C. for 1 hour. The infected *E. coli* is inoculated to a plate of 225 mm×225 mm. Next, phages are collected from cultures of the inoculated *E. coli* to prepare a phage library solution.

In the second and subsequent rounds of panning, the phages are enriched with antigen-binding ability or pH-dependent binding ability as an index. Specifically, 40 pmol of biotin-labeled antigens is added to the prepared phage library solution and thereby contacted with the phage library solution at room temperature for 60 minutes. After addition of BSA- or skim milk-blocked magnetic beads, the antigen-phage complexes are attached to the magnetic beads at room temperature for 15 minutes. The beads are washed with 1 mL of TBST and TBS. For the enrichment with antigen-binding ability as an index, the beads supplemented with 0.5 mL of 1 mg/mL trypsin are suspended at room temperature for 15 minutes, immediately after which the beads are separated using a magnetic stand to recover a phage solution. For the enrichment with pH-dependent antigen-binding ability as an index, the beads supplemented with 0.1 mL of 50 mM MES/1.2 mM $CaCl_2$/150 mM NaCl (pH 5.5) are suspended at room temperature. Immediately thereafter, the beads are separated using a magnetic stand to recover a phage solution. The addition of 5 μL of 100 mg/mL trypsin to the collected phage solution cleaved the pIII proteins (helper phage-derived pIII proteins) of non-Fab-displaying phages to cancel the ability of the non-Fab-displaying phages to infect *E. coli*. The collected phages are added to 10 mL of an *E. coli* strain ER2738 in a logarithmic growth phase (OD600: 0.4-0.7). The *E. coli* strain is infected by the phages through the gentle spinner culture of the strain at 37° C. for 1 hour. The infected *E. coli* is inoculated to a plate of 225 mm×225 mm. Next, phages are collected from cultures of the inoculated *E. coli* to recover a phage library solution. The panning with antigen-binding ability or pH-dependent binding ability as an index is repeated several times.

(5-2) Evaluation by Phage ELISA

A phage-containing culture supernatant is collected according to a conventional method (Methods Mol. Biol. (2002) 178, 133-145) from each single colony of the *E. coli* obtained by the above method.

After addition of BSA and $CaCl_2$, the phage-containing culture supernatant was subjected to ELISA by the following procedures: StreptaWell 96 microtiter plate (F. Hoffmann-La Roche Ltd.) is coated overnight with 100 μL of PBS containing biotin-labeled antigens. Each well of the plate is washed with PBST to remove unbound antigens. Then, the well is blocked with 250 μL of 4% BSA-TBS for 1 hour or longer. After removal of 4% BSA-TBS, the prepared culture supernatant is added to each well, and the plate is left standing at 37° C. for 1 hour to associate phage-displayed antibodies with the antigens contained in each well. Each well is washed with 1.2 mM $CaCl_2$/TBST, and 1.2 mM $CaCl_2$/TBS (pH 7.6) or 1.2 mM $CaCl_2$/TBS (pH 5.5) is added thereto. The plate is left standing at 37° C. for 30 minutes for incubation. After washing with 1.2 mM $CaCl_2$/TBST, HRP-conjugated anti-M13 antibodies (Amersham Pharmacia Biotech Inc.) diluted with TBS having 4% BSA and an ionized calcium concentration of 1.2 mM are added to each well. The plate is incubated for 1 hour. After washing with 1.2 mM $CaCl_2$/TBST, TMB single solution (ZYMED Laboratories, Inc.) is added to the well. The chromogenic reaction of the solution in each well is terminated by the addition of sulfuric acid. Then, the developed color is assayed on the basis of absorbance at 450 nm.

Genes of antibody fragments judged as having pH-dependent antigen-binding ability as a result of the phage ELISA are amplified as a template using specific primers and then analyzed for their nucleotide sequences.

(5-3) Antibody Expression and Purification

The gene of each clone judged as having pH-dependent antigen-binding ability as a result of the phage ELISA is introduced to plasmids for expression in animal cells. Antibody expression is performed by the following method: a human embryonic kidney cell-derived FreeStyle 293-F line (Invitrogen Corp.) is suspended in FreeStyle 293 Expression Medium (Invitrogen Corp.). The suspension having a cell density of $1.33 \times 10^6$ cells/mL is inoculated at a concentration of 3 mL/well to a 6-well plate. The prepared plasmids are transferred to the cells by lipofection. The cells are cultured for 4 days in a $CO_2$ incubator (37° C., 8% $CO_2$, 90 rpm). Antibodies are purified from the obtained culture supernatant by a method generally known to those skilled in the art using rProtein A Sepharose™ Fast Flow (Amersham Biosciences, Inc.). The absorbance of the purified antibody solution is measured at 280 nm using a spectrophotometer. The antibody concentration is calculated from the obtained measurement value by use of an extinction coefficient calculated by PACE (Protein Science (1995) 4, 2411-2423).

(5-4) Evaluation of Obtained Antibody for its pH-Dependent Binding Ability Against Human IL-6 Receptor In order to judge the pH dependence of the human IL-6 receptor-binding activity of the antibodies obtained in Example 5, these antibodies are analyzed for their interaction with human IL-6 receptors using Biacore T100 (GE Healthcare Bio-Sciences Corp.). Tocilizumab (heavy chain: SEQ ID NO: 24 and light chain: SEQ ID NO: 25) is used as a control antibody having no pH-dependent binding activity against human IL-6 receptors. The interaction of antigen-antibody reaction is analyzed in solutions of pH 7.4 and pH 6.0 as neutral pH and acidic pH conditions, respectively. Each antibody of interest is captured onto Sensor chip CM5 (GE Healthcare Bio-Sciences Corp.) with protein A/G (Invitrogen Corp.) immobilized thereon in an appropriate amount by the amine coupling method. Two types of buffer solutions are used as running buffers: 20 mM ACES, 150 mM NaCl, 0.05% (w/v) Tween 20, and 1.2 mM $CaCl_2$) (pH 7.4); and 20 mM ACES, 150 mM NaCl, 0.05% (w/v) Tween 20, and 1.2 mM $CaCl_2$) (pH 6.0). The human IL-6 receptors are also diluted with each of these buffers. Assay is all carried out at 37° C.

In the analysis on the interaction of antigen-antibody reaction using the control antibody tocilizumab and the antibodies obtained in Example 5, the diluted IL-6 receptor solution or a blank running buffer is injected to interact the IL-6 receptors with the antibodies captured on the sensor chip. Then, 10 mM glycine-HCl (pH 1.5) is injected thereto at a flow rate of 30 µL/min for 30 seconds to regenerate the sensor chip. Sensorgrams under the condition of pH 6.0 are also obtained by a similar method.

[Example 6] Search for Human Germline Sequence Binding to Calcium Ion (6-1) Antibody Binding to Antigen in Calcium-Dependent Manner An antibody binding to an antigen in a calcium-dependent manner (calcium-dependent antigen-binding antibody) is an antibody whose interaction with the antigen is changed depending on the concentration of calcium ion. Since the calcium-dependent antigen-binding antibody is considered to bind to the antigen via calcium ions, amino acids constituting antigen epitopes are negatively charged amino acids capable of chelating the calcium ions or amino acids that can serve as hydrogen-bonding acceptors (FIG. 4B). Because of the properties of such epitope-constituting amino acids, the calcium-dependent antigen-binding antibody is capable of targeting an epitope other than that for the pH-dependent antigen-binding molecule prepared by the introduction of histidine residues as shown in FIG. 4A. In addition, use of antigen-binding molecules having the property of binding to antigens in both calcium-dependent and pH-dependent manners as shown in FIG. 4C can achieve preparation of antigen-binding molecules capable of individually targeting diverse epitopes having a wide range of properties. This suggests that the calcium-dependent antigen-binding antibody can be obtained efficiently if a set of molecules comprising calcium-binding motifs (Ca library) is constructed and antigen-binding molecules are obtained from this set of molecules.

(6-2) Obtainment of Human Germline Sequence

A possible example of the set of molecules comprising calcium-binding motifs is a set of antibodies as the molecules. In other words, a possible example of the Ca library is an antibody library comprising calcium-binding motifs.

None of previously reported antibodies comprising human germline sequences bind to calcium ions. Thus, in order to determine whether or not antibodies comprising human germline sequences bound to calcium ions, the germline sequence DNAs of antibodies comprising human germline sequences were cloned using, as a template, cDNAs prepared from Human Fetal Spleen Poly RNA (Clontech Laboratories, Inc.). The cloned DNA fragments were inserted to expression vectors for animal cells. The obtained expression vectors were sequenced by a method generally known to those skilled in the art. SEQ ID NOs of amino acid sequences encoded by the determined nucleotide sequences are shown in Table 7. A polynucleotide encoding the sequence of SEQ ID NO: 6 (Vk1), SEQ ID NO: 7 (Vk2), SEQ ID NO: 8 (Vk3), SEQ ID NO: 9 (Vk4), or SEQ ID NO: 1 (Vk5) was linked by PCR to a polynucleotide encoding a natural kappa chain constant region (SEQ ID NO: 26). The resulting DNA fragments were separately incorporated into vectors for expression in animal cells. Also, a heavy chain variable region polynucleotide encoding the sequence of SEQ ID NO: 27 (Vk1), SEQ ID NO: 28 (Vk2), SEQ ID NO: 29 (Vk3), or SEQ ID NO: 30 (Vk4) was linked by PCR to a polynucleotide encoding IgG1 lacking C-terminal 2-amino acids in the sequence of SEQ ID NO: 14. The resulting DNA fragments were separately incorporated into vectors for expression in animal cells. The sequences of the prepared modified forms were confirmed by a method generally known to those skilled in the art. In this context, human Vk1 is also referred to as hVk1; human Vk2 is also referred to as hVk2; human Vk3 is also referred to as hVk3; and human Vk4 is also referred to as hVk4.

TABLE 7

| Light chain germline sequence | SEQ ID NO of heavy chain variable region | SEQ ID NO of light chain variable region |
|---|---|---|
| Vk1 | 27 | 6 |
| Vk2 | 28 | 7 |
| Vk3 | 29 | 8 |
| Vk4 | 30 | 9 |
| Vk5 | 4 | 1 |

(6-3) Antibody Expression and Purification

The vectors for expression in animal cells having the DNA fragment insert encoding each of 5 types of human germline sequences thus obtained were transfected to animal cells. Antibody expression was performed by the following method: a human embryonic kidney cell-derived FreeStyle 293-F line (Invitrogen Corp.) was suspended in FreeStyle 293 Expression Medium (Invitrogen Corp.). The suspension having a cell density of $1.33 \times 10^6$ cells/mL was inoculated at a concentration of 3 mL/well to a 6-well plate. The prepared plasmids were transferred to the cells by lipofection. The cells were cultured for 4 days in a $CO_2$ incubator (37° C., 8% $CO_2$, 90 rpm). Antibodies were purified from the obtained culture supernatant by a method generally known to those skilled in the art using rProtein A Sepharose™ Fast Flow (Amersham Biosciences, Inc.). The absorbance of the purified antibody solution was measured at 280 nm using a spectrophotometer. The antibody concentration was calculated from the obtained measurement value by use of an extinction coefficient calculated by PACE (Protein Science (1995) 4, 2411-2423).

(6-4) Evaluation of Antibody Comprising Human Germline Sequence for its Calcium Ion-Binding Activity The purified antibodies were evaluated for their calcium ion-binding activity. Thermal denaturation midpoint temperature (Tm) was measured by differential scanning calorimetry (DSC) (MicroCal VP-Capillary DSC, MicroCal) as an index for evaluating the calcium ion binding of the antibodies. The thermal denaturation midpoint temperature (Tm) serves as an index for stability and becomes higher when a protein is stabilized through calcium ion binding, compared with the thermal denaturation midpoint temperature (Tm) of a calcium ion-unbound protein (J. Biol. Chem. (2008) 283, 37, 25140-25149). In order to evaluate the binding activity of the antibody against calcium ions, change in the Tm value of each antibody according to change in calcium ion concentration in the antibody solution was evaluated. The purified antibodies were dialyzed (EasySEP, Tomy Seiko Co., Ltd.) against a solution containing 20 mM Tris-HCl, 150 mM NaCl, and 2 mM $CaCl_2$ (pH 7.4) or containing 20 mM Tris-HCl, 150 mM NaCl, and 3 µM $CaCl_2$ (pH 7.4) as an external solution. Each antibody solution was adjusted to approximately 0.1 mg/mL with the solution used in the dialysis and subjected as a test substance to DSC assay at 20° C. to 115° C. with the rate of temperature rise set to 240° C./hr. Table 8 shows the thermal denaturation midpoint temperature (Tm) of each antibody Fab domain calculated on the basis of the obtained DSC denaturation curve.

TABLE 8

| Light chain germline sequence | Calcium ion concentration | | ΔTm (° C.) |
|---|---|---|---|
| | 3 µm | 2 mM | 2 mM-3 µM |
| hVk1 | 80.32 | 80.78 | 0.46 |
| hVk2 | 80.67 | 80.61 | −0.06 |
| hVk3 | 81.64 | 81.36 | −0.28 |
| hVk4 | 70.74 | 70.74 | 0 |
| hVk5 | 71.52 | 74.17 | 2.65 |

As a result, the Tm value of the Fab domain of the antibody comprising the hVk1, hVk2, hVk3, or hVk4 sequence did not vary depending on the concentration of calcium ions in the solution containing the Fab domain. By contrast, the Tm value of the Fab domain of the antibody comprising the hVk5 sequence varied depending on the concentration of calcium ions in the antibody solution containing the Fab domain, showing that the hVk5 sequence binds to calcium ions.

(6-5) Evaluation of hVk5-2 Sequence for Calcium Binding

In addition to Vk5-2 (SEQ ID NO: 1 fused with SEQ ID NO: 26), Vk5-2 variant 1 (SEQ ID NO: 2) and Vk5-2 variant 2 (SEQ ID NO: 3) classified as Vk5-2 were obtained in Example 6(6-2). These variants were also evaluated for their calcium binding. The DNA fragments of Vk5-2, Vk5-2 variant 1, and Vk5-2 variant 2 were separately incorporated into expression vectors for animal cells. The obtained expression vectors were sequenced by a method generally known to those skilled in the art. Animal cells were cotransfected with each expression vector for animal cells having the insert of the Vk5-2, Vk5-2 variant 1, or Vk5-2 variant 2 DNA fragment and a vector for expression in animal cells having a DNA insert encoding a heavy chain CIM_H (SEQ ID NO: 4) to be expressed, by the method described in Example 6(6-3). The obtained antibodies were purified. The purified antibodies were evaluated for their calcium ion-binding activity. The purified antibodies were dialyzed (EasySEP, Tomy Seiko Co., Ltd.) against a solution containing 20 mM Tris-HCl, 150 mM NaCl, and 2 mM $CaCl_2$ (pH 7.5) or containing 20 mM Tris-HCl and 150 mM NaCl (pH 7.5) (the latter solution is indicated by "Calcium ion concentration": 0 mM in Table 9) as an external solution. Each antibody solution was adjusted to approximately 0.1 mg/mL with the solution used in the dialysis and subjected as a test substance to DSC assay at 20° C. to 115° C. with the rate of temperature rise set to 240° C./hr. Table 9 shows the thermal denaturation midpoint temperature (Tm) of each antibody Fab domain calculated on the basis of the obtained DSC denaturation curve.

TABLE 9

| Light chain | Calcium ion concentration | | ΔTm (° C.) 2 mM- 0 mM |
|---|---|---|---|
| | 0 mM | 2 mM | |
| Vk5-2 | 71.65 | 74.38 | 2.73 |
| Vk5-2 variant 1 | 65.75 | 72.24 | 6.49 |
| Vk5-2 variant 2 | 66.46 | 72.24 | 5.78 |

As a result, the Tm value of the Fab domain of the antibody comprising the Vk5-2, Vk5-2 variant 1, or Vk5-2 variant 2 sequence varied depending on the concentration of calcium ions in the antibody solution containing the Fab domain, showing that the antibody having the sequence classified into Vk5-2 binds to calcium ions.

[Example 7] Evaluation of Human Vk5 (hVk5) Sequence (7-1) hVk5 Sequence

Only the hVk5-2 sequence is registered as an hVk5 sequence in the Kabat database. Hereinafter, hVk5 and hVk5-2 will be treated synonymously. WO2010136598 discloses that the abundance ratio of the hVk5-2 sequence is 0.4% among germline sequences. Other reports also state that the abundance ratio of the hVk5-2 sequence is 0 to 0.06% among germline sequences (J. Mol. Biol. (2000) 296, 57-86; and Proc. Natl. Acad. Sci. (2009) 106, 48, 20216-20221). Since the hVk5-2 sequence has low frequency of appearance among germline sequences as described above, the obtainment of calcium-binding antibodies from an antibody library constituted by human germline sequences or from B cells obtained by the immunization of human antibody-expressing mice seemed to be inefficient. This might make it reasonable to design a Ca library comprising human hVk5-2 sequences. Previously reported synthetic antibody libraries (WO2010105256 or WO2010136598), however, did not include the hVk5 sequence. In addition, the physicochemical properties of the hVk5-2 sequence had not been reported, and the feasibility thereof was unknown.

(7-2) Construction, Expression, and Purification of Non-Glycosylated hVk5-2 Sequence The hVk5-2 sequence has a sequence with a potential N-glycosylated amino acid at position 20 (defined by the Kabat numbering). It is desirable from the viewpoint of substance homogeneity that proteins should avoid to be glycosylated, because sugar chains added to proteins cause heterogeneity. Thus, a modified form hVk5-2_L65 (SEQ ID NO: 5) was prepared by the substitution of the Asn (N) residue at position 20 (defined by the Kabat numbering) by a Thr (T) residue. The amino acid substitution was performed by a method generally known to those skilled in the art using QuikChange Site-Directed Mutagenesis Kit (Stratagene Corp.). DNA encoding the modified form hVk5-2_L65 was incorporated into vectors for expression in animal cells. Animal cells were cotransfected with the prepared vector for expression in animal cells having the DNA insert of the modified form hVk5-2_L65 and a vector for expression in animal cells having a DNA insert encoding a heavy chain CIM_H (SEQ ID NO: 4) to be expressed, by the method described in Example 6. An antibody comprising hVk5-2_L65 and CIM_H was expressed by the transfected animal cells and purified by the method described in Example 6.

Figure 5:
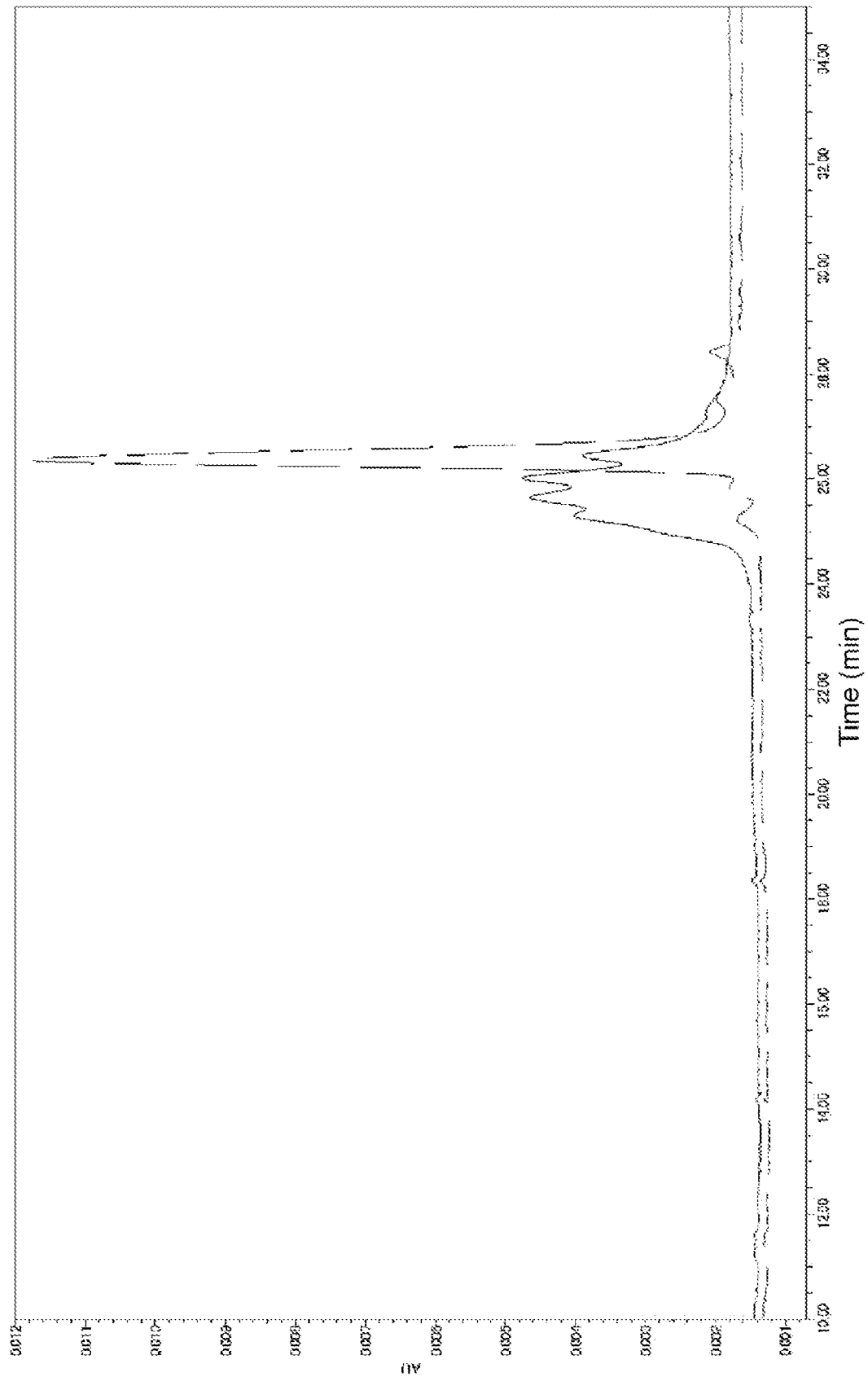
FIG. 5 shows the ion-exchange chromatograms of an antibody comprising a human Vk5-2 sequence and an antibody comprising an hVk5-2_L65 sequence modified from the human Vk5-2 sequence at the glycosylation sequence. The solid line represents the chromatogram of the antibody comprising a human Vk5-2 sequence (heavy chain: CIM_H (SEQ ID NO: 4) and light chain: hVk5-2 (SEQ ID NO: 1 fused with SEQ ID NO: 26)). The broken line represents the chromatogram of the antibody having an hVk5-2 L65 sequence (heavy chain: CIM_H (SEQ ID NO: 4) and light chain: hVk5-2_L65 (SEQ ID NO: 5)).

(7-3) Evaluation of Antibody Comprising Non-Glycosylated hVk5-2 Sequence for its Physicochemical Properties Whether or not the heterogeneity of the obtained antibody comprising the modified sequence hVk5-2_L65 was reduced with respect to that of an antibody comprising the original hVk5-2 sequence subjected to the modification was analyzed using ion-exchange chromatography. The ion-exchange chromatography was performed by a method shown in Table 10. The analysis results demonstrated that, as shown in FIG. 5, hVk5-2_L65 modified at the glycosylation site from original hVk5-2 sequence has less heterogeneity than that of the original hVk5-2 sequence.

TABLE 10

| | Conditions |
|---|---|
| Column | TOSOH TSKgel DEAE-NPR |
| Mobile phase | A; 10 mM Tris-HCl, 3 μM $CaCl_2$ (pH 8.0) B; 10 mM Tris-HCl, 500 mM NaCl, 3 μM $CaCl_2$ (pH 8.0) |
| Gradient schedule | % B = 0-(5 min)-0-2%/1 min |
| Column temperature | 40° C. |
| Detection | 280 nm |
| Injection quantity | 100 μL, (5 μg) |

Next, the antibody comprising the hVk5-2_L65 sequence having reduced heterogeneity was evaluated for its ability to bind to calcium ions by the method described in Example 6. As a result, as shown in Table 11, the Tm value of the Fab domain of the antibody comprising hVk5-2_L65 modified at the glycosylation site also varied depending on change in the concentration of calcium ions in the antibody solution. This showed that calcium ions bind to the Fab domain of the antibody comprising hVk5-2_L65 modified at the glycosylation site.

TABLE 11

| Light chain | Glycosylated sequence | Calcium ion concentration | | ΔTm (° C.) 2 mM- |
|---|---|---|---|---|
| | | 3 μM | 2 mM | 3 μM |
| hVk5-2 | Present | 71.52 | 74.17 | 2.65 |
| hVk5-2_L65 | Absent | 71.51 | 73.66 | 2.15 |

[Example 8] Evaluation of Antibody Molecule Comprising hVk5-2 CDR Sequence for its Calcium Ion-Binding Activity (8-1) Preparation, Expression, and Purification of Engineered Antibody Comprising hVk5-2 CDR Sequence The hVk5-2_L65 sequence is a sequence modified from the human Vk5-2 sequence by amino acid substitution at the glycosylation site in the framework region. Example 7 showed that calcium ions bind to even the antibody comprising the sequence modified at the glycosylation site. Germline sequences were generally desirable as framework sequences from the viewpoint of immunogenicity. Thus, study was made on whether or not to be able to substitute the framework sequences of an antibody by non-glycosylated germline framework sequences while the calcium ion-binding activity of the antibody was maintained.

A polynucleotide encoding a sequence modified from the chemically synthesized hVk5-2 sequence by the replacement of its framework sequences with hVk1, hVk2, hVk3, or hVk4 sequences (the modified sequences were designated as CaVk1 (SEQ ID NO: 31), CaVk2 (SEQ ID NO: 32), CaVk3 (SEQ ID NO: 33), and CaVk4 (SEQ ID NO: 34), respectively) was linked by PCR to a polynucleotide encoding a natural kappa chain constant region (SEQ ID NO: 26). The resulting DNA fragments were separately incorporated into vectors for expression in animal cells. The sequences of the prepared modified forms were confirmed by a method generally known to those skilled in the art. Animal cells were cotransfected with each plasmid thus prepared and a plasmid having an insert of a polynucleotide encoding CIM_H (SEQ ID NO: 4), by the method described in Example 6. The desired antibody molecules thus expressed were purified from culture fluid of the transfected animal cells.

(8-2) Evaluation of Engineered Antibody Comprising hVk5-2 CDR Sequence for its Calcium Ion-Binding Activity The engineered antibodies comprising the framework sequences of the germline sequence (hVk1, hVk2, hVk3, or hVk4) other than the hVk5-2 sequence and the CDR sequences of the hVk5-2 sequence were evaluated for their ability to bind to calcium ions by the method described in Example 6. The evaluation results are shown in Table 12. The Tm value of the Fab domain of each engineered antibody was shown to vary depending on change in calcium ion concentration in the antibody solution. These results demonstrated that the antibody comprising the framework sequences other than the hVk5-2 framework sequences also binds to calcium ions.

TABLE 12

| Germline (light chain framework sequence) | Calcium ion concentration | | ΔTm (° C.) |
|---|---|---|---|
| | 3 μM | 2 mM | 2 mM-3 μM |
| hVk1 | 77.51 | 79.79 | 2.28 |
| hVk2 | 78.46 | 80.37 | 1.91 |
| hVk3 | 77.27 | 79.54 | 2.27 |
| hVk4 | 80.35 | 81.38 | 1.03 |
| hVk5-2 | 71.52 | 74.17 | 2.65 |

As is further evident from the results, the thermal denaturation temperature (Tm), an index for thermal stability, of the Fab domain of each antibody modified so as to comprise the framework sequences of the germline sequence (hVk1, hVk2, hVk3, or hVk4) other than the hVk5-2 sequence and the CDR sequences of the hVk5-2 sequence was higher than that of the Fab domain of the antibody comprising the original hVk5-2 sequence subjected to the modification. From this result, the antibody comprising the hVk1, hVk2, hVk3, or hVk4 framework sequences and the hVk5-2 CDR sequences was found to be a molecule that had the property of binding to calcium ions and was also excellent from the viewpoint of thermal stability.

[Example 9] Identification of Calcium Ion-Binding Site Present in Human Germline hVk5-2 Sequence (9-1) Design of Mutation Site in CDR Sequence of hVk5-2 Sequence As described in Example 8, the antibodies comprising light chains with the CDR domains of the hVk5-2 sequence introduced in the framework sequences of a different germline sequence were also shown to bind to calcium ions.

This result suggested that the calcium ion-binding site present in hVk5-2 was located in CDR. Examples of amino acids binding to calcium ions, i.e., chelating calcium ions, include negatively charged amino acids and amino acids that can serve as hydrogen-bonding acceptors. Thus, antibodies comprising a variant hVk5-2 sequence mutated from the hVk5-2 sequence by the substitution of Asp (D) and/or Glu (E) residues in the CDR sequences by Ala (A) residues were evaluated for their ability to bind to calcium ions.

(9-2) Preparation of Ala-Substituted Variant of hVk5-2 Sequence and Antibody Expression and Purification Antibody molecules were prepared, which comprised light chains with Ala residues modified from the Asp and/or Glu residues present in the hVk5-2 CDR sequences. As described in Example 7, the non-glycosylated modified form hVk5-2_L65 maintained calcium ion binding and therefore appears to be equivalent to the hVk5-2 sequence from the viewpoint of the property of binding to calcium ions. In this Example, amino acid substitution was performed with hVk5-2_L65 as a template sequence. The prepared modified forms are shown in Table 13. The amino acid substitution was performed by a method generally known to those skilled in the art using QuikChange Site-Directed Mutagenesis Kit (Stratagene Corp.), PCR, In fusion Advantage PCR cloning kit (Takara Bio Inc.), or the like. Expression vectors for the light chains modified by the amino acid substitution were constructed.

TABLE 13

| Name of modified light chain | Modification site (Kabat numbering) | SEQ ID NO |
|---|---|---|
| hVk5-2_L65 | Wild-type | 5 |
| hVk5-2_L66 | 30 | 35 |
| hVk5-2_L67 | 31 | 36 |
| hVk5-2_L68 | 32 | 37 |
| hVk5-2_L69 | 50 | 38 |
| hVk5-2_L70 | 30, 32 | 39 |
| hVk5-2_L71 | 30, 50 | 40 |
| hVk5-2_L72 | 30, 32, 50 | 41 |
| hVk5-2_L73 | 92 | 42 |

The obtained expression vectors were sequenced by a method generally known to those skilled in the art. Human embryonic kidney cell-derived HEK293H line (Invitrogen Corp.) or FreeStyle 293 cells (Invitrogen Corp.) were transiently cotransfected with the prepared expression vector for each modified light chain and an expression vector for a heavy chain CIM_H (SEQ ID NO: 4) to express antibodies. Each antibody was purified from the obtained culture supernatant by a method generally known to those skilled in the art using rProtein A Sepharose™ Fast Flow (GE Healthcare Bio-Sciences Corp.). The absorbance of the purified antibody solution was measured at 280 nm using a spectrophotometer. The antibody concentration was calculated from the obtained measurement value by use of an extinction coefficient calculated by PACE (Protein Science (1995) 4, 2411-2423).

(9-3) Evaluation of Antibody Comprising Ala-Substituted Variant of hVk5-2 Sequence for its Calcium Ion-Binding Activity Whether or not the obtained purified antibodies bound to calcium ions was determined by the method described in Example 6. The results are shown in Table 14. The Tm values of the Fab domains of some antibodies did not vary depending on change in calcium ion concentration in the antibody solutions, as a result of substituting the Asp and/or Glu residues present in the CDR sequences of the hVk5-2 sequence by Ala residues, which were unable to participate in the binding or chelating of calcium ions. The substitution sites that did not cause variations in Tm values even by substitution by Ala (positions 32 and 92 (defined by the Kabat numbering)) were shown to be particularly important for the calcium ion binding of the antibodies.

TABLE 14

| Name of modified light chain | Modification site (Kabat numbering) | Calcium ion concentration 0 mM | Calcium ion concentration 2 mM | ΔTm (° C.) 2 mM-0 mM |
|---|---|---|---|---|
| hVk5-2_L65 | Wild-type | 71.71 | 73.69 | 1.98 |
| hVk5-2_L66 | 30 | 71.65 | 72.83 | 1.18 |
| hVk5-2_L67 | 31 | 71.52 | 73.30 | 1.78 |
| hVk5-2_L68 | 32 | 73.25 | 74.03 | 0.78 |
| hVk5-2_L69 | 50 | 72.00 | 73.97 | 1.97 |
| hVk5-2_L70 | 30, 32 | 73.42 | 73.60 | 0.18 |
| hVk5-2_L71 | 30, 50 | 71.84 | 72.57 | 0.73 |
| hVk5-2_L72 | 30, 32, 50 | 75.04 | 75.17 | 0.13 |
| hVk5-2_L73 | 92 | 75.23 | 75.04 | −0.19 |

[Example 10] Evaluation of Antibody Comprising hVk1 Sequence Having Calcium Ion-Binding Motif (10-1) Preparation of hVk1 Sequence Having Calcium Ion-Binding Motif and Antibody Expression and Purification The results about the calcium-binding activity of the Ala-substituted variants described in Example 9 showed that Asp and Glu residues in the CDR sequences of the hVk5-2 sequence are important for calcium binding. Thus, antibodies prepared by the introduction of only residues 30, 31, 32, 50, and 92 (defined by the Kabat numbering) into the variable region sequence of a different germline sequence were evaluated for their ability to bind to calcium ions. Specifically, a modified form LfVk1_Ca (SEQ ID NO: 43) was prepared by the substitution of residues 30, 31, 32, 50, and 92 (defined by the Kabat numbering) in the human germline sequence hVk1 by residues 30, 31, 32, 50, and 92 (defined by the Kabat numbering) in the hVk5-2 sequence. The presence or absence of calcium-binding ability was determined as to an antibody comprising the hVk1 sequence with only these five hVk5-2 sequence-derived residues introduced therein. The preparation of the modified form was performed in the same way as in Example 9. The modified light chain LfVk1_Ca thus obtained or LfVk1 (SEQ ID NO: 44) comprising the light chain hVk1 sequence was coexpressed with a heavy chain CIM_H (SEQ ID NO: 4). Antibody expression and purification were carried out in the same way as in Example 9.

(10-2) Evaluation of Antibody Comprising Human hVk1 Sequence Having Calcium Ion-Binding Motif for its Calcium Ion-Binding Activity Whether or not the purified antibodies thus obtained bound to calcium ions was determined by the method described in Example 6. The results are shown in Table 15. The Tm value of the Fab domain of the antibody comprising LfVk1 having the hVk1 sequence did not vary depending on change in calcium concentration in the antibody solution. By contrast, the Tm value of the antibody sequence comprising LfVk1_Ca was changed by 1° C. or more depending on change in calcium concentration in the antibody solution, showing that the antibody comprising LfVk1_Ca binds to calcium. These results demonstrated that not the whole hVk5-2 CDR sequence is required for calcium ion binding and only the residues introduced for constructing the LfVk1_Ca sequence suffice for the binding.

TABLE 15

| Modified light chain | Calcium ion concentration | | ΔTm (° C.) |
|---|---|---|---|
| | 3 μM | 2 mM | 2 mM-3 μM |
| LfVk1 | 83.18 | 83.81 | 0.63 |
| LfVk1_Ca | 79.83 | 82.24 | 2.41 |

(10-3) Construction, Expression, and Purification of Anti-Degradation LfVk1_Ca Sequence In Example 10(10-1), the modified form LfVk1_Ca (SEQ ID NO: 43) was prepared by the substitution of residues 30, 31, 32, 50, and 92 (defined by the Kabat numbering) in the human germline sequence hVk1 by residues 30, 31, 32, 50, and 92 (defined by the Kabat numbering) in the hVk5-2 sequence, and shown to bind to calcium ions. This might make it reasonable to design a Ca library comprising LfVk1_Ca sequences. Since the physicochemical properties of the LfVk1_Ca sequence had not been reported, the feasibility thereof was unknown. The LfVk1_Ca sequence contained Asp at positions 30, 31, and 32 (defined by the Kabat numbering) and contained, in its CDR1 sequence, an Asp-Asp sequence reportedly degradable in an acidic condition (J. Pharm. Biomed. Anal. (2008) 47 (1), 23-30). From the viewpoint of stability during storage, it is desirable to avoid degradation under the acidic condition. Thus, modified forms LfVk1 Ca1 (SEQ ID NO: 45), LfVk1_Ca2 (SEQ ID NO: 46), and LfVk1_Ca3 (SEQ ID NO: 47) were prepared by the substitution of degradable Asp (D) residues by Ala (A) residues. The amino acid substitution was performed by a method generally known to those skilled in the art using QuikChange Site-Directed Mutagenesis Kit (Stratagene Corp.). DNA encoding each modified form was incorporated into vectors for expression in animal cells. Animal cells were cotransfected with the prepared vector for expression in animal cells having the DNA insert of each modified form and a vector for expression in animal cells having a DNA insert encoding a heavy chain GC_H (SEQ ID NO: 48) to be expressed, by the method described in Example 6. Antibodies expressed in the transfected animal cells were purified by the method described in Example 6.

Figure 6:
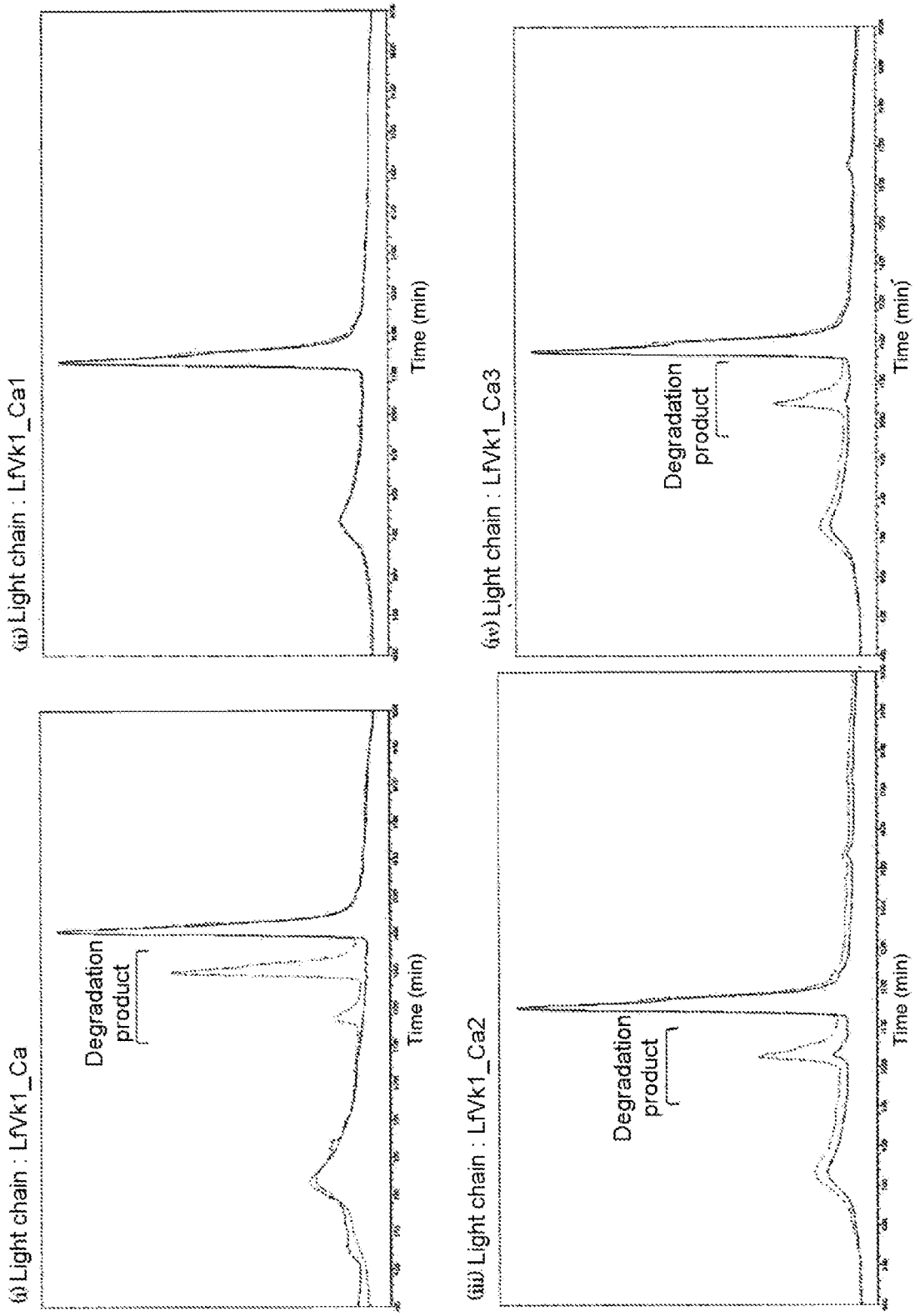
FIG. 6 shows the ion-exchange chromatograms of an antibody comprising a LfVk1_Ca sequence (heavy chain: GC_H (SEQ ID NO: 48) and light chain: LfVk1_Ca (SEQ ID NO: 43)) and an antibody comprising a sequence modified from the LfVk1_Ca sequence by the replacement of an Asp (D) residue with Ala (A) residue after storage at 5° C. (solid line) or after storage at 50° C. (dotted line). The highest peak in each ion-exchange chromatogram after storage at 5° C. is defined as a main peak. In the diagram, the y-axis was normalized with the main peak.

(10-4) Stability Evaluation on Antibody Comprising Anti-Degradation LfVk1_Ca Sequence Whether or not the degradation of each antibody obtained in Example 10(10-3) was reduced in a solution of pH 6.0 compared with an antibody comprising the original LfVk1_Ca sequence subjected to the modification was evaluated by the comparison of heterogeneity after thermal acceleration among the antibodies. Each antibody was dialyzed overnight against a solution containing 20 mM histidine-HCl and 150 mM NaCl (pH 6.0) under conditions of 4° C. The dialyzed antibody was adjusted to 0.5 mg/mL and stored at 5° C. or 50° C. for 3 days. Each antibody thus stored was subjected to ion-exchange chromatography by the method described in Example 7. The analysis results demonstrated that, as shown in FIG. 6, LfVk1 Ca1 modified at the degradation site has less heterogeneity than that of the original LfVk1_Ca sequence and its degradation by thermal acceleration is significantly reduced. These results demonstrated that degradation occurs at the Asp (D) residue located at position 30 in the LfVk1_Ca sequence and can be avoided by amino acid modification.

(10-5) Preparation of Anti-Asp30 Residue-Degradation Light Chain LVk1_Ca Sequence and Antibody Expression and Purification The results of anti-degradation of the Ala-substituted variant described in Example 10(10-4) showed that degradation under the acidic condition occurs at the Asp (D) residue at position 30 (defined by the Kabat numbering) in the CDR sequence of the LfVk1_Ca sequence and can be inhibited by the substitution of the residue 30 (defined by the Kabat numbering) by another amino acid (in Example 10(10-4), by an Ala (A) residue). Thus, a sequence (referred to as LfVk1_Ca6; SEQ ID NO: 49) prepared by the substitution of the residue 30 (defined by the Kabat numbering) by a Ser (S) residue, a typical residue capable of chelating calcium ions, was evaluated for the presence or absence of inhibition of degradation. The preparation of the modified form was performed in the same way as in Example 10. The obtained modified light chain LfVk1_Ca6 or the light chain LfVk1_Ca sequence was coexpressed with a heavy chain GC_H (SEQ ID NO: 48). Antibody expression and purification were carried out in the same way as in Example 10.

(10-6) Evaluation of Anti-Asp30 Residue-Degradation Light Chain LVk1_Ca Sequence The preservation stability of the purified antibodies thus obtained under the acidic condition was determined by the method described in Example 10(10-4). The results demonstrated that, as shown in FIG. 7, the degradation of the antibody comprising the LfVk1_Ca6 sequence is more inhibited than the antibody comprising the original LfVk1_Ca sequence.

In addition, whether or not the antibody comprising the LfVk1_Ca sequence and the antibody comprising the LfVk1_Ca6 sequence bound to calcium ions was determined by the method described in Example 6. The results are shown in Table 16. The Tm values of the Fab domains of the antibody comprising the LfVk1_Ca sequence and the antibody comprising the anti-degradation LfVk1_Ca6 sequence were each changed by 1° C. or more depending on change in calcium concentration in the antibody solutions.

TABLE 16

| Modified light chain | Calcium ion concentration | | ΔTm (° C.) |
|---|---|---|---|
| | 3 μM | 2 mM | 2 mM-3 μM |
| LfVk1_Ca | 78.45 | 80.06 | 1.61 |
| LfVk1_Ca6 | 78.44 | 79.74 | 1.30 |

[Example 11] Design of Pool (Ca Library) of Antibody Molecules Containing Calcium Ion-Binding Motifs in Variable Regions, which Permits Efficient Obtainment of Binding Antibody that Binds to Antigen in Calcium Ion Concentration-Dependent Manner Preferred examples of calcium-binding motifs include an hVk5-2 sequence and its CDR sequences, and further, narrowed-down residues 30, 31, 32, 50, and 92 (defined by the Kabat numbering). In addition, the EF hand motif (calmodulin, etc.) of a calcium-binding protein and a C-type lectin (ASGPR, etc.) also corresponds to the calcium-binding motifs.

The Ca library is constituted by heavy and light chain variable regions. The heavy chain variable regions used were human antibody sequences, while the calcium-binding motifs were introduced to the light chain variable regions.

An hVk1 sequence was selected as a light chain variable region template sequence for calcium-binding motif introduction. As shown in Example 10, the antibody comprising the LfVk1_Ca sequence in which the hVk5-2 CDR sequence was introduced as a calcium-binding motif in the hVk1 sequence was shown to bind to calcium ions. Various amino acids were allowed to appear at each given position in the template sequence to expand the diversity of the antigen-binding molecules constituting the library. Surface-exposed positions in the variable regions that were likely to interact with antigens were selected as the position at which the plurality of amino acids appeared. Specifically, positions 30, 31, 32, 34, 50, 53, 91, 92, 93, 94, and 96 (defined by the Kabat numbering) were selected as such flexible residues.

Next, the types and incidences of the amino acid residues to appear were set. The amino acids at the flexible residues were analyzed for their frequency of appearance in the sequences of hVk1 and hVk3 registered in the Kabat database (KABAT, E. A. et al.: 'Sequences of proteins of immunological interest', vol. 91, 1991, NIH PUBLICATION). On the basis of the analysis results, the types of amino acids appearing in the Ca library were selected from among amino acids with high frequency of appearance at each position. In this procedure, amino acids confirmed to have low frequency of appearance from the analysis results were also selected so as to prevent amino acid properties from being unbalanced. The frequency of appearance of the selected amino acids was set with reference to the analysis results of the Kabat database.

In consideration of the amino acids thus selected and the frequency of appearance thereof, the following Ca library was designed: a Ca library that placed emphasis on sequence diversity so as to comprise the calcium-binding motifs and a plurality of amino acids at each residue other than the motifs. The detailed design of the Ca library is shown in Tables 17 and 18 ("Position" in each table represents the Kabat numbering). The frequency of amino acid appearance described in Tables 17 and 18 can adopt Leu (L) instead of Ser (S) at position 94 defined by the Kabat numbering in the case of Asn (N) at position 92.

TABLE 17

| CDR | Position | 70% of whole | | | |
|---|---|---|---|---|---|
| CDR1 | 28 | S; 100% | | | |
| | 29 | I; 100% | | | |
| | 30 | E; 72% | H; 14% | S; 14% | |
| | 31 | D; 100% | | | |
| | 32 | D; 100% | | | |
| | 33 | L; 100% | | | |
| | 34 | A; 70% | N; 30% | | |
| CDR2 | 50 | E; 100% | | | |
| | 51 | A; 100% | | | |
| | 52 | S; 100% | | | |
| | 53 | H; 5% | N; 25% | S; 45% | T; 25% |
| | 54 | L; 100% | | | |
| | 55 | Q; 100% | | | |
| | 56 | S; 100% | | | |
| CDR3 | 90 | Q; 100% | | | |
| | 91 | H; 25% | S; 15% | R; 15% | Y; 45% |
| | 92 | D; 80% | N; 10% | S; 10% | |
| | 93 | D; 5% | G; 10% | N; 25% | S; 50% | R; 10% |
| | 94 | S; 50% | Y; 50% | | |
| | 95 | P; 100% | | | |
| | 96 | L; 50% | Y; 50% | | |

TABLE 18

| CDR | Position | 30% amino acid of whole | | | |
|---|---|---|---|---|---|
| CDR1 | 28 | S: 100% | | | |
| | 29 | I: 100% | | | |
| | 30 | E: 83% | S: 17% | | |
| | 31 | D: 100% | | | |
| | 32 | D: 100% | | | |
| | 33 | L: 100% | | | |
| | 34 | A: 70% | N: 30% | | |
| CDR2 | 50 | H: 100% | | | |
| | 51 | A: 100% | | | |
| | 52 | S: 100% | | | |
| | 53 | H: 5% | N: 25% | S: 45% | T: 25% |
| | 54 | L: 100% | | | |
| | 55 | Q: 100% | | | |
| | 56 | S: 100% | | | |
| CDR3 | 90 | Q: 100% | | | |
| | 91 | H: 25% | S: 15% | R: 15% | Y: 45% |
| | 92 | D: 80% | N: 10% | S: 10% | |
| | 93 | D: 5% | G: 10% | N: 25% | S: 50% | R: 10% |
| | 94 | S: 50% | Y: 50% | | |
| | 95 | P: 100% | | | |
| | 96 | L: 50% | Y: 50% | | |

[Example 12] Preparation of Ca Library

A gene library of antibody heavy chain variable regions was amplified by PCR using poly-A RNA prepared from human PBMC, commercially available human poly-A RNA, or the like as a template. The light chain portions of antibody variable regions were designed so as to enhance the frequency of appearance of antibodies that maintained calcium-binding motifs and were capable of binding to antigens in a calcium concentration-dependent manner, as described in Example 11. A library of antibody light chain variable regions was designed with reference to information about the frequency of appearance of amino acids in natural human antibodies (KABAT, E. A. et al.: 'Sequences of proteins of immunological interest', vol. 91, 1991, NIH PUBLICATION) so that amino acids with high frequency of appearance in the natural human antibody sequences were evenly distributed as amino acid residues other than the calcium-binding motif-introduced residues among the flexible residues. Combinations of the sequences in the gene library of antibody heavy chain variable regions and the gene library of antibody light chain variable regions thus prepared were inserted into phagemid vectors. A human antibody phage display library displaying Fab domains composed of human antibody sequences (Methods Mol Biol. (2002) 178, 87-100) was constructed.

Figure 8:
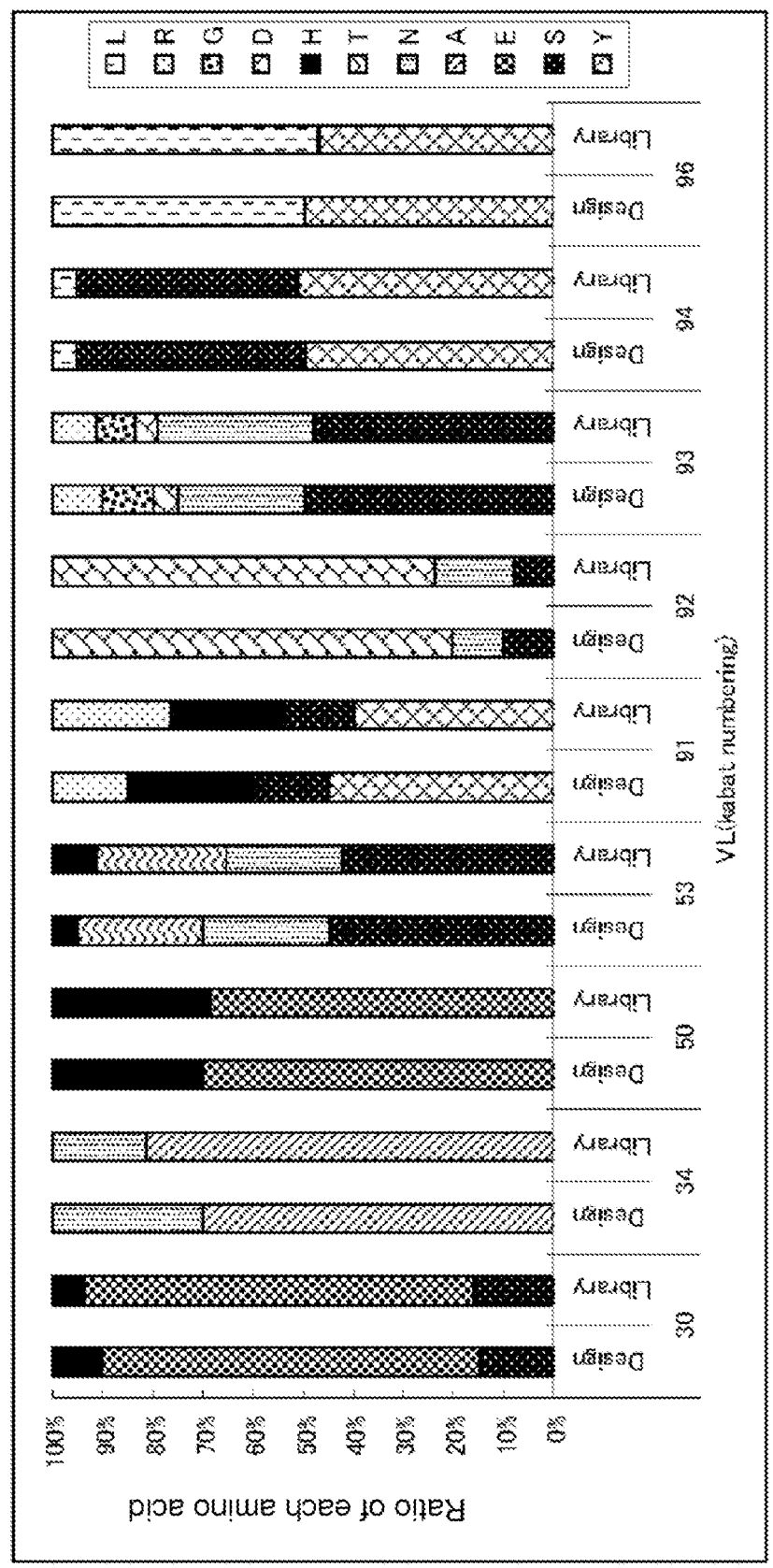
FIG. 8 is a graph showing the relationship between the amino acid distribution (indicated by Library) of sequence information about 290 clones isolated from *E. coli* transformed with a gene library of antibodies binding to antigens in a Ca-dependent manner and a designed amino acid distribution (indicated by Design). The abscissa represents an amino acid position defined by the Kabat numbering. The ordinate represents the ratio of each amino acid in the distribution.

Antibody gene portions isolated from *E. coli* transformed with the antibody gene library were sequenced according to the method described in Example 2. FIG. 8 shows an amino acid distribution in the sequences of 290 types of clones thus obtained and the designed amino acid distribution.

[Example 13] Evaluation of Molecule Contained in Ca Library for its Calcium Ion-Binding Activity (13-1) Calcium Ion-Binding Activity of Molecule Contained in Ca Library Since the hVk5-2 sequence shown to bind to calcium ions has low frequency of appearance among germline sequences as shown in Example 7, the obtainment of calcium-binding antibodies from an antibody library constituted by human germline sequences or from B cells obtained by the immunization of human antibody-expressing mice seemed to be inefficient. Thus, the Ca library was constructed in Example 12. The constructed Ca library was evaluated for the presence or absence of clones exhibiting calcium binding.

(13-2) Antibody Expression and Purification

The gene of each clone contained in the Ca library was introduced to plasmids for expression in animal cells. Antibody expression was performed by the following method: a human embryonic kidney cell-derived FreeStyle 293-F line (Invitrogen Corp.) was suspended in FreeStyle 293 Expression Medium (Invitrogen Corp.). The suspension having a cell density of $1.33 \times 10^6$ cells/mL was inoculated at a concentration of 3 mL/well to a 6-well plate. The prepared plasmids were transferred to the cells by lipofection. The cells were cultured for 4 days in a $CO_2$ incubator (37° C., 8% $CO_2$, 90 rpm). Antibodies were purified from the obtained culture supernatant by a method generally known to those skilled in the art using rProtein A Sepharose™ Fast Flow (Amersham Biosciences, Inc.). The absorbance of the purified antibody solution was measured at 280 nm using a spectrophotometer. The antibody concentration was calculated from the obtained measurement value by use of an extinction coefficient calculated by PACE (Protein Science (1995) 4, 2411-2423).

(13-3) Evaluation of Obtained Antibody for its Calcium Ion Binding

Whether or not the purified antibodies thus obtained bound to calcium ions were determined by the method described in Example 6. The results are shown in Table 19. The Tm values of the Fab domains of a plurality of antibodies contained in the Ca library varied depending on calcium ion concentration, showing that the Ca library contains molecules binding to calcium ions.

TABLE 19

| Antibody | SEQ ID NO | | Calcium ion concentration | | ΔTm (° C.) |
|---|---|---|---|---|---|
| | Heavy chain | Light chain | 3 µM | 2 mM | 2 mM-3 µM |
| Ca_B01 | 50 | 61 | 70.88 | 71.45 | 0.57 |
| Ca_E01 | 51 | 62 | 84.31 | 84.95 | 0.64 |
| Ca_H01 | 52 | 63 | 77.87 | 79.49 | 1.62 |
| Ca_D02 | 53 | 64 | 78.94 | 81.1 | 2.16 |
| Ca_E02 | 54 | 65 | 81.41 | 83.18 | 1.77 |
| Ca_H02 | 55 | 66 | 72.84 | 75.13 | 2.29 |
| Ca_D03 | 56 | 67 | 87.39 | 86.78 | −0.61 |
| Ca_C01 | 57 | 68 | 74.74 | 74.92 | 0.18 |
| Ca_G01 | 58 | 69 | 65.21 | 65.87 | 0.66 |
| Ca_A03 | 59 | 70 | 80.64 | 81.89 | 1.25 |
| Ca_B03 | 60 | 71 | 93.02 | 93.75 | 0.73 |

[Example 14] Obtainment of Antibody Binding to IL-6 Receptor in Ca-Dependent Manner (14-1) Obtainment of Antibody Fragment Binding to Antigen in Ca-Dependent Manner from Library by Bead Panning Method The first round of screening of the constructed Ca library was carried out by the enrichment of only antibody fragments having antigen (IL-6 receptor)-binding ability.

Phages were produced from *E. coli* carrying the constructed phagemid for phage display. 2.5 M NaCl/10% PEG was added to cultures of *E. coli* that had produced phages, and a pool of the phages thus precipitated was diluted with TBS to obtain a phage library solution. Next, BSA and $CaCl_2$) (final concentration: 4% BSA and 1.2 mM calcium ion) were added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of biotin-labeled antigens was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed three times with 1 mL of 1.2 mM $CaCl_2$)/TBST (TBST containing 1.2 mM $CaCl_2$)) and then further washed twice with 1 mL of 1.2 mM $CaCl_2$)/TBS (TBS containing 1.2 mM $CaCl_2$)). After addition of 0.5 mL of 1 mg/mL trypsin, the beads were suspended at room temperature for 15 minutes, immediately after which the beads were separated using a magnetic stand to collect a phage solution. The collected phage solution was added to 10 mL of an *E. coli* strain ER2738 in a logarithmic growth phase (OD600: 0.4-0.7). The *E. coli* strain was infected by the phages through the gentle spinner culture of the strain at 37° C. for 1 hour. The infected *E. coli* was inoculated to a plate of 225 mm×225 mm. Next, phages were collected from cultures of the inoculated *E. coli* to prepare a phage library solution.

In the second round of panning, the phages were enriched with antigen-binding ability or Ca-dependent binding ability as an index.

Specifically, for the enrichment with antigen-binding ability as an index, 40 pmol of biotin-labeled antigens was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed three times with 1 mL of 1.2 mM $CaCl_2$)/TBST and two times with 1.2 mM $CaCl_2$)/TBS. Then, the beads supplemented with 0.5 mL of 1 mg/mL trypsin were suspended at room temperature for 15 minutes, immediately after which the beads were separated using a magnetic stand to collect a phage solution. The addition of 5 µL of 100 mg/mL trypsin to the collected phage solution cleaved the pIII proteins (helper phage-derived pIII proteins) of non-Fab-displaying phages to cancel the ability of the non-Fab-displaying phages to infect *E. coli*. The collected phage solution was added to 10 mL of an *E. coli* strain ER2738 in a logarithmic growth phase (OD600: 0.4-0.7). The *E. coli* strain was infected by the phages through the gentle spinner culture of the strain at 37° C. for 1 hour. The infected *E. coli* was inoculated to a plate of 225 mm×225 mm. Next, phages were collected from cultures of the inoculated *E. coli* to prepare a phage library solution.

For the enrichment with Ca-dependent binding ability as an index, 40 pmol of biotin-labeled antigens was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed with 1 mL of 1.2 mM $CaCl_2$)/TBST and 1.2 mM $CaCl_2$/TBS. Then, the beads supplemented with 0.1 mL of 2 mM EDTA/TBS (TBS containing 2 mM EDTA) were suspended at room temperature. Immediately thereafter, the beads were separated using a magnetic stand to collect a phage solution. The addition of 5 μL of 100 mg/mL trypsin to the colcected phage solution cleaved the pIII proteins (helper phage-derived pIII proteins) of non-Fab-displaying phages to cancel the ability of the non-Fab-displaying phages to infect E. coli. The collected phage solution was added to 10 mL of an E. coli strain ER2738 in a logarithmic growth phase (OD600: 0.4-0.7). The E. coli strain was infected by the phages through the gentle spinner culture of the strain at 37° C. for 1 hour. The infected E. coli was inoculated to a plate of 225 mm×225 mm. Next, phages were collected from cultures of the inoculated E. coli to prepare a phage library solution.

(14-2) Evaluation by Phage ELISA

A phage-containing culture supernatant was collected according to a conventional method (Methods Mol. Biol. (2002) 178, 133-145) from each single colony of the E. coli obtained by the above method.

After addition of BSA and $CaCl_2$), the phage-containing culture supernatant was subjected to ELISA by the following procedures: StreptaWell 96 microtiter plate (F. Hoffmann-La Roche Ltd.) was coated overnight with 100 μL of PBS containing biotin-labeled antigens. Each well of the plate was washed with PBST to remove unbound antigens. Then, the well was blocked with 250 μL of 4% BSA-TBS for 1 hour or longer. After removal of 4% BSA-TBS, the prepared culture supernatant was added to each well, and the plate was left standing at 37° C. for 1 hour to associate phage-displayed antibodies with the antigens contained in each well. Each well was washed with 1.2 mM $CaCl_2$/TBST, and 1.2 mM $CaCl_2$/TBS or 1 mM EDTA/TBS was added thereto. The plate was left standing at 37° C. for 30 minutes for incubation. After washing with 1.2 mM $CaCl_2$/TBST, HRP-conjugated anti-M13 antibodies (Amersham Pharmacia Biotech Inc.) diluted with TBS having an ionized calcium concentration of 1.2 mM were added to each well. The plate was incubated for 1 hour. After washing with 1.2 mM $CaCl_2$/TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm.

Genes of the clones subjected to the phage ELISA were amplified using specific primers and then analyzed for their nucleotide sequences. The results of phage ELISA and sequence analysis are shown in the following Table 20.

TABLE 20

| Enrichment index | Library | |
|---|---|---|
| | Ca library Antigen-binding ability | Ca library Dependent antigen-binding ability |
| Number of panning campaigns | 2 | 2 |
| Number of clones tested | 85 | 86 |
| ELISA-positive | 77 | 75 |
| Type of ELISA-positive clone sequence | 74 | 72 |
| Type of Ca-dependent binding clone sequence | 13 | 47 |

(14-3) Antibody Expression and Purification

The gene of each clone judged as having Ca-dependent antigen-binding ability as a result of the phage ELISA was introduced to plasmids for expression in animal cells. Antibody expression was performed by the following method: a human embryonic kidney cell-derived FreeStyle 293-F line (Invitrogen Corp.) was suspended in FreeStyle 293 Expression Medium (Invitrogen Corp.). The suspension having a cell density of $1.33 \times 10^6$ cells/mL was inoculated at a concentration of 3 mL/well to a 6-well plate. The prepared plasmids were transferred to the cells by lipofection. The cells were cultured for 4 days in a $CO_2$ incubator (37° C., 8% $CO_2$, 90 rpm). Antibodies were purified from the obtained culture supernatant by a method generally known to those skilled in the art using rProtein A Sepharose™ Fast Flow (Amersham Biosciences, Inc.). The absorbance of the purified antibody solution was measured at 280 nm using a spectrophotometer. The antibody concentration was calculated from the obtained measurement value by use of an extinction coefficient calculated by PACE (Protein Science (1995) 4, 2411-2423).

(14-4) Evaluation of Obtained Antibody for its Ca-Dependent Binding Ability Against Human IL-6 Receptor In order to judge the Ca dependence of the human IL-6 receptor-binding activity of antibodies 6RC1IgG_010 (heavy chain: SEQ ID NO: 72 and light chain: SEQ ID NO: 73), 6RC1IgG_012 (heavy chain: SEQ ID NO: 74 and light chain: SEQ ID NO: 75), and 6RC1IgG_019 (heavy chain: SEQ ID NO: 76 and light chain: SEQ ID NO: 77) obtained in Example 14, these antibodies were analyzed for their interaction with human IL-6 receptors using Biacore T100 (GE Healthcare Bio-Sciences Corp.). Tocilizumab (heavy chain: SEQ ID NO: 24 and light chain: SEQ ID NO: 25) was used as a control antibody having no Ca-dependent binding activity against human IL-6 receptors. The interaction was analyzed in solutions of 1.2 mM and 3 μM calcium ion concentrations as high-calcium ion concentration and low-calcium ion concentration conditions, respectively. Each antibody of interest was captured onto Sensor chip CM5 (GE Healthcare Bio-Sciences Corp.) with protein A/G (Invitrogen Corp.) immobilized thereon in an appropriate amount by the amine coupling method. Two types of buffer solutions were used as running buffers: 20 mM ACES, 150 mM NaCl, 0.05% (w/v) Tween 20, and 1.2 mM $CaCl_2$) (pH 7.4); and 20 mM ACES, 150 mM NaCl, 0.05% (w/v) Tween 20, and 3 μM $CaCl_2$) (pH 7.4). The human IL-6 receptors were also diluted with each of these buffers. These assays were all carried out at 37° C.

In the analysis on the interaction of antigen-antibody reaction using the control antibody tocilizumab, the 6RC1IgG_010 antibody, the 6RC1IgG_012 antibody, and the 6RC1IgG_019 antibody, the diluted IL-6 receptor solution or a blank running buffer was injected at a flow rate of 5 μL/min for 3 minutes to interact the IL-6 receptors with the tocilizumab antibody, the 6RC1IgG_010 antibody, the 6RC1IgG_012 antibody, or the 6RC1IgG_019 antibody captured on the sensor chip. Then, 10 mM glycine-HCl (pH 1.5) was injected thereto at a flow rate of 30 μL/min for 30 seconds to regenerate the sensor chip.

Figure 9:
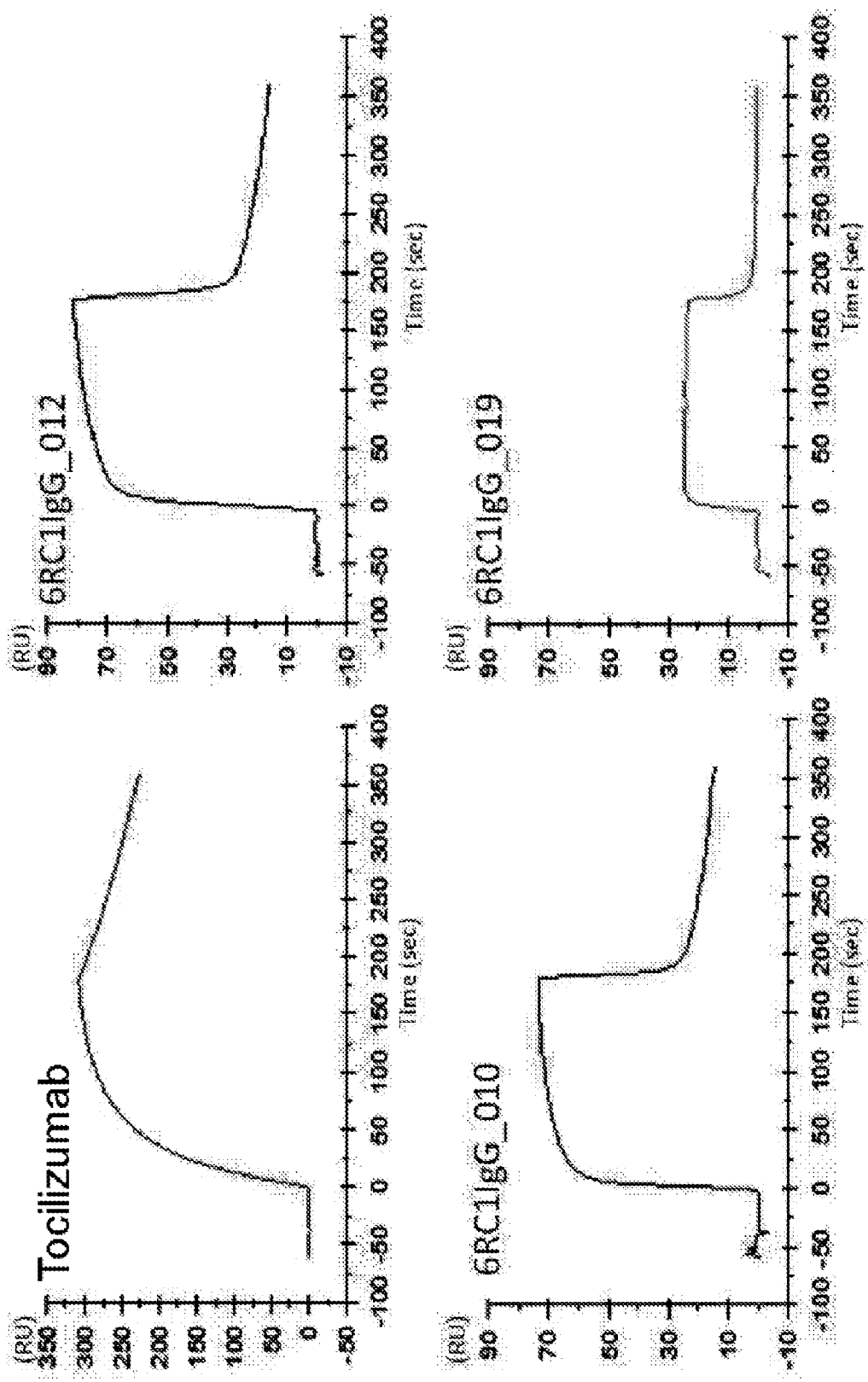
FIG. 9 shows the sensorgrams of an anti-IL-6R antibody (tocilizumab), a 6RC1IgG_010 antibody, a 6RC1IgG_012 antibody, and a 6RC1IgG_019 antibody under a high-calcium ion concentration condition (1.2 mM). The abscissa represents time. The ordinate represents RU values.

FIG. 9 shows the sensorgrams of the antibodies assayed at the high calcium ion concentration by this method.

Figure 10:
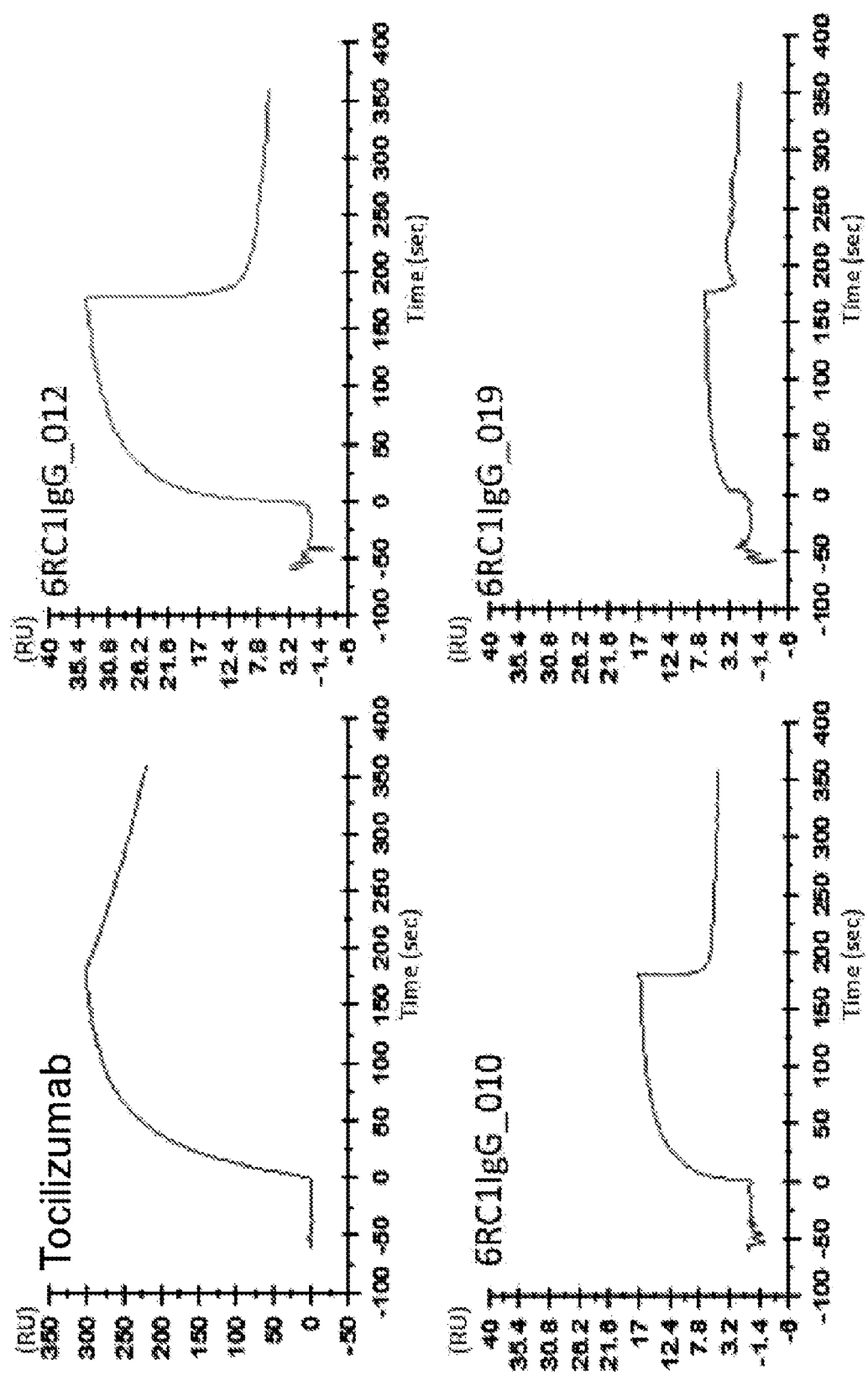
FIG. 10 shows the sensorgrams of the anti-IL-6R antibody (tocilizumab), the 6RC1IgG_010 antibody, the 6RC1IgG_012 antibody, and the 6RC1IgG_019 antibody under a low-calcium ion concentration condition (3 µM). The abscissa represents time. The ordinate represents RU values.

The sensorgrams of the antibody, tocilizumab, the 6RC1IgG_010 antibody, the 6RC1IgG_012 antibody, and the 6RC1IgG_019 antibody under the low-calcium ion concentration condition were also obtained by a similar method. FIG. 10 shows the sensorgrams of the antibodies at the low calcium ion concentration.

As a result, the IL6 receptor-binding ability of the 6RC1IgG_010 antibody, the 6RC1IgG_012 antibody, and the 6RC1IgG_019 antibody was observed to be drastically reduced by the change of the calcium ion concentration in the buffer from 1.2 mM to 3 μM.

[Example 15] Obtainment of Antibody Binding to IL-6 Receptor in Ca-Dependent Manner from Human Antibody Library Using Phage Display Technique (15-1) Preparation of Naive Human Antibody Phage Display Library A human antibody phage display library consisting of a plurality of phages displaying Fab domains having distinct human antibody sequences was constructed according to a method generally known to those skilled in the art using poly-A RNA prepared from human PBMC, commercially available human poly-A RNA, or the like as a template.

(15-2) Obtainment of Antibody Fragment Binding to Antigen in Ca-Dependent Manner from Library by Bead Panning Method The first round of screening of the constructed naive human antibody phage display library was carried out by the enrichment of only antibody fragments having antigen (IL-6 receptor)-binding ability or by the enrichment of antibody fragments with Ca concentration-dependent antigen (IL-6 receptor)-binding ability as an index. The enrichment of antibody fragments with Ca concentration-dependent antigen (IL-6 receptor)-binding ability as an index was carried out by the elution of phages from the phage library bound with IL-6 receptors in the presence of Ca ions using EDTA chelating Ca ions. The antigens used were biotin-labeled IL-6 receptors.

Phages were produced from $E.\ coli$ carrying the constructed phagemid for phage display. 2.5 M NaCl/10% PEG was added to cultures of $E.\ coli$ that had produced phages, and a pool of the phages thus precipitated was diluted with TBS to obtain a phage library solution. Next, BSA and $CaCl_2$ (final concentration: 4% BSA and 1.2 mM calcium ion) were added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of biotin-labeled antigens was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed once with 1 mL of 1.2 mM $CaCl_2$/TBS (TBS containing 1.2 mM $CaCl_2$)). Then, a phage solution was collected by elution according to a general method for the enrichment of the antibody fragments having IL-6 receptor-binding ability or by elution from the beads suspended in 2 mM EDTA/TBS (TBS containing 2 mM EDTA) for the enrichment of the antibody fragments with Ca concentration-dependent IL-6 receptor-binding ability as an index. The collected phage solution was added to 10 mL of an $E.\ coli$ strain TG1 in a logarithmic growth phase (OD600: 0.4-0.7). The $E.\ coli$ strain was infected by the phages through the gentle spinner culture of the strain at 37° C. for 1 hour. The infected $E.\ coli$ was inoculated to a plate of 225 mm×225 mm. Next, phages were collected from cultures of the inoculated $E.\ coli$ to prepare a phage library solution.

In the second and subsequent rounds of panning, the phages were enriched with Ca-dependent binding ability as an index. Specifically, 40 pmol of biotin-labeled antigens was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed with 1 mL of 1.2 mM $CaCl_2$)/TBST and 1.2 mM $CaCl_2$)/TBS. Then, the beads supplemented with 0.1 mL of 2 mM EDTA/TBS were suspended at room temperature. Immediately thereafter, the beads were separated using a magnetic stand to collect a phage solution. The collected phage solution was added to 10 mL of an $E.\ coli$ strain TG1 in a logarithmic growth phase (OD600: 0.4-0.7). The $E.\ coli$ strain was infected by the phages through the gentle spinner culture of the strain at 37° C. for 1 hour. The infected $E.\ coli$ was inoculated to a plate of 225 mm×225 mm. Next, phages were collected from cultures of the inoculated $E.\ coli$ to collect a phage library solution. The panning with Ca-dependent binding ability as an index was repeated several times.

(15-3) Evaluation by Phage ELISA

A phage-containing culture supernatant was collected according to a conventional method (Methods Mol. Biol. (2002) 178, 133-145) from each single colony of the $E.\ coli$ obtained by the above method.

After addition of BSA and $CaCl_2$) (final concentration: 4% BSA and 1.2 mM calcium ion), the phage-containing culture supernatant was subjected to ELISA by the following procedures: StreptaWell 96 microtiter plate (F. Hoffmann-La Roche Ltd.) was coated overnight with 100 μL of PBS containing biotin-labeled antigens. Each well of the plate was washed with PBST to remove unbound antigens. Then, the well was blocked with 250 μL of 4% BSA-TBS for 1 hour or longer. After removal of 4% BSA-TBS, the prepared culture supernatant was added to each well, and the plate was left standing at 37° C. for 1 hour to associate phage-displayed antibodies with the antigens contained in each well. Each well was washed with 1.2 mM $CaCl_2$/TBST, and 1.2 mM $CaCl_2$/TBS or 1 mM EDTA/TBS was added thereto. The plate was left standing at 37° C. for 30 minutes for incubation. After washing with 1.2 mM $CaCl_2$/TBST, HRP-conjugated anti-M13 antibodies (Amersham Pharmacia Biotech Inc.) diluted with TBS having 4% BSA and an ionized calcium concentration of 1.2 mM (all were indicated by final concentrations) were added to each well. The plate was incubated for 1 hour. After washing with 1.2 mM $CaCl_2$/TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm.

Genes of antibody fragments judged as having Ca-dependent antigen-binding ability as a result of the phage ELISA were amplified as a template using specific primers and then analyzed for their nucleotide sequences.

(15-4) Antibody Expression and Purification

The gene of each clone judged as having Ca-dependent antigen-binding ability as a result of the phage ELISA was introduced to plasmids for expression in animal cells. Antibody expression was performed by the following method: a human embryonic kidney cell-derived FreeStyle 293-F line (Invitrogen Corp.) was suspended in FreeStyle 293 Expression Medium (Invitrogen Corp.). The suspension having a cell density of $1.33 \times 10^6$ cells/mL was inoculated at a concentration of 3 mL/well to a 6-well plate. The prepared plasmids were transferred to the cells by lipofection. The cells were cultured for 4 days in a $CO_2$ incubator (37° C., 8%

$CO_2$, 90 rpm). Antibodies were purified from the obtained culture supernatant by a method generally known to those skilled in the art using rProtein A Sepharose™ Fast Flow (Amersham Biosciences, Inc.). The absorbance of the purified antibody solution was measured at 280 nm using a spectrophotometer. The antibody concentration was calculated from the obtained measurement value by use of an extinction coefficient calculated by PACE (Protein Science (1995) 4, 2411-2423).

[Example 16] Evaluation of Obtained Antibody for its Ca-Dependent Binding Ability Against Human IL-6 Receptor In order to judge the Ca dependence of the human IL-6 receptor-binding activity of antibodies 6RL #9-IgG1 (heavy chain: SEQ ID NO: 78 (sequence of SEQ ID NO: 10 linked to an IgG1-derived constant region) and light chain: SEQ ID NO: 79) and FH4-IgG1 (heavy chain: SEQ ID NO: 80 and light chain: SEQ ID NO: 81) obtained in Example 15, these antibodies were kinetically analyzed for their antigen-antibody reaction with human IL-6 receptors using Biacore T100 (GE Healthcare Bio-Sciences Corp.). H54/L28-IgG1 described in WO2009125825 (heavy chain: SEQ ID NO: 82 and light chain: SEQ ID NO: 83) was used as a control antibody having no Ca-dependent binding activity against human IL-6 receptors. The antigen-antibody reaction was kinetically analyzed in solutions of 2 mM and 3 μM calcium ion concentrations as high-calcium ion concentration and low-calcium ion concentration conditions, respectively. Each antibody of interest was captured onto Sensor chip CM4 (GE Healthcare Bio-Sciences Corp.) with protein A (Invitrogen Corp.) immobilized thereon in an appropriate amount by the amine coupling method. Two types of buffer solutions were used as running buffers: 10 mM ACES, 150 mM NaCl, 0.05% (w/v) Tween 20, and 2 mM $CaCl_2$ (pH 7.4); and 10 mM ACES, 150 mM NaCl, 0.05% (w/v) Tween 20, and 3 μmol/L $CaCl_2$ (pH 7.4). The human IL-6 receptors were also diluted with each of these buffers. Assay was all carried out at 37° C.

In the kinetic analysis on the antigen-antibody reaction using the H54/L28-IgG1 antibody, the diluted IL-6 receptor solution or a blank running buffer was injected at a flow rate of 20 μL/min for 3 minutes to interact the IL-6 receptors with the H54/L28-IgG1 antibody captured on the sensor chip. Then, a running buffer was injected at flow rate of 20 μL/min for 10 minutes, and the dissociation of the IL-6 receptors was observed. Then, 10 mM glycine-HCl (pH 1.5) was injected thereto at a flow rate of 30 μL/min for 30 seconds to regenerate the sensor chip. An associate rate constant ka (1/Ms) and a dissociation rate constant kd (1/s) were calculated as kinetic parameters from the sensorgram obtained in the assay. These values were used to calculate the dissociation constant KD (M) of the H54/L28-IgG1 antibody for the human IL-6 receptor. Each parameter was calculated using Biacore T100 Evaluation Software (GE Healthcare Bio-Sciences Corp.).

In the kinetic analysis on the antigen-antibody reaction using the FH4-IgG1 antibody and the 6RL #9-IgG1 antibody, the diluted IL-6 receptor solution or a blank running buffer was injected at a flow rate of 5 μL/min for 15 minutes to interact the IL-6 receptors with the FH4-IgG1 antibody or the 6RL #9-IgG1 antibody captured on the sensor chip. Then, 10 mM glycine-HCl (pH 1.5) was injected thereto at a flow rate of 30 μL/min for 30 seconds to regenerate the sensor chip. The dissociation constant KD (M) was calculated using Steady State Affinity Model from the sensorgrams obtained in the assay. Each parameter was calculated using Biacore T100 Evaluation Software (GE Healthcare Bio-Sciences Corp.).

Table 21 shows the dissociation constant KD of each antibody for the IL-6 receptor determined by this method in the presence of 2 mM $CaCl_2$).

TABLE 21

| Antibody | H54/L28-IgG1 | FH4-IgG1 | 6RL#9-IgG1 |
|---|---|---|---|
| kD (M) | 1.9E−9 | 5.9E−7 | 2.6E−7 |

KD of the H54/L28-IgG1 antibody under the Ca concentration condition of 3 μM can be calculated in the same way as in the presence of Ca having a concentration of 2 mM. The FH4-IgG1 antibody and the 6RL #9-IgG1 antibody were hardly observed to bind to the IL-6 receptor under the Ca concentration condition of 3 μM. Thus, KD is difficult to calculate by the above method. Instead, the KD values of these antibodies under the Ca concentration condition of 3 μM can be calculated according to the following expression 1 (Biacore T100 Software Handbook, BR-1006-48, AE January 2007).

$$Req = C \times Rmax/(KD+C) + RI \qquad \text{[Expression 1]}$$

In the above expression 1, each symbol is defined as follows:
Req (RU): Steady state binding levels
Rmax (RU): Analyte binding capacity of the surface
RI (RU): Bulk refractive index contribution in the sample
C (M): Analyte concentration
KD (M): Equilibrium dissociation constant Table 22 shows results of roughly estimating the dissociation constant KD of each antibody for the IL-6 receptor at the Ca concentration of 3 μmol/L according to the expression 1. In Table 22, Req, Rmax, RI, and C represent values hypothesized on the basis of the assay results.

TABLE 22

| Antibody | H54/L28-IgG1 | FH4-IgG1 | 6RL#9-IgG1 |
|---|---|---|---|
| Req (RU) |  | 5 | 10 |
| Rmax (RU) |  | 39 | 72 |
| RI (RU) |  | 0 | 0 |
| C (M) |  | 5E−06 | 5E−06 |
| KD (M) | 2.2E−9 | 3.4E−05 | 3.1E−05 |

As a result, the FH4-IgG1 antibody and the 6RL #9-IgG1 antibody were predicted to have KD values for the IL-6 receptor that were increased by approximately 60 times and approximately 120 times, respectively (affinity were reduced by 60 times and 120 times or more) as the $CaCl_2$) concentration in the buffer was decreased from 2 mM to 3 μM.

Table 23 summarizes the KD values of three types of antibodies, H54/L28-IgG1, FH4-IgG1, and 6RL #9-IgG1, in the presence of 2 mM $CaCl_2$) and in the presence of 3 μM $CaCl_2$), and the Ca dependency of the KD values.

TABLE 23

| Antibody | H54/L28-IgG1 | FH4-IgG1 | 6RL#9-IgG1 |
|---|---|---|---|
| KD (M) (2 mM $CaCl_2$) | 1.9E−9 | 5.9E−7 | 2.6E−7 |
| KD (M) (3 μM $CaCl_2$) | 2.2E−9 | 3.4E−5 or more | 3.1E−5 or more |

TABLE 23-continued

| Antibody | H54/L28-IgG1 | FH4-IgG1 | 6RL#9-IgG1 |
|---|---|---|---|
| Ca dependence | Approximately 1 time | Approximately 60 times or more | Approximately 120 times or more |

The H54/L28-IgG1 antibody was not observed to differ in IL-6 receptor binding depending on the difference in Ca concentration. By contrast, significant attenuation of IL-6 receptor binding was observed in the FH4-IgG1 antibody and the 6RL #9-IgG1 antibody under the low-Ca concentration condition (Table 23).

[Example 17] Evaluation of Obtained Antibody for its Calcium Ion Binding

Next, thermal denaturation midpoint temperature (Tm) was measured by differential scanning calorimetry (DSC) (MicroCal VP-Capillary DSC, MicroCal) as an index for evaluating the calcium ion binding of the antibodies. The thermal denaturation midpoint temperature (Tm) serves as an index for stability and becomes higher when a protein is stabilized through calcium ion binding, compared with the thermal denaturation midpoint temperature (Tm) of a calcium ion-unbound protein (J. Biol. Chem. (2008) 283, 37, 25140-25149). Change in the Tm value of each antibody according to change in calcium ion concentration in the antibody solution was evaluated to evaluate the binding activity of the antibody against calcium ions. The purified antibodies were dialyzed (EasySEP, Tomy Seiko Co., Ltd.) against a solution containing 20 mM Tris-HCl, 150 mM NaCl, and 2 mM $CaCl_2$) (pH 7.4) or containing 20 mM Tris-HCl, 150 mM NaCl, and 3 µM $CaCl_2$) (pH 7.4) as an external solution. Each antibody solution was adjusted to approximately 0.1 mg/mL of antibody with the solution used in the dialysis and subjected as a test substance to DSC assay at 20° C. to 115° C. with the rate of temperature rise set to 240° C./hr. Table 24 shows the thermal denaturation midpoint temperature (Tm) of each antibody Fab domain calculated on the basis of the obtained (DSC) denaturation curve.

TABLE 24

| Antibody | Calcium ion concentration | | ΔTm (° C.) |
|---|---|---|---|
| | 3 µM | 2 mM | 2 mM-3 µM |
| H54/L28-IgG1 | 92.87 | 92.87 | 0.00 |
| FH4-IgG1 | 74.71 | 78.97 | 4.26 |
| 6RL#9-IgG1 | 77.77 | 78.98 | 1.21 |

The results of Table 24 showed that the Tm values of the Fab domains of the FH4-IgG1 antibody and the 6RL #9-IgG1 antibody exhibiting calcium-dependent binding ability varied depending on change in calcium ion concentration, whereas the Tm value of the Fab domain of the H54/L28-IgG1 antibody exhibiting no calcium-dependent binding ability did not vary depending on change in calcium ion concentration. Such variations in the Tm values of the Fab domains of the FH4-IgG1 antibody and the 6RL #9-IgG1 antibody indicate that the Fab domains were stabilized through the binding of calcium ions to these antibodies. These results demonstrated that the FH4-IgG1 antibody and the 6RL #9-IgG1 antibody bind to calcium ions, whereas the H54/L28-IgG1 antibody does not bind to calcium ions.

[Example 18] Identification of Calcium Ion-Binding Site in 6RL #9 Antibody by X-Ray Crystal Structure Analysis (18-1) X-Ray Crystal Structure Analysis As shown in Example 17, the thermal denaturation temperature Tm assay suggested that the 6RL #9 antibody bound to calcium ions. However, the site via which the 6RL #9 antibody bound to calcium ions was unpredictable. Thus, a residue responsible for the interaction with calcium ions was identified in the sequence of the 6RL #9 antibody by use of the approach of X-ray crystal structure analysis.

(18-2) 6RL #9 Antibody Expression and Purification

The 6RL #9 antibody expressed for use in X-ray crystal structure analysis was purified. Specifically, animal cells were transiently transfected with plasmids for expression in animal cells prepared so as to permit respective expression of the heavy chain (SEQ ID NO: 78) and the light chain (SEQ ID NO: 79) of the 6RL #9 antibody. The prepared plasmids were transfected by lipofection to 800 mL of a human embryonic kidney cell-derived FreeStyle 293-F line (Invitrogen Corp.) suspended at a final cell density of $1×10^6$ cells/mL in FreeStyle 293 Expression Medium (Invitrogen Corp.). The cells transfected with the plasmids were cultured for 5 days in a $CO_2$ incubator (37° C., 8% $CO_2$, 90 rpm). Antibodies were purified from the obtained culture supernatant according to a method generally known to those skilled in the art using rProtein A Sepharose™ Fast Flow (Amersham Biosciences, Inc.). The absorbance of the purified antibody solution was measured at 280 nm using a spectrophotometer. The antibody concentration was calculated from the measurement value by use of an extinction coefficient calculated by PACE (Protein Science (1995) 4, 2411-2423).

(18-3) Purification of Fab Fragment from 6RL #9 Antibody

The 6RL #9 antibody was concentrated to 21 mg/mL using an ultrafiltration membrane having a molecular weight cutoff of 10000 MWCO. The antibody was diluted to 5 mg/mL with 4 mM L-cysteine, 5 mM EDTA, and a 20 mM sodium phosphate buffer solution (pH 6.5) to prepare 2.5 mL of an antibody sample. After addition of 0.125 mg of papain (Roche Applied Science), the sample was stirred and then left standing at 35° C. for 2 hours. The sample thus left standing was further supplemented with one tablet of Protease Inhibitor Cocktail Mini, EDTA-Free (Roche Applied Science) dissolved in 10 mL of a 25 mM MES buffer solution (pH 6), and left standing on ice to terminate the protease reaction with papain. Next, the sample was added to a 1 mL-size cation-exchange column HiTrap SP HP (GE Healthcare Bio-Sciences Corp.) (equilibrated with a 25 mM MES buffer solution (pH 6)) connected in tandem with a downstream 1 mL-size protein A carrier column HiTrap MabSelect Sure (GE Healthcare Bio-Sciences Corp.). A purified fraction of the 6RL #9 antibody Fab fragment was obtained by elution on a linear gradient of NaCl concentration up to 300 mM in this buffer solution. Next, the obtained purified fraction was concentrated to approximately 0.8 mL using a 5000 MWCO ultrafiltration membrane. The concentrate was added to a gel filtration column Superdex 200 10/300 GL (GE Healthcare Bio-Sciences Corp.) equilibrated with a 100 mM HEPES buffer solution (pH 8) containing 50 mM NaCl. The purified 6RL #9 antibody Fab fragment for crystallization was eluted from the column using this buffer solution. The column operation was all carried out at a low temperature of 6 to 7.5° C.

(18-4) Crystallization of Fab Fragment of 6RL #9 Antibody in Presence of Calcium Ion Seed crystals of the 6RL #9 Fab fragment were obtained in advance under generally set conditions. Next, the purified 6RL #9 antibody Fab fragment was adjusted to 5 mM by the addition of $CaCl_2$) and concentrated to 12 mg/mL using a 5000 MWCO ultrafiltration membrane. Subsequently, the sample thus concentrated was crystallized by the hanging-drop vapor diffusion method. A 100 mM HEPES buffer solution (pH 7.5) containing 20 to 29% PEG4000 was used as a reservoir solution. The seed crystals were disrupted in a 100 mM HEPES buffer solution (pH 7.5) containing 29% PEG4000 and 5 mM $CaCl_2$) and diluted 100- to 10000-fold, and 0.2 µl of each solution of this dilution series was added to a mixed solution of 0.8 µl of the reservoir solution and 0.8 µl of the concentrated sample on a glass cover to prepare crystallization drops. The crystallization drops were left standing at 20° C. for 2 days to 3 days. X-ray diffraction data on the obtained thin plate-like crystals was determined.

(18-5) Crystallization of Fab Fragment of 6RL #9 Antibody in Absence of Calcium Ion The purified 6RL #9 antibody Fab fragment was concentrated to 15 mg/mL using a 5000 MWCO ultrafiltration membrane. Subsequently, the sample thus concentrated was crystallized by the hanging-drop vapor diffusion method. A 100 mM HEPES buffer solution (pH 7.5) containing 18 to 25% PEG4000 was used as a reservoir solution. Crystals of the 6RL #9 antibody Fab fragment obtained in the presence of Ca were disrupted in a 100 mM HEPES buffer solution (pH 7.5) containing 25% PEG4000 and diluted 100- to 10000-fold, and 0.2 µl of each solution of this dilution series was added to a mixed solution of 0.8 µl of the reservoir solution and 0.8 µl of the concentrated sample on a glass cover to prepare crystallization drops. The crystallization drops were left standing at 20° C. for 2 days to 3 days. X-ray diffraction data on the obtained thin plate-like crystals was assayed.

(18-6) Collection of X-Ray Diffraction Data on Crystal of 6RL #9 Antibody Fab Fragment Obtained in Presence of Calcium Ion One of the monocrystals (obtained in the presence of Ca) of the 6RL #9 antibody Fab fragment dipped in a 100 mM HEPES buffer solution (pH 7.5) containing 35% PEG4000 and 5 mM $CaCl_2$) was scooped out, together with the external solution, using very small nylon loop pin and frozen in liquid nitrogen. The X-ray diffraction data on the frozen crystal was assayed using beam line BL-17A from Photon Factory, Institute Materials Structure Science, High Energy Accelerator Research Organization (KEK). During the assay, the frozen crystal was left at all times in a nitrogen stream of −178° C. to maintain its frozen state. A total of 180 diffraction images were collected, with the crystal rotated by 1° for each image, using a CCD detector Quantum 315r (Area Detector Systems Corporation (ADSC)) equipped with the beam line. The determination of a lattice constant, the indexing of diffraction spots, and the processing of the diffraction date were performed using a program Xia2 (CCP4 Software Suite), XDS Package (Wolfgang Kabsch), and Scala (CCP4 Software Suite). Finally, diffraction intensity data up to a resolution of 2.2 angstroms was obtained. This crystal belonged to the space group $P2_12_12_1$ and had lattice constants a=45.47 angstroms, b=79.86 angstroms, c=116.25 angstroms, $\alpha=90°$, $\beta=90°$, and $\gamma=90°$.

(18-7) Collection of X-Ray Diffraction Data on Crystal of 6RL #9 Antibody Fab Fragment Obtained in Absence of Calcium Ion One of the monocrystals (obtained in the absence of Ca) of the 6RL #9 antibody Fab fragment dipped in a 100 mM HEPES buffer solution (pH 7.5) containing 35% PEG4000 was scooped out, together with the external solution, using very small nylon loop pin and frozen in liquid nitrogen. The X-ray diffraction data on the frozen crystal was assayed using beam line BL-5A from Photon Factory, Institute Materials Structure Science, High Energy Accelerator Research Organization (KEK). During the assay, the frozen crystal was left at all times in a nitrogen stream of −178° C. to maintain its frozen state. A total of 180 diffraction images were collected, with the crystal rotated by 1° for each image, using a CCD detector Quantum 210r (Area Detector Systems Corporation (ADSC)) equipped with the beam line. The determination of a lattice constant, the indexing of diffraction spots, and the processing of the diffraction date were performed using a program Xia2 (CCP4 Software Suite), XDS Package (Wolfgang Kabsch), and Scala (CCP4 Software Suite). Finally, diffraction intensity data up to a resolution of 2.3 angstroms was obtained. This crystal, which was the same type of the crystal obtained in the presence of Ca, belonged to the space group $P2_12_12_1$ and had lattice constants a=45.40 angstroms, b=79.63 angstroms, c=116.07 angstroms, $\alpha=90°$, $\beta=90°$, and $\gamma=90°$.

(18-8) Structural Analysis of Crystal of 6RL #9 Antibody Fab Fragment Obtained in Presence of Calcium Ion The structure of the crystal of the 6RL #9 antibody Fab fragment obtained in the presence of Ca was determined by the molecular replacement method using a program Phaser (CCP4 Software Suite). The number of molecules in the asymmetric unit was presumed to be one from the size of the obtained crystal lattice and the molecular weight of the 6RL #9 antibody Fab fragment. On the basis of homology on the primary sequence, amino acid residues at positions 112 to 220 in the chain A and at positions 116 to 218 in the chain B retrieved from the structure coordinate of PDB code: 1ZA6 were selected as model molecules for search for CL and CH1 regions. Next, amino acid residues at positions 1 to 115 in the chain B retrieved from the structure coordinate of PDB code: 1ZA6 were selected as a model molecule for search for a VH region. Finally, amino acid residues at positions 3 to 147 in the light chain retrieved from the structure coordinate of PDB code: 2A9M were selected as a model molecule for search for a VL region. According to this order, the orientation and position of each model molecule for search in the crystal lattice were determined by rotation and translation functions to obtain an initial structural model of the 6RL #9 antibody Fab fragment. The initial structural model was subjected to rigid body refinement moving each of the VH, VL, CH1, and CL domains to obtain a crystallographic reliability factor R of 46.9% and a Free R value of 48.6% for reflection data of 25-3.0 angstroms. In addition, the model was refined by model correction on a repetition program Coot (Paul Emsley) with reference to electron density maps of coefficients 2Fo-Fc and Fo-Fc calculated through the use of structure refinement using a program Refmac5 (CCP4 Software Suite), an experimentally determined structure factor Fo, a structure factor Fc calculated from the model, and a phase. Final refinement was performed using a program Refmac5 (CCP4 Software Suite) by the incorporation of Ca ion and water molecules into the model on the basis of the electron density maps of coefficients 2Fo-Fc and Fo-Fc. Finally, a crystallographic reliability factor R of 20.0% and a Free R value of 27.9% were obtained for the model of 3440 atoms by use of 21020 reflection data with a resolution of 25-2.2 angstroms.

(18-9) A Structural Analysis of Crystal of 6RL #9 Antibody Fab Fragment Obtained in Aabsence of Calcium Ion The structure of the crystal of the 6RL #9 antibody Fab fragment obtained in the absence of Ca was determined using the structure of the crystal, which was the same type thereas, obtained in the presence of Ca. Water and Ca ion molecules were excluded from the structure coordinate of the crystal of the 6RL #9 antibody Fab fragment obtained in the presence of Ca, followed by rigid body refinement moving each of the VH, VL, CH1, and CL domains to obtain a crystallographic reliability factor R of 30.3% and a Free R value of 31.7% for reflection data of 25-3.0 angstroms. In addition, the model was refined by model correction on a repetition program Coot (Paul Emsley) with reference to electron density maps of coefficients 2Fo-Fc and Fo-Fc calculated through the use of structure refinement using a program Refmac5 (CCP4 Software Suite), an experimentally determined structure factor Fo, a structure factor Fc calculated from the model, and a phase. Final refinement was performed using a program Refmac5 (CCP4 Software Suite) by the incorporation of water molecules into the model on the basis of the electron density maps of coefficients 2Fo-Fc and Fo-Fc. Finally, a crystallographic reliability factor R of 20.9% and a Free R value of 27.7% were obtained for the model of 3351 atoms by use of 18357 reflection data with a resolution of 25-2.3 angstroms.

(18-10) X-Ray Diffraction Data Comparison Between Crystals of 6RL #9 Antibody Fab Fragment Obtained in Presence of Ca and in Absence of Ca As a result of structural comparison between the crystals of the 6RL #9 antibody Fab fragment obtained in the presence of Ca and in the absence of Ca, large change was seen in heavy chain CDR3. FIG. 11 shows the structure of the heavy chain CDR3 of the 6RL #9 antibody Fab fragment determined by X-ray crystal structure analysis. Specifically, a calcium ion was present at the central portion of the heavy chain CDR3 loop portion in the crystal of the 6RL #9 antibody Fab fragment obtained in the presence of Ca. The calcium ion was considered to interact with amino acid residues 95, 96, and 100a (defined by the Kabat numbering) in the heavy chain CDR3. This suggested that, in the presence of Ca, the heavy chain CDR3 loop, which is important for antigen binding, is stabilized through binding to calcium to take a structure optimum for antigen binding. None of previous reports show that calcium binds to antibody heavy chain CDR3. This structure of antibody heavy chain CDR3 bound with calcium is a novel structure.

The calcium-binding motifs present in heavy chain CDR3, which were revealed from the structure of the 6RL #9 antibody Fab fragment, may also serve as new factors for the design of the Ca library as described in Example 11. Although the calcium-binding motifs were introduced to the light chain variable region in Example 11, another possible library comprises, for example, the heavy chain CDR3 of the 6RL #9 antibody and comprises flexible residues in the other CDRs including light chain CDRs.

[Example 19] Obtainment of Antibody Binding to IL-6 in Ca-Dependent Manner from Human Antibody Library Using Phage Display Technique (19-1) Preparation of Naive Human Antibody Phage Display Library A human antibody phage display library consisting of a plurality of phages displaying Fab domains having distinct human antibody sequences was constructed according to a method generally known to those skilled in the art using poly-A RNA prepared from human PBMC, commercially available human poly-A RNA, or the like as a template.

(19-2) Obtainment of Antibody Fragment Binding to Antigen in Ca-Dependent Manner from Library by Bead Panning Method The first round of screening of the constructed naive human antibody phage display library was carried out by the enrichment of only antibody fragments having antigen (IL-6)-binding ability. The antigens used were biotin-labeled IL-6.

Phages were produced from $E.\ coli$ carrying the constructed phagemid for phage display. 2.5 M NaCl/10% PEG was added to cultures of $E.\ coli$ that had produced phages, and a pool of the phages thus precipitated was diluted with TBS to obtain a phage library solution. Next, BSA and $CaCl_2$) (final concentration: 4% BSA and 1.2 mM calcium ion) were added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of biotin-labeled antigens was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed three times with 1.2 mM $CaCl_2$)/TBST (TBST containing 1.2 mM $CaCl_2$)) and then further washed twice with 1 mL of 1.2 mM $CaCl_2$)/TBS (TBS containing 1.2 mM $CaCl_2$)). After addition of 0.5 mL of 1 mg/mL trypsin, the beads were suspended at room temperature for 15 minutes, immediately after which the beads were separated using a magnetic stand to collect a phage solution. The collected phage solution was added to 10 mL of an $E.\ coli$ strain TG1 in a logarithmic growth phase (OD600: 0.4-0.7). The $E.\ coli$ strain was infected by the phages through the gentle spinner culture of the strain at 37° C. for 1 hour. The infected $E.\ coli$ was inoculated to a plate of 225 mm×225 mm. Next, phages were collected from cultures of the inoculated $E.\ coli$ to prepare a phage library solution.

In the second and subsequent rounds of panning, the phages were enriched with Ca-dependent binding ability as an index. Specifically, 40 pmol of biotin-labeled antigens was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed with 1 mL of 1.2 mM $CaCl_2$)/TBST and 1.2 mM $CaCl_2$)/TBS. Then, the beads supplemented with 0.1 mL of 2 mM EDTA/TBS were suspended at room temperature. Immediately thereafter, the beads were separated using a magnetic stand to collect a phage solution. The addition of 5 μL of 100 mg/mL trypsin to the collected phage solution cleaved the pIII proteins (helper phage-derived pIII proteins) of non-Fab-displaying phages to cancel the ability of the non-Fab-displaying phages to infect $E.\ coli$. The phages collected from the trypsin-treated phage solution were added to 10 mL of an $E.\ coli$ strain TG1 in a logarithmic growth phase (OD600: 0.4-0.7). The *E. coli* strain was infected by the phages through the gentle spinner culture of the strain at 37° C. for 1 hour. The infected *E. coli* was inoculated to a plate of 225 mm×225 mm. Next, phages were collected from cultures of the inoculated *E. coli* to collect a phage library solution. This panning with Ca-dependent binding ability as an index was performed 3 rounds in total.

(19-3) Evaluation by Phage ELISA

A phage-containing culture supernatant was collected according to a conventional method (Methods Mol. Biol. (2002) 178, 133-145) from each single colony of the *E. coli* obtained by the above method.

After addition of BSA and $CaCl_2$ (final concentration: 4% BSA and 1.2 mM calcium ion), the phage-containing culture supernatant was subjected to ELISA by the following procedures: StreptaWell 96 microtiter plate (F. Hoffmann-La Roche Ltd.) was coated overnight with 100 μL of PBS containing biotin-labeled antigens. Each well of the plate was washed with PBST to remove unbound antigens. Then, the well was blocked with 250 μL of 4% BSA-TBS for 1 hour or longer. After removal of 4% BSA-TBS, the prepared culture supernatant was added to each well, and the plate was left standing at 37° C. for 1 hour to associate phage-displayed antibodies with the antigens contained in each well. Each well was washed with 1.2 mM $CaCl_2$/TBST, and 1.2 mM $CaCl_2$/TBS or 1 mM EDTA/TBS was added thereto. The plate was left standing at 37° C. for 30 minutes for incubation. After washing with 1.2 mM $CaCl_2$/TBST, HRP-conjugated anti-M13 antibodies (Amersham Pharmacia Biotech Inc.) diluted with TBS having 4% BSA and an ionized calcium concentration of 1.2 mM (all were indicated by final concentrations) were added to each well. The plate was incubated for 1 hour. After washing with 1.2 mM $CaCl_2$/TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm.

A 6KC4-1 #85 antibody having Ca-dependent IL-6-binding ability was obtained by phage ELISA using 96 isolated clones. The gene of the antibody fragment judged as having Ca-dependent antigen-binding ability as a result of the phage ELISA was amplified as a template using specific primers and then analyzed for its nucleotide sequence. The sequence of the heavy chain variable region of the 6KC4-1 #85 antibody is shown in SEQ ID NO: 11, and the sequence of the light chain variable region thereof is shown in SEQ ID NO: 84. A polynucleotide encoding the heavy chain variable region (SEQ ID NO: 11) of the 6KC4-1 #85 antibody was linked by PCR to a polynucleotide encoding an IgG1-derived sequence. The resulting DNA fragment was incorporated into vectors for expression in animal cells to construct vectors that permits expression of a heavy chain represented by SEQ ID NO: 85. A polynucleotide encoding the light chain variable region (SEQ ID NO: 84) of the 6KC4-1 #85 antibody was linked by PCR to a polynucleotide encoding a natural kappa chain constant region (SEQ ID NO: 26). The resulting DNA fragment was incorporated into vectors for expression in animal cells. The sequence of the prepared modified form was confirmed by a method generally known to those skilled in the art. The sequence of the prepared modified form was confirmed by a method generally known to those skilled in the art.

(19-4) Antibody Expression and Purification

The gene of the clone 6KC4-1 #85 judged as having Ca-dependent antigen-binding ability as a result of the phage ELISA was introduced to plasmids for expression in animal cells. Antibody expression was performed by the following method: a human embryonic kidney cell-derived FreeStyle 293-F line (Invitrogen Corp.) was suspended in FreeStyle 293 Expression Medium (Invitrogen Corp.). The suspension having a cell density of $1.33 \times 10^6$ cells/mL was inoculated at a concentration of 3 mL/well to a 6-well plate. The prepared plasmids were transferred to the cells by lipofection. The cells were cultured for 4 days in a $CO_2$ incubator (37° C., 8% $CO_2$, 90 rpm). Antibodies were purified from the obtained culture supernatant by a method generally known to those skilled in the art using rProtein A Sepharose™ Fast Flow (Amersham Biosciences, Inc.). The absorbance of the purified antibody solution was measured at 280 nm using a spectrophotometer. The antibody concentration was calculated from the obtained measurement value by use of an extinction coefficient calculated by PACE (Protein Science (1995) 4, 2411-2423).

[Example 20] Evaluation of 6KC4-1 #85 Antibody for its Calcium Ion Binding

The calcium-dependent antigen-binding antibody 6KC4-1 #85 obtained from the human antibody library was evaluated for its calcium binding. Whether or not a measured Tm value varied under different ionized calcium concentrations was evaluated by the method described in Example 6.

Table 25 shows the Tm value of the Fab domain of the 6KC4-1 #85 antibody. As shown in Table 25, the Tm value of the Fab domain of the 6KC4-1 #85 antibody varied depending on calcium ion concentration, demonstrating that the 6KC4-1 #85 antibody binds to calcium.

TABLE 25

| Antibody | Calcium ion concentration | | ΔTm (° C.) |
| --- | --- | --- | --- |
| | 3 μM | 2 mM | 2 mM-3 μM |
| 6KC4-1#85 | 71.49 | 75.39 | 3.9 |

[Example 21] Identification of Calcium Ion-Binding Site in 6KC4-1 #85 Antibody

As shown in Example 20, the 6KC4-1 #85 antibody was shown to bind to calcium ions, but did not have the calcium-binding motifs revealed by the study on the hVk5-2 sequence. Thus, in order to confirm that calcium ions bound to the heavy or light chain of the 6KC4-1 #85 antibody, or both, engineered antibodies comprising either heavy or light chain replaced with the corresponding chain of an anti-glypican 3 antibody (heavy chain sequence GC_H (SEQ ID NO: 48) and light chain sequence GC_L (SEQ ID NO: 86)) unable to bind to calcium ions were evaluated for their calcium ion binding. Table 26 shows the Tm values of the engineered antibodies measured according to the method shown in Example 6. As a result, the Tm value of the engineered antibody having the heavy chain of the 6KC4-1 #85 antibody was changed depending on calcium ion concentration, suggesting that the 6KC4-1 #85 antibody binds to calcium via its heavy chain.

TABLE 26

| Heavy chain | Light chain | Calcium concentration | | ΔTm (° C.) |
|---|---|---|---|---|
| | | 3 μM | 2 mM | 2 mM-3 μM |
| 6KC4-1#85 | 6KC4-1#85 | 71.46 | 75.18 | 3.72 |
| 6KC4-1#85 | GC_L | 78.87 | 80.01 | 1.14 |
| GC_H | 6KC4-1#85 | 75.69 | 75.94 | 0.25 |
| GC_H | GC_L | 79.94 | 80.01 | 0.07 |

In order to further identify the residue via which the heavy chain of the 6KC4-1 #85 antibody bound to calcium ions, modified heavy chains (6_H1-11 (SEQ ID NO: 87), 6_H1-12 (SEQ ID NO: 88), 6_H1-13 (SEQ ID NO: 89), 6_H1-14 (SEQ ID NO: 90), and 6_H1-15 (SEQ ID NO: 91)) or modified light chains (6 L1-5 (SEQ ID NO: 92) and 6_L1-6 (SEQ ID NO: 93)) were prepared by the substitution of Asp (D) residues present in CDRs of the 6KC4-1 #85 antibody by Ala (A) residues, which were unable to participate in the binding or chelating of calcium ions. The engineered antibodies were purified according to the method described in Example 19 from cultures of animal cells transfected with expression vectors comprising the engineered antibody genes. The calcium binding of the purified engineered antibodies was assayed according to the method described in Example 6. The assay results are shown in Table 27. As shown in Table 27, the 6KC4-1 #85 antibody lost its calcium-binding ability by the substitution of residue 95 or 101 (defined by the Kabat numbering) in its heavy chain CDR3 by the Ala residue, suggesting that these residues are important for calcium binding. The calcium-binding motifs present near the base of the loop of heavy chain CDR3 in the 6KC4-1 #85 antibody, which were revealed from the calcium binding property of the engineered antibody of the 6KC4-1 #85 antibody, may also serve as new factors for the design of the Ca library as described in Example 11. Although the calcium-binding motifs were introduced to the light chain variable region in Example 11, another possible library comprises, for example, the heavy chain CDR3 of the 6KC4-1 #85 antibody and comprises flexible residues in the other CDRs including light chain CDRs.

TABLE 27

| Heavy chain | Light chain | Modified residue | Calcium ion concentration | | ΔTm (° C.) |
|---|---|---|---|---|---|
| | | | 3 μM | 2 mM | 2 mM-3 μM |
| 6KC4-1#85 | 6KC4-1#85 | Wild-type | 71.49 | 75.39 | 3.9 |
| 6H1-11 | 6KC4-1#85 | H chain position 61 (Kabat numbering) | 71.73 | 75.56 | 3.83 |
| 6H1-12 | 6KC4-1#85 | H chain position 95 (Kabat numbering) | 72.9 | 73.43 | 0.53 |
| 6H1-13 | 6KC4-1#85 | H chain position 100a (Kabat numbering) | 70.94 | 76.25 | 5.31 |
| 6H1-14 | 6KC4-1#85 | H chain position 100g (Kabat numbering) | 73.95 | 75.14 | 1.19 |
| 6H1-15 | 6KC4-1#85 | H chain position 101 (Kabat numbering) | 65.37 | 66.25 | 0.87 |
| 6KC4-1#85 | 6L1-5 | L chain position 50 (Kabat numbering) | 71.92 | 76.08 | 4.16 |
| 6KC4-1#85 | 6L1-6 | L chain position 92 (Kabat numbering) | 72.13 | 78.74 | 6.61 |

[Example 22] Obtainment of Antibody Binding to Human IgA in Ca-Dependent Manner (22-1) Preparation of MRA-hIgA, GC-hIgA, and Biotinylated Human IgA-Fc MRA-hIgA (heavy chain: SEQ ID NO: 97 and light chain: SEQ ID NO: 25), GC-hIgA (heavy chain: SEQ ID NO: 98 and light chain: SEQ ID NO: 99), and biotinylated human IgA-Fc (also referred to as biotin-labeled hIgA-Fc; hIgA_CH2-CH3-Avitag: SEQ ID NO: 100) were prepared as human IgA as follows:

(22-1-1) Preparation of MRA-hIgA

Recombinant human IgA MRA-hIgA (hereinafter, referred to as MRA-hIgA) was prepared as follows: expressed hIgA comprising H(WT)-IgA1 (SEQ ID NO: 97) and L(WT) (SEQ ID NO: 25) was purified by a method generally known to those skilled in the art using ion-exchange chromatography and gel filtration chromatography.

(22-1-2) Preparation of GC-hIgA

Recombinant human IgA GC-hIgA was prepared as follows: a gene fragment encoding GC-hIgA (heavy chain: SEQ ID NO: 98 and light chain: SEQ ID NO: 99) was incorporated into a vector for expression in animal cells. FreeStyle 293 (Invitrogen Corp.) was cotransfected with the constructed plasmid vector and a gene encoding EBNA1 to be expressed using 293Fectin (Invitrogen Corp.). Then, the cells transfected with these genes were cultured at 37° C. for 6 days in an 8% $CO_2$ atmosphere to secrete GC-hIgA proteins into the culture supernatant.

The GC-hIgA-containing cell cultures were filtered through a 0.22-μm bottle-top filter to obtain a culture supernatant. The culture supernatant was diluted with 20 mM Tris-HCl (pH 8.0) and loaded onto HiTrap Q HP (GE Healthcare Bio-Sciences Corp.) equilibrated with this solution, followed by elution of GC-hIgA on a NaCl concentration gradient. Then, the removal of associates by gel filtration chromatography using Superdex 200 and the replacement of the buffer with 20 mM His-HCl and 150 mM NaCl (pH 6.0) were performed to obtain purified GC-hIgA.

(22-1-3) Preparation of Biotin-Labeled hIgA-Fc

In order to add biotin to the C terminus of the protein of interest (human IgA-Fc), a gene fragment encoding a specific sequence (Avitag sequence) for biotin ligase-mediated biotinylation was linked downstream of a gene fragment encoding the human IgA-Fc region. The gene fragment encoding a protein of the human IgA linked to the Avitag sequence (hIgA_CH2-CH3-Avitag (SEQ ID NO: 100)) was incorporated into vectors for expression in animal cells. FreeStyle 293 (Invitrogen Corp.) was transfected with the constructed plasmid vectors using 293Fectin (Invitrogen Corp.). This transfection was performed simultaneously with a gene encoding EBNA1 to be expressed and a gene encoding biotin ligase (BirA) to be expressed for biotinylation to biotin-label the protein. The cells transfected with these genes according to the above procedures were cultured at 37° C. for 6 days in an 8% $CO_2$ atmosphere to secrete the protein of interest into the culture supernatant.

The cell cultures containing the human IgA-Fc of interest were filtered through a 0.22-μm bottle-top filter to obtain a culture supernatant. The culture supernatant was diluted with 20 mM Tris-HCl (pH 7.4) and loaded onto HiTrap Q HP (GE Healthcare Bio-Sciences Corp.) equilibrated with this solution, followed by elution of the human IgA-Fc of interest on a NaCl concentration gradient. The HiTrap Q HP eluate was diluted with 50 mM Tris-HCl (pH 8.0) and loaded onto SoftLink Avidin column equilibrated with this solution, followed by elution with 5 mM biotin, 150 mM NaCl, and 50 mM Tris-HCl (pH 8.0). Then, the removal of associates by gel filtration chromatography using Superdex 200 and the replacement of the buffer with 20 mM His-HCl and 150 mM NaCl (pH 6.0) were performed to obtain purified human IgA-Fc.

(22-2) Obtainment of Antibody Fragment Binding to Antigen in Ca-Dependent Manner from Ca Library by Bead Panning The first round of screening of the constructed Ca-dependent antigen-binding antibody library (Ca library) was carried out with antigen (human IgA-Fc)-binding ability as an index.

Phages were produced from *E. coli* carrying the constructed phagemid for phage display. 2.5 M NaCl/10% PEG was added to cultures of *E. coli* that had produced phages, and a pool of the phages thus precipitated was diluted with TBS to obtain a phage library solution. Next, BSA or skim milk and $CaCl_2$ (final concentration: 4% BSA and 1.2 mM calcium ion; or 3% skim milk and 1.2 mM calcium ion) were added to the phage library solution to prepare a blocked phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of biotin-labeled antigens (biotin-labeled IgA-Fc) was added to the prepared phage library solution and thereby contacted with the phage library solution at room temperature for 60 minutes. After addition of BSA- or skim milk-blocked magnetic beads, the antigen-phage complexes were attached to the magnetic beads at room temperature for 15 minutes. The beads were washed with 1 mL of 1.2 mM $CaCl_2$/TBST (TBS containing 1.2 mM $CaCl_2$ and 0.1% Tween 20) and 1 mL of 1.2 mM $CaCl_2$/TBS (TBS containing 1.2 mM $CaCl_2$)). After addition of 0.5 mL of 1 mg/mL trypsin, the beads were suspended at room temperature for 15 minutes, immediately after which the beads were separated using a magnetic stand to collect a phage solution. The collected phage solution was added to 10 mL of an *E. coli* strain ER2738 in a logarithmic growth phase (OD600: 0.4-0.7). The *E. coli* strain was infected by the phages through the gentle spinner culture of the strain at 37° C. for 1 hour. The infected *E. coli* was inoculated to a plate of 225 mm×225 mm. Next, phages were collected from cultures of the inoculated *E. coli* to prepare a phage library solution.

In the second and third rounds of panning, the phages were enriched with Ca ion concentration-dependent antigen-binding ability as an index. Specifically, 40 pmol of biotin-labeled antigens was added to the phage library solution prepared by blocking in the same way as in the first round of panning, and thereby contacted with the phage library solution at room temperature for 60 minutes. After addition of BSA-blocked magnetic beads, the antigen-phage complexes were attached to the magnetic beads at room temperature for 15 minutes. The beads were washed with 1 mL of 1.2 mM $CaCl_2$/TBST and 1.2 mM $CaCl_2$/TBS. Then, the beads supplemented with 0.1 mL of 2 mM EDTA/TBS (TBS containing 2 mM EDTA) were suspended at room temperature. Immediately thereafter, the beads were separated using a magnetic stand to collect a phage solution. The addition of 5 µL of 100 mg/mL trypsin to the collected phage solution cleaved the pIII proteins (helper phage-derived pIII proteins) of non-Fab-displaying phages to cancel the ability of the non-Fab-displaying phages to infect *E. coli*. The collected phage solution was added to 10 mL of an *E. coli* strain ER2738 in a logarithmic growth phase (OD600: 0.4-0.7). The *E. coli* strain was infected by the phages through the gentle spinner culture of the strain at 37° C. for 1 hour. The infected *E. coli* was inoculated to a plate of 225 mm×225 mm. Next, phages were collected from cultures of the inoculated *E. coli* to collect a phage library solution.

(22-3) Screening of Human IgA-Binding Antibody by Using Biacore

Antibody fragment genes extracted from phagemids obtained from the *E. coli* obtained after the completion of the second round of panning were inserted to vectors for expression in animal cells. Antibody expression was performed by the following method: a human embryonic kidney cell-derived FreeStyle 293-F line (Invitrogen Corp.) was suspended in FreeStyle 293 Expression Medium (Invitrogen Corp.). The suspension having a cell density of $2.63 \times 10^5$ cells/mL was inoculated at a concentration of 190 µL/well to a 96-well plate. The prepared plasmids were transferred to the cells by lipofection. The cells were cultured for 4 days in a $CO_2$ incubator (37° C., 8% $CO_2$).

The culture supernatant obtained by the above method was used to analyze GC-hIgA-binding ability using Biacore A100. Antibodies in the culture supernatant were immobilized onto Sensor chip CM5 (GE Healthcare Bio-Sciences Corp.) with protein A (Invitrogen Corp.) immobilized thereon in an appropriate amount by the amine coupling method. A buffer solution containing 20 mM ACES, 150 mM NaCl, 0.05% (w/v) Tween 20, and 1.2 mM $CaCl_2$) (pH 7.4) were used as a running buffer. GC-hIgA was also diluted with this buffer. Assay was all carried out at 25° C.

Genes of antibodies judged as having GC-hIgA-binding ability as a result of the IgG Biacore binding ability analysis were amplified using specific primers from the vectors for expression in animal cells used in the expression thereof, and then analyzed for their nucleotide sequences.

(22-4) Screening of hIgA-Binding Antibody by Phage ELISA

A phage-containing culture supernatant was collected by phage culture according to a conventional method (Methods Mol. Biol. (2002) 178, 133-145) from each single colony of the *E. coli* obtained after the third round of panning carried out in the step (22-2). After addition of BSA and $CaCl_2$) (final concentration: 4% BSA and 1.2 mM calcium ion), the phage-containing culture supernatant was subjected to ELISA by the following procedures: StreptaWell 96 microtiter plate (F. Hoffmann-La Roche Ltd.) was coated overnight with 100 µL of PBS containing biotin-labeled IgA-Fc. Each well of the plate was washed with PBST to remove unbound antigens. Then, the well was blocked with 250 µL of 4% BSA-TBS for 1 hour or longer. After removal of 4% BSA-TBS, the prepared culture supernatant was added to each well, and the plate was left standing at 37° C. for 1 hour to associate phage-displayed antibodies with IgA-Fc contained in each well. Each well was washed with 1.2 mM $CaCl_2$/TBST, and 1.2 mM $CaCl_2$/TBS or 1 mM EDTA/TBS was added thereto. The plate was left standing at 37° C. for 30 minutes for incubation. After washing with 1.2 mM $CaCl_2$/TBST, HRP-conjugated anti-M13 antibodies (Amersham Pharmacia Biotech Inc.) diluted with TBS having 4% BSA and an ionized calcium concentration of 1.2 mM (all were indicated by final concentrations) were added to each well. The plate was incubated for 1 hour. After washing with 1.2 mM $CaCl_2$/TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm.

Clones judged as having IgA-Fc-binding ability changed depending on Ca ion concentration as a result of the phage ELISA were analyzed for the nucleotide sequences of their antibody fragment genes.

(22-5) Obtainment of Antibody Fragment Binding to Antigen in Ca-Dependent Manner from Ca Library by Solid-Phase Panning The first round of screening of the constructed Ca-dependent antigen-binding antibody library (Ca library) was carried out with antigen (human IgA-Fc)-binding ability as an index.

Phages were produced from $E.$ $coli$ carrying the constructed phagemid for phage display. 2.5 M NaCl/10% PEG was added to cultures of $E.$ $coli$ that had produced phages, and a pool of the phages thus precipitated was diluted with TBS to obtain a phage library solution. Next, BSA or skim milk and $CaCl_2$ (final concentration: 4% BSA and 1.2 mM calcium ion; or 3% skim milk and 1.2 mM calcium ion) were added to the phage library solution to prepare a blocked phage library solution. In the first round of panning, the panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of biotin-labeled antigens (biotin-labeled IgA-Fc) was added to the prepared phage library solution and thereby contacted with the phage library solution at room temperature for 60 minutes. After addition of skim milk-blocked magnetic beads, the antigen-phage complexes were attached to the magnetic beads at room temperature for 15 minutes. The beads were washed with 1 mL of 1.2 mM $CaCl_2$/TBST (TBS containing 1.2 mM $CaCl_2$ and 0.1% Tween 20) and 1 mL of 1.2 mM $CaCl_2$/TBS (TBS containing 1.2 mM $CaCl_2$)). After addition of 0.5 mL of 1 mg/mL trypsin, the beads were suspended at room temperature for 15 minutes, immediately after which the beads were separated using a magnetic stand to collect a phage solution. The collected phage solution was added to 10 mL of an $E.$ $coli$ strain ER2738 in a logarithmic growth phase (OD600: 0.4-0.7). The $E.$ $coli$ strain was infected by the phages through the gentle spinner culture of the strain at 37° C. for 1 hour. The infected $E.$ $coli$ was inoculated to a plate of 225 mm×225 mm. Next, phages were collected from cultures of the inoculated $E.$ $coli$ to prepare a phage library solution.

The second round of panning was performed using antigens immobilized on a plate. Specifically, biotin-labeled antigens were added at a concentration of 5 pmol/well to a streptavidin-coated 10-well plate (StreptaWell, F. Hoffmann-La Roche Ltd.) and contacted therewith at room temperature for 60 minutes. Then, the plate was washed three times with TBST (TBS containing 0.1% Tween 20) to prepare an antigen-immobilized plate. The phage library blocked with skim milk containing 1.2 mM Ca was added thereto and thereby contacted with the antigens at room temperature for 60 minutes. The plate was washed three times with 1.2 mM $CaCl_2$/TBST using a plate washer (Skan WASHER, SKARON). Then, the plate was further dipped in 2 L of 1.2 mM $CaCl_2$/TBST and gently shaken for 60 minutes. The phages in each well supplemented with 0.1 mL of 2 mM EDTA/TBS (TBS containing 2 mM EDTA) were suspended at room temperature, followed by collection of a phage solution. The addition of 5 nt of 100 mg/mL trypsin to the collected phage solution cleaved the pIII proteins (helper phage-derived pIII proteins) of non-Fab-displaying phages to cancel the ability of the non-Fab-displaying phages to infect $E.$ $coli$. The collected phage solution was added to 10 mL of an $E.$ $coli$ strain ER2738 in a logarithmic growth phase (OD600: 0.4-0.7). The $E.$ $coli$ strain was infected by the phages through the gentle spinner culture of the strain at 37° C. for 1 hour. The infected $E.$ $coli$ was inoculated to a plate of 225 mm×225 mm.

(22-6) Screening for hIgA-Binding Antibody by Phage ELISA

A phage-containing culture supernatant was collected by phage culture according to a conventional method (Methods Mol. Biol. (2002) 178, 133-145) from each single colony of the $E.$ $coli$ obtained after the panning. Phage ELISA was carried out by the method described in the step (22-4). Genes of clones judged as having Ca-dependent antigen-binding ability were analyzed for their nucleotide sequences, then inserted to vectors for expression in animal cells, and expressed as antibodies, which were then purified.

[Example 23] Evaluation of Obtained Antibody for its Ca-Dependent Binding Ability Against Human IgA (23-1) Expression and Purification of Obtained Anti-Human IgA Antibody Of the obtained antibodies judged as having human IgA-binding ability in Example 22, antibodies GA1-IgG1 (obtained in the step (22-3); heavy chain: SEQ ID NO: 101 and light chain: SEQ ID NO: 102), GA2-IgG1 (obtained in the step (22-4); heavy chain: SEQ ID NO: 103 and light chain: SEQ ID NO: 104), GA3-IgG1 (obtained in the step (22-6); heavy chain: SEQ ID NO: 105 and light chain: SEQ ID NO: 106), and GA4-IgG1 (obtained in the step (22-3); heavy chain: SEQ ID NO: 107 and light chain: SEQ ID NO: 108) were expressed using the following method and then purified: a human embryonic kidney cell-derived FreeStyle 293-F line (Invitrogen Corp.) was suspended in FreeStyle 293 Expression Medium (Invitrogen Corp.). The suspension having a cell density of $1.33 \times 10^6$ cells/mL was inoculated at a concentration of 3 mL/well to a 6-well plate. The prepared plasmids were transfected to the cells by lipofection. The cells were cultured for 4 days in a $CO_2$ incubator (37° C., 8% $CO_2$, 90 rpm). Antibodies were purified from the obtained culture supernatant by a method generally known to those skilled in the art using rProtein A Sepharose™ Fast Flow (Amersham Biosciences, Inc.). The absorbance of the purified antibody solution was measured at 280 nm using a spectrophotometer. The antibody concentration was calculated from the obtained measurement value by use of an extinction coefficient calculated by PACE (Protein Science (1995) 4, 2411-2423).

(23-2) Evaluation of Obtained Antibody for its Ca-Dependent Binding Ability Against Human IgA The antibodies (GA1-IgG1, GA2-IgG1, GA3-IgG1, and GA4-IgG1) obtained in the step (23-1) were evaluated for their human IgA-binding activity (dissociation constant KD (M)) using Biacore T200 (GE Healthcare Bio-Sciences Corp.). The binding activity was assayed using 0.05% Tween 20, 20 mmol/l ACES, and 150 mmol/l NaCl containing 3 μM or 1.2 mM $CaCl_2$) (pH 7.4 and pH 5.8) or 0.05% Tween 20, 20 mmol/l ACES, and 150 mmol/l NaCl (pH 8.0) containing 0.1 µM or 10 mM $CaCl_2$) as a running buffer.

Figure 12:
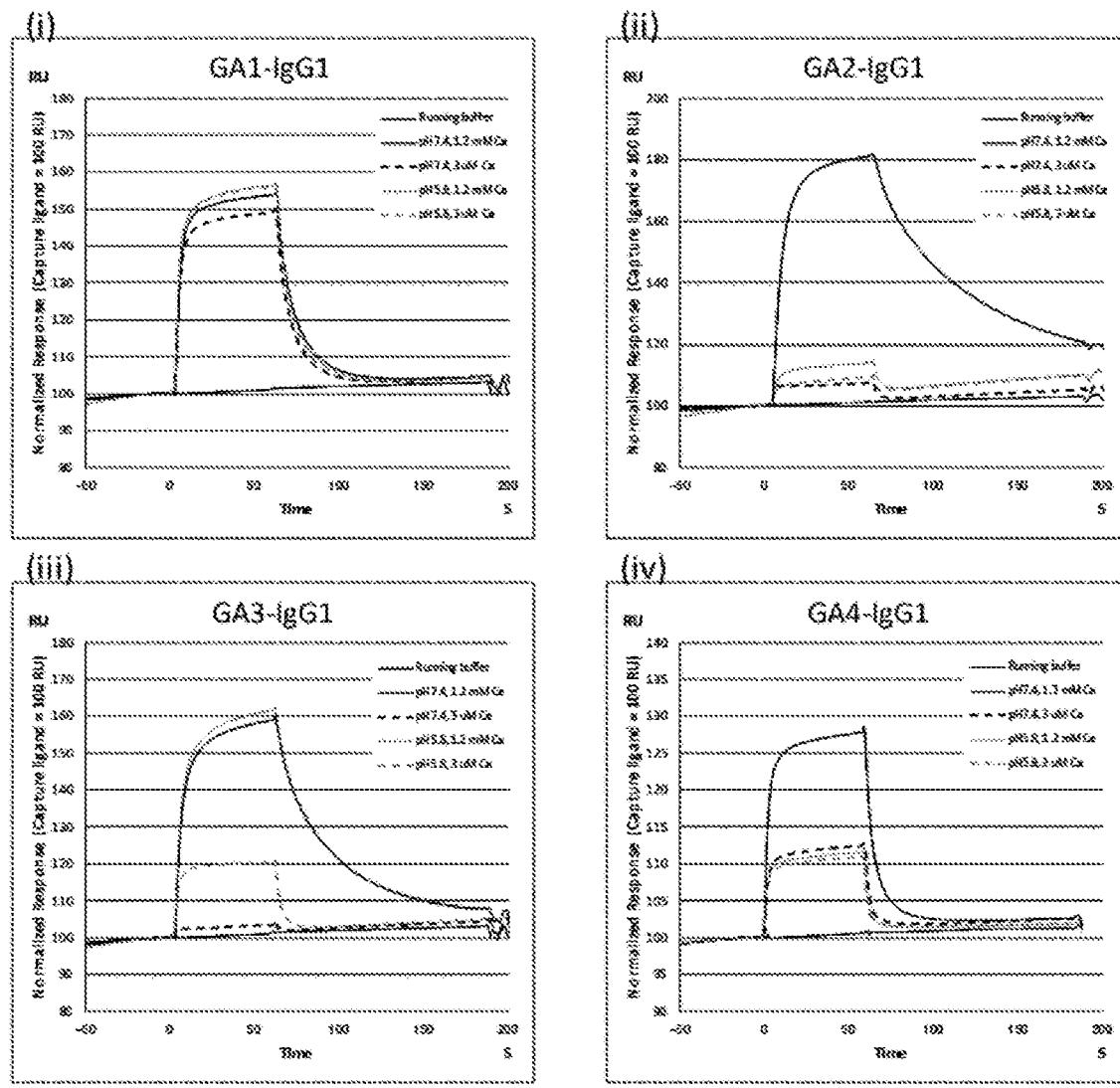
FIG. 12 shows a sensorgram depicting the interaction between an anti-human IgA antibody and human IgA at 1.2 mM $Ca^{2+}$ and at 3 µM $Ca^{2+}$ using Biacore.

Each antibody was associated with recombinant protein A/G (Thermo Fisher Scientific K.K.) immobilized in an appropriate amount onto Sensor chip CM5 (GE Healthcare Bio-Sciences Corp.) by the amine coupling method. An appropriate concentration of MRA-hIgA (described in the step (22-1)) was injected thereto as an analyte and interacted with the antibody on the sensor chip. Then, 10 mmol/L glycine-HCl (pH 1.5) was injected thereto to regenerate the sensor chip. The assay was performed at 37° C. The dissociation constant KD (M) was calculated by the curve fitting analysis and equilibrium value analysis of the assay results using Biacore T200 Evaluation Software (GE Healthcare Bio-Sciences Corp.). The results are shown in Table 28. Also, the obtained sensorgrams are shown in FIG. 12. As is evidently shown, GA2-IgG1, GA3-IgG1, and GA4-IgG1 strongly bind to human IgA at the $Ca^{2+}$ concentration of 1.2 mM, but weakly bind to human IgA at the Ca ion concentration of 3 µM.

TABLE 28

| Antibody name | Conditions | Fit | ka | kd | KD [M] |
|---|---|---|---|---|---|
| GA1-IgG1 | pH 8.0, 10 mM Ca | 1:1 binding model | 1.2E+06 | 1.2E−01 | 1.0E−07 |
| | pH 8.0, 0.1 µM Ca | 1:1 binding model | 1.1E+06 | 2.4E−01 | 2.2E−07 |
| | pH 7.4, 1.2 mM Ca | 1:1 binding model | 5.7E+05 | 8.4E−02 | 1.5E−07 |
| | pH 7.4, 3 µM Ca | 1:1 binding model | 6.4E+05 | 1.2E−01 | 1.9E−07 |
| | pH 5.8, 1.2 mM Ca | 1:1 binding model | 6.8E+05 | 9.9E−02 | 1.4E−07 |
| | pH 5.8, 3 µM Ca | 1:1 binding model | 7.1E+05 | 1.1E−01 | 1.5E−07 |
| GA2-IgG1 | pH 7.4, 1.2 mM Ca | 1:1 binding model | 4.0E+05 | 1.6E−02 | 3.9E−08 |
| | pH 7.4, 3 µM Ca | Steady State Affinity | — | — | 6.7E−06 |
| | pH 5.8, 1.2 mM Ca | Steady State Affinity | — | — | 4.0E−06 |
| | pH 5.8, 3 µM Ca | Steady State Affinity | — | — | 5.0E−06 |
| GA3-IgG1 | pH 7.4, 1.2 mM Ca | 1:1 binding model | 4.3E+05 | 3.3E−02 | 7.9E−08 |
| | pH 7.4, 3 µM Ca | Steady State Affinity | — | — | — |
| | pH 5.8, 1.2 mM Ca | 1:1 binding model | 4.4E+05 | 3.5E−02 | 8.1E−08 |
| | pH 5.8, 3 µM Ca | Steady State Affinity | — | — | 1.1E−06 |
| GA4-IgG1 | pH 7.4, 1.2 mM Ca | Steady State Affinity | — | — | 4.2E−07 |
| | pH 7.4, 3 µM Ca | Steady State Affinity | — | — | 8.9E−07 |
| | pH 5.8, 1.2 mM Ca | Steady State Affinity | — | — | 1.1E−06 |
| | pH 5.8, 3 µM Ca | Steady State Affinity | — | — | 1.5E−06 |

Although antibodies whose interaction with antigens (IL6 receptors) was changed depending on Ca ion concentration were obtained from the Ca library in Example 14, it was revealed that the antibodies binding to antigens in a Ca ion concentration-dependent manner can be obtained not only using the IL6 receptors but using human IgA.

[Example 24] Obtainment of Antibody Binding to Human Glypican 3 (GPC3) in Ca-Dependent Manner (24-1) Preparation of Human Glypican 3

Recombinant human glypican 3 (hereinafter, referred to as GPC3) for use as an antigen was prepared as follows: a culture supernatant was collected from CHO cells stably transfected with plasmids for expression of a transmembrane region-free amino acid sequence of human glypican 3 linked to 6 histidine residues (SEQ ID NO: 109). The obtained culture supernatant was purified by ion-exchange chromatography, then affinity-purified on the basis of the His tag, and purified by gel filtration chromatography to obtain GPC3. The GPC3 was biotin-labeled using EZ-Link NHS-PEG4-Biotin (Thermo Fisher Scientific K.K.) to prepare biotin-labeled GPC3.

(24-2) Obtainment of Antibody Fragment Binding to Antigen in Ca-Dependent Manner from Library by Bead Panning The first round of screening of the constructed Ca-dependent GPC3-binding antibody library was carried out with antigen (GPC3)-binding ability as an index.

Phages were produced from E. coli carrying the constructed phagemid for phage display. 2.5 M NaCl/10% PEG was added to cultures of E. coli that had produced phages, and a pool of the phages thus precipitated was diluted with TBS to obtain a phage library solution. Next, BSA or skim milk and $CaCl_2$) (final concentration: 4% BSA and 1.2 mM calcium ion; or 3% skim milk and 1.2 mM calcium ion) were added to the phage library solution to prepare a blocked phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of biotin-labeled antigens (biotin-labeled GPC3) was added to the prepared phage library solution and thereby contacted with the phage library solution at room temperature for 60 minutes. After addition of BSA- or skim milk-blocked magnetic beads, the antigen-phage complexes were attached to the magnetic beads at room temperature for 15 minutes. The beads were washed with 1 mL of 1.2 mM $CaCl_2$/TBST (TBST containing 1.2 mM $CaCl_2$)) and 1 mL of 1.2 mM $CaCl_2$/TBS (TBS containing 1.2 mM $CaCl_2$)). After addition of 0.5 mL of 1 mg/mL trypsin, the beads were suspended at room temperature for 15 minutes, immediately after which the beads were separated using a magnetic stand to collect a phage solution. The collected phage solution was added to 10 mL of an E. coli strain ER2738 in a logarithmic growth phase (OD600: 0.4-0.7). The E. coli strain was infected by the phages through the gentle spinner culture of the strain at 37° C. for 1 hour. The infected E. coli was inoculated to a plate of 225 mm×225 mm. Next, phages were collected from cultures of the inoculated E. coli to prepare a phage library solution.

In the second and subsequent rounds of panning, the phages were enriched with Ca-dependent binding ability as an index. Specifically, 40 pmol of biotin-labeled antigens was added to the phage library solution prepared by blocking in the same way as in the first round of panning, and thereby contacted with the phage library solution at room temperature for 60 minutes. After addition of BSA- or skim milk-blocked magnetic beads, the antigen-phage complexes were attached to the magnetic beads at room temperature for 15 minutes. The beads were washed with 1 mL of 1.2 mM $CaCl_2$)/TBST and 1.2 mM $CaCl_2$)/TBS. Then, the beads supplemented with 0.1 mL of 2 mM EDTA/TBS (TBS containing 2 mM EDTA) were suspended at room temperature. Immediately thereafter, the beads were separated using a magnetic stand to collect a phage solution. The addition of 5 μL of 100 mg/mL trypsin to the collected phage solution cleaved the pIII proteins (helper phage-derived pIII proteins) of non-Fab-displaying phages to cancel the ability of the non-Fab-displaying phages to infect E. coli. The collected phage solution was added to 10 mL of an E. coli strain ER2738 in a logarithmic growth phase (OD600: 0.4-0.7). The E. coli strain was infected by the phages through the gentle spinner culture of the strain at 37° C. for 1 hour. The infected E. coli was inoculated to a plate of 225 mm×225 mm. Next, phages were collected from cultures of the inoculated E. coli to collect a phage library solution.

(24-3) Screening for GPC3-Binding Antibody by Phage ELISA

A phage-containing culture supernatant was collected by phage culture according to a conventional method (Methods Mol. Biol. (2002) 178, 133-145) from each single colony of the E. coli obtained after the second and third rounds of panning carried out by the above method.

After addition of BSA and $CaCl_2$) (final concentration: 4% BSA and 1.2 mM calcium ion), the phage-containing culture supernatant was subjected to ELISA by the following procedures: StreptaWell 96 microtiter plate (F. Hoffmann-La Roche Ltd.) was coated overnight with 100 μL of PBS containing biotin-labeled antigens. Each well of the plate was washed with PBST (PBS containing 0.1% Tween 20) to remove unbound antigens. Then, the well was blocked with 250 μL of 4% BSA-TBS for 1 hour or longer. After removal of 4% BSA-TBS, the prepared culture supernatant was added to each well, and the plate was left standing at 37° C. for 1 hour to associate phage-displayed antibodies with the antigens contained in each well. Each well was washed with 1.2 mM $CaCl_2$)/TBST, and 1.2 mM $CaCl_2$)/TBS or 1 mM EDTA/TBS was added thereto. The plate was left standing at 37° C. for 30 minutes for incubation. After washing with 1.2 mM $CaCl_2$)/TBST, HRP-conjugated anti-M13 antibodies (Amersham Pharmacia Biotech Inc.) diluted with TBS having 4% BSA and an ionized calcium concentration of 1.2 mM (all were indicated by final concentrations) were added to each well. The plate was incubated for 1 hour. After washing with 1.2 mM $CaCl_2$)/TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm.

Genes of antibody fragments judged as having Ca-dependent antigen-binding ability as a result of the phage ELISA were amplified as a template using specific primers and then analyzed for their nucleotide sequences.

(24-4) Expression and Purification of Antibody Binding to Human GPC3

The genes of four antibodies judged as having Ca-dependent antigen-binding ability as a result of the phage ELISA, i.e., CSCM-01_005 (heavy chain sequence: 110 and light chain sequence: 111), CSCM-01_009 (heavy chain sequence: 112 and light chain sequence: 113), CSCM-01_015 (heavy chain sequence: 114 and light chain sequence: 115), and CSCM-01_023 (heavy chain sequence: 116 and light chain sequence: 117), and anti-human GPC3 antibody GC-IgG1 (heavy chain sequence: 118 and light chain sequence: 119) as a control were separately inserted to plasmids for expression in animal cells. These antibodies were expressed using the following method: a human embryonic kidney cell-derived FreeStyle 293-F line (Invitrogen Corp.) was suspended in FreeStyle 293 Expression Medium (Invitrogen Corp.). The suspension having a cell density of $1.33 \times 10^6$ cells/mL was inoculated at a concentration of 3 mL/well to a 6-well plate. The prepared plasmids were transferred to the cells by lipofection. The cells were cultured for 4 days in a $CO_2$ incubator (37° C., 8% $CO_2$, 90 rpm). Antibodies were purified from the obtained culture supernatant by a method generally known to those skilled in the art using rProtein A Sepharose™ Fast Flow (Amersham Biosciences, Inc.). The absorbance of the purified antibody solution was measured at 280 nm using a spectrophotometer. The antibody concentration was calculated from the obtained measurement value by use of an extinction coefficient calculated by PACE (Protein Science (1995) 4, 2411-2423). The GC-IgG1 antibody was purified in the same way as above from a culture supernatant of CHO cells steadily expressing the GC-IgG1 antibody, and its concentration was calculated.

(24-5) Evaluation of Obtained Antibody for its Ca-Dependent Binding Ability Against Human GPC3

The obtained antibodies were subjected to ELISA by the following procedures: StreptaWell 96 microtiter plate (F. Hoffmann-La Roche Ltd.) was coated overnight with 100 μL of PBS containing biotin-labeled antigens. Each well of the plate was washed with ACES buffer (10 mM ACES, 150 mM NaCl, 100 mM $CaCl_2$), and 0.05% Tween 20 (pH 7.4)) to remove unbound antigens. Then, the well was blocked with 250 μL of ACES buffer containing 2% BSA for 1 hour or longer. After removal of the ACES buffer containing 2% BSA, 100 μL of each of 4-fold serial dilutions of purified IgG diluted in advance from 10 μg/mL was added to each well, and the plate was left standing for 1 hour to associate IgG with the antigens contained in each well. Each well was washed with ACES buffer, and "10 mM ACES, 150 mM NaCl, and 1.2 mM $CaCl_2$) (pH 7.4)", "10 mM ACES, 150 mM NaCl, and 3 μM $CaCl_2$) (pH 7.4)", "10 mM ACES, 150 mM NaCl, and 1.2 mM $CaCl_2$) (pH 5.8)", or "10 mM ACES, 150 mM NaCl, and 3 μM $CaCl_2$) (pH 5.8)" were added thereto. The plate was left standing at 37° C. for 30 minutes for incubation. After washing with ACES buffer, HRP-conjugated anti-human IgG antibodies (BioSource International, Inc.) diluted with ACES buffer containing 2% BSA were added to each well. The plate was incubated for 1 hour. After washing with ACES buffer, TMB single solution (ZYMED Laboratories, Inc.) was added to the well. The chromogenic reaction of the solution in each well was terminated by the addition of sulfuric acid. Then, the developed color was assayed on the basis of absorbance at 450 nm.

The assay results are shown in FIG. 13. The absorbance was constant for GC-IgG1 regardless of calcium ion concentration, whereas the absorbance was significantly lower for CSCM-01_005, CSCM-01_009, CSCM-01_015, and CSCM-01_023 at the calcium ion concentration of 3 μM (low calcium ion concentration) than that at the calcium ion concentration of 1.2 mM (high calcium ion concentration). From these results, CSCM-01_005, CSCM-01_009, CSCM-01_015, and CSCM-01_023 were shown to have the antigen-binding property that was changed depending on calcium ion concentration, demonstrating that the calcium-dependent antibody can also be obtained against human glypican 3.

[Example 25] Obtainment of Antibody Binding to Mouse IgA in pH-Dependent Manner (25-1) Preparation of GC-mIgA and Biotinylated Mouse IgA-Fc GC-mIgA (heavy chain: SEQ ID NO: 120 and light chain: SEQ ID NO: 121) and biotinylated mouse IgA-Fc (also referred to as biotin-labeled mIgA-Fc; mIgA_CH2-CH3-Avitag: SEQ ID NO: 122) were prepared as mouse IgA as follows:

(25-1-1) Preparation of GC-mIgA

Recombinant mouse IgA GC-mIgA was prepared as follows: a gene fragment encoding GC-mIgA (heavy chain: SEQ ID NO: 120 and light chain: SEQ ID NO: 121) was incorporated into a vector for expression in animal cells. FreeStyle 293 (Invitrogen Corp.) was cotransfected with the constructed plasmid vector and a gene encoding EBNA1 to be expressed using 293Fectin (Invitrogen Corp.). Then, the cells transfected with these genes were cultured at 37° C. for 4 days in an 8% $CO_2$ atmosphere to secrete GC-mIgA proteins into the culture supernatant.

The GC-mIgA-containing cell cultures were filtered through a 0.22-µm bottle-top filter to obtain a culture supernatant. The culture supernatant was diluted with 20 mM Tris-HCl (pH 8.0) and loaded onto HiTrap Q HP (GE Healthcare Bio-Sciences Corp.) equilibrated in advance with this solution, followed by elution of GC-mIgA on a NaCl concentration gradient. Then, associates were removed by gel filtration chromatography using Superdex 200, and the resulting GC-mIgA-containing buffer was replaced with 20 mM His-HCl and 150 mM NaCl (pH 6.0) to obtain purified GC-mIgA.

(25-1-2) Preparation of Biotin-Labeled mIgA-Fc

In order to add biotin to the C terminus of the protein of interest (mouse IgA-Fc), a gene fragment encoding a specific sequence (Avitag sequence) for biotin ligase-mediated biotinylation was linked downstream of a gene fragment encoding the mouse IgA-Fc region. The gene fragment encoding a protein of the mouse IgA linked to the Avitag sequence (mIgA_CH2-CH3-Avitag (SEQ ID NO: 122)) was incorporated into vectors for expression in animal cells. FreeStyle 293 (Invitrogen Corp.) was transfected with the constructed plasmid vectors using 293Fectin (Invitrogen Corp.). This transfection was performed simultaneously with a gene encoding EBNA1 to be expressed and a gene encoding biotin ligase (BirA) to be expressed for biotinylation to biotin-label the protein. The cells transfected with these genes according to the above procedures were cultured at 37° C. for 6 days in an 8% $CO_2$ atmosphere to secrete the protein of interest into the culture supernatant.

The cell cultures containing the mouse IgA-Fc of interest were filtered through a 0.22-µm bottle-top filter to obtain a culture supernatant. The culture supernatant was diluted with 20 mM Tris-HCl (pH 7.4) and loaded onto HiTrap Q HP (GE Healthcare Bio-Sciences Corp.) equilibrated in advance with this solution, followed by elution of the mouse IgA-Fc of interest on a NaCl concentration gradient. Next, the HiTrap Q HP eluate was diluted with 50 mM Tris-HCl (pH 8.0) and loaded onto SoftLink Avidin column equilibrated in advance with this solution, followed by elution of the mouse IgA-Fc of interest with 5 mM biotin, 150 mM NaCl, and 50 mM Tris-HCl (pH 8.0). Then, associates were removed by gel filtration chromatography using Superdex 200, and the resulting mouse IgA-Fc-containing buffer was replaced with 20 mM His-HCl and 150 mM NaCl (pH 6.0) to obtain purified mouse IgA-Fc.

(25-2) Obtainment of Antibody Fragment Binding to Antigen in pH-Dependent Manner from his Library by Bead Panning The first round of screening of the constructed pH-dependent antigen-binding antibody library (His library 1) was carried out with antigen (mouse IgA-Fc)-binding ability as an index.

Phages were produced from *E. coli* carrying the constructed phagemid for phage display. 2.5 M NaCl/10% PEG was added to cultures of *E. coli* that had produced phages, and a pool of the phages thus precipitated was diluted with TBS to obtain a phage library solution. Next, skim milk (final concentration: 3% skim milk) was added to the phage library solution to prepare a blocked phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, biotin-labeled antigens (biotin-labeled mIgA-Fc) were added to the prepared phage library solution and thereby contacted with the phage library solution at room temperature for 60 minutes. The biotin-labeled antigens were used in panning in amounts of 250 pmol for the first round, 40 pmol for the second round, and 10 pmol for the third round. After addition of skim milk-blocked magnetic beads, the antigen-phage complexes were attached to the magnetic beads at room temperature for 15 minutes. The beads were washed with 1 mL of 1.2 mM $CaCl_2$/TBST (TBS containing 1.2 mM $CaCl_2$) and 0.1% Tween 20 (pH 7.6)) and 1 mL of 1.2 mM $CaCl_2$/TBS (TBS containing 1.2 mM $CaCl_2$) (pH 7.6)). After addition of 0.5 mL of 1 mg/mL trypsin, the beads were suspended at room temperature for 15 minutes, immediately after which the beads were separated using a magnetic stand to collect a phage solution. The collected phage solution was added to 10 mL of an *E. coli* strain ER2738 in a logarithmic growth phase (OD600: 0.4-0.7). The *E. coli* strain was infected by the phages through the gentle spinner culture of the strain at 37° C. for 1 hour. The infected *E. coli* was inoculated to a plate of 225 mm×225 mm. Next, phages were collected from cultures of the inoculated *E. coli* to prepare a phage library solution. This panning was performed 3 rounds in total.

(25-3) Evaluation of Mouse IgA-Binding Antibody for its Binding Ability Using Biacore Antibody fragment genes extracted from phagemids obtained from the *E. coli* obtained after the completion of the third round of panning were inserted to vectors for expression in animal cells. Antibody expression was performed by the following method: a human embryonic kidney cell-derived FreeStyle 293-F line (Invitrogen Corp.) was suspended in FreeStyle 293 Expression Medium (Invitrogen Corp.). The suspension having a cell density of $2.63 \times 10^5$ cells/mL was inoculated at a concentration of 190 µL/well to a 96-well plate. The prepared plasmids were transferred to the cells by lipofection. The cells were cultured for 4 days in a $CO_2$ incubator (37° C., 8% $CO_2$).

The culture supernatant obtained by the above method was used to analyze GC-mIgA-binding ability using Biacore A100. Antibodies in the culture supernatant were captured onto Sensor chip CM5 (GE Healthcare Bio-Sciences Corp.) with protein A/G (Pierce Biotechnology Inc.) immobilized thereon in an appropriate amount by the amine coupling method. Two types of buffer solutions were used as running buffers: 20 mM ACES, 150 mM NaCl, 0.05% (w/v) Tween 20, and 1.2 mM $CaCl_2$) (pH 7.4); and 20 mM ACES, 150 mM NaCl, 0.05% (w/v) Tween 20, and 1.2 mM $CaCl_2$) (pH 5.8). The interaction of antigen-antibody reaction was analyzed under neutral pH and acidic pH conditions. GC-mIgA was also diluted with each of these buffers and injected at a flow rate of 10 μL/min for 60 seconds to interact the antigen with the antibodies captured on the sensor chip. Then, 10 mM glycine-HCl (pH 1.5) was injected thereto at a flow rate of 30 μL/min for 30 seconds to regenerate the sensor chip. Assay was all carried out at 25° C.

Figure 14:
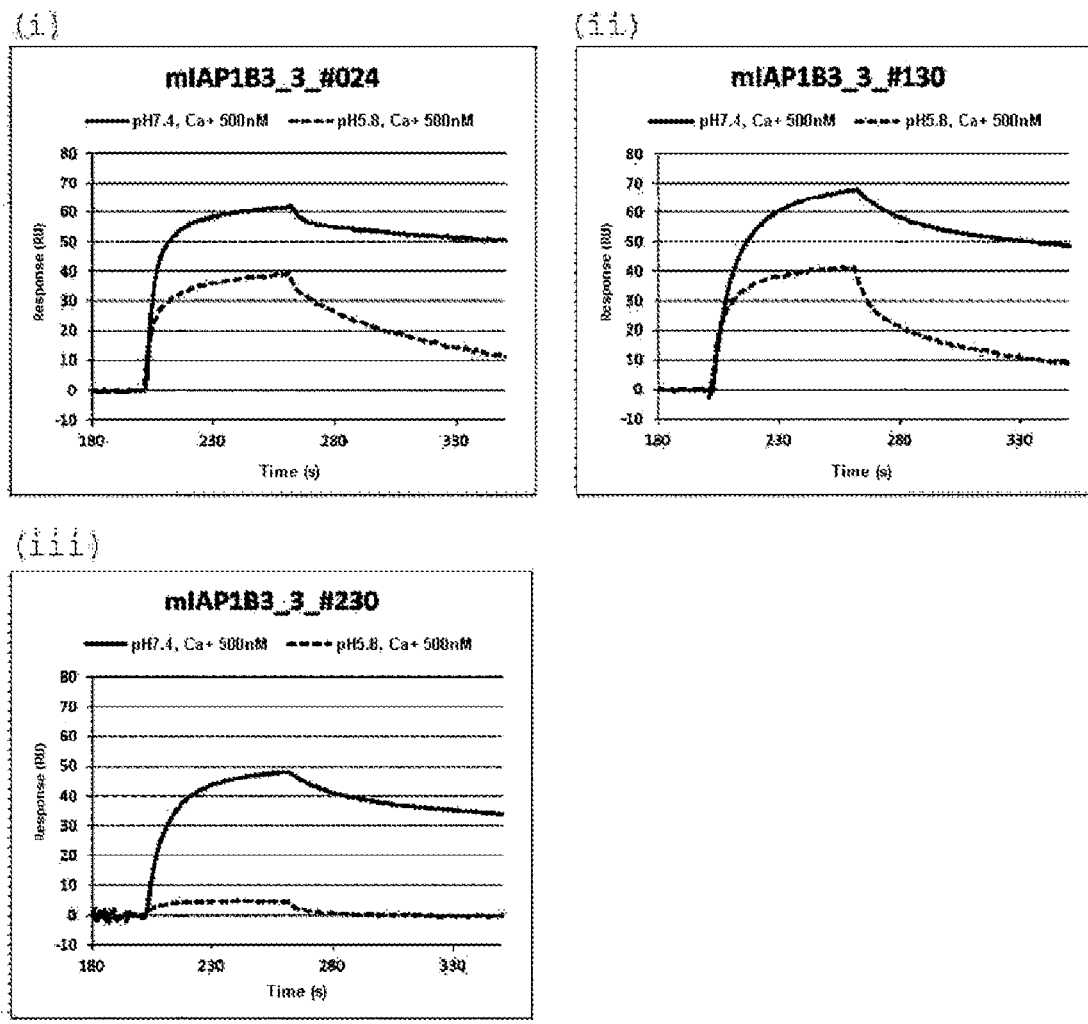
FIG. 14 shows a sensorgram depicting the interaction between an anti-mouse IgA antibody and mouse IgA at pH 7.4 and at pH 5.8 using Biacore. The solid line represents the results about the condition of pH 7.4. The broken line represents the results about the condition of pH 5.8.

As a result of the Biacore binding evaluation, mIAP1B3-3_#024 (heavy chain: SEQ ID NO: 123 and light chain: SEQ ID NO: 124), mIAP1B3-3_#130 (heavy chain: SEQ ID NO: 125 and light chain: SEQ ID NO: 126), and mIAP1B3-3_#230 (heavy chain: SEQ ID NO: 127 and light chain: SEQ ID NO: 128) were obtained as antibodies judged as having pH-dependent binding ability against GC-mIgA. FIG. 14 shows the sensorgrams of these antibodies at pH 7.4 and pH 5.8. The mouse IgA-binding ability of these antibodies was observed to be reduced by the change of the buffer pH from pH 7.4 to pH 5.8.

Genes of these antibodies from the vectors for expression in animal cells used in the expression thereof were analyzed for their nucleotide sequences.

Although antibodies whose interaction with antigens (IL-6R) was changed depending on pH were obtained from the His library 1 in Example 3, it was revealed that the antibodies binding to antigens in a pH-dependent manner can be obtained not only using the IL-6R but using mouse IgA.

[Example 26] Obtainment of Antibody Binding to Human HMGB1 in pH-Dependent Manner (26-1) Preparation of Human HMGB1 and Biotinylated Human HMGB1

Human HMGB1 (SEQ ID NO: 129) and biotinylated human HMGB1-Avi (also referred to as biotin-labeled hHMGB1; hHMGB1-Avitag: SEQ ID NO: 130) were prepared as follows:

(26-1-1) Preparation of Human HMGB1

Recombinant human HMGB1 hHMGB1 was prepared as follows: a gene fragment encoding hHMGB1 (SEQ ID NO: 129) was incorporated into a vector for expression in animal cells. FreeStyle 293 (Invitrogen Corp.) was cotransfected with the constructed plasmid vector and a gene encoding EBNA1 to be expressed using 293Fectin (Invitrogen Corp.). Then, the cells transfected with these genes were cultured at 37° C. in an 8% $CO_2$ atmosphere to secrete hHMGB1 proteins into the culture supernatant. The culture supernatant thus obtained was loaded onto HiTrap SP Sepharose HP (GE Healthcare Bio-Sciences Corp.) equilibrated in advance with PBS, and the column was washed with PBS, followed by elution of proteins adsorbed on the column on a linear concentration gradient of sodium chloride. After equilibration with 20 mM histidine-HCl (pH 5.0), the hHMGB1-containing eluted fraction diluted 3-fold with this buffer solution was loaded onto the column. The column was washed with this buffer solution, followed by elution of proteins adsorbed on the column on a linear concentration gradient of sodium chloride. The hHMGB1-containing fraction was concentrated through an ultrafiltration membrane and then loaded onto Superdex 200 column (GE Healthcare Bio-Sciences Corp.) equilibrated with 300 mM NaCl and 20 mM histidine (pH 6.0). A purified hHMGB1 fraction was obtained by separation using the same buffer solution.

(26-1-2) Preparation of Biotin-Labeled Human HMGB1

In order to add biotin to the C terminus of the protein of interest (human HMGB1), a gene fragment encoding a specific sequence (Avitag sequence) for biotin ligase-mediated biotinylation was linked downstream of a gene fragment encoding the human HMGB1 region. The gene fragment encoding a protein of the human HMGB1 linked to the Avitag sequence (hHMGB1-Avitag (SEQ ID NO: 130)) was incorporated into vectors for expression in animal cells. FreeStyle 293 (Invitrogen Corp.) was transfected with the constructed plasmid vectors using 293Fectin (Invitrogen Corp.). This transfection was performed simultaneously with a gene encoding EBNA1 to be expressed and a gene encoding biotin ligase (BirA) to be expressed for biotinylation to biotin-label the protein. The cells transfected with these genes according to the above procedures were cultured at 37° C. in an 8% $CO_2$ atmosphere to secrete the protein of interest into the culture supernatant.

The culture supernatant thus obtained was loaded onto HiTrap SP Sepharose HP (GE Healthcare Bio-Sciences Corp.) equilibrated in advance with PBS, and the column was washed with PBS, followed by elution of proteins adsorbed on the column on a linear concentration gradient of sodium chloride. The HMGB1-Avi-containing fraction diluted 2-fold with 100 mM Tris-HCl (pH 7.4) was loaded onto SoftLink Soft Release Avidin Resin column (Promega Corp.) equilibrated with TBS. The column was washed with TBS, followed by elution of proteins adsorbed on the column using TBS (pH 8.0) containing 5 mM biotin. The HMGB1-Avi-containing fraction was concentrated through an ultrafiltration membrane and then loaded onto Superdex 200 column (GE Healthcare Bio-Sciences Corp.) equilibrated with 300 mM NaCl and 20 mM histidine (pH 6.0). A purified biotinylated HMGB1-Avi fraction was obtained by separation using the same buffer solution.

(26-2) Obtainment of Antibody Fragment Binding to Antigen in pH-Dependent Manner from his Library by Bead Panning The first round of screening of the constructed pH-dependent antigen-binding antibody library (His library 1) was carried out with antigen (human HMGB1)-binding ability as an index.

Phages were produced from E. coli carrying the constructed phagemid for phage display. 2.5 M NaCl/10% PEG was added to cultures of E. coli that had produced phages, and a pool of the phages thus precipitated was diluted with TBS to obtain a phage library solution. Next, BSA, and $CaCl_2$) (final concentration: 4% BSA and 1.2 mM calcium ion) were added to the phage library solution to prepare a blocked phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of biotin-labeled antigens (biotin-labeled hHMGB1) was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed with 1 mL of 1.2 mM $CaCl_2$/TBST (50 mM Tris, 300 mM NaCl, 1.2 mM $CaCl_2$, and 0.1% Tween 20 (pH 7.6)) and 1 mL of 1.2 mM CaCl$_2$)/TBS (50 mM Tris, 300 mM NaCl, and 1.2 mM CaCl$_2$) (pH 7.6)). After addition of 0.5 mL of 1 mg/mL trypsin, the beads were suspended at room temperature for 15 minutes, immediately after which the beads were separated using a magnetic stand to collect a phage solution. The collected phage solution was added to 10 mL of an *E. coli* strain ER2738 in a logarithmic growth phase (OD600: 0.4-0.7). The *E. coli* strain was infected by the phages through the gentle spinner culture of the strain at 37° C. for 1 hour. The infected *E. coli* was inoculated to a plate of 225 mm×225 mm. Next, phages were collected from cultures of the inoculated *E. coli* to prepare a phage library solution.

In the second and subsequent rounds of panning, the phages were enriched with antigen-binding ability or pH-dependent binding ability as an index. Specifically, 40 pmol of biotin-labeled antigens was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed several times with 1 mL of 1.2 mM CaCl$_2$)/TBST and 1.2 mM CaCl$_2$)/TBS. For the enrichment with antigen-binding ability as an index, the beads supplemented with 0.5 mL of 1 mg/mL trypsin were suspended at room temperature for 15 minutes, immediately after which the beads were separated using a magnetic stand to collect a phage solution. For the enrichment with pH-dependent antigen-binding ability as an index, 0.4 mL (round 2) or 0.1 mL (round 3 or later) of 50 mM MES/1.2 mM CaCl$_2$)/150 mM NaCl (pH 5.5) was added to the beads, and the resulting beads were suspended at room temperature. Then, the beads were separated using a magnetic stand to recover a phage solution. The addition of 20 μL (round 2) or 5 μL (round 3 or later) of 100 mg/mL trypsin to the collected phage solution cleaved the pIII proteins (helper phage-derived pIII proteins) of non-Fab-displaying phages to cancel the ability of the non-Fab-displaying phages to infect *E. coli*. The collected phages were added to 10 mL of an *E. coli* strain ER2738 in a logarithmic growth phase (OD600: 0.4-0.7). The *E. coli* strain was infected by the phages through the gentle spinner culture of the strain at 37° C. for 1 hour. The infected *E. coli* was inoculated to a plate of 225 mm×225 mm. Next, phages were collected from cultures of the inoculated *E. coli* to collect a phage library solution. This panning with antigen-binding ability or pH-dependent binding ability as an index was performed 3 rounds in total.

(26-3) Screening for Human HMGB1-Binding Antibody by Phage ELISA

A phage-containing culture supernatant was collected by phage culture according to a conventional method (Methods Mol. Biol. (2002) 178, 133-145) from each single colony of the *E. coli* obtained after the third and fourth rounds of panning carried out in the step (26-2). After addition of BSA and CaCl$_2$) (final concentration: 4% BSA and 1.2 mM calcium ion), the phage-containing culture supernatant was subjected to ELISA by the following procedures: StreptaWell 96 microtiter plate (F. Hoffmann-La Roche Ltd.) was coated for 4 hours or longer with 100 μL of PBS containing biotin-labeled hHMGB1. Each well of the plate was washed with PBST to remove unbound antigens. Then, the well was blocked with 250 μL of 4% BSA-TBS (50 mM Tris, 300 mM NaCl, 2.5 mM CaCl$_2$), and 4% BSA) for 1 hour or longer. After removal of 4% BSA-TBS, the prepared culture supernatant was added to each well, and the plate was left standing at 37° C. for 1 hour to associate phage-displayed antibodies with the HMGB1 contained in each well. Each well was washed with 1.2 mM CaCl$_2$)/TBST (pH 7.6), and 1.2 mM CaCl$_2$)/TBS (pH 7.6) or 1.2 mM CaCl$_2$)/150 mM NaCl/50 mM MES (pH 5.5) was added thereto. The plate was left standing at 37° C. for 30 minutes for incubation. After washing with 1.2 mM CaCl$_2$)/TBST (pH 7.6), HRP-conjugated anti-M13 antibodies (Amersham Pharmacia Biotech Inc.) diluted with 4% BSA-TBS were added to each well. The plate was incubated for 1 hour. After washing with 1.2 mM CaCl$_2$)/TBST (pH 7.6), TMB single solution (Invitrogen Corp.) was added to the well. The chromogenic reaction of the solution in each well was terminated by the addition of sulfuric acid. Then, the developed color was assayed on the basis of absorbance at 450 nm.

Antibody fragment genes contained in clones judged as having human HMGB1-binding ability changed depending on pH as a result of the phage ELISA were analyzed for their nucleotide sequences.

(26-4) Expression and Purification of Antibody Binding to Human HMGB1

The genes of three antibodies judged as having pH-dependent antigen-binding ability as a result of the phage ELISA, i.e., HM_3_2_R_017 (heavy chain: SEQ ID NO: 131 and light chain: SEQ ID NO: 132), HM_3_2_R_054 (heavy chain: SEQ ID NO: 133 and light chain: SEQ ID NO: 134), and HM_4_1_R_001 (heavy chain: SEQ ID NO: 135 and light chain: SEQ ID NO: 136), were separately inserted to plasmids for expression in animal cells. These antibodies were expressed using the following method: a human embryonic kidney cell-derived FreeStyle 293-F line (Invitrogen Corp.) was suspended in FreeStyle 293 Expression Medium (Invitrogen Corp.). The suspension having a cell density of 1.33×10$^6$ cells/mL was inoculated at a concentration of 3 mL/well to a 6-well plate. The prepared plasmids were transferred to the cells by lipofection. The cells were cultured for 4 days in a CO$_2$ incubator (37° C., 8% CO$_2$, 90 rpm). Antibodies were purified from the obtained culture supernatant by a method generally known to those skilled in the art using rProtein A Sepharose™ Fast Flow (Amersham Biosciences, Inc.). The absorbance of the purified antibody solution was measured at 280 nm using a spectrophotometer. The antibody concentration was calculated from the obtained measurement value by use of an extinction coefficient calculated by PACE (Protein Science (1995) 4, 2411-2423).

(26-5) Evaluation of Obtained Antibody for its pH-Dependent Binding Ability Against Human HMGB1

In order to judge the pH dependence of hHMGB1-binding activity of the antibodies HM_3_2_R_017 (heavy chain: SEQ ID NO: 131 and light chain: SEQ ID NO: 132), HM_3_2_R_054 (heavy chain: SEQ ID NO: 133 and light chain: SEQ ID NO: 134), and HM_4_1_R_001 (heavy chain: SEQ ID NO: 135 and light chain: SEQ ID NO: 136) obtained in the step (26-4), these antibodies were analyzed for their interaction with hHMGB1 using Biacore T100 (GE Healthcare Bio-Sciences Corp.). The interaction of antigen-antibody reaction was analyzed in solutions of pH 7.4 and pH 5.8 as neutral pH and acidic pH conditions, respectively. Approximately of 200 RU of each antibody of interest was captured onto Sensor chip CM4 (GE Healthcare Bio-Sciences Corp.) with protein A/G (Pierce Biotechnology Inc.) immobilized thereon in an appropriate amount by the amine coupling method. Two types of buffer solutions were used as running buffers: 20 mM ACES, 150 mM NaCl, 0.05% (w/v) Tween 20, and 1.2 mM CaCl$_2$) (pH 7.4); and 20 mM ACES, 150 mM NaCl, 0.05% (w/v) Tween 20, and 1.2 mM CaCl$_2$) (pH 5.8). hHMGB1 was also diluted with each of these buffers. Assay was all carried out at 25° C.

In the analysis on the interaction of antigen-antibody reaction using the HM_3_2_R_017 antibody, the HM_3_2_R_054 antibody, and the HM_4_1_R_001 antibody, the diluted hHMGB1 solution or a blank running buffer was injected at a flow rate of 10 μL/min for 60 seconds to capture the antigen onto the sensor chip. The HM_3_2_R_017 antibody, the HM_3_2_R_054 antibody, and the HM_4_1_R_001 antibody were interacted with hHMGB1. Then, 10 mM glycine-HCl (pH 1.5) was injected thereto at a flow rate of 30 μL/min for 30 seconds to regenerate the sensor chip.

Figure 15:
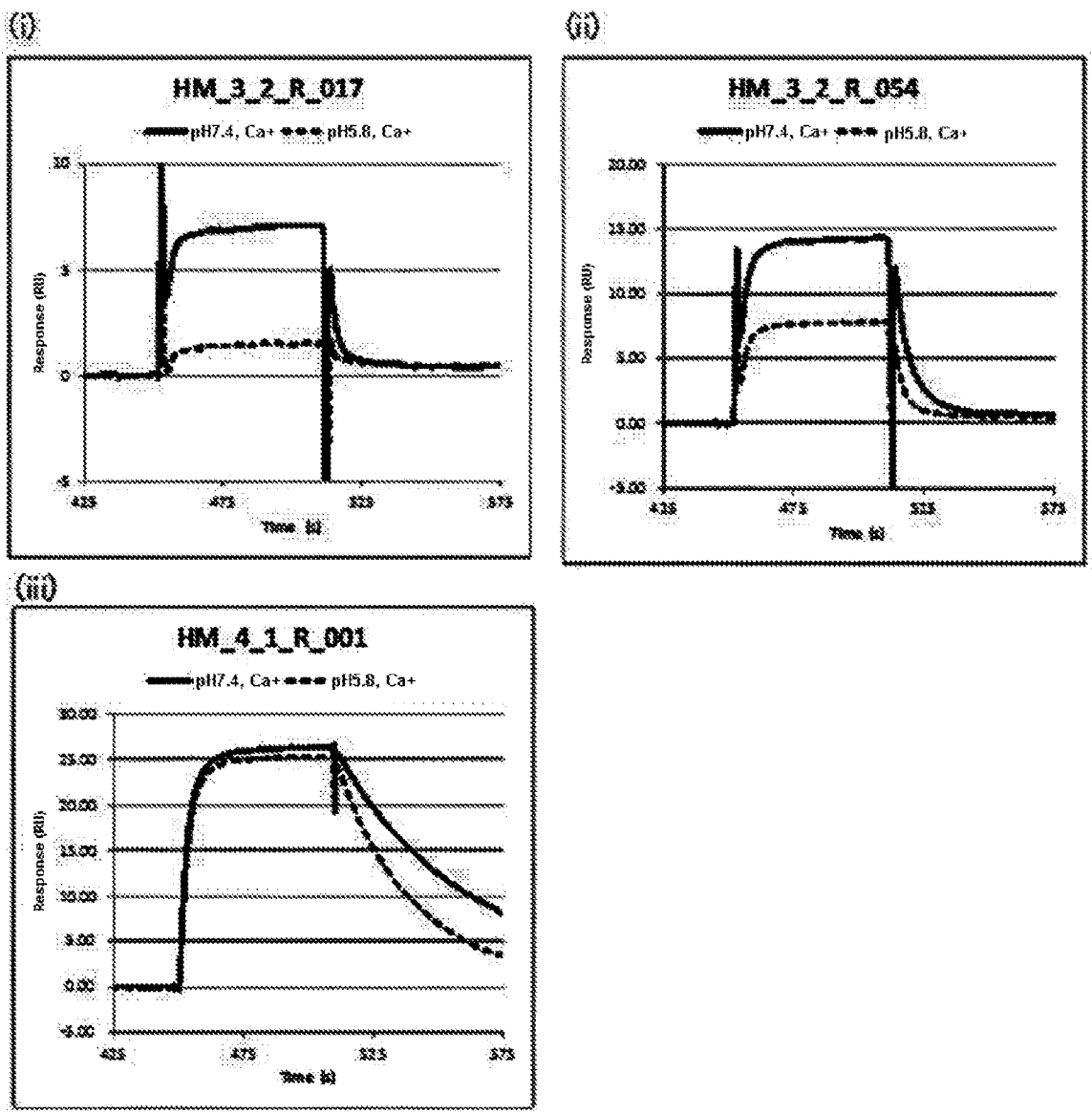
FIG. 15 shows a sensorgram depicting the interaction between an anti-human HMGB1 antibody and human HMGB1 at pH 7.4 and at pH 5.8 using Biacore. The solid line represents the results about the condition of pH 7.4. The broken line represents the results about the condition of pH 5.8.

FIG. 15 shows the sensorgrams of these antibodies assayed by the above method at pH 7.4 and pH 5.8.

From these results, the hHMGB1-binding ability of the HM_3_2_R_017 antibody, the HM_3_2_R_054 antibody, and the HM_4_1_R_001 antibody was observed to be reduced by the change of the buffer pH from pH 7.4 to pH 5.8, showing that pH-dependent binding antibodies can also be obtained against human HMGB1.

[Reference Example 1] Evaluation of Ca-Dependent Binding Antibody for its Influence on Plasma Retention of Antigen Using Normal Mouse (1-1) In Vivo Test Using Normal Mouse hsIL-6R (soluble human IL-6 receptor; prepared in Reference Example 4) was administered alone or simultaneously with each anti-human IL-6 receptor antibody to each normal mouse (C57BL/6J mouse, Charles River Laboratories Japan, Inc.). Then, the hsIL-6R and the anti-human IL-6 receptor antibody were evaluated for their pharmacokinetics in vivo. The hsIL-6R solution (5 μg/mL) or a mixed solution of hsIL-6R and the anti-human IL-6 receptor antibody was administered at a single dose of 10 mL/kg to the tail vein. The anti-human IL-6 receptor antibody used was H54/L28-IgG1, 6RL #9-IgG1, or FH4-IgG1 described above.

The mixed solution had an hsIL-6R concentration fixed to 5 μg/mL, but had an anti-human IL-6 receptor antibody concentration differing among the antibodies: 0.1 mg/mL for H54/L28-IgG1 and 10 mg/mL for 6RL #9-IgG1 and FH4-IgG1. In this case, an excessive amount of the anti-human IL-6 receptor antibody is present in mixed solution to be sufficient for binding to hsIL-6R. The great majority of the hsIL-6R antigens therefore seem to be bound with the antibodies. Blood was collected 15 minutes, 7 hours, 1 day, 2 days, 4 days, 7 days, 14 days, 21 days, and 28 days after the administration. The collected blood was immediately centrifuged at 12,000 rpm at 4° C. for 15 minutes to obtain plasma. The separated plasma was stored in a refrigerator set to −20° C. or lower until practice of assay.

Figure 16:
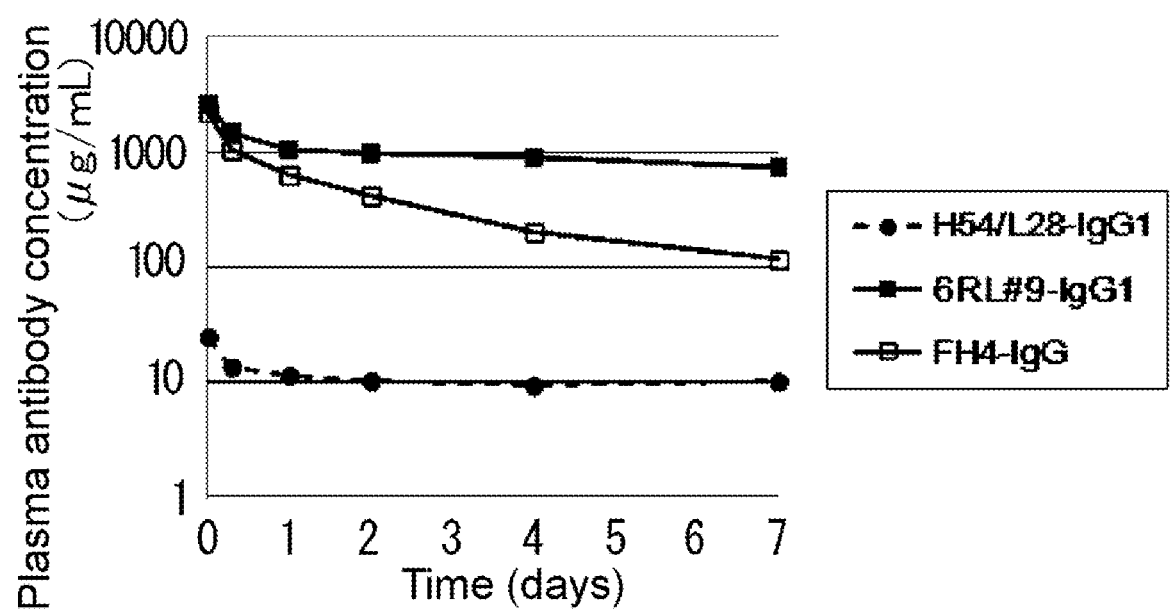
FIG. 16 is a diagram showing the plasma concentration of an H54/L28-IgG1 antibody, an FH4-IgG1 antibody, and a 6RL #9-IgG1 antibody in normal mouse.

(1-2) Measurement of Anti-Human IL-6 Receptor Antibody Concentration in Normal Mouse Plasma by ELISA The anti-human IL-6 receptor antibody concentration in the mouse plasma was measured by ELISA. First, Anti-Human IgG (γ-chain specific) F(ab')2 Fragment of Antibody (Sigma-Aldrich Corp.) was dispensed to Nunc-Immuno Plate, MaxiSoup (Nalge Nunc International) and left standing overnight at 4° C. to prepare an anti-human IgG solid-phase plate. Calibration curve samples having a plasma concentration of 0.64, 0.32, 0.16, 0.08, 0.04, 0.02, or 0.01 μg/mL and mouse plasma assay samples diluted 100-fold or more were each dispensed to the anti-human IgG solid-phase plate, which was then incubated at 25° C. for 1 hour. Then, Biotinylated Anti-human IL-6 R Antibody (R&D Systems, Inc.) was reacted therewith at 25° C. for 1 hour. Then, Streptavidin-PolyHRP80 (Stereospecific Detection Technologies GmbH) was reacted therewith at 25° C. for 0.5 hours. TMB One Component HRP Microwell Substrate (BioFX Laboratories Inc.) was used as a substrate in chromogenic reaction. The chromogenic reaction was terminated by the addition of 1 N sulfuric acid (Showa Chemical Industry Co., Ltd.). Then, the absorbance of the developed color solution was measured at 450 nm using a microplate reader. The antibody concentration in the mouse plasma was calculated with reference to the absorbance of the calibration curve using analysis software SOFTmax PRO (Molecular Devices, LLC). FIG. 16 shows change in the concentrations of the H54/L28-IgG1, 6RL #9-IgG1, and FH4-IgG1 antibodies measured by this method in the plasma of the normal mice after intravenous administration.

Figure 17:
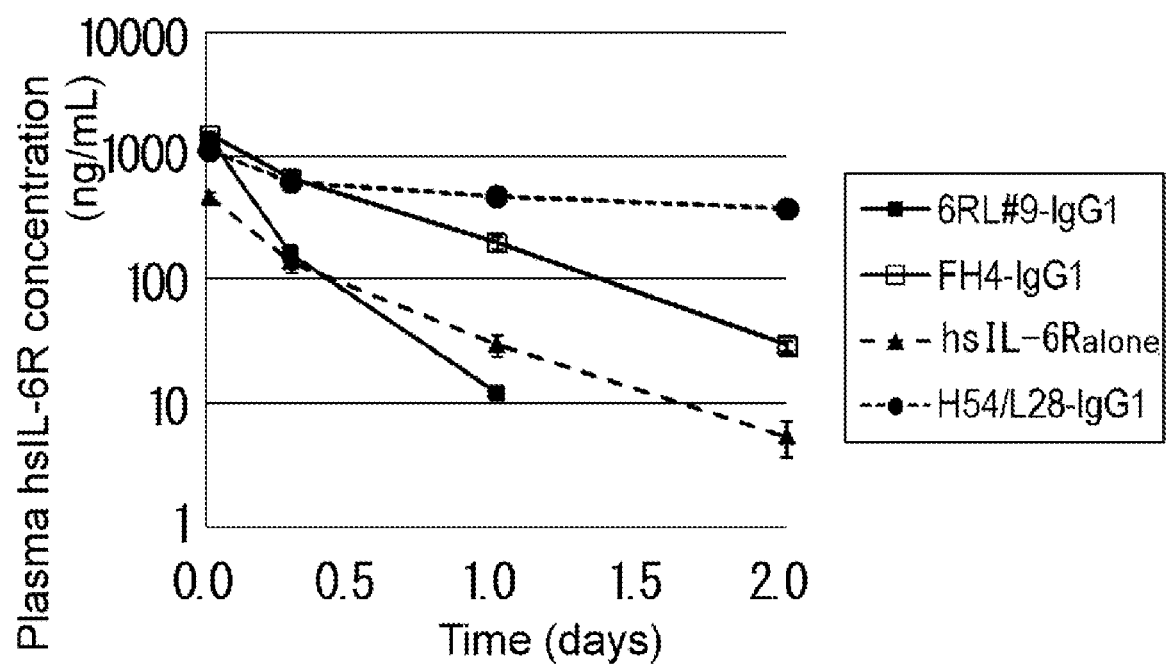
FIG. 17 is a diagram showing the concentration of a soluble human IL-6 receptor (hsIL-6R) in the plasma of a normal mouse that received the H54/L28-IgG1 antibody, the FH4-IgG1 antibody, or the 6RL #9-IgG1 antibody.

(1-3) Measurement of hsIL-6R Concentration in Plasma by Electrochemiluminescent Method The hsIL-6R concentration in the mouse plasma was measured by the electrochemiluminescent method. hsIL-6R calibration curve samples adjusted to 2000, 1000, 500, 250, 125, 62.5, or 31.25 pg/mL and mouse plasma assay samples diluted 50-fold or more were reacted overnight at 4° C. with a mixed solution of Monoclonal Anti-human IL-6R Antibody (R&D Systems, Inc.) labeled with ruthenium using SULFO-TAG NHS Ester (Meso Scale Discovery), Biotinylated Anti-human IL-6 R Antibody (R&D Systems, Inc.), and a tocilizumab (heavy chain: SEQ ID NO: 24 and light chain: SEQ ID NO: 25) solution. Free Ca concentration in the samples was decreased to allow almost all of the hsIL-6R antigens in the samples to be dissociated from 6RL #9-IgG1 or FH4-IgG1 and then associated with the added tocilizumab. For this purpose, the assay buffer contained 10 mM EDTA. Then, the reaction solution was dispensed to MA400 PR Streptavidin Plate (Meso Scale Discovery). After further reaction at 25° C. for 1 hour, each well of the plate was washed, and Read Buffer T (×4) (Meso Scale Discovery) was then dispensed to each well. Immediately thereafter, the reaction solution was assayed using SECTOR PR 400 reader (Meso Scale Discovery). The hsIL-6R concentration was calculated from the response of the calibration curve using analysis software SOFTmax PRO (Molecular Devices, LLC). FIG. 17 shows change in the concentration of hsIL-6R measured by this method in the plasma of the normal mice after intravenous administration.

As a result, hsIL-6R alone was cleared from blood rapidly, whereas the simultaneous administration thereof with the conventional antibody H54/L28-IgG1 having no Ca-dependent hsIL-6R binding drastically prolonged the clearance of the hsIL-6R. By contrast, the simultaneous administration thereof with the antibody 6RL #9-IgG1 or FH4-IgG1 having 100-fold or higher Ca-dependent hsIL-6R binding drastically accelerated the clearance of the hsIL-6R. The antibodies 6RL #9-IgG1 and FH4-IgG1 simultaneously administered with hsIL-6R reduced the plasma hsIL-6R concentration after 1 day by 39 times and 2 times, respectively, compared with H54/L28-IgG1 simultaneously administered therewith. This demonstrated that the calcium-dependent binding antibody can accelerate the clearance of antigens from plasma.

[Reference Example 2] Study on Improvement in Antigen Clearance-Accelerating Effect of Ca-Dependent Antigen-Binding Antibody (Preparation of Antibody)

(2-1) Regarding FcRn Binding of IgG Antibody

The IgG antibody has long plasma retention through its binding to FcRn. The binding between IgG and FcRn is observed only in an acidic condition (pH 6.0) and is hardly observed in a neutral condition (pH 7.4). The IgG antibody is nonspecifically taken up into cells, but recycled onto cell surface through binding to endosomal FcRn under the acidic condition in endosome and dissociated from FcRn under the neutral condition in plasma. IgG that has lost FcRn binding under the acidic condition by the mutation of the Fc region is no longer recycled into plasma from endosome, resulting in significantly impaired plasma retention of the antibody.

Previously reported methods for improving the plasma retention of the IgG antibody involve improving its FcRn binding under the acidic condition. Amino acid substitution is introduced to the Fc region of the IgG antibody to improve the FcRn binding under the acidic condition, thereby enhancing the efficiency of recycling of the IgG antibody from endosome into plasma. As a result, the plasma retention of the IgG antibody is improved. It has been considered important for the introduction of amino acid substitution not to enhance the FcRn binding under the neutral condition. It has been believed that the plasma retention of such an IgG antibody binding to FcRn under the neutral condition is rather impaired because this IgG antibody may be recycled onto cell surface through binding to FcRn under the acidic condition in endosome, but can be neither dissociated from FcRn under the neutral condition in plasma nor recycled into plasma.

As described by, for example, Dall'Acqua et al. (J. Immunol. (2002) 169 (9), 5171-5180), an IgG1 antibody that has become able to bind to mouse FcRn under the neutral condition (pH 7.4) by the introduction of amino acid substitution reportedly exhibits deteriorated plasma retention, when administered to a mouse. As described by Yeung et al. (J. Immunol. (2009) 182 (12), 7663-7671), Datta-Mannan et al. (J. Biol. Chem. (2007) 282 (3), 1709-1717), and Dall' Acqua et al. (J. Immunol. (2002) 169 (9), 5171-5180), an engineered IgG1 antibody having the improved ability to bind to human FcRn under the acidic condition (pH 6.0) as a result of the introduction of amino acid substitution was also confirmed to bind to human FcRn under the neutral condition (pH 7.4). According to the reports, the antibody administered to a cynomolgus monkey did not exhibit improvement in plasma retention or change in plasma retention. The conventional antibody engineering techniques of improving antibody functions have been focused on improvement in the plasma retention of antibodies by enhancing binding to human FcRn under the acidic condition without enhancing binding to human FcRn under the neutral condition (pH 7.4). Specifically, none of the previous reports have made mention about the advantages of the IgG1 antibody having the enhanced binding to human FcRn under the neutral condition (pH 7.4) by the introduction of amino acid substitution to the Fc region.

Ca-dependent antigen-binding antibodies are very useful because of their effects of accelerating the clearance of soluble antigens and binding to the soluble antigens repeatedly by one antibody molecule. A method of enhancing FcRn binding under the neutral condition (pH 7.4) was tested in order to further improve this antigen clearance-accelerating effect.

(2-2) Preparation of Ca-Dependent Human IL-6 Receptor-Binding Antibody Having FcRn-Binding Activity Under Neutral Condition Amino acids in the Fc regions of FH4-IgG1 and 6RL #9-IgG1 having calcium-dependent antigen-binding ability and H54/L28-IgG1 used as a control having no calcium-dependent antigen-binding ability were mutated to prepare modified forms having FcRn binding under the neutral condition (pH 7.4). The amino acid mutation was performed by PCR using a method generally known to those skilled in the art. Specifically, FH4-N434W (heavy chain: SEQ ID NO: 94 and light chain: SEQ ID NO: 81), 6RL #9-N434W (heavy chain: SEQ ID NO: 95 and light chain: SEQ ID NO: 79), and H54/L28-N434W (heavy chain: SEQ ID NO: 96 and light chain: SEQ ID NO: 83) were prepared by the substitution of Asn at amino acid 434 defined by the EU numbering in an IgG1 heavy chain constant region by Trp. Expression vectors for animal cells having an insert of a polynucleotide encoding each of these amino acid substitution variants were prepared using QuikChange Site-Directed Mutagenesis Kit (Stratagene Corp.) according to a method described in the instruction manual attached to the kit. Antibody expression and purification and concentration measurement were carried out by the method described in Example 15.

[Reference Example 3] Evaluation of Ca-Dependent Binding Antibody for its Disappearance-Accelerating Effect Using Normal Mouse (3-1) In Vivo Test Using Normal Mouse hsIL-6R (soluble human IL-6 receptor; prepared in Reference Example 4) was administered alone or simultaneously with each anti-human IL-6 receptor antibody to each normal mouse (C57BL/6J mouse, Charles River Laboratories Japan, Inc.). Then, the hsIL-6R and the anti-human IL-6 receptor antibody were evaluated for their in vivo kinetics. The hsIL-6R solution (5 µg/mL) or a mixed solution of hsIL-6R and the anti-human IL-6 receptor antibody was administered at a single dose of 10 mL/kg to the tail vein. The anti-human IL-6 receptor antibody used was H54/L28-N434W, 6RL #9-N434W, or FH4-N434W described above.

The mixed solution had an hsIL-6R concentration fixed to 5 µg/mL, but had an anti-human IL-6 receptor antibody concentration differing among the antibody types: 0.042 mg/mL for H54/L28-N434W, 0.55 mg/mL for 6RL #9-N434W, and 1 mg/mL for FH4-N434W. In this case, the anti-human IL-6 receptor antibody is present in an excessive amount sufficient for hsIL-6R. The great majority of the hsIL-6R antigens therefore seem to be bound with the antibodies. Blood was collected 15 minutes, 7 hours, 1 day, 2 days, 4 days, 7 days, 14 days, 21 days, and 28 days after the administration. The collected blood was immediately centrifuged at 12,000 rpm at 4° C. for 15 minutes to obtain plasma. The separated plasma was stored in a refrigerator set to −20° C. or lower until practice of assay.

Figure 18:
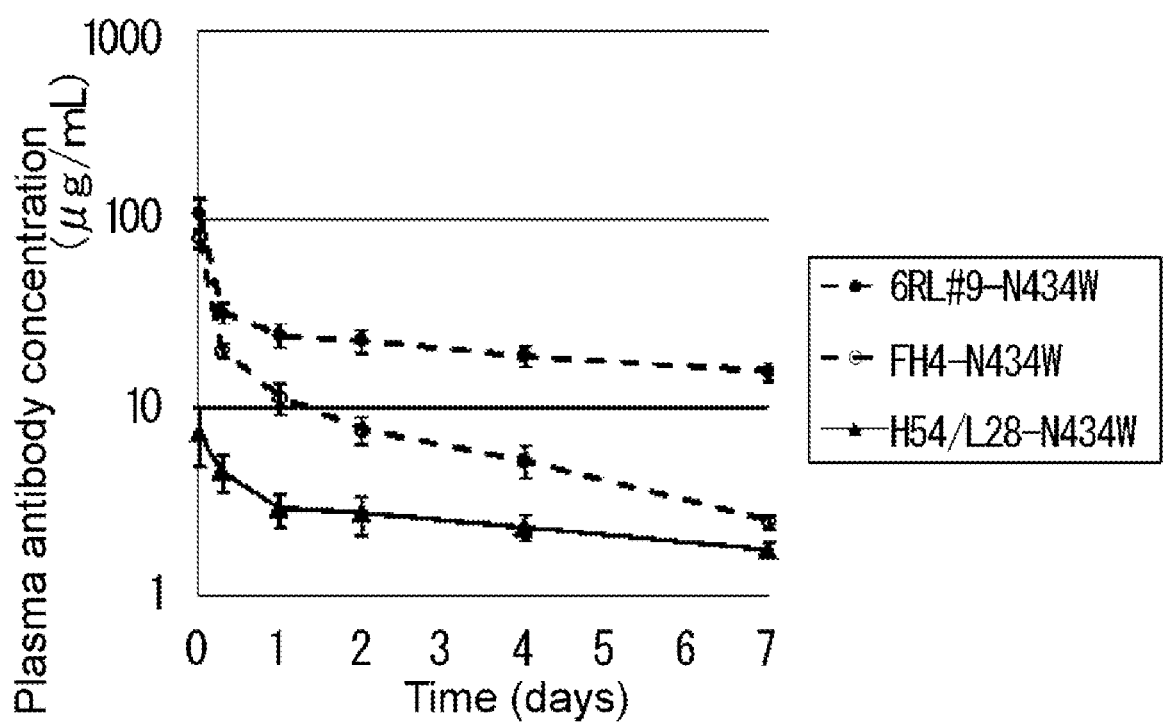
FIG. 18 is a diagram showing the plasma concentrations of an H54/L28-N434W antibody, an FH4-N434W antibody, and a 6RL #9-N434W antibody in normal mouse.

(3-2) Measurement of Anti-Human IL-6 Receptor Antibody Concentration in Normal Mouse Plasma by ELISA The anti-human IL-6 receptor antibody concentration in the mouse plasma was measured by ELISA in the same way as in Reference Example 1. FIG. 18 shows change in the concentrations of the H54/L28-N434W, 6RL #9-N434W, and FH4-N434W antibodies measured by this method in the plasma of the normal mice after intravenous administration.

Figure 19:
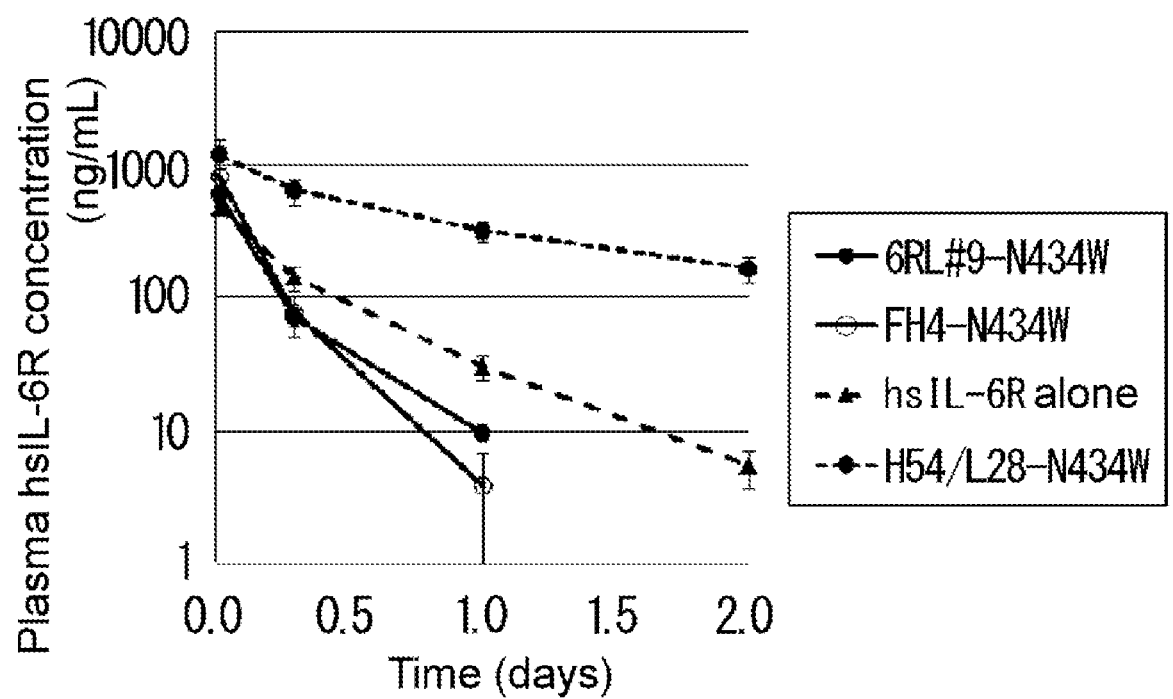
FIG. 19 is a diagram showing the concentration of a soluble human IL-6 receptor (hsIL-6R) in the plasma of a normal mouse that received the H54/L28-N434W antibody, the FH4-N434W antibody, and the 6RL #9-N434W antibody.

(3-3) Measurement of hsIL-6R Concentration in Plasma by Electrochemiluminescent Method The hsIL-6R concentration in the mouse plasma was measured by the electrochemiluminescent method. hsIL-6R calibration curve samples adjusted to 2000, 1000, 500, 250, 125, 62.5, or 31.25 pg/mL and mouse plasma assay samples diluted 50-fold or more were reacted overnight at 4° C. with a mixed solution of Monoclonal Anti-human IL-6R Antibody (R&D Systems, Inc.) labeled with ruthenium using SULFO-TAG NHS Ester (Meso Scale Discovery) and Biotinylated Anti-human IL-6 R Antibody (R&D Systems, Inc.). Free Ca concentration in the samples was decreased to allow almost all of the hsIL-6R antigens in the samples to be dissociated from 6RL #9-N434W or FH4-N434W to assume free forms. For this purpose, the assay buffer contained 10 mM EDTA. Then, the reaction solution was dispensed to MA400 PR Streptavidin Plate (Meso Scale Discovery). After further reaction at 25° C. for 1 hour, each well of the plate was washed, and Read Buffer T (×4) (Meso Scale Discovery) was then dispensed to each well. Immediately thereafter, the reaction solution was assayed using SECTOR PR 400 reader (Meso Scale Discovery). The hsIL-6R concentration was calculated from the response of the calibration curve using analysis software SOFTmax PRO (Molecular Devices, LLC). FIG. 19 shows change in the concentration of hsIL-6R measured by this method in the plasma of the normal mice after intravenous administration.

As a result, the simultaneous administration of hsIL-6R with the H54/L28-N434W antibody having FcRn-binding activity at pH 7.4 but no Ca-dependent binding activity against hsIL-6R drastically prolonged the disappearance of the hsIL-6R, compared with the administration of the hsIL-6R alone. By contrast, the simultaneous administration thereof with the 6RL #9-N434W antibody or the FH4-N434W antibody having 100-fold or higher Ca-dependent hsIL-6R binding and also FcRn binding at pH 7.4 accelerated the disappearance of the hsIL-6R, compared with the administration of the hsIL-6R alone. The 6RL #9-N434W antibody and the FH4-N434W antibody simultaneously administered with hsIL-6R reduced the plasma hsIL-6R concentration by 3 times and 8 times in one day after the administration, respectively, compared with the hsIL-6R administered alone. These results demonstrated that the calcium-dependent antigen-binding antibody provided with FcRn-binding activity at pH 7.4 can further accelerate the disappearance of antigens from plasma.

The 6RL #9-IgG1 antibody or the FH4-IgG1 antibody having 100-fold or higher Ca-dependent hsIL-6R-binding activity was confirmed to have the effect of increasing the disappearance of hsIL-6R, compared with the H54/L28-IgG1 antibody having no Ca-dependent hsIL-6R binding. The 6RL #9-N434W antibody or the FH4-N434W antibody having 100-fold or higher Ca-dependent hsIL-6R-binding activity and also FcRn binding at pH 7.4 was confirmed to accelerate the disappearance of hsIL-6R, compared with hsIL-6R administered alone. These data suggests that, as with the pH-dependent antigen-binding antibody, the Ca-dependent antigen-binding antibody is dissociated from the antigen in endosome.

[Reference Example 4] Preparation of Soluble Human IL-6 Receptor (hsIL-6R)

A recombinant antigen of the human IL-6 receptor was prepared as follows: a CHO cell line stably expressing a soluble human IL-6 receptor (hereinafter, referred to as hsIL-6R) composed of an N-terminal amino acid sequence from positions 1 to 357 as reported by Mullberg et al. (J. Immunol. (1994) 152, 4958-4968) was constructed by a method generally known to those skilled in the art. The expressing line was cultured to express hsIL-6R. hsIL-6R was purified from the obtained culture supernatant by Blue Sepharose 6 FF column chromatography and gel filtration column chromatography. A fraction eluted as a main peak in the final step was used as a final purified product.

[Reference Example 5] NMR Analysis of Antibody Comprising Human hVk1 Sequence Having Calcium Ion-Binding Motif for its Calcium Ion-Binding Activity (5-1) Antibody Expression and Purification An antibody comprising LfVk1_Ca and an antibody comprising LfVk1 were expressed for use in NMR assay and purified. Specifically, animal cells were transiently transfected with plasmids for expression in animal cells prepared so as to permit respective expression of the heavy chain (SEQ ID NO: 24) and the light chain (SEQ ID NO: 43) of the antibody comprising LfVk1_Ca (also referred to as an LfVk1_Ca antibody). Also, animal cells were transiently transfected with plasmids for expression in animal cells prepared so as to permit respective expression of the heavy chain (SEQ ID NO: 24) and the light chain (SEQ ID NO: 44) of the antibody comprising LfVk1 (also referred to as an LfVk1 antibody). Labeling amino acids were added to 100 mL of a cell suspension of a human embryonic kidney cell-derived FreeStyle 293-F line (Invitrogen Corp.) suspended at a final cell density of $1 \times 10^6$ cells/mL in FreeStyle 293 Expression Medium (Invitrogen Corp.). Specifically, for the Asp/Glu/Gln/Asn label, L-aspartic acid-$^{13}C_4$, $^{15}N$ (10 mg), L-glutamic acid-$^{13}C_5$, $^{15}N$ (2.5 mg), L-glutamine-$^{13}C_5$, $^{15}N_2$ (60 mg), L-asparagine-$^{13}C_4$, $^{15}N_2 \cdot H_2O$ (2.5 mg), and β-chloro-L-alanine (6 mg) were suspended in 10 mL of water, and the resulting solution was filtered through a 0.22-μm filter and then added thereto. For the Leu label, L-leucine-$^{15}N$ (30 mg) and β-chloro-L-alanine (6 mg) were suspended in 10 mL of water, and the resulting solution was filtered through a 0.22-μm filter and then added thereto. The prepared plasmids were transferred to the cells by lipofection. The cells transfected with the plasmids were cultured for 5 days in a $CO_2$ incubator (37° C., 8% $CO_2$, 90 rpm). Antibodies were purified from the obtained culture supernatant according to a method generally known to those skilled in the art using rProtein A Sepharose™ Fast Flow (Amersham Biosciences, Inc.). The absorbance of the purified antibody solution was measured at 280 nm using a spectrophotometer. The antibody concentration was calculated from the obtained measurement value by use of an extinction coefficient calculated by PACE (Protein Science (1995) 4, 2411-2423).

(5-2) Preparation of Fab Fragment

Each antibody was concentrated to 8.2 to 11.8 mg/mL using an ultrafiltration membrane having a molecular weight cutoff of 30,000 MWCO. The antibody was diluted to 8 mg/mL with 1 mM L-cysteine, 2 mM EDTA, and 50 mM acetic acid/125 mM tris buffer solution (pH 6.8) to prepare an antibody sample. After addition of papain (Roche Applied Science) in 1/40 of the amount of each antibody, the sample was stirred and then left standing at 37° C. for 1 hour. The sample thus left standing was added to a Gly-Gly-Tyr-Arg (Sigma-Aldrich Corp.) peptide-conjugated 1 mL-size HiTrap NHS-activated HP (GE Healthcare Bio-Sciences Corp.) (equilibrated with 50 mM acetic acid/125 mM tris buffer solution (pH 6.8)) connected in tandem with a downstream 1 mL-size protein A carrier column HiTrap MabSelect Sure (GE Healthcare Bio-Sciences Corp.). The activated papain was removed by the upstream Gly-Gly-Tyr-Arg peptide, while Fc fragments and undigested antibodies were removed by the downstream protein A carrier column to obtain a purified fraction of the Fab fragment. A 10 μM cysteine protease inhibitor E64 (Sigma-Aldrich Corp.) was added to the Fab fraction to prevent the activation of the inactive papain contained in the Fab fraction. The column operation was all carried out at room temperature of 20 to 25° C.

(5-3) Preparation of NMR Samples of LfVk1_Ca and LfVk1 Antibody Fab Fragments

Each antibody solution was concentrated to 0.5 mL by centrifugation using a MWCO 5000 ultrafilter Vivaspin (Sartorius). Next, Diafiltration Cup was placed in the ultrafilter, and the buffer solution was replaced with a buffer solution for NMR: 5 mM d-BisTris, 20 mM NaCl, 0.001% (w/v) $NaN_3$, and 5% (v/v)$^2H_2O$ (pH 7.0) (pH-adjusted using NaOH or HCl) (5 mL of the buffer solution was added to the Diafiltration Cup, the contents of which were concentrated to 0.5 mL by centrifugation; this operation was repeated three times). The resulting solution was finally concentrated to 0.25 mL. Finally, the ultrafilter was thoroughly washed with the NMR buffer solution. The washes were combined with the concentrate to prepare 420 µL of an LfVk1_Ca antibody solution and 270 µL of an LfVk1 antibody solution. At this stage, the pH of each solution was confirmed again and adjusted, if necessary, to pH 7.0 with NaOH or HCl. The absorbance was measured at 280 nm using a UV meter Nanodrop (Thermo Fisher Scientific K.K.). Each Fab fragment was quantified with the molar extinction coefficient at 280 nm set to 70000 $M^{-1} \cdot cm^{-1}$ and consequently determined to be 0.12 mM for the Leu-labeled LfVk1_Ca antibody and the Leu-labeled LfVk1 antibody and 0.24 mM for the Asp/Glu/Asn/Gln-labeled LfVk1_Ca antibody and the Asp/Glu/Asn/Gln-labeled LfVk1 antibody. Of these samples, each LfVk1_Ca antibody was charged into an NMR sample tube (Shigemi Co., Ltd.) of 5 mm in diameter, while each LfVk1 antibody was charged into a symmetrical microsample tube for aqueous solutions (Shigemi Co., Ltd.) of 5 mm in diameter using a Pasteur pipette. In the $Ca^{2+}$ titration experiment of the LfVk1_Ca antibody, $CaCl_2$) solutions were sequentially added to the antibody solution at 1, 2, 5, 10, and 20 molar equivalents of $Ca^{2+}$ to the antibody. The $CaCl_2$) solutions used in the addition were prepared as 10, 20, 50, and 100 mM solutions of $CaCl_2$) dissolved in an NMR buffer. The necessary amounts of the $CaCl_2$) solutions were directly added at volumes in the range of 3 to 10 µL to the antibody solutions charged in the NMR sample tubes using a special-order microsyringe (Ito Corp.) with a syringe portion extended from the ready-made one. The sample tubes were stirred using a vortex mixer and then centrifuged in a manual centrifuge (Shimadzu Corp.).

(5-3) NMR Analysis for Observing Amide Group Signals of LfVk1_Ca and LfVk1_Ca Antibody Fab Fragments The NMR analysis was performed using an NMR spectroscope DRX750 (Bruker Biospin K.K.) equipped with TCI CryoProbe. The temperature was set to 307 K (gas flow: 535 L/h). $^1H$-$^{15}N$ HSQC was used in the NMR assay for observing amide group signals. $^1H$-$^{15}N$ FHSQC involving the simultaneous $^{13}C$ decoupling of α-carbon and carbonyl carbon in the $^{15}N$ evolution period, and 3-9-19 pulse train for cancelation of solvent water signals was used in the assay method. For control thereof, the pulse program included as standard by the manufacturer (Bruker Biospin K.K.) was used. The NMR assay conditions were as follows: spectrum width: 12019 Hz (f2) and 1976 Hz (f1), and the number of data points: 2048 (f2) and 128 (f1). Topspin 3.0 (Bruker Biospin K.K.) was used for data processing. The data processing conditions were as follows: for both f2 and f1, the data was multiplied with a shifted sine (QSINE)-bell window function and zero-filled to double the number of data points, followed by Fourier transform. The chemical shifts of the signals were calculated using NMR analysis software Sparky (UCSF).

(5-4) Attribution of NMR Signal of Main Chain Amide Group

80% of NMR signals have been attributed so far to main chain amide groups in the Fab fragment of tocilizumab (heavy chain: SEQ ID NO: 24 and light chain: SEQ ID NO: 25) (data not published). The amino acid sequence of the LfVk1_Ca antibody Fab fragment is the same as that of the tocilizumab Fab fragment except for a portion of light chain CDR1, CDR2, and CDR3 and light chain amino acid residues 73 and 83. Since the NMR signals of the same parts in the amino acid sequences of these antibodies have identical or similar chemical shifts, attribution information about tocilizumab was able to be migrated to the LfVk1_Ca antibody. The attribution of light chain residues 11, (33), (46), (47), (54), (78), 125, 135, 136, 154, 175, 179, 181, and 201 and heavy chain residues 18, 46, 64, 71, 81, 83, 114, 144, 147, 165, 176, 181, 184, and 195 was able to be migrated to the Leu-labeled sample. The numbers without parentheses represent residue numbers to which the attribution was able to be migrated because of their chemical shifts identical to those of tocilizumab. The numbers in parentheses represent residue numbers to which the attribution was able to be migrated because of their chemical shifts similar to those of tocilizumab and the absence of the other signals having similar chemical shifts. For the Asp/Glu/Asn/Gln-labeled sample, four signals were newly observed in LfVk1_Ca by the spectral comparison between the LfVk1_Ca antibody and the LfVk1 antibody. These signals were successfully classified as signals derived from any 4 of 5 residues introduced as $Ca^{2+}$-binding motifs, i.e., Asp30, Asp31, Asp32, Asp92, and Glu50, in the light chain differing in sequence between the antibodies, among the Asp, Glu, Asn, and Gln residues.

(5-5) Identification of $Ca^{2+}$-Binding Site on LfVk1_Ca Antibody

Signals having change in chemical shift were extracted by the $^1H$-$^{15}N$ HSQC spectral comparison between the LfVk1_Ca antibody Fab fragment unsupplemented with $Ca^{2+}$ and the Fab fragment supplemented with 20 molar equivalents of $Ca^{2+}$. The results about the Leu-labeled samples demonstrated that light chain Leu33 is involved in the binding, whereas the other Leu residues are not involved in the binding. The results about the Asp/Glu/Asn/Gln-labeled samples demonstrated that any 4 of the 5 residues (light chain Asp30, Asp31, Asp32, Asp92, and Glu50) are involved in the binding, whereas the other Asp, Glu, Asn, and Gln residues except for 1 residue are not involved in the binding. From these results, amino acids in at least light chain CDR1 in the amino acid sequence introduced as the $Ca^{2+}$-binding motifs as well as in one or both of light chain CDR2 and CDR3 were identified to participate in $Ca^{2+}$ binding. This was consistent with the results confirmed in Example 15 showing that important for calcium ion binding is that 4 of residues 30, 31, 32, 50, and 92 (defined by the Kabat numbering) are amino acids of the hVk5-2 sequence.

(5-6) Calculation of $Ca^{2+}$ Dissociation Constant in Titration Experiment $^1H$-$^{15}N$ HSQC spectra were used, which were obtained when the $Ca^{2+}$ concentration was 0, 1, 2, 5, 10, or 20 molar equivalents to the LfVk1_Ca antibody Fab fragment. A $^1H$ or $^{15}N$ chemical shift in the signal of light chain Leu33 identified as a binding site was plotted on the ordinate, while the above molar equivalents of $Ca^{2+}$ were plotted on the abscissa. The data was fit to a function represented by the following expression 2 using graph creation software Gnuplot:

$$f(x)=s\times[1-0.5/a\times\{(a\times x+a+Kd)-((a\times x+a+Kd)2-4\times x\times a2)0.5\}]+t\times[0.5/a\times\{(a\times x+a+Kd)-((a\times x+a+Kd)^2-4\times x\times a^2)^{0.5}\}$$ [Expression 2]

In the function represented by the expression 2, s and t represent a chemical shift [ppm] in the absence of bound $Ca^{2+}$ and a putative chemical shift [ppm] in the presence of saturation-bound $Ca^{2+}$, respectively; a represents the concentration [M] of the antibody Fab fragment; Kd represents a dissociation constant; and x represents the molar equivalent of $Ca^{2+}$ added to the antibody Fab fragment. For the fitting, s, t, and Kd were used as fitting parameters. As a result, $Kd=7.1\times10^{-5}$ [M] was estimated from the $^1H$ chemical shift, and $Kd=5.9\times10^{-5}$ [M] was estimated from the $^{15}N$ chemical shift.

---

The invention claimed is:

1. A library for screening an antigen-binding molecule, which binds to an antigen of interest, consisting essentially of a plurality of antigen-binding molecules differing in sequence from each other and that bind different antigens, wherein the antigen-binding domain in each of the antigen-binding molecules is a heavy chain variable region and a light chain variable region of an antibody and comprises at least one histidine residue at any one or more of positions 27, 31, 32, 33, 35, 50, 52, 53, 55, 57, 58, 59, 61, 62, 95, 96, 97, 98, 99, 100a, 100b, 100d, 100f, 100h, 102, and 107 defined by the Kabat numbering in the heavy chain variable region or a histidine residue at any one or more of positions 24, 27, 28, 30, 31, 32, 34, 50, 51, 52, 53, 54, 55, 56, 89, 90, 91, 92, 93, 94, and 95a defined by the Kabat numbering in the light chain variable region.

2. The library according to claim 1, wherein an amino acid sequence except for the amino acid residue at any one or more of positions 27, 31, 32, 33, 35, 50, 52, 53, 55, 57, 58, 59, 61, 62, 95, 96, 97, 98, 99, 100a, 100b, 100d, 100f, 100h, 102, and 107 defined by the Kabat numbering in the heavy chain variable region comprises the amino acid sequence of a naive sequence.

3. The library according to claim 1, wherein a light chain variable region of the antigen-binding molecule comprises a germline sequence.

4. The library according to claim 1, wherein the histidine residue is contained in CDR1 of the light chain variable region.

5. The library according to claim 4, wherein the histidine residue is located at any one or more of positions 24, 27, 28, 30, 31, 32, and 34 defined by the Kabat numbering in the light chain CDR1.

6. The library according to claim 1, wherein the histidine residue is contained in the light chain CDR2.

7. The library according to claim 6, wherein the histidine residue is located at any one or more of positions 50, 51, 52, 53, 54, 55, and 56 defined by the Kabat numbering in the light chain CDR2.

8. The library according to claim 1, wherein the histidine residue is contained in light chain CDR3.

9. The library according to claim 8, wherein the histidine residue is located at any one or more of positions 89, 90, 91, 92, 93, 94, and 95a defined by the Kabat numbering in the light chain CDR3.

10. The library according to claim 1, wherein the antigen-binding domain in each of the antigen-binding molecules is an antigen binding fragment of an antibody.

11. The library according to claim 1, wherein the antigen-binding domain in each of the antigen-binding molecules is a Fab, F(ab')2, or scFv.

* * * * *